US011013441B2

(12) United States Patent
Samadani

(10) Patent No.: US 11,013,441 B2
(45) Date of Patent: *May 25, 2021

(54) METHODS AND KITS FOR DIAGNOSING, ASSESSING OR QUANTITATING DRUG USE, DRUG ABUSE AND NARCOSIS, INTERNUCLEAR OPHTHALMOPLEGIA, ATTENTION DEFICIT HYPERACTIVITY DISORDER (ADHD), CHRONIC TRAUMATIC ENCEPHALOPATHY, SCHIZOPHRENIA SPECTRUM DISORDERS AND ALCOHOL CONSUMPTION

(71) Applicant: NEW YORK UNIVERSITY, New York, NY (US)

(72) Inventor: Uzma Samadani, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 339 days.

This patent is subject to a terminal disclaimer.

(21) Appl. No.: 15/501,273

(22) PCT Filed: Jul. 31, 2015

(86) PCT No.: PCT/US2015/043083
§ 371 (c)(1),
(2) Date: Feb. 2, 2017

(87) PCT Pub. No.: WO2016/022414
PCT Pub. Date: Feb. 11, 2016

(65) Prior Publication Data
US 2017/0367633 A1    Dec. 28, 2017

Related U.S. Application Data

(60) Provisional application No. 62/032,769, filed on Aug. 4, 2014, provisional application No. 62/065,057, filed
(Continued)

(51) Int. Cl.
A61B 5/16        (2006.01)
A61B 5/00        (2006.01)
(Continued)

(52) U.S. Cl.
CPC ............. *A61B 5/163* (2017.08); *A61B 3/113* (2013.01); *A61B 5/1075* (2013.01);
(Continued)

(58) Field of Classification Search
None
See application file for complete search history.

(56) References Cited

U.S. PATENT DOCUMENTS 4,576,184 A * 3/1986 Westerman .......... A61B 5/0496
600/546
4,838,681 A    6/1989 Pavlidis
(Continued)

FOREIGN PATENT DOCUMENTS

CA    2 754 835      4/2013
CN    1300407 A      6/2001
(Continued)

OTHER PUBLICATIONS

Office Action issued in Chinese Patent Application No. 201580055076.7 dated May 21, 2018, 41 pages.
(Continued)

*Primary Examiner* — Bruk A Gebremichael
(74) *Attorney, Agent, or Firm* — Wei & Sleman LLP

(57) ABSTRACT

The invention provides methods for diagnosing, assessing or quantitating drug use, drug abuse or narcosis or for differentiating drug use, drug abuse or narcosis from brain injury in a subject by tracking eye movement of at least one eye of the subject, analyzing eye movement of at least one eye of the subject, comparing eye movement of at least one eye of the subject the normal or mean eye movement; and, option-
(Continued)

Left eye

Right eye ally calculating a standard deviation or p value for eye movement of at least one eye of the subject as compared to the normal or mean eye movement.

13 Claims, 57 Drawing Sheets

Related U.S. Application Data on Oct. 17, 2014, provisional application No. 62/068,047, filed on Oct. 24, 2014, provisional application No. 62/102,164, filed on Jan. 12, 2015.

(51) Int. Cl.
| | | |
|---|---|---|
| *A61B 5/107* | (2006.01) | |
| *G16H 40/63* | (2018.01) | |
| *G16H 50/20* | (2018.01) | |
| *G16H 20/10* | (2018.01) | |
| *A61B 3/113* | (2006.01) | |

(52) U.S. Cl.
CPC .......... *A61B 5/4058* (2013.01); *A61B 5/4845* (2013.01); *A61B 5/7275* (2013.01); *G16H 20/10* (2018.01); *G16H 40/63* (2018.01); *G16H 50/20* (2018.01)

(56) References Cited

U.S. PATENT DOCUMENTS

| | | | |
|---|---|---|---|
| 5,422,690 A * | 6/1995 | Rothberg | A61B 3/112 |
| | | | 351/209 |
| 5,961,448 A | 10/1999 | Swenson et al. | |
| 6,346,887 B1 * | 2/2002 | Van Orden | A61B 5/18 |
| | | | 180/272 |
| 7,384,399 B2 | 6/2008 | Ghajar | |
| 7,496,174 B2 | 2/2009 | Gertner et al. | |
| 7,703,921 B2 | 4/2010 | Dick et al. | |
| 7,708,700 B2 | 5/2010 | Ghajar | |
| 7,792,249 B2 | 9/2010 | Gertner et al. | |
| 7,819,818 B2 | 10/2010 | Ghajar | |
| 8,585,589 B1 | 11/2013 | Cinberg | |
| 8,732,795 B2 | 5/2014 | Skeel et al. | |
| 8,808,179 B1 | 8/2014 | Cinberg | |
| 8,951,046 B2 | 2/2015 | Stack | |
| 9,004,687 B2 | 4/2015 | Stack | |
| 9,101,312 B2 | 8/2015 | Waldorf et al. | |
| 9,229,227 B2 | 1/2016 | Border et al. | |
| 9,265,416 B2 | 2/2016 | Klin et al. | |
| 9,265,458 B2 | 2/2016 | Stack | |
| 9,380,976 B2 | 7/2016 | Stack | |
| 9,439,592 B2 | 9/2016 | Stack et al. | |
| 9,459,451 B2 | 10/2016 | Saarikko | |
| 9,642,522 B2 | 5/2017 | Samadani et al. | |
| 9,721,476 B2 | 8/2017 | Ghajar et al. | |
| 9,958,939 B2 | 5/2018 | Ghajar | |
| 2001/0056359 A1 | 12/2001 | Abreu | |
| 2002/0024633 A1 | 2/2002 | Kim et al. | |
| 2002/0099305 A1 * | 7/2002 | Fukushima | A61B 3/112 |
| | | | 600/558 |
| 2003/0028081 A1 | 2/2003 | Blazey et al. | |
| 2007/0008151 A1 | 1/2007 | Victor et al. | |
| 2007/0273611 A1 | 11/2007 | Torch | |
| 2010/0119112 A1 * | 5/2010 | Helfman | G16B 30/00 |
| | | | 382/103 |
| 2010/0277693 A1 | 11/2010 | Martinez-Conde et al. | |
| 2010/0298735 A1 | 11/2010 | Suffin | |
| 2011/0228224 A1 | 9/2011 | Siminou | |
| 2012/0010474 A1 | 1/2012 | Olsen et al. | |
| 2012/0081666 A1 | 4/2012 | Kiderman et al. | |
| 2012/0238903 A1 | 9/2012 | Martinez-Conde et al. | |
| 2013/0044291 A1 * | 2/2013 | Kato | A61B 3/0025 |
| | | | 351/209 |
| 2013/0144185 A1 | 6/2013 | Fuller et al. | |
| 2013/0208952 A1 | 8/2013 | Auchinleck | |
| 2013/0278899 A1 | 10/2013 | Waldorf et al. | |
| 2014/0148728 A1 | 5/2014 | Eizenman et al. | |
| 2014/0171756 A1 * | 6/2014 | Waldorf | A61B 3/032 |
| | | | 600/301 |
| 2015/0190050 A1 | 7/2015 | Samadani et al. | |
| 2015/0326570 A1 | 11/2015 | Publicover et al. | |
| 2016/0278716 A1 | 9/2016 | Samadani | |
| 2017/0091392 A1 | 3/2017 | White et al. | |
| 2017/0135577 A1 | 5/2017 | Komogortsev | |
| 2017/0172408 A1 | 6/2017 | Samadani et al. | |
| 2017/0364732 A1 | 12/2017 | Komogortsev | |
| 2017/0367633 A1 | 12/2017 | Samadani et al. | |
| 2018/0092531 A1 | 4/2018 | Samadani et al. | |
| 2018/0110410 A1 | 4/2018 | Samadani et al. | |
| 2018/0116512 A1 | 5/2018 | Bitoun | |
| 2018/0235530 A1 | 8/2018 | Samadani et al. | |

FOREIGN PATENT DOCUMENTS

| | | |
|---|---|---|
| EP | 1 260 177 | 11/2002 |
| EP | 1 260 777 A2 | 11/2002 |
| WO | 2007075460 | 7/2007 |
| WO | 2010042557 A2 | 4/2010 |
| WO | 2013148557 | 10/2013 |
| WO | 2013148557 A1 | 10/2013 |
| WO | 2014204904 | 12/2014 |
| WO | 2015051272 | 4/2015 |
| WO | 2015057321 | 4/2015 |
| WO | 2016022414 | 2/2016 |
| WO | 2016118453 | 7/2016 |

OTHER PUBLICATIONS

Extended European Search Report issued in European Patent Application No. 15830656.3 dated May 11, 2018, 9 pages.
Samadani et al., U.S. Appl. No. 62/403,440, filed Oct. 3, 2016, 31 pages.
Samadani et al., U.S. Appl. No. 62/410,754, filed Oct. 20, 2016, 24 pages.
Samadani et al., U.S. Appl. No. 62/558,069, filed Sep. 13, 2017, 51 pages.
Samadani et al., U.S. Appl. No. 15/786,759, filed Oct. 18, 2017, 137 pages.
International Search Report and Written Opinion for Application No. PCT/US2018/050650, dated Nov. 30, 2018.
Samadani et al., U.S. Appl. No. 15/716,826, filed Sep. 27, 2017, 127 pages.
Serra et al., "Diagnosing disconjugate eye movements. Phase-plane analysis of horizontal saccades", Neurology, 2008, 71:1167-1175.

* cited by examiner

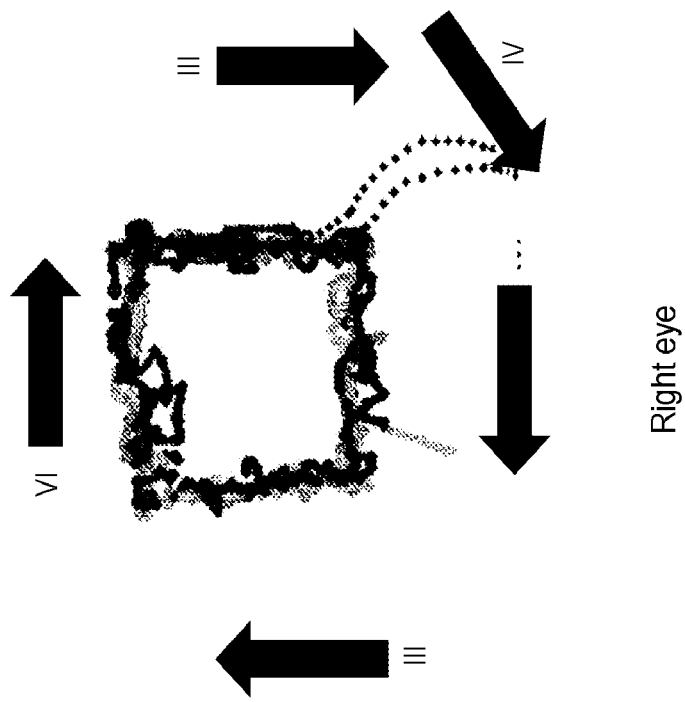
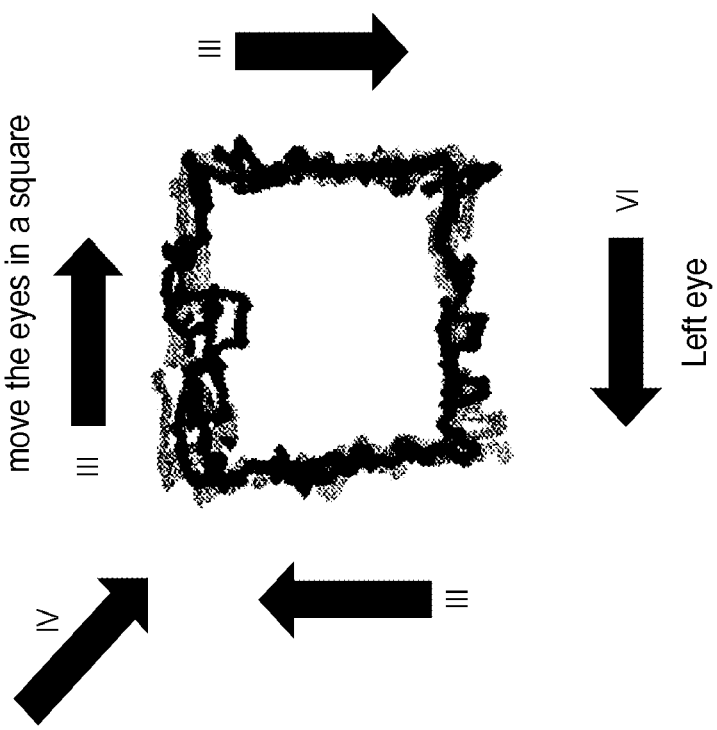

Age as a function of Conjugate Gaze

Relationship of Vertical and Horizontal Conjugacy of Gaze

Test/Retest Reliability

A

A

Postoperative film

A

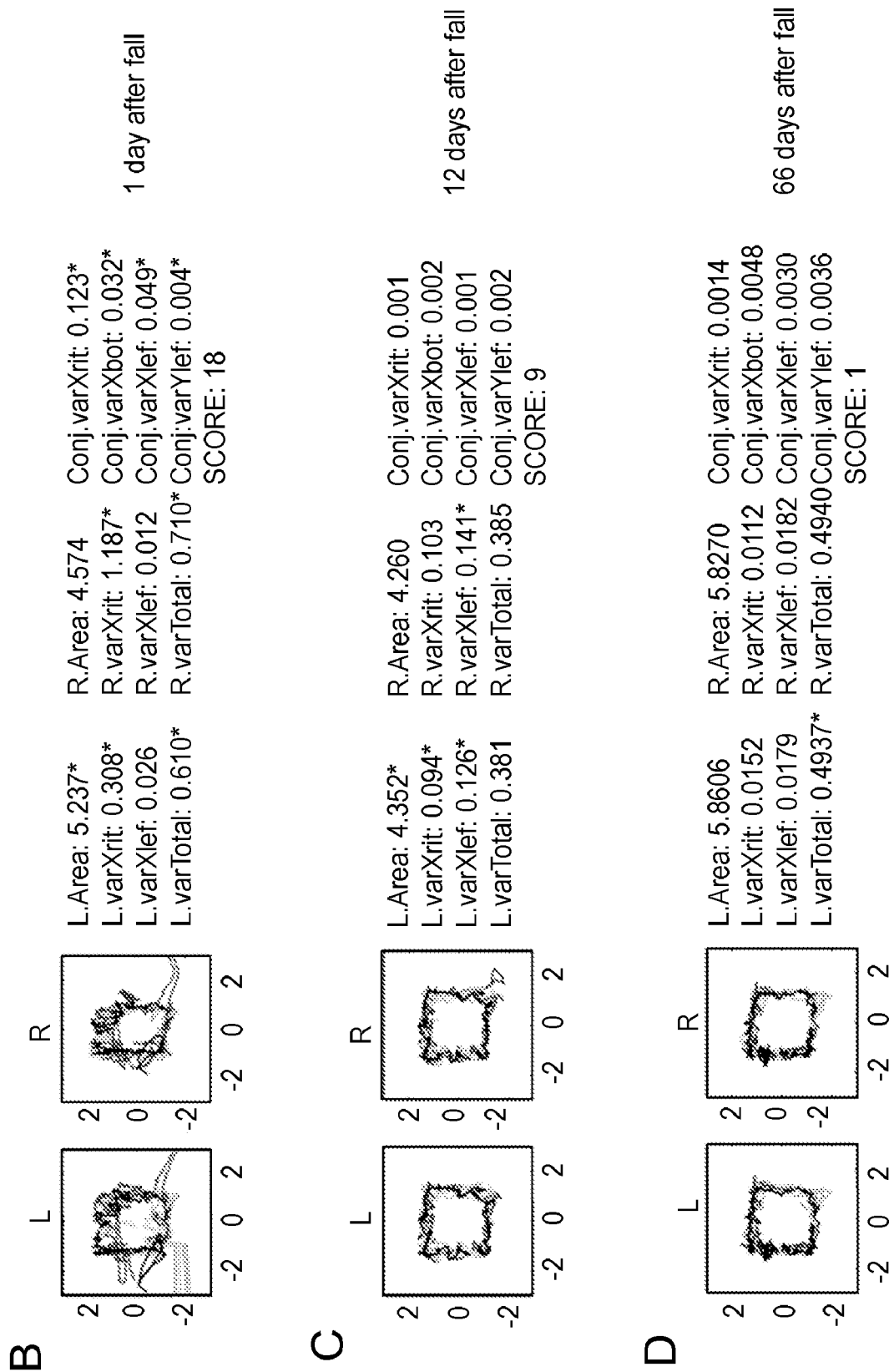

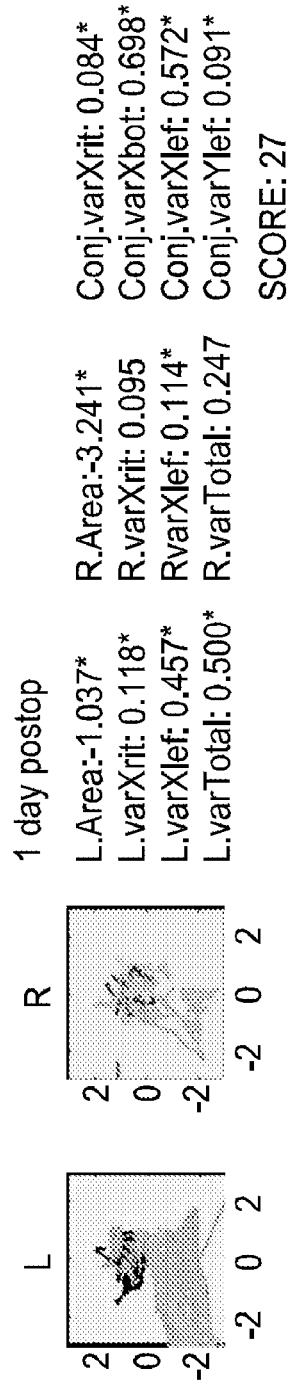

FIG. 17A 1 day postop

L.Area:-1.037*  R.Area:-3.241*  Conj.varXrit: 0.084*
L.varXrit: 0.118*  R.varXrit: 0.095  Conj.varXbot: 0.698*
L.varXlef: 0.457*  RvarXlef: 0.114*  Conj.varXlef: 0.572*
L.varTotal: 0.500*  R.varTotal: 0.247  Conj.varYlef: 0.091*

SCORE: 27

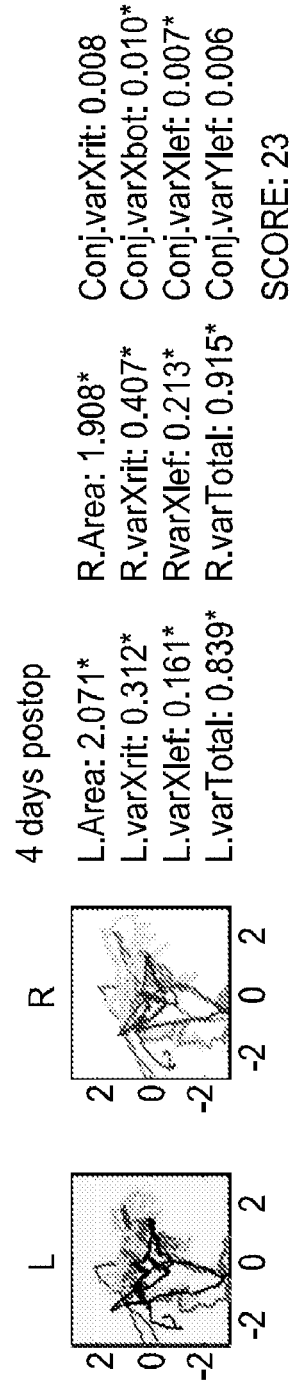

FIG. 17B 4 days postop

L.Area: 2.071*  R.Area: 1.908*  Conj.varXrit: 0.008
L.varXrit: 0.312*  R.varXrit: 0.407*  Conj.varXbot: 0.010*
L.varXlef: 0.161*  RvarXlef: 0.213*  Conj.varXlef: 0.007*
L.varTotal: 0.839*  R.varTotal: 0.915*  Conj.varYlef: 0.006

SCORE: 23

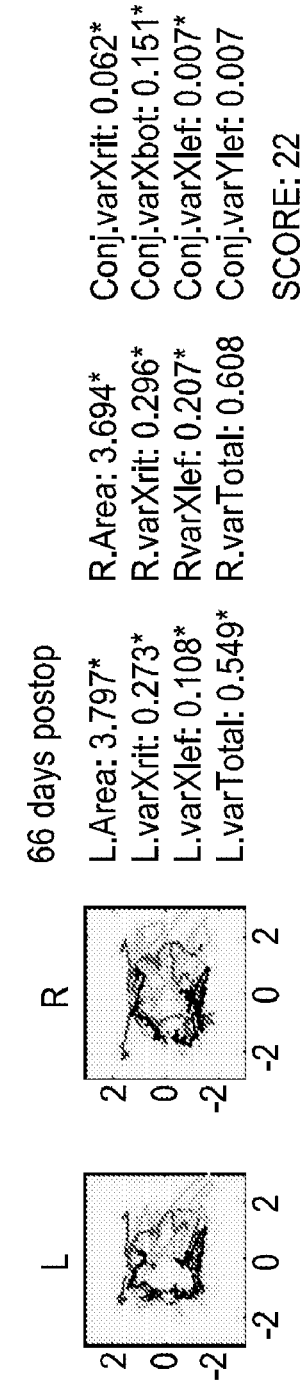

FIG. 17C 66 days postop

L.Area: 3.797*  R.Area: 3.694*  Conj.varXrit: 0.062*
L.varXrit: 0.273*  R.varXrit: 0.296*  Conj.varXbot: 0.151*
L.varXlef: 0.108*  RvarXlef: 0.207*  Conj.varXlef: 0.007*
L.varTotal: 0.549*  R.varTotal: 0.608  Conj.varYlef: 0.007

SCORE: 22

L Aspect: 1.0076 (0.9374 to 1.1018)   R Aspect: 1.0133 (0.9370 to 1.0881)

L Aspect: 1.521*
(0.9374 to 1.1018)

R Aspect: 0.8462*
(0.9370 to 1.0881)

— Left-X —— Left-Y
—·— Right-X ---- Right-Y

—— Left-X —— Left-Y
—·— Right-X ----- Right-Y

FIG. 24B
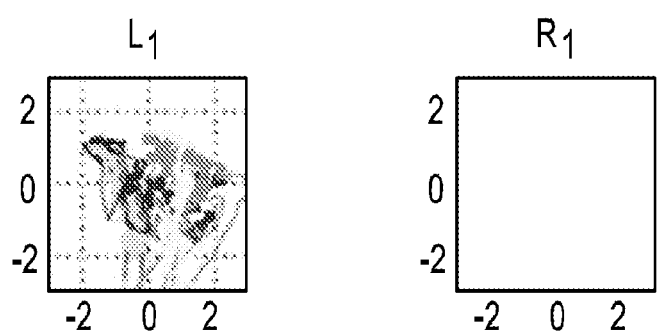
FIG. 24C
L Aspect: -22.9424*  R Aspect: NaN
(0.9374 to 1.1018)  (0.9370 to 1.0881)
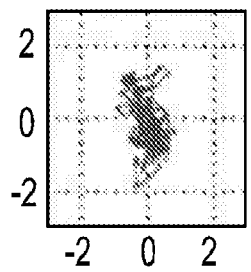 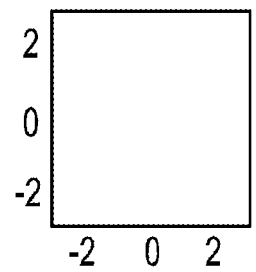

— Left-X    — Left-Y
--- Right-X  ---- Right-Y

FIG. 25A
Case: 19 year old male with ADHD
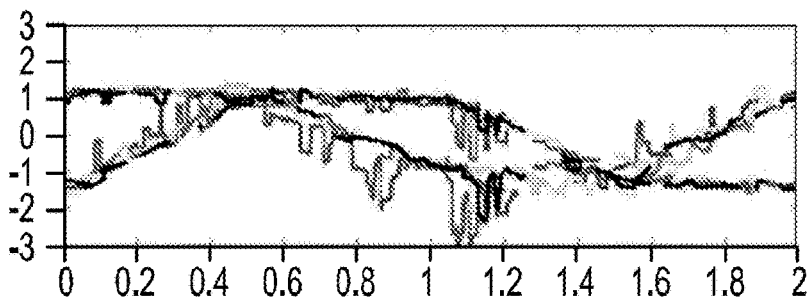
Red, green, cyan, magenta, blue
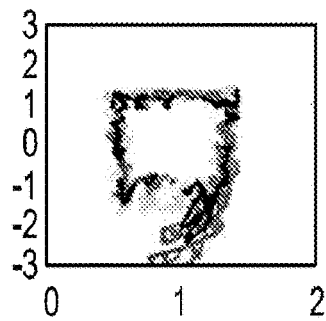
Aspect Ratio
0.97912
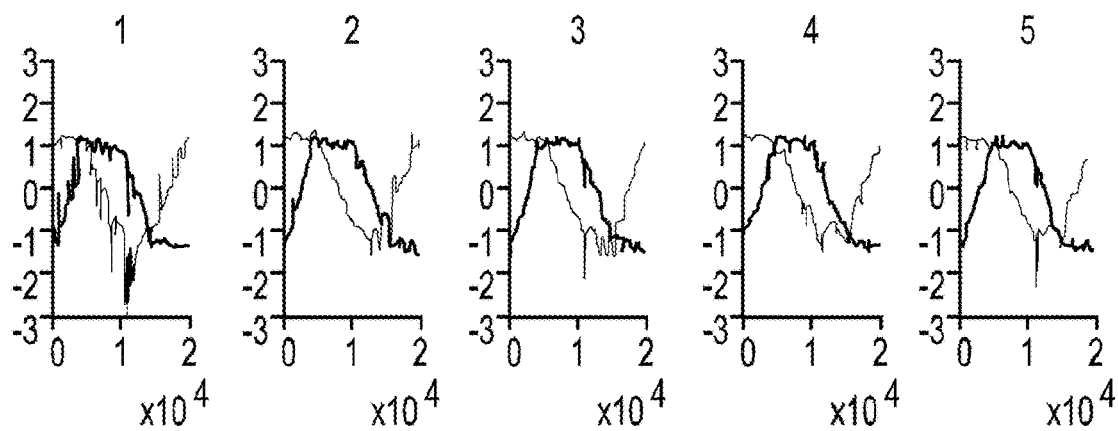
| Red | Green | Cyan | Magenta | Blue |
|---|---|---|---|---|
| 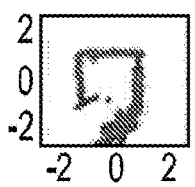 | 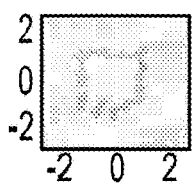 | 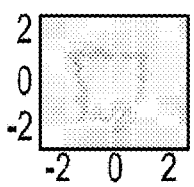 | 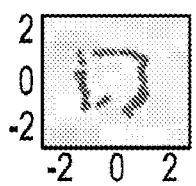 | 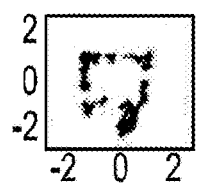 |

FIG. 25B
Case: 19 year old male with ADHD
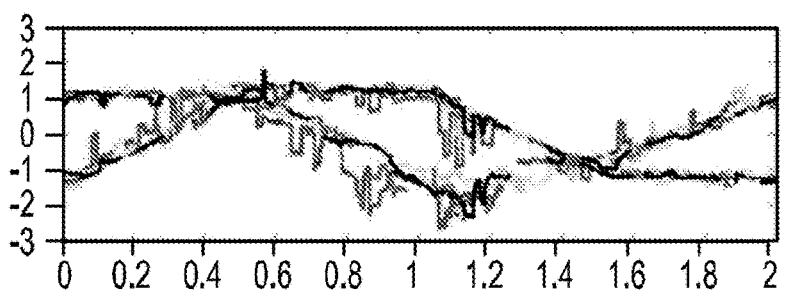
Red, green, cyan, magenta, blue
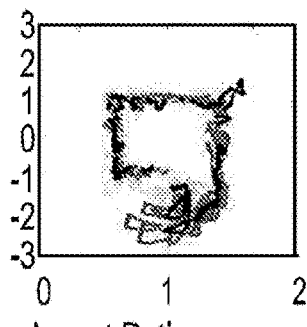
Aspect Ratio
0.97109
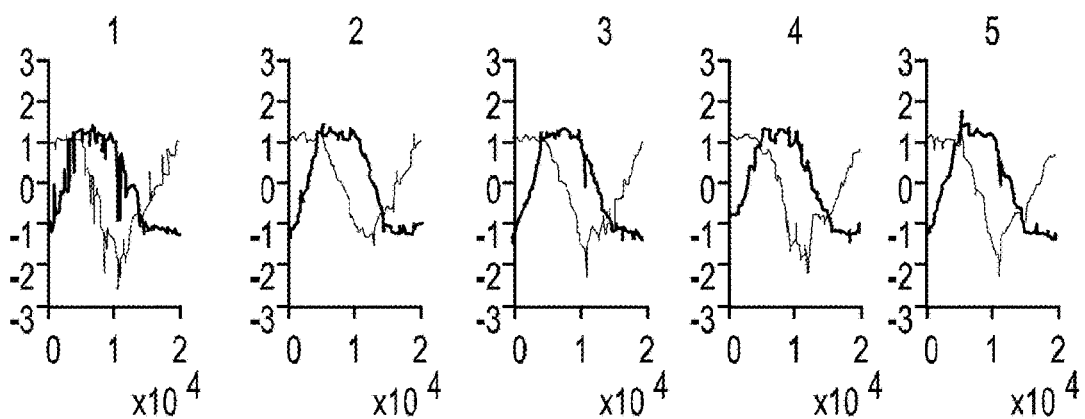
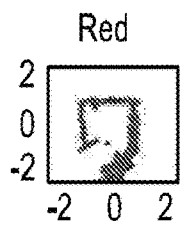
Red
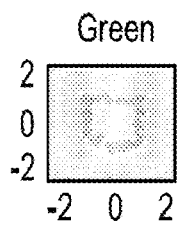
Green
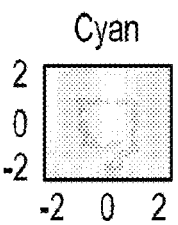
Cyan
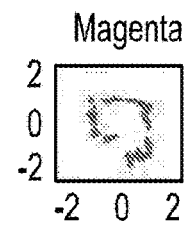
Magenta
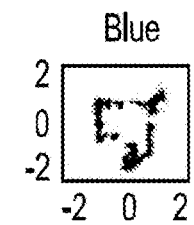
Blue Conjugacy for case 1

FIG. 27A
Case: 19 year old male with ADHD
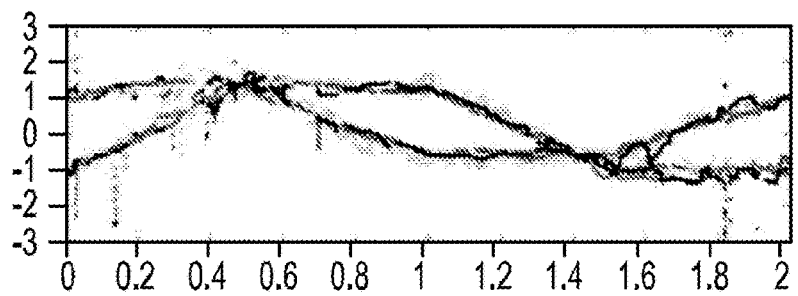
Red, green, cyan, magenta, blue
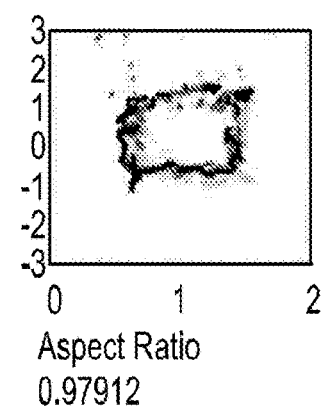
Aspect Ratio
0.97912
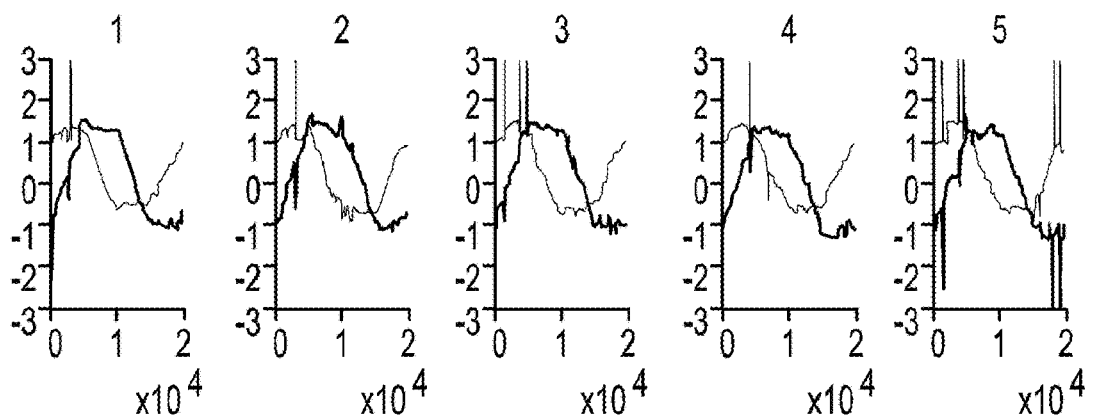
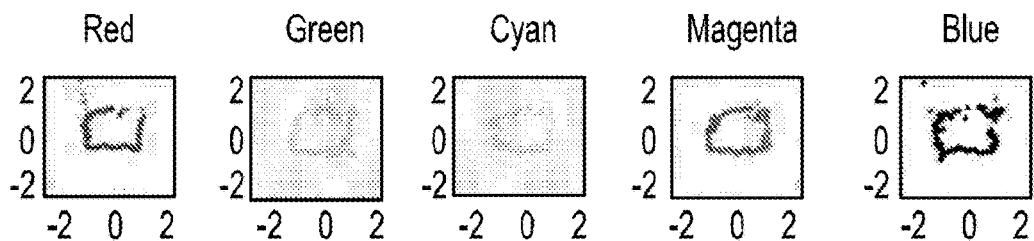

FIG. 27B
Case: 19 year old male with ADHD
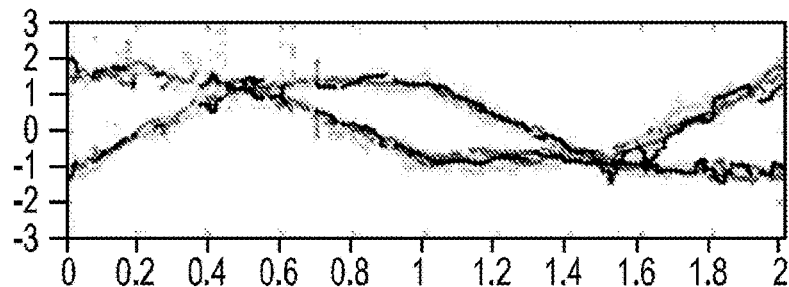
Red, green, cyan, magenta, blue
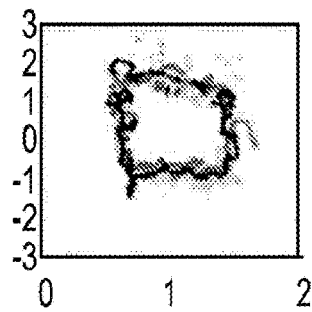
Aspect Ratio
0.97912
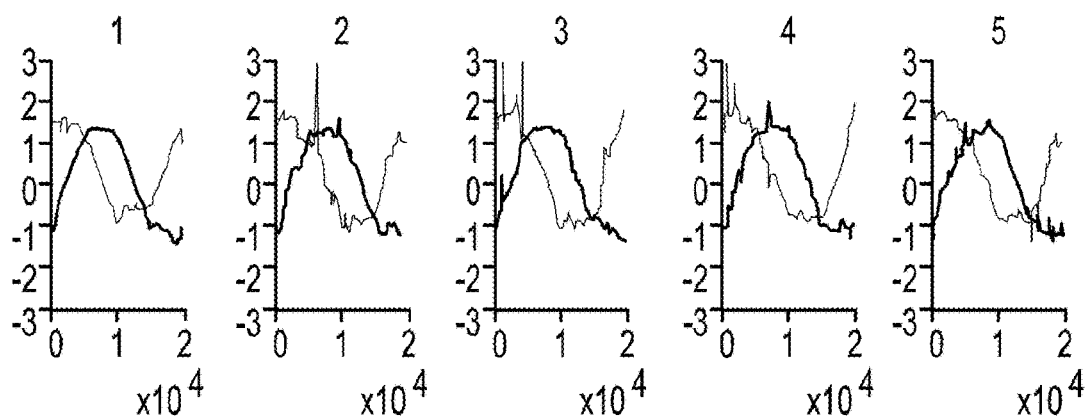
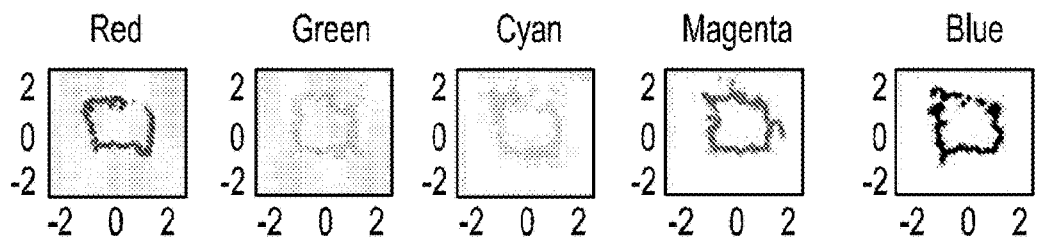

Conjugacy for case 2

FIG. 29A
Case 3
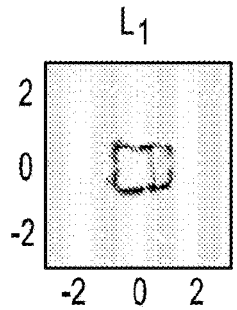
$L_1$
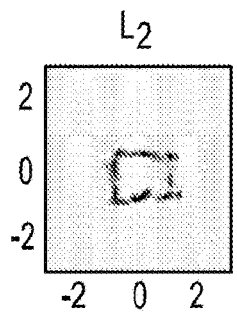
$L_2$
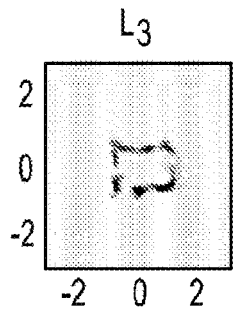
$L_3$
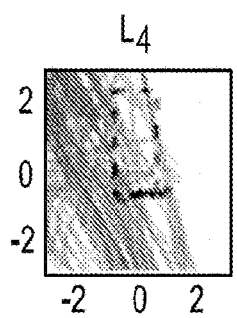
$L_4$
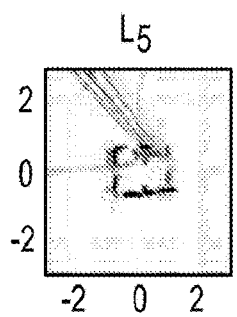
$L_5$
FIG. 29B
Case 3
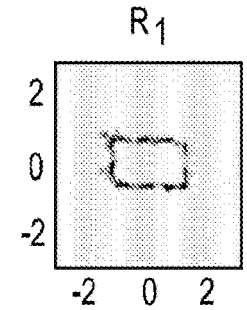
$R_1$
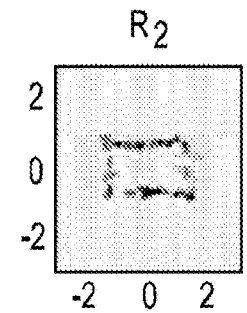
$R_2$
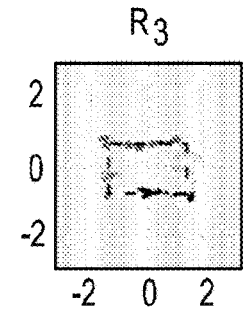
$R_3$
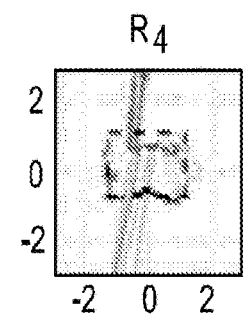
$R_4$
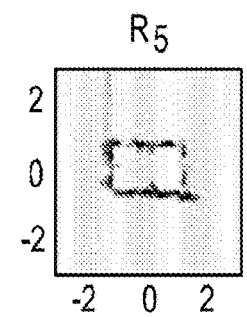
$R_5$

FIG. 29C
$L_{1-4}$
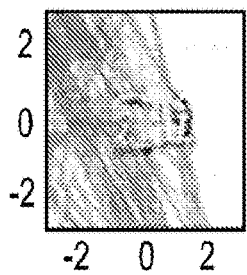
L Aspect: 1:0156 (0.9374 to 1.1018)
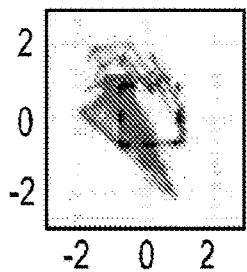
FIG. 29D
$R_{1-4}$
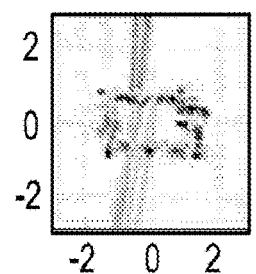
R Aspect: 0.6236* (0.9370 to 1.0881)
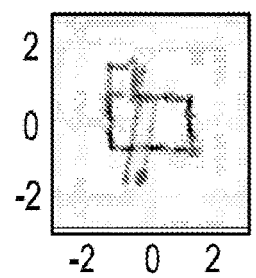

FIG. 30A
Retesting of Case 3
$L_1$-AR: 0.4563 (NaN to NaN)
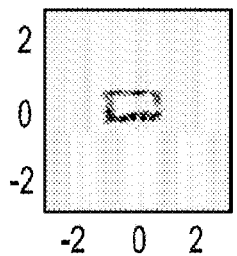
$L_2$-AR: 0.4798 (NaN to NaN)
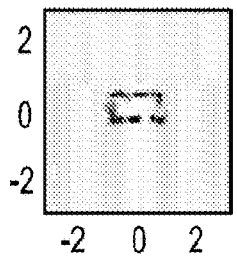
$L_3$-AR: 0.4448 (NaN to NaN)
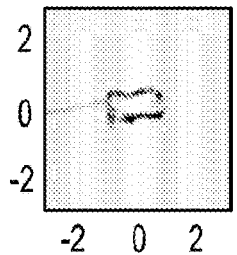
$L_4$-AR: 0.3222 (NaN to NaN)
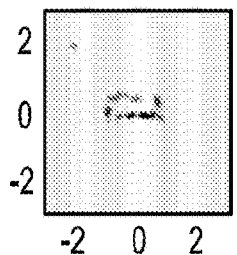
$L_5$-AR: 0.2058 (NaN to NaN)
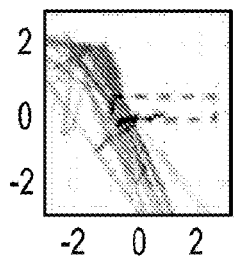
FIG. 30B
Retesting of Case 3
$R_1$-AR: 0.3869 (NaN to NaN)
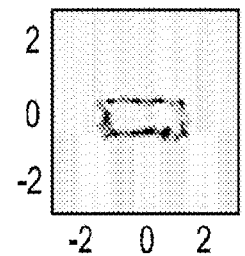
$R_2$-AR: 0.4205 (NaN to NaN)
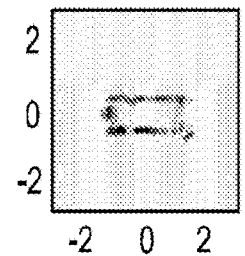
$R_3$-AR: 0.2773 (NaN to NaN)
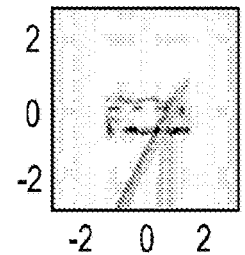
$R_4$-AR: 0.4971 (NaN to NaN)
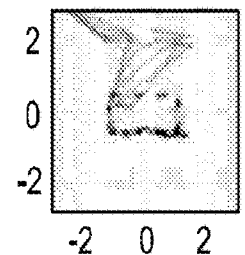
$R_5$-AR: 1.5548 (NaN to NaN)
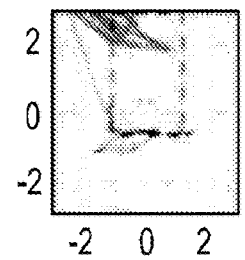

FIG. 30C
$L_{1-5}$
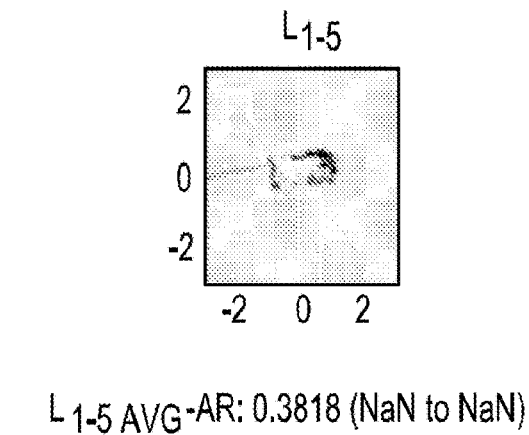
$L_{1-5\ AVG}$-AR: 0.3818 (NaN to NaN)
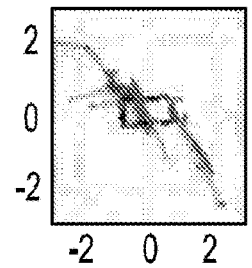
FIG. 30D
$R_{1-5}$
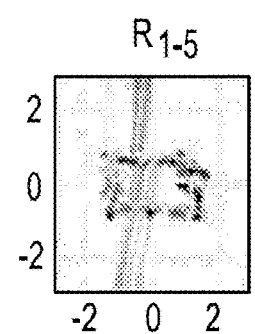
$R_{1-5\ AVG}$-AR: 0.6273 (NaN to NaN)
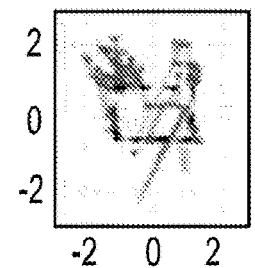

FIG. 31A
Subject 1: 31 year old male
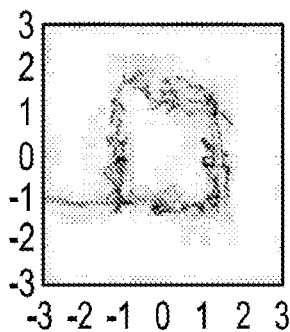
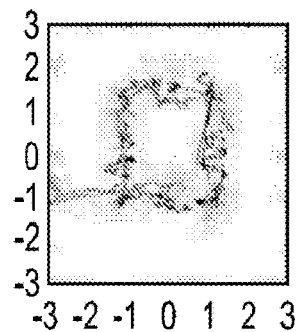
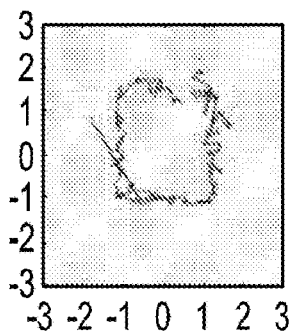
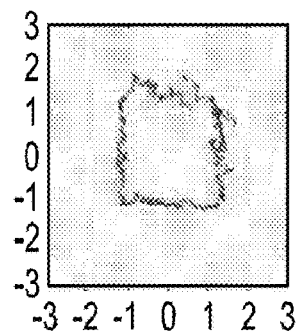
Pre Drinking
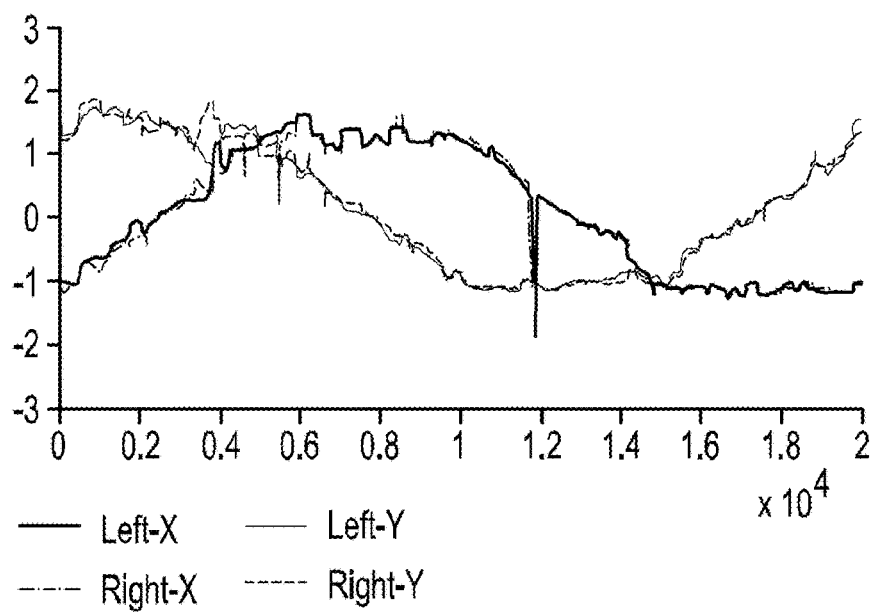
— Left-X  — Left-Y
--- Right-X  --- Right-Y

FIG. 31B
Subject 1: 31 year old male
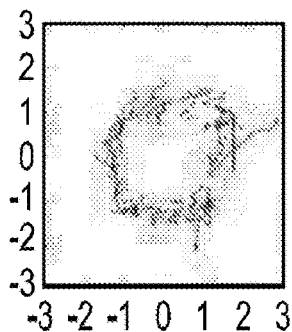
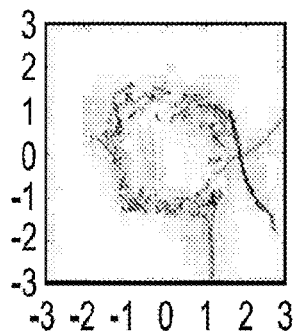
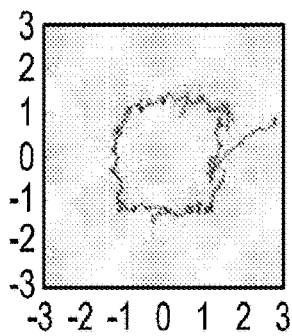
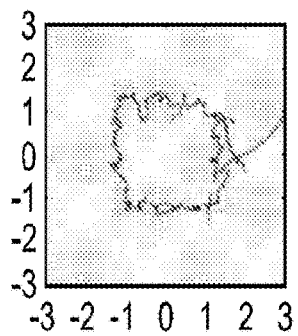
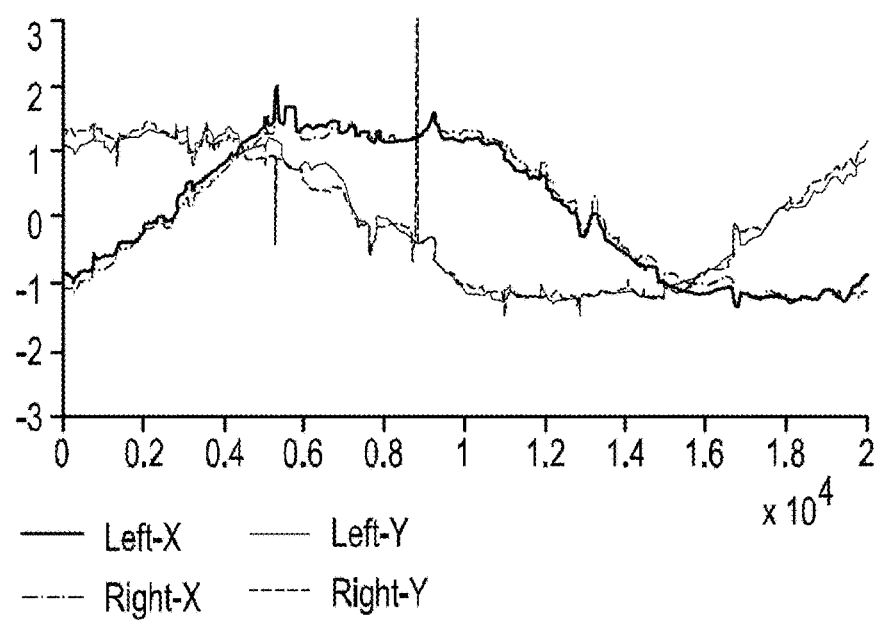
Post Drinking

FIG. 32A
Subject 2: 34 year old female
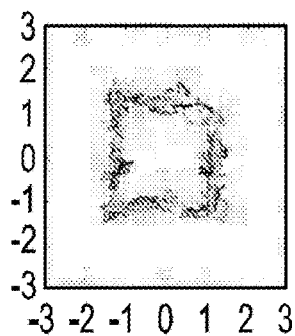
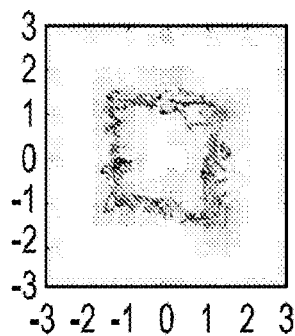
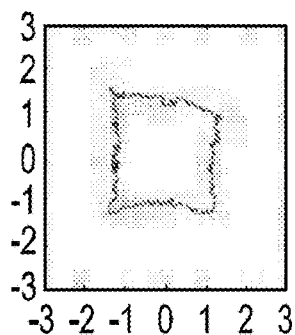
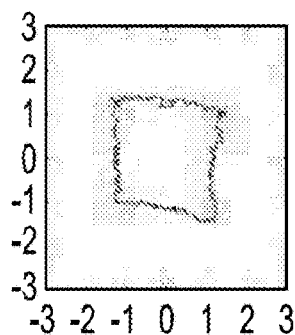
Pre Drinking
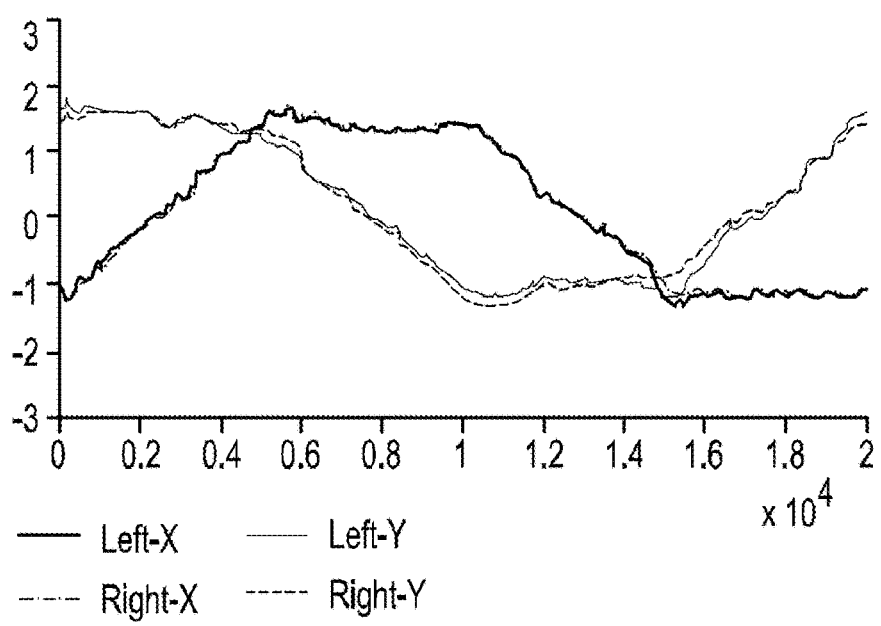
— Left-X   — Left-Y
---- Right-X   ----- Right-Y

FIG. 32B
Subject 2: 34 year old female
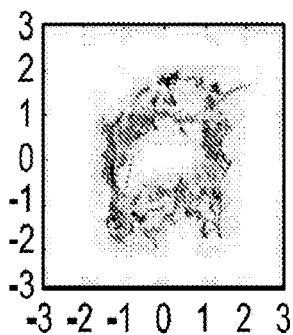
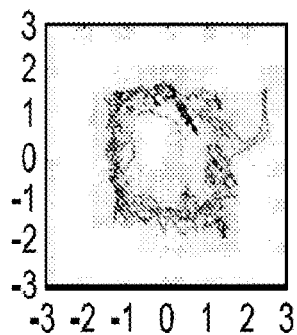
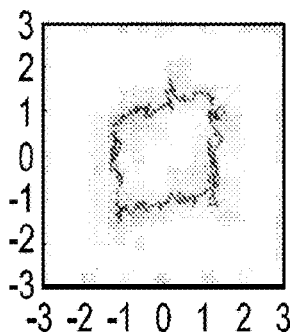
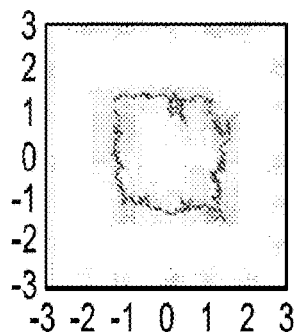
Post Drinking
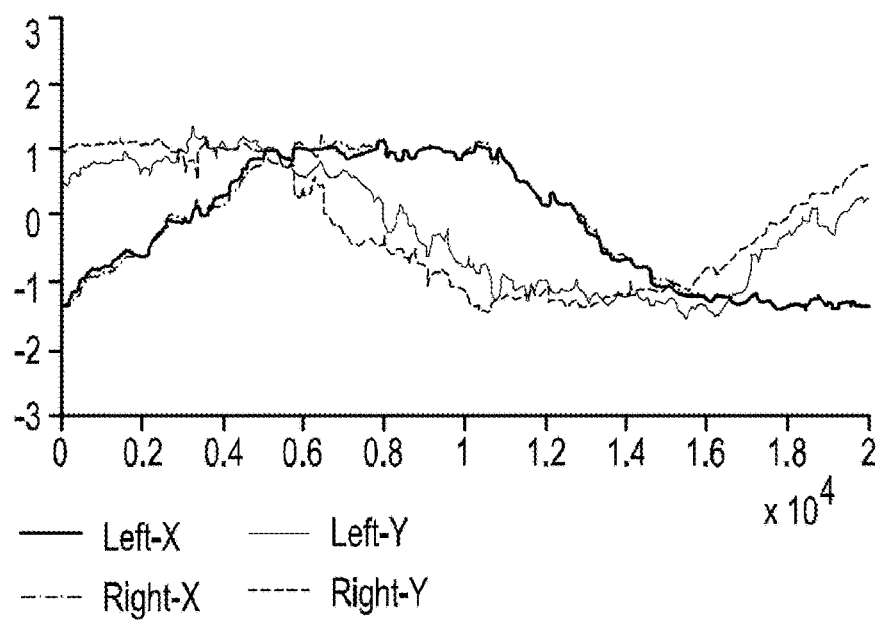
— Left-X — Left-Y
--- Right-X ----- Right-Y

METHODS AND KITS FOR DIAGNOSING, ASSESSING OR QUANTITATING DRUG USE, DRUG ABUSE AND NARCOSIS, INTERNUCLEAR OPHTHALMOPLEGIA, ATTENTION DEFICIT HYPERACTIVITY DISORDER (ADHD), CHRONIC TRAUMATIC ENCEPHALOPATHY, SCHIZOPHRENIA SPECTRUM DISORDERS AND ALCOHOL CONSUMPTION

FIELD OF THE INVENTION

The present invention relates to methods and kits for diagnosing, assessing or quantitating drug use, drug abuse, and narcosis and for differentiating narcosis from brain injury such as structural and non-structural traumatic brain injury and for screening for, diagnosing, and assessing the same, for diagnosing and assessing internuclear ophthalmoplegia (INO) in a subject by tracking eye movement, for diagnosing and assessing attention deficit hyperactivity disorder (ADHD), chronic traumatic encephalopathy, and schizophrenia spectrum disorders in a subject by tracking eye movement, and for detecting, screening for or quantifying alcohol consumption and intoxication in a subject by tracking eye movement.

BACKGROUND OF THE INVENTION

Automated Eye Movement Tracking

Automated eye movement tracking has been used for marketing and advertising research, the development of assistive devices for immobile individuals, and for video games. Spatial calibration of the device requires the subject to have relatively intact ocular motility that implies function of cranial nerves II (optic), III (oculomotor), IV (trochlear) and VI (abducens) and their associated nuclei as well as sufficient cerebral function to enable cognition and volition for calibration.

Others have successfully demonstrated the clinical applications of eye movement data (Lee et al., *Brain Research.* 2011; 1399:59-65; Contreras et al., *Brain Research* 2011; 1398:55-63; Maruta et al., *The Journal of Head Trauma Rehabilitation* 2010; 25(4):293-305). Trojano et al., *J Neurol* 2012; (published online; ahead of print) recently described uncalibrated eye movement measurements in a population of minimally conscious and persistently vegetative patients. They report data from 11 healthy control subjects evaluating chronic disorders of consciousness, not acute changes in intracranial pressure. They sample eye movements at 60 Hz rather than 500 Hz, effectively reducing the power of their data 100-fold, and they report differences in on-target and off-target fixations between the groups without spatially calibrated data. Moreover, they use static stimuli moving in a quasi-periodic way.

Eye movement tracking for neuropsychiatric and brain injury research (Heitger, et al., *Brain,* 2009; 132: 2850-2870; Maruta, et al., *J Head Trauma Rehabil.,* 2010; 25: 293-305) has been performed for nearly 30 years and can evaluate smooth pursuit, saccades, fixation, pupil size and other aspects of gaze. Spatial calibration of the eye tracker is generally performed for each individual being tracked. With calibration, the eye-tracker measures the relative position of pupil and corneal reflection for a period of about 400-800 ms while the subject looks at a target or targets of known position to generate meaningful spatial coordinates during subsequent pupil movement. The process of spatial calibration implies relatively preserved neurologic function because it requires that the subject is able to follow commands and look at specific points.

It is conceivable that the process of spatial calibration may mask deficits in ocular motility. If there is a persistent and replicable weakness in movement of an eye, the camera will interpret the eye's ability to move in the direction of that weakness as the full potential range of motion in that direction due to the calibration process. In other words if the subject is directed to look at a position but consistently only moves halfway there, the calibration process will account for that when tracking subsequent eye movements and interpret movements to the halfway point as occurring at the full range of normal motion. If during calibration one eye only makes it halfway to the target, but the other eye is fully there, the camera will interpret both eyes as being together when one performs half the eye movement as the other. Thus binocular spatial calibration may preclude detection of disconjugate gaze unless each eye is calibrated separately using a dichoptic apparatus (Schotter, et al., *PLoS One,* 2012; 7: e35608).

Conjugacy of Eye Movement

Conjugate gaze is the motion of both eyes in the same direction at the same time. Conjugate gaze is believed to be controlled by the following four different mechanisms: the saccadic system that allows for voluntary direction of the gaze, the pursuit system that allows the subject to follow a moving object, the optokinetic system that restores gaze despite movements of the outside world, and the vestibulo-ocular reflex system (VOR system) that corrects for the movements of the head to preserve the stable visual image of the world.

Disconjugate gaze or strabismus is a failure of the eyes to turn together in the same direction. Normal coordinated movements of the eyes produces conjugate gaze, in which the eyes are aligned for binocular 3-dimensional vision. Misalignment results in loss of this vision. With the visual axis of each eye fixated on a different point, diplopia (or double vision) usually results and may be perceived as a blurred image if the two images are very closely aligned. However, if the image from the weaker eye is suppressed by higher cortical centers, there is only one image with loss of visual acuity (or a blurred image). Pathology usually resides either in the oculomotor muscles or their neuronal pathways including the medial longitudinal fasiculus, the paramedian pontine reticular formation, the medullary reticular formation, the superior colliculus, or the cranial nerves III, IV, or VI or their nuclei.

Assessment of eye movement conjugacy is commonly performed by primary care physicians, neurologists, ophthalmologists, neurosurgeons, emergency medicine doctors, and trauma surgeons to rapidly assess global neurologic functioning. In stable patients, ophthalmologists and neurologists perform more detailed examination to assess the alignment of the eyes such as the cover test and Hirschberg corneal reflex test. Other tests used to assess binocular conjugacy include the Titmus House Fly test, Lang's stereo test, the Hess screen, red-filter test, Maddox rod evaluation and Lancaster red-green test. In young children, who may be less cooperative with an examiner, binocular gaze conjugacy may only be assessable with simpler algorithms, such as following an object moving in a set trajectory (Cavezian, et al., *Res Dev Disabil.,* 2010; 31: 1102-1108). When such tests are performed in conjunction with the remainder of the neurophthalmic and physical evaluation, one can localize neurologic lesions and quantitate ocular motility deficits with great accuracy. Despite this capability, these tests are not used routinely in the emergency setting due to the need for a trained practitioner to administer them, the requirement for sophisticated equipment, and the urgent nature of many neurologic disorders.

Assessment of binocular gaze conjugacy in primates for research purposes is performed with the magnetic search coil technique requiring coils implanted into the bulbar conjunctiva (Schultz, et al., *J Neurophysiol.*, 2013; 109: 518-545). This technique was first described by Fuchs and Robinson in 1966 (Fuchs, et al., *J Appl Physiol.*, 1966; 21: 1068-1070) and can also be performed in humans fitted with sclera search coils designed specifically for tracking eye movements.

Experimentally, spatially calibrated eye movement tracking using the Bouis oculometer (Bach, et al., *J Neurosci Methods*, 1983; 9: 9-14), which requires that the head is rigidly fixed, shows that healthy seven year old children have increased disconjugacy of eye movement during saccades relative to adults while both perform a reading task (Bucci, et al., *Vision Res.*, 2006; 46: 457-466). Research on disconjugacy during reading can be performed using a dichoptic apparatus in which the individual eyes are spatially calibrated separately and presented with stimuli to assess movements separately for simultaneous comparison to each other (Schotter, et al., *PLoS One*, 2012; 7: e35608). U.S. Provisional Application No. 61/881,014, filed Sep. 23, 2013, the disclosure of which is herein incorporated by reference in its entirety, teaches methods for tracking eye movement, and methods and kits for assessing conjugacy and disconjugacy of gaze and strabismus.

Brain Injury

One of the problems associated with the study of outcomes after brain injury, is the heterogeneous nature of such injury in terms of etiology, anatomic sequelae, and physiologic and psychologic impact. The etiology of injury affects the anatomic sequelae and ranges from global mechanisms such as acceleration/deceleration and blast, to potentially more focal mechanisms such as blunt impact and penetrating trauma. Some injury mechanisms result in structural changes to the brain that can be visualized using conventional imaging such as MRI and CT scan, while other injuries appear radiographically normal.

Acceleration/deceleration injury may result in structurally visible coup/contrecoup injuries and less visible diffuse axonal injury (DAI) (Cecil, et al., *Journal of Neurosurgery*, 1998; 88: 795-801) Acceleration/deceleration is also thought to be one of the potential mechanisms for concussion which is the most common form of civilian radiographically normal brain injury (Bayly, et al., *Journal of Neurotrauma*, 2005; 22: 845-856; Daneshvar, et al., *Physical Medicine and Rehabilitation Clinics of North America*, 2011; 22: 683-700). Concussion is brain injury, most often resulting from blunt impact, in the absence of structural abnormality by conventional radiographic imaging such as computed tomography (CT) scan (McCrory, et al., *The Physician and Sports Medicine*, 2009; 37: 141-159). Concussion may include transient loss or disruption of neurologic function. The term "subconcussion" may be used to describe the sequelae of brain injury in the absence of transient loss or disruption of neurologic function. Both concussion and subconcussion as well as blast injury may be termed "nonstructural" brain injury.

Blast injury resembles blunt impact brain injury in that both may be associated with radiographically apparent cerebral edema and intracranial hemorrhage, however with blast injury the edema onset may be more rapid and severe, and there is greater likelihood of clinical vasospasm (Armonda, et al., *Neurosurgery*, 2006; 59: 1215-1225). Blast injury is very frequently radiographically normal, yet mild or moderate blast injury is strongly associated with post-traumatic stress disorder and other cognitive dysfunctions (Cernak, et al., *The Journal of Trauma*, 2001; 50: 695-706). The actual cause of blast brain injury is suspected to be multifactorial and often results in DAI (Leung, et al., *Mol Cell Biomech*, 2008; 5: 155-168). A shock wave resulting from pressure changes caused by the explosion impacts, both cranial and non-cranial structures (Courtney, et al., *Medical Hypotheses*, 2009; 72: 76-83; Bauman, et al., *Journal of Neurotrauma*, 2009; 26: 841-860). Blast injury affects the brain through several mechanisms: primary brain injury caused by blastwave induced changes in atmospheric pressure directly impacting the brain; secondary injury resulting from objects put in motion by the blast that impact the head, and tertiary injury resulting from the victim striking the head upon falling or being propelled into a solid object (Warden, *The Journal of Head Trauma Rehabilitation*, 2006; 21: 398-402).

Blunt impact and penetrating trauma can result in both diffuse and focal injury. One mechanism by which focal brain injury leads to neurologic damage is cortical spreading depression (Hartings, et al., *Journal of Neurotrauma*, 2009; 26: 1857-1866), which is currently only thought measurable using invasive means.

Brain injury may be associated with short term sequelae including headaches and memory problems, and longer term problems including dementia, Parkinsonism and motor-neuron disease (Daneshvar, et al., *Physical Medicine and Rehabilitation Clinics of North America*, 2011; 22: 683-700). Both concussion and mild blast injury may be associated with post-traumatic stress disorder and cognitive impairment (Taber, et al., *The Journal of Neuropsychiatry and Clinical Neurosciences*, 2006; 18: 141-145). Clinical tests for concussion show poor test reliability (Broglio, et al., *Journal of Athletic Training*, 2007; 42: 509-514) and thus concussion remains a diagnosis that is difficult to treat because it is difficult to detect. Traumatic brain injury can impact eye movement through a multitude of mechanisms including direct compression of cranial nerves, trauma to cranial nerves, injury to cranial nerve nuclei and supranuclear impacts.

Many cases of trauma result in elevated intracranial pressure. If untreated, acute elevations in intracranial pressure (ICP) due to brain injury can result in permanent neurologic impairment or death. Double vision and other ocular disturbances associated with elevated ICP were first described by Hippocrates in approximately 400 B.C. (Aronyk, *Neurosurgery Clinics of North America*, 1993; 4: 599-609). Papilledema, and its association with elevated ICP was described by Albrecht von Graefe in 1860 (Pearce, *European Neurology*, 2009; 61: 224-249). In the post-radiographic era, acute and chronic pathology of the optic nerve and disc, and of ocular motility are well characterized in people with elevated ICP (Dennis, et al., *Archives of Neurology*, 1981; 38: 607-615; Zeiner, et al., *Child's Nerv. Syst.*, 1985; 1: 115-122; Altintas, et al., *Graefe's Archive for Clinical and Experimental Ophthalmology*, 2005; 243: 1213-1217). Clinically apparent disruption of ocular motility may precede computed tomography (CT) findings in some subjects with acutely elevated ICP (Tzekov, et al., *Pediatric Neurosurgery*, 1991; 17: 317-320; Chou, et al., *Neurosurgery Clinics of North America*, 1999; 10: 587-608).

Elevated Intracranial Pressure

Several potential mechanisms may contribute to cranial nerve dysfunction due to elevated intracranial pressure. The IIIrd nerve (oculomotor) may be directly compressed by the medial aspect of the temporal lobe with frontal or temporal mass lesions, or diffuse supratentorial mass effect. The VIth nerve (abducens) is anatomically vulnerable to infratentorial mass effect at the prepontine cistern and to hydrocephalus from stretch as it traverses the tentorial edge.

Elevated intracranial pressure slows axoplasmic transport along cranial nerves (Balarratnasingam, et al., *Brain Research*, 2011; 1417: 67-76). The optic nerve (II) is most frequently analyzed because it can be visualized directly with ophthalmoscopy, and indirectly with ultrasound. Edema of the optic nerve appears earlier than ocular fundus changes, and resolves after treatment of elevated ICP Gangemi, et al., *Neurochirurgia,* 1987; 30: 53-55). Fluctuating elevated neural pressure leads to impaired axonal transport along the optic nerve after as little as 30 minutes in a rabbit model (Balarratnasingam, et al., *Brain Research,* 2011; 1417: 67-76). Axoplasmic flow stasis and intraneuronal ischemia may occur in the optic nerve exposed to chronically elevated ICP (Lee, et al., *Current Neurology and Neuroscience Reports,* 2012). Among the nerves impacting ocular motility, the trochlear nerve (IV), followed by oculomotor (III) and then abducens (VI), has the greatest length of exposure to the subarachnoid space with the narrowest diameter, and thus may be most vulnerable to a pressure induced palsy (Hanson, et al., *Neurology,* 2004; 62: 33-36; Adler, et al., *Journal of Neurosurgery,* 2002; 96: 1103-1113). The optic nerve (II) has approximately the same length of exposure as the abducens (Murali, et al., in Head Injury (ed. Paul Cooper and John Golfinos) (McGraw-Hill, 2000)), and thus papilledema, or swelling of the optic disc apparent on ophthalmoscopic examination may be a relatively late indicator of elevated ICP (Killer, et al., *Clinical & Experimental Ophthalmology,* 2009; 37: 444-447; Nazir, et al., *J Aapos,* 2009; 13: 62-66). Papilledema is not always a sensitive marker for hydrocephalus leading to elevated ICP, and in one study was present in as few as 14% of patients with a shunt malfunction (Nazir, et al., *J Aapos,* 2009; 13: 62-66) consistent with the relatively short intracranial course of II compared to cranial nerves III and IV. Compartmentalization of subarachnoid spaces is hypothesized to explain why papilledema may be present in a patient without elevated ICP, and not occur in patients with elevated ICP (Killer, et al., *Clinical & Experimental Ophthalmology,* 2009; 37: 444-447).

Effect of Drugs and Narcotics on Eye Movement

Methadone has been shown to impact ocular movements during both smooth pursuit and saccades, and is thought to impact function of the superior colliculus (Rothenberg et al., *Psychopharmacology* (Berl) 1980; 67:221-227; Rothenberg et al., *Psychopharmacology* (Berl) 1980; 67:229-234, 1980). Narcotic naïve subjects administered methadone had decreased smooth pursuit eye movement gain in horizontal pursuit tracking, but showed no significant decrease in gain in vertical pursuit tracking. There was a significant increase in vertical cross correlation measurements but none in horizontal cross correlation. No phase difference between subjects given methadone and control was present, signifying that the difference in gain was not due to failure of eye movement during parts of eye tracking trial or a difference in frequency of eye motion compared to target motion. The lack of vertical pursuit gain in methadone dose subjects may be due to contamination of vertical data from eyelid motion, as eyelid motion occurs with vertical eye motion when movement is greater than 5 degrees from central position. Methadone may have induced loss of eyelid control, resulting in contamination of vertical pursuit tracking. Methadone did not significantly alter maximum saccade velocity. However, initial saccade accuracy is significantly decreased with more pronounced saccade undershoot after use of methadone. In addition, the latency to onset of initial saccade was also significantly increased.

Similar results may be seen with other pharmacologic agents. Diazepam is one of the class of benzodiazepines. Subjects given diazepam showed significant decrease in smooth pursuit gain in a dose dependent manner; 5 mg diazepam significantly reduced gain at 0.4 Hz and 10 mg diazepam at 0.4, 0.6, 0.8, 1.0, 1.2, and 1.6 Hz. In contrast to methadone, diazepam induced changes in cross-correlation as function of drug as well. Phase of smooth pursuit did not show a significant change upon administration of diazepam (Rothenberg et al., *Psychopharmacology* (Berl) 1981; 74:232-236; Rothenberg et al., *Psychopharmacology* (Berl) 1981; 74:237-240). The dose dependent effects of diazepam on different frequencies of motion track suggest that smooth pursuit eye tracking after diazepam administration may be dependent on stimulus velocity. Saccadic pursuit replaces smooth pursuit upon administration of diazepam. Diazepam may induce the above eye movement changes by its binding to visual CNS benzodiazepine binding sites that are important for oculomotor control. Compared to methadone, diazepam administration shows a greater reduction in amplitude and replacement of smooth pursuit with saccadic pursuit.

Lorazepam is another of the class of benzodiazepines. When administered to subjects undergoing saccade tasks, the gap between successive images were temporally overlapped with the original image still on the screen before the next image appeared. In normal subjects, latency increases with temporal overlap compared to images separated by 200 ms gap. With lorazepam administration, subjects showed significant change during the temporal overlap but not with 200 ms gap (Masson et al., *Behav Brain Res* 2000; 108: 169-180). Temporal overlap had no significant effect on saccadic peak velocity and amplitude in normal subjects. In lorazepam administered subjects, saccadic peak velocity and the amplitude of first saccadic eye movement significantly decreased. With smooth pursuit eye movement, lorazepam showed increased latency and longer reaction time compared to control. In addition, lorazepam significantly decreased eye velocity. Results also indicate that tracking errors in smooth pursuit induced by lorazepam are compensated for by saccadic movements of the eyes.

Alcohol consumption also impacts eye movements. Drinking subjects show decreased gain during smooth pursuit eye movement in a dose dependent manner. In one study subjects were given 0.4 and 0.8 g/kg of alcohol and eye tracking was done on two time points: T1 at 60 min. and T2 at 180 min. after beverage consumption (Roche et al., *Psychopharmacology* (Berl) 2010; 212:33-44). In smooth pursuit eye tracking, high dose affected gain at both time points while low dose did not have an effect on gain for the latter time point. For pro-saccade, latency was also impaired in a similar, dose dependent manner. Ocular velocity and accuracy decreased only after high dose consumption. Anti-saccade showed similar presentation as pro-saccade with the exception that high dose improved accuracy at T1 and decreased by T2.

Alcohol significantly affected both pro and anti-saccade accuracy; however, greater accuracy for high dose alcohol at T1 may be due to alcohol increasing the amplitude of anti-saccade relative to normal conditions and not that alcohol is improving anti-saccade functioning. This suggests that high dose alcohol may be affecting neurocircuitry required for rapid processing of visuospatial information. High dose and low dose alcohol consumption show similar impairment in smooth pursuit gain and anti-saccade functions; however, high dose patients have less awareness of the impact of this dysfunction, placing them in higher risk for injuries.

Internuclear Ophthalmoplegia (INO)

The medial longitudinal fasciculus is a bilateral axonal bundle that functionally coordinates the actions of cranial nerves III, IV and VI, and receives inputs from the frontal eye fields, cerebellar flocculus, superior colliculus, accessory oculomotor nuclei, pontine reticular formation, fastigial nucleus and cranial nerve VIII (Reulen et al., *Brain* 1983; 106 (Pt 1):121-140). It enables saccadic and reflexive eye movements and carries the descending tectospinal and medial vestibulospinal tracts into the cervical spinal cord.

Internuclear ophthalmoplegia (INO) results from impaired function of the medial longtitudinal fasciculus (Zee et al., *Baillieres Clin Neurol* 1992; 1:455-470) and can be either unilateral or bilateral. The most common causes of INO are multiple sclerosis and stroke/ischemic injury. Other causes are trauma, tentorial herniation, infection, tumor, iatrogenic injury, hemorrhage, vasculitis, and other (Keane et al., *Arch Neurol* 2005; 62:714-717).

INO can be difficult to detect in patients with mild or intermediate slowing of adduction and a variety of technologies have been proposed to increase the accuracy of detection, such as quantitative infrared oculography (Frohman et al., *Neurology* 2003; 61:848-850), saccade testing and electrooculography (Jozefowicz-Korczynska et al., *J Neurol* 2008; 255:1006-1011) and oculo-vestibular evoked myogenic potentials (Rosengren et al., *Clin Neurophysiol* 2011; 122:1264-1267). MRI sequences in patients with INO may also reveal lesions in the MLF (McNulty et al., *Clin Neuroradiol* 2014).

INO can also be difficult to differentiate from infranuclear palsies of cranial nerves such as a partial third nerve palsy, or disorders such as myasthenia gravis or Guillain Barre or ocular globe trauma. A method for quantitation of INO would be a useful outcome measure for assessing the efficacy of treatments for INO. Since INO is often seen in multiple sclerosis such a method may also be useful for assessing the efficacy of treatments for multiple sclerosis (MS).

Chronic Traumatic Encephalopathy

Chronic traumatic encephalopathy (CTE) is a form of encephalopathy that is a progressive degenerative disease, which can currently only be definitively diagnosed postmortem, in individuals with a history of multiple concussions and other forms of head injury. In March 2014, researchers announced the discovery of an exosome particle created by the brain which has been shown to contain trace proteins indicating the presence of the disease, however, a test is not yet available. The disease was previously called dementia pugilistica (DP), as it was initially found in those with a history of boxing. CTE has been most commonly found in professional athletes participating in American football, ice hockey, professional wrestling and other contact sports who have experienced repetitive brain trauma. It has also been found in soldiers exposed to a blast or a concussive injury, in both cases resulting in characteristic degeneration of brain tissue and the accumulation of tau protein. (Individuals with CTE may show symptoms of dementia, such as memory loss, aggression, confusion and depression, which generally appear years or many decades after the trauma.

Repeated concussions and injuries less serious than concussions ("sub-concussions") incurred during the play of contact sports over a long period have not yet been found to result in CTE. In the case of blast injury, a single exposure to a blast and the subsequent violent movement of the head in the blast wind can cause the condition.

CTE is a neurological degenerative disease found in individuals who have been subjected to repetitive traumatic brain injuries by way of the acceleration of the head on impact and the subsequent damage to axons. (McKee et al., *J. Neuropathol. Exp. Neurol.* 68 (7): 709-35) While repetitive brain trauma is thought to be necessary to cause CTE, it is not sufficient, meaning that not everyone exposed to repetitive brain trauma will get the disease. Other risk factors are possible but have not yet been reported, due to the donated brains in the brain bank at the Boston University School of Medicine and elsewhere, which consists mostly of the brains of athletes with a history of professional participation in contact sports. (Saulle et al., "Chronic Traumatic Encephalopathy: A Review," *Rehabilitation Research and Practice* 2012: 1) Professional level athletes are the largest demographic to suffer from CTE due to frequent concussions from play in contact-sport. These contact-sports include American football, ice hockey, rugby, boxing, and wrestling. (Daneshvar et al., *Clin Sports Med* 2011; 30(1): 1-17) Other individuals that have been diagnosed with CTE were involved in military service, had a previous history of chronic seizures, victims of domestic abuse, and or were involved in activities resulting in repetitive head collisions. (Daneshvar et al., *Phys Med Rehabil Clin N Am* 2011; 22(4): 683-700) Reports of CTE have steadily increased in younger athletes, most likely due to increased awareness of the issue and perhaps due in part to athletes becoming bigger and stronger producing greater magnitudes of force in collision.

The primary physical manifestations of CTE include a reduction in brain weight, associated with atrophy of the frontal and temporal cortices and medial temporal lobe. The lateral ventricles and the third ventricle are often enlarged, with rare instances of dilation of the fourth ventricle. (Baugh et al., *Brain Imaging and Behavior* 2012; 6(2): 244-254) Other physical manifestations of CTE include anterior cavum septi pellucidi and posterior fenestrations, pallor of the substantia nigra and locus ceruleus, and atrophy of the olfactory bulbs, thalamus, mammillary bodies, brainstem and cerebellum. (Jancin, "Chronic traumatic encephalopathy test sought," *Internal Medicine News*. December 2013) As CTE progresses, there may be marked atrophy of the hippocampus, entorhinal cortex, and amygdala. (McKee et al., *J. Neuropathol. Exp. Neurol.* 2009; 68(7):709-35)

On a microscopic scale the pathology includes neuronal loss, tau deposition, TAR DNA-binding Protein 43 (TDP 43) beta-amyloid deposition, white matter changes, and other abnormalities. The tau deposition occurs as dense neurofibrillary tangles (NFT), neurites, and glial tangles, which are made up of astrocytes and other glial cells[7] Beta-amyloid deposition is a relatively uncommon feature of CTE. (McKee et al., (2012) "The Spectrum of Disease in Chronic Traumatic Encephalopathy" *Brain:* 1-22)

A small group of individuals with CTE have chronic traumatic encephalomyopathy (CTEM), characterized by motor neuron disease symptoms and mimics Amyotrophic Lateral Sclerosis (ALS) (known in the United States as Lou Gehrig's disease). Progressive muscle weakness and balance and gait problems seem to be early signs of CTEM.

Effects of Alcohol on Eye Movement

A substantial percentage of trauma subjects are simultaneously intoxicated with alcohol: (Dinh et al., *Emerg Med J* 2014; 31:390-393; O'Keeffe et al., *J Trauma* 2009; 66:495-498) Alcohol impedes assessment of patients with acute trauma by decreasing the Glasgow coma scale score and obfuscating the clinical examination. (Jurkovich et al.,

*JAMA* 1993; 270:51-56; Rundhaug et al., *J Neurosurg* 2014; 1:1-8) The impact of alcohol intoxication on eye movements has been well-described. Alcohol intoxication (0.6 g/kg for men and 0.55 g/kg for women) inhibits volitional antisaccades, impairs smooth pursuit and impacts the latency and accuracy of pro- and anti-saccades in a dose dependent manner. (Roche et al., *Psychopharmacology* (Berl) 2010; 212:33-44; Roche et al., *Alcohol Clin Exp Res* 2014; 38:844-852; Fogt et al., *Aviat Space Environ Med* 2001; 72:579-585; Fransson et al., *Clin Neurophysiol* 2010; 121:2134-2142) Alcohol also alters saccadic velocity. (King et al., *J Stud Alcohol* 2004; 65:27-36) These findings correlate closely with self-report of intoxication.

All publications, patent applications, patents and other reference material mentioned are incorporated by reference in their entirety, for instance, Patent Cooperation Treaty Application No. PCT/US2013/033672 filed Mar. 25, 2013 and Patent Cooperation Treaty Application No. PCT/US2014/042645 filed Jun. 17, 2014, and U.S. provisional applications 61/835,927, filed Jun. 17, 2013, 61/881,014, filed Sep. 23, 2013, 61/929,238, filed Jan. 20, 2014, 62/032,769, filed Aug. 4, 2014, and 62/065,057, filed Oct. 17, 2014, 62/068,047 filed Oct. 24, 2014, and 62/102,164 filed Jan. 12, 2015. In addition, the materials, methods and examples are only illustrative and are not intended to be limiting. The citation of references herein is not to be construed as an admission that the references are prior art to the present invention.

SUMMARY OF THE INVENTION

In a first aspect, the invention provides methods for diagnosing, assessing or quantitating drug use, drug abuse or narcosis in a subject by
  a) Tracking eye movement of at least one eye of the subject;
  b) Analyzing eye movement of at least one eye of the subject;
  c) Comparing eye movement of at least one eye of the subject to a normal or mean eye movement; and, optionally
  d) Calculating a standard deviation or p value for eye movement of at least one eye of the subject as compared to the normal or mean eye movement.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L \cdot \text{var } Y\text{top} = \text{Var}(\bar{y}_{1,average\ k=1:5,1}) \quad (13)$$

$$R \cdot \text{var } Y\text{top} = \text{Var}(\bar{y}_{2,average\ k=1:5,1}) \quad (14)$$

$$L \cdot \text{var } X\text{rit} = \text{Var}(\bar{x}_{1,average\ k=1:5,2}) \quad (15)$$

$$R \cdot \text{var } X\text{rit} = \text{Var}(\bar{x}_{2,average\ k=1:5,2}) \quad (16)$$

$$L \cdot \text{var } Y\text{bot} = \text{Var}(\bar{y}_{1,average\ k=1:5,3}) \quad (17)$$

$$R \cdot \text{var } Y\text{bot} = \text{Var}(\bar{y}_{2,average\ k=1:5,3}) \quad (18)$$

$$L \cdot \text{var } X\text{lef} = \text{Var}(\bar{x}_{1,average\ k=1:5,4}) \quad (19)$$

$$R \cdot \text{var } X\text{lef} = \text{Var}(\bar{x}_{2,average\ k=1:5,4}) \quad (20)$$

$$L \cdot \text{varTotal} = \text{Average}(\text{Var}(\bar{x}_{1,average\ k=1:5}) + \text{Var}(\bar{y}_{1,average\ k=1:5})) \quad (21)$$

$$R \cdot \text{varTotal} = \text{Average}(\text{Var}(\bar{y}_{2,average\ k=1:5}) + \text{Var}(\bar{y}_{2,average\ k=1:5})) \quad (22)$$

or segment standard deviation and segment skew such as, for instance, $$L \cdot \text{SkewTop} = \text{Skew}(\bar{y}_{1,average\ k=1:5,1}) \quad (27)$$

$$R \cdot \text{SkewTop} = \text{Skew}(\bar{y}_{2,average\ k=1:5,1}) \quad (28)$$

$$L \cdot \text{SkewRit} = \text{Skew}(\bar{x}_{1,average\ k=1:5,2}) \quad (29)$$

$$R \cdot \text{SkewRit} = \text{Skew}(\bar{x}_{2,average\ k=1:5,2}) \quad (30)$$

$$L \cdot \text{SkewBot} = \text{Skew}(\bar{y}_{1,average\ k=1:5,3}) \quad (31)$$

$$R \cdot \text{SkewBot} = \text{Skew}(\bar{y}_{2,average\ k=1:5,3}) \quad (32)$$

$$L \cdot \text{SkewLef} = \text{Skew}(\bar{x}_{1,average\ k=1:5,4}) \quad (33)$$

$$R \cdot \text{SkewLef} = \text{Skew}(\bar{x}_{2,average\ k=1:5,4}) \quad (34)$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}}, \quad (35)$$

$$\text{SkewNorm}(\bar{y}_{j,k,l}) = \frac{\text{Skew}(\bar{y}_{j,k,l})}{\sigma_{\bar{y}_{j,k,l}}}. \quad (36)$$

$$L \cdot \text{SkewTopNorm} = \text{SkewNorm}(\bar{y}1, \text{average } k=1:5,1) \quad (37)$$

$$R \cdot \text{SkewTopNorm} = \text{SkewNorm}(\bar{y}2, \text{average } k=1:5,1) \quad (38)$$

$$L \cdot \text{SkewRitNorm} = \text{SkewNorm}(\bar{x}1, \text{average } k=1:5,2) \quad (39)$$

$$R \cdot \text{SkewRitNorm} = \text{SkewNorm}(\bar{x}2, \text{average } k=1:5,2) \quad (40)$$

$$L \cdot \text{SkewBotNorm} = \text{SkewNorm}(\bar{y}1, \text{average } k=1:5,3) \quad (41)$$

$$R \cdot \text{SkewBotNorm} = \text{SkewNorm}(\bar{y}2, \text{average } k=1:5,3) \quad (42)$$

$$L \cdot \text{SkewLefNorm} = \text{SkewNorm}(\bar{x}1, \text{average } k=1:5,4) \quad (43)$$

$$R \cdot \text{SkewLefNorm} = \text{SkewNorm}(\bar{x}2, \text{average } k=1:5,4) \quad (44)$$

The method may also feature calculating box height, box width, box area, or box aspect ratio.

Box Height $$\text{BoxHeight}_{j,k} = \overline{y}_{j,k,1} - \overline{y}_{j,k,3} \quad (45)$$

Box Width $$\text{BoxWidth}_{j,k} = \overline{x}_{j,k,2} - \overline{x}_{j,k,4} \quad (46)$$

Box Aspect Ratio $$\text{AspectRatio}_{j,k} = \frac{\text{BoxHeight}_{j,k}}{\text{BoxWidth}_{j,k}} \quad (47)$$

Box Area $$\text{BoxArea}_{j,k} = \text{BoxHeight}_{j,k} \times \text{BoxWidth}_{j,k} \quad (48)$$

The method may also feature calculating conjugacy of eye movement or variance from perfect conjugacy of eye movement, such as, for example, $$\text{Conj varXtop} = \frac{\sum (\hat{x}_1)^2 - 0}{\sum \hat{x}_1}, \quad (57)$$

$$\text{Conj varXrit} = \frac{\sum (\hat{x}_2)^2 - 0}{\sum \hat{x}_2}, \quad (58)$$

$$\text{Conj varXbot} = \frac{\sum (\hat{x}_3)^2 - 0}{\sum \hat{x}_3}, \quad (59)$$

$$\text{Conj varXlef} = \frac{\sum (\hat{x}_4)^2 - 0}{\sum \hat{x}_4}, \quad (60)$$

$$\text{Conj varYtop} = \frac{\sum (\hat{y}_1)^2 - 0}{\sum \hat{y}_1}, \quad (61)$$

$$\text{ConjvarYrit} = \frac{\sum (\hat{y}_2)^2 - 0}{\sum \hat{y}_2}, \quad (62)$$

$$\text{Conj varYbot} = \frac{\sum (\hat{y}_3)^2 - 0}{\sum \hat{y}_3}, \quad (63)$$

$$\text{Conj varYrit} = \frac{\sum (\hat{y}_4)^2 - 0}{\sum \hat{y}_4}, \quad (64)$$

$$\text{Conj CorrXYtop} = \frac{\sum \hat{x}_1 \hat{y}_1}{\sum \hat{x}_1 - 1}, \quad (65)$$

$$\text{Conj CorrXYrit} = \frac{\sum \hat{x}_2 \hat{y}_2}{\sum \hat{x}_2 - 1}, \quad (66)$$

$$\text{Conj CorrXYbot} = \frac{\sum \hat{x}_3 \hat{y}_3}{\sum \hat{x}_3 - 1}, \quad (67)$$

$$\text{Conj CorrXYlef} = \frac{\sum \hat{x}_4 \hat{y}_4}{\sum \hat{x}_4 - 1}, \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting that a subject has been using or consuming a drug or narcotic, is under the influence of a drug or narcotic, is experiencing an impaired mental state because of a drug or narcotic, or is in a state of narcosis. In some instances, two, three, four, five, six, seven, eight, nine, ten or more metrics may be observed or determined.

In some instances, the method may feature calculating velocity of eye movement. In such instances, the distance ($z_1$) traveled by the pupil between times 1 and 2 may be determined as the square root of:

$$(x_2-x_1)^2+(y_2-y_1)^2$$

where the coordinates of the pupil at time 1 are $x_1$, $y_1$, and the coordinates of the pupil at time 2 are $x_2$, $y_2$.

The sum of the z's may be obtained to determine the distance traveled by the eye pupil over any time period of interest. The sum of the z's over, for instance, 1, 2, 3, 5, 7, 10, 15, 20, 25, 30, 60 or 90 or so second intervals may be obtained to determine the distance traveled during each segment of a box eye movement trajectory. Pupil velocity may be determined by dividing by the time in seconds.

The method may also feature determining whether eye pupil velocity changes in different directions of eye movement reflected in an eye movement box trajectory. In some instances, one or more of a $z_{total}$, $z_{top}$, $z_{left}$, $z_{right}$, $z_{bottom}$ may be determined with reference to an eye movement box trajectory. In some instances, one or more of such a $z_{total}$, $z_{top}$, $z_{left}$, $z_{right}$, $z_{bottom}$ may be provided for each eye. Further, in some instances Wilcoxon statistical analysis may be employed to analyze groups of data.

The velocity of eye pupil movement may be slower by 5, 10, 25, 30, 35, 40, 50, 60, 70, 75% or more in a subject using or abusing a drug such as a narcotic or in a subject in a state of narcosis compared to a control, a normal, a subject not using or abusing a drug such as a narcotic and not in a state of narcosis, or compared to the velocity of eye pupil movement in the same subject at a time when that subject is not using or abusing a drug such as a narcotic or when that subject is not in a state of narcosis. In some such instances, the velocity of eye pupil movement may be only about 25, 30, 40, 50, 60, 70, 75, 80 or 90% as fast. In some instances, when eye pupil movement is represented in an eye movement trajectory box, and the top or bottom or left or right segment of the eye movement trajectory box may demonstrate more or less slowing of velocity of eye pupil movement than the other segments. For instance, in many instances, the top segment of the eye movement trajectory box may demonstrate more slowing of velocity of eye pupil movement than the other three segments of the eye movement trajectory box.

A standard deviation or p value of 0.05, 0.10, 0.25, 0.3, 0.4, 0.5, 0.75. 0.8, 0.9, 1.0, 1.5, 2.0, 2.5 or more may reflect that a subject has been using or consuming a drug or narcotic, is under the influence of a drug or narcotic, is experiencing an impaired mental state because of a drug or narcotic, or is in a state of narcosis. As such, the methods described herein may be used to detect drug use, drug abuse, and narcosis and assess or determine the severity of the same.

In some instances, the drug or narcotic may be a psychoactive compound with sleep-inducing properties or a drug that is illegal or prohibited. In some instances, the drug or narcotic may be one or more of an opiate, an opioid, morphine, heroin, and their derivatives, such as hydrocodone, or *Cannabis*, alcohol, or any other substance classified as a controlled substance by the United States Controlled Substances Act. In some instances, the drug or narcotic may be a prescription medication such as, for instance, a benzodiazepine or barbiturate.

In a second aspect, the invention provides methods for differentiating between drug use, drug abuse or narcosis and brain injury or a disease characterized by or featuring brain injury in a subject by
  a) Tracking eye movement of at least one eye of the subject;
  b) Analyzing eye movement of at least one eye of the subject;
  c) Comparing eye movement of at least one eye of the subject to a normal or mean eye movement; and, optionally
  d) Calculating a standard deviation or p value for eye movement of at least one eye of the subject.

In some instances, the normal or mean eye movement of c) may be obtained from or observed in a subject suffering from a brain injury. The brain injury may be, for instance, a structural or a non-structural traumatic brain injury such as, for instance, a concussion, a subconcussion or a blast injury.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L \cdot \text{var } Y\text{top} = \text{Var}(\bar{y}_{1, average\ k=1:5,1}) \tag{13}$$

$$R \cdot \text{var } Y\text{top} = \text{Var}(\bar{y}_{2, average\ k=1:5,1}) \tag{14}$$

$$L \cdot \text{var } X\text{rit} = \text{Var}(\bar{x}_{1, average\ k=1:5,2}) \tag{15}$$

$$R \cdot \text{var } X\text{rit} = \text{Var}(\bar{x}_{2, average\ k=1:5,2}) \tag{16}$$

$$L \cdot \text{var } Y\text{bot} = \text{Var}(\bar{y}_{1, average\ k=1:5,3}) \tag{17}$$

$$R \cdot \text{var } Y\text{bot} = \text{Var}(\bar{y}_{2, average\ k=1:5,3}) \tag{18}$$

$$L \cdot \text{var } X\text{lef} = \text{Var}(\bar{x}_{1, average\ k=1:5,4}) \tag{19}$$

$$R \cdot \text{var } X\text{lef} = \text{Var}(\bar{x}_{2, average\ k=1:5,4}) \tag{20}$$

$$L \cdot \text{varTotal} = \text{Average}(\text{Var}(\bar{x}_{1, average\ k=1:5}) + \text{Var}(\bar{y}_{1, average\ k=1:5})) \tag{21}$$

$$R \cdot \text{varTotal} = \text{Average}(\text{Var}(\bar{y}_{2, average\ k=1:5}) + \text{Var}(\bar{y}_{2, average\ k=1:5})) \tag{22}$$

or segment standard deviation and segment skew such as, for instance, $$L \cdot \text{SkewTop} = \text{Skew}(\bar{y}_{1, average\ k=1:5,1}) \tag{27}$$

$$R \cdot \text{SkewTop} = \text{Skew}(\bar{y}_{2, average\ k=1:5,1}) \tag{28}$$

$$L \cdot \text{SkewRit} = \text{Skew}(\bar{x}_{1, average\ k=1:5,2}) \tag{29}$$

$$R \cdot \text{SkewRit} = \text{Skew}(\bar{x}_{2, average\ k=1:5,2}) \tag{30}$$

$$L \cdot \text{SkewBot} = \text{Skew}(\bar{y}_{1, average\ k=1:5,3}) \tag{31}$$

$$R \cdot \text{SkewBot} = \text{Skew}(\bar{y}_{2, average\ k=1:5,3}) \tag{32}$$

$$L \cdot \text{SkewLef} = \text{Skew}(\bar{x}_{1, average\ k=1:5,4}) \tag{33}$$

$$R \cdot \text{SkewLef} = \text{Skew}(\bar{x}_{2, average\ k=1:5,4}) \tag{34}$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}}, \tag{35}$$

$$\text{SkewNorm}(\bar{y}_{j,k,l}) = \frac{\text{Skew}(\bar{y}_{j,k,l})}{\sigma_{\bar{y}_{j,k,l}}}. \tag{36}$$

$$L \cdot \text{SkewTopNorm} = \text{SkewNorm}(\hat{y}1, \text{average } k=1:5,1) \tag{37}$$

$$R \cdot \text{SkewTopNorm} = \text{SkewNorm}(\bar{y}2, \text{average } k=1:5,1) \tag{38}$$

$$L \cdot \text{SkewRitNorm} = \text{SkewNorm}(\bar{x}1, \text{average } k=1:5,2) \tag{39}$$

$$R \cdot \text{SkewRitNorm} = \text{SkewNorm}(\bar{x}2, \text{average } k=1:5,2) \tag{40}$$

$$L \cdot \text{SkewBotNorm} = \text{SkewNorm}(\bar{y}1, \text{average } k=1:5,3) \tag{41}$$

$$R \cdot \text{SkewBotNorm} = \text{SkewNorm}(\bar{y}2, \text{average } k=1:5,3) \tag{42}$$

$$L \cdot \text{SkewLefNorm} = \text{SkewNorm}(\bar{x}1, \text{average } k=1:5,4) \tag{43}$$

$$R \cdot \text{SkewLefNorm} = \text{SkewNorm}(\bar{x}2, \text{average } k=1:5,4) \tag{44}$$

The method may also feature calculating box height, box width, box area, or box aspect ratio.

Box Height $$\text{BoxHeight}_{j,k} = \bar{y}_{j,k,1} - \bar{y}_{j,k,3} \tag{45}$$

Box Width $$\text{BoxWidth}_{j,k} = \bar{x}_{j,k,2} - \bar{x}_{j,k,4} \tag{46}$$

Box Aspect Ratio $$\text{AspectRatio}_{j,k} = \frac{\text{BoxHeight}_{j,k}}{\text{BoxWidth}_{j,k}} \tag{47}$$

Box Area $$\text{BoxArea}_{j,k} = \text{BoxHeight}_{j,k} \times \text{BoxWidth}_{j,k} \tag{48}$$

The method may also feature calculating conjugacy of eye movement or variance from perfect conjugacy of eye movement, such as, for example, $$\text{Conj } var X top = \frac{\sum (\hat{x}_1)^2 - 0}{\sum \hat{x}_1}, \tag{57}$$

$$Conj\ varXrit = \frac{\sum (\hat{x}_2)^2 - 0}{\sum \hat{x}_2}, \qquad (58)$$

$$Conj\ varXbot = \frac{\sum (\hat{x}_3)^2 - 0}{\sum \hat{x}_3}, \qquad (59)$$

$$Conj\ varXlef = \frac{\sum (\hat{x}_4)^2 - 0}{\sum \hat{x}_4}, \qquad (60)$$

$$Conj\ varYtop = \frac{\sum (\hat{y}_1)^2 - 0}{\sum \hat{y}_1}, \qquad (61)$$

$$ConjvarYrit = \frac{\sum (\hat{y}_2)^2 - 0}{\sum \hat{y}_2}, \qquad (62)$$

$$Conj\ varYbot = \frac{\sum (\hat{y}_3)^2 - 0}{\sum \hat{y}_3}, \qquad (63)$$

$$Conj\ varYrit = \frac{\sum (\hat{y}_4)^2 - 0}{\sum \hat{y}_4}, \qquad (64)$$

$$Conj\ CorrXYtop = \frac{\sum \hat{x}_1 \hat{y}_1}{\sum \hat{x}_1 - 1}, \qquad (65)$$

$$Conj\ CorrXYrit = \frac{\sum \hat{x}_2 \hat{y}_2}{\sum \hat{x}_2 - 1}, \qquad (66)$$

$$Conj\ CorrXYbot = \frac{\sum \hat{x}_3 \hat{y}_3}{\sum \hat{x}_3 - 1}, \qquad (67)$$

$$Conj\ CorrXYlef = \frac{\sum \hat{x}_4 \hat{y}_4}{\sum \hat{x}_4 - 1} \qquad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing drug use, drug abuse or narcosis. In some instances, two, three, four, five, six, seven, eight, nine, ten or more metrics may be observed or determined.

In some instances, the method may feature calculating velocity of eye movement. In such instances, the distance ($z_1$) traveled by the pupil between times 1 and 2 may be determined as the square root of:

$$(x_2-x_1)^2+(y_2-y_1)^2$$

where the coordinates of the pupil at time 1 are $x_1$, $y_1$, and the coordinates of the pupil at time 2 are $x_2$, $y_2$.

In some instances, the sum of the z's may be obtained to determine the distance traveled by the eye pupil over any time period of interest. The sum of the z's over, for instance, 1, 2, 3, 5, 7, 10, 15, 20, 25, 30, 60 or 90 or so second intervals may be obtained to determine at the distance traveled during each segment of a box eye movement trajectory. Pupil velocity may be determined by dividing by the time in seconds.

The method may feature determining whether eye pupil velocity changes in different directions of eye movement reflected in an eye movement box trajectory. In some instances, one or more of a $z_{total}$, $z_{top}$, $z_{left}$, $z_{right}$, $z_{bottom}$ may be determined with reference to an eye movement box trajectory. In some instances, one or more of such a $z_{total}$, $z_{top}$, $z_{left}$, $z_{right}$, $z_{bottom}$ may be provided for each eye. Further, in some instances Wilcoxon statistical analysis may be employed to analyze groups of data.

The velocity of eye pupil movement may be slower by 5, 10, 25, 30, 35, 40, 50, 60, 70, 75% or more in a subject using or abusing a drug such as a narcotic or in a subject in a state of narcosis compared to a control, a normal, a subject not using or abusing a drug such as a narcotic and not in a state of narcosis, compared to the velocity of eye pupil movement in the same subject at a time when that subject is not using or abusing a drug such as a narcotic or when that subject is not in a state of narcosis, or compared to a subject suffering from or experiencing brain injury, such as, for instance, structural or non-structural traumatic brain injury. In some such instances, the velocity of eye pupil movement may be only about 25, 30, 40, 50, 60, 70, 75, 80 or 90% as fast. In some instances, when eye pupil movement is represented in an eye movement trajectory box, and the top or bottom or left or right segment of the eye movement trajectory box may demonstrate more or less slowing of velocity of eye pupil movement than the other segments. For instance, in many instances, the top segment of the eye movement trajectory box may demonstrate more slowing of velocity of eye pupil movement than the other three segments of the eye movement trajectory box.

A standard deviation or p value of 0.05, 0.10, 0.25, 0.3, 0.4, 0.5, 0.75. 0.8, 0.9, 1.0, 1.5, 2.0, 2.5 or more may reflect that a subject has been using or consuming a drug or narcotic, is under the influence of a drug or narcotic, is experiencing an impaired mental state because of a drug or narcotic, or is in a state of narcosis. In some instances the eye movement is tracked for about 30, 60, 90, 100, 120, 150, 180, 200, 220, 240, 270, 300, 360 or more seconds.

In some instances, the drug or narcotic may be a psychoactive compound with sleep-inducing properties or a drug that is illegal or prohibited. In some instances, the drug or narcotic may be one or more of an opiate, an opioid, morphine, heroin, and their derivatives, such as hydrocodone, or *Cannabis*, alcohol, or any other substance classified as a controlled substance by the United States Controlled Substances Act. In some instances, the drug or narcotic may be a prescription medication such as, for instance, a benzodiazepine or barbiturate.

In a third aspect, the invention provides methods for diagnosing, assessing or quantitating drug use, drug abuse or narcosis in a subject by
 a) Tracking eye movement of at least one eye of the subject;
 b) collecting raw x and y cartesian coordinates of pupil position;
 c) normalizing the raw x and y Cartesian coordinates; and
 d) calculating one or more individual metric.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In instances where the eye movement of both eyes are tracked, the method may additionally feature sorting the data by eye.

The one or more individual metric may be any one of $$L \cdot var\ Ytop = Var(\bar{y}_{1,average\ k=1:5,1}) \qquad (13)$$

$$R \cdot var\ Ytop = Var(\bar{y}_{2,average\ k=1:5,1}) \qquad (14)$$

$$L\cdot\text{var }X\text{rit}=\text{Var}(\overline{x}_{1,average\ k=1:5,2}) \quad (15)$$

$$R\cdot\text{var }X\text{rit}=\text{Var}(\overline{x}_{2,average\ k=1:5,2}) \quad (16)$$

$$L\cdot\text{var }Y\text{bot}=\text{Var}(\overline{y}_{1,average\ k=1:5,3}) \quad (17)$$

$$R\cdot\text{var }Y\text{bot}=\text{Var}(\overline{y}_{2,average\ k=1:5,3}) \quad (18)$$

$$L\cdot\text{var }X\text{lef}=\text{Var}(\overline{x}_{1,average\ k=1:5,4}) \quad (19)$$

$$R\cdot\text{var }X\text{lef}=\text{Var}(\overline{x}_{2,average\ k=1:5,4}) \quad (20)$$

$$L\cdot\text{varTotal}=\text{Average}(\text{Var}(\overline{x}_{1,average\ k=1:5})+\text{Var}(\overline{y}_{1,average\ k=1:5})) \quad (21)$$

$$R\cdot\text{varTotal}=\text{Average}(\text{Var}(\overline{y}_{2,average\ k=1:5})+\text{Var}(\overline{y}_{2,average\ k=1:5})) \quad (22)$$

or segment standard deviation and segment skew such as, for instance, $$L\cdot\text{SkewTop}=\text{Skew}(\overline{y}_{1,average\ k=1:5,1}) \quad (27)$$

$$R\cdot\text{SkewTop}=\text{Skew}(\overline{y}_{2,average\ k=1:5,1}) \quad (28)$$

$$L\cdot\text{SkewRit}=\text{Skew}(\overline{x}_{1,average\ k=1:5,2}) \quad (29)$$

$$R\cdot\text{SkewRit}=\text{Skew}(\overline{x}_{2,average\ k=1:5,2}) \quad (30)$$

$$L\cdot\text{SkewBot}=\text{Skew}(\overline{y}_{1,average\ k=1:5,3}) \quad (31)$$

$$R\cdot\text{SkewBot}=\text{Skew}(\overline{y}_{2,average\ k=1:5,3}) \quad (32)$$

$$L\cdot\text{SkewLef}=\text{Skew}(\overline{x}_{1,average\ k=1:5,4}) \quad (33)$$

$$R\cdot\text{SkewLef}=\text{Skew}(\overline{x}_{2,average\ k=1:5,4}) \quad (34)$$

or segment normalized skew, such as, for instance, $$\text{SkewNorm}(\overline{x}_{j,k,l}) = \frac{\text{Skew}(\overline{x}_{j,k,l})}{\sigma_{\overline{x}_{j,k,l}}}, \quad (35)$$

$$\text{SkewNorm}(\overline{y}_{j,k,l}) = \frac{\text{Skew}(\overline{y}_{j,k,l})}{\sigma_{\overline{y}_{j,k,l}}}. \quad (36)$$

$$L\cdot\text{SkewTopNorm}=\text{SkewNorm}(\overline{y}1,average\ k=1:5,1) \quad (37)$$

$$R\cdot\text{SkewTopNorm}=\text{SkewNorm}(\overline{y}2,average\ k=1:5,1) \quad (38)$$

$$L\cdot\text{SkewRitNorm}=\text{SkewNorm}(\overline{x}1,average\ k=1:5,2) \quad (39)$$

$$R\cdot\text{SkewRitNorm}=\text{SkewNorm}(\overline{x}2,average\ k=1:5,2) \quad (40)$$

$$L\cdot\text{SkewBotNorm}=\text{SkewNorm}(\overline{y}1,average\ k=1:5,3) \quad (41)$$

$$R\cdot\text{SkewBotNorm}=\text{SkewNorm}(\overline{y}2,average\ k=1:5,3) \quad (42)$$

$$L\cdot\text{SkewLefNorm}=\text{SkewNorm}(\overline{x}1,average\ k=1:5,4) \quad (43)$$

$$R\cdot\text{SkewLefNorm}=\text{SkewNorm}(\overline{x}2,average\ k=1:5,4) \quad (44)$$

The method may also feature calculating box height, box width, box area, or box aspect ratio.

Box Height $$\text{BoxHeight}_{j,k}=\overline{y}_{j,k,1}-\overline{y}_{j,k,3} \quad (45)$$

Box Width $$\text{BoxWidth}_{j,k}=\overline{x}_{j,k,2}-\overline{x}_{j,k,4} \quad (46)$$

Box Aspect Ratio $$\text{AspectRatio}_{j,k} = \frac{\text{BoxHeight}_{j,k}}{\text{BoxWidth}_{j,k}} \quad (47)$$

Box Area $$\text{BoxArea}_{j,k}=\text{BoxHeight}_{j,k}\times\text{BoxWidth}_{j,k} \quad (48)$$

The method may also feature calculating conjugacy of eye movement or variance from perfect conjugacy of eye movement, such as, for example, or variance x ratio top/bottom (conjugacy), variance y ratio top/bottom (conjugacy), variance x ratio left/right (conjugacy), or variance y ratio left/right (conjugacy).

$$\text{Conj varXtop} = \frac{\sum (\hat{x}_1)^2 - 0}{\sum \hat{x}_1}, \quad (57)$$

$$\text{Conj varXrit} = \frac{\sum (\hat{x}_2)^2 - 0}{\sum \hat{x}_2}, \quad (58)$$

$$\text{Conj varXbot} = \frac{\sum (\hat{x}_3)^2 - 0}{\sum \hat{x}_3}, \quad (59)$$

$$\text{Conj varXlef} = \frac{\sum (\hat{x}_4)^2 - 0}{\sum \hat{x}_4}, \quad (60)$$

$$\text{Conj varYtop} = \frac{\sum (\hat{y}_1)^2 - 0}{\sum \hat{y}_1}, \quad (61)$$

$$\text{ConjvarYrit} = \frac{\sum (\hat{y}_2)^2 - 0}{\sum \hat{y}_2}, \quad (62)$$

$$\text{Conj varYbot} = \frac{\sum (\hat{y}_3)^2 - 0}{\sum \hat{y}_3}, \quad (63)$$

$$\text{Conj varYrit} = \frac{\sum (\hat{y}_4)^2 - 0}{\sum \hat{y}_4}, \quad (64)$$

$$\text{Conj CorrXYtop} = \frac{\sum \hat{x}_1 \hat{y}_1}{\sum \hat{x}_1 - 1}, \quad (65)$$

$$\text{Conj CorrXYrit} = \frac{\sum \hat{x}_2 \hat{y}_2}{\sum \hat{x}_2 - 1}, \quad (66)$$

$$\text{Conj CorrXYbot} = \frac{\sum \hat{x}_3 \hat{y}_3}{\sum \hat{x}_3 - 1}, \quad (67)$$

$$\text{Conj CorrXYlef} = \frac{\sum \hat{x}_4 \hat{y}_4}{\sum \hat{x}_4 - 1} \quad (68)$$

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing drug use, drug abuse or narcosis. In some instances, two, three, four, five, six, seven, eight, nine, ten or more metrics may be observed or determined.

In some instances, the method may feature calculating velocity of eye movement. In such instances, the distance ($z_1$) traveled by the pupil between times 1 and 2 may be determined as the square root of:

$$(x_2-x_1)^2+(y_2-y_1)^2$$

where the coordinates of the pupil at time 1 are $x_1$, $y_1$, and the coordinates of the pupil at time 2 are $x_2$, $y_2$.

In some instances, the sum of the z's may be obtained to determine the distance traveled by the eye pupil over any time period of interest. The sum of the z's over, for instance, 1, 2, 3, 5, 7, 10, 15, 20, 25, 30, 60 or 90 or so second intervals may be obtained to determine at the distance traveled during each segment of a box eye movement trajectory. Pupil velocity may be determined by dividing by the time in seconds.

The method may feature determining whether eye pupil velocity changes in different directions of eye movement reflected in an eye movement box trajectory. In some instances, one or more of a $z_{total}$, $z_{top}$, $z_{left}$, $z_{right}$, $z_{bottom}$ may be determined with reference to an eye movement box trajectory. In some instances, one or more of such a $z_{total}$, $z_{top}$, $z_{left}$, $z_{right}$, $z_{bottom}$ may be provided for each eye. Further, in some instances Wilcoxon statistical analysis may be employed to analyze groups of data.

The velocity of eye pupil movement may be slower by 5, 10, 25, 30, 35, 40, 50, 60, 70, 75% or more in a subject using or abusing a drug such as a narcotic or in a subject in a state of narcosis compared to a control, a normal, a subject not using or abusing a drug such as a narcotic and not in a state of narcosis, or compared to the velocity of eye pupil movement in the same subject at a time when that subject is not using or abusing a drug such as a narcotic or when that subject is not in a state of narcosis. In some such instances, the velocity of eye pupil movement may be only about 25, 30, 40, 50, 60, 70, 75, 80 or 90% as fast. In some instances, when eye pupil movement is represented in an eye movement trajectory box, and the top or bottom or left or right segment of the eye movement trajectory box may demonstrate more or less slowing of velocity of eye pupil movement than the other segments. For instance, in many instances, the top segment of the eye movement trajectory box may demonstrate more slowing of velocity of eye pupil movement than the other three segments of the eye movement trajectory box.

A standard deviation or p value of 0.05, 0.10, 0.25, 0.3, 0.4, 0.5, 0.75. 0.8, 0.9, 1.0, 1.5, 2.0, 2.5 or more may reflect that a subject has been using or consuming a drug or narcotic, is under the influence of a drug or narcotic, is experiencing an impaired mental state because of a drug or narcotic, or is in a state of narcosis. In some instances the eye movement is tracked for about 30, 60, 90, 100, 120, 150, 180, 200, 220, 240, 270, 300, 360 or more seconds.

In some instances, the drug or narcotic may be a psychoactive compound with sleep-inducing properties or a drug that is illegal or prohibited. In some instances, the drug or narcotic may be one or more of an opiate, an opioid, morphine, heroin, and their derivatives, such as hydrocodone, or *Cannabis*, alcohol, or any other substance classified as a controlled substance by the United States Controlled Substances Act. In some instances, the drug or narcotic may be a prescription medication such as, for instance, a benzodiazepine or barbiturate.

In a fourth aspect, the invention provides a kit useful for detecting, screening for or quantitating drug use, drug abuse or narcosis in a subject, containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a fifth aspect, the invention provides methods for diagnosing or assessing internuclear ophthalmoplegia (INO) in a subject by
  a) Tracking eye movement of both eyes of the subject;
  b) Analyzing eye movement of both eyes of the subject;
  c) Comparing eye movement of a first eye of the subject to eye movement of a second eye of the subject; and
  d) Identifying the subject as having eye movement of a first eye that is significantly different from eye movement of a second eye.

The method may further feature
  e) Tracking eye movement of each eye of the subject separately.

The method may also further feature
  f) Identifying the subject as having substantially normal eye movement of each eye when eye movement of each eye of the subject is tracked separately.

A diagnosis of internuclear ophthalmoplegia (INO) may be made or provided as a possibility or the status of internuclear ophthalmoplegia (INO) may be evaluated or internuclear ophthalmoplegia (INO) may be assessed if the subject is d) identified as having eye movement of a first eye that is significantly different from eye movement of a second eye when tracking eye Movement of both eyes of the subject and if the subject is also t) identified as having substantially normal eye movement of each eye when eye movement of each eye of the subject is tracked separately. The method is useful for differentiating internuclear ophthalmoplegia (INO) from infranuclear nerve palsies or other disorders affecting the muscles associated with ocular motility.

In a sixth aspect, the invention provides methods for diagnosing or assessing internuclear ophthalmoplegia (INO) in a subject by
  a) Tracking eye movement of both eyes of the subject;
  b) Analyzing eye movement of both eyes of the subject;
  c) Comparing the x or y Cartesian coordinates at any time point for the eye movement of a first eye of the subject to the respective x or y Cartesian coordinates at the time point for the eye movement of a second eye of the subject;
  d) Providing a sum of the differences between all of the x coordinates of the first eye compared to the second eye over the time tested or providing a sum of the differences in y coordinates of the first eye compared to the second eye over the time tested or both; and, optionally
  e) Providing a total sum of the differences between both x and y coordinates of the first eye compared to the second eye over the time tested.

The method may further feature
  f) Tracking eye movement of each eye of the subject separately.

The method may also further feature
  g) Identifying the subject as having substantially normal eye movement of each eye when eye movement of each eye of the subject is tracked separately.

In some instances, the subject suffering from the internuclear ophthalmoplegia (INO) may have a total sum of the differences between both x and y coordinates of the first eye compared to the second eye over the time tested that is 10%, 20%, 30%, 40%, 50%, 60%, 70%, 80%, 90%, 100%, 150%, 200%, or two, three, four, five, six, eight, ten or more times greater than the total sum of the differences between both x and y coordinates of the first eye compared to the second eye over the time tested in a healthy control or in a reference value based upon one or more healthy controls or based upon the subject at a time before the internuclear ophthalmoplegia (INO).

A diagnosis of internuclear ophthalmoplegia (INO) may be made or provided as a possibility or the status of internuclear ophthalmoplegia (INO) may be evaluated or internuclear ophthalmoplegia (INO) may be assessed if the subject is d) identified as having eye movement of a first eye that is significantly different from eye movement of a second eye when tracking eye movement of both eyes of the subject and if the subject is also f) identified as having substantially normal eye movement of each eye when eye movement of each eye of the subject is tracked separately. The method is useful for differentiating internuclear ophthalmoplegia (INO) from infranuclear nerve palsies.

In a seventh aspect, the invention provides methods for assessing or quantitating or diagnosing internuclear ophthalmoplegia (INO) in a subject by
  a) Tracking eye movement of both eyes of the subject;
  b) collecting raw x and y cartesian coordinates of pupil position;
  c) normalizing the raw x and y Cartesian coordinates; and
  d) calculating one or more individual metric.
The method may further feature
  e) Tracking eye movement of each eye of the subject separately.
The method may still further feature
  f) calculating one or more second or additional individual metric.
The method may also further feature
  g) Identifying the subject as having substantially normal eye movement of each eye when eye movement of each eye of the subject is tracked separately.

A diagnosis of internuclear ophthalmoplegia (INO) may be made or provided as a possibility or the status of internuclear ophthalmoplegia (INO) may be evaluated or internuclear ophthalmoplegia (INO) may be assessed if the subject is identified as having normal motility or aspect ratio in the eyes assessed separately and abnormal aspect ratio or conjugacy when the eye movement of both eyes is tracked together. The method is useful for differentiating internuclear ophthalmoplegia (INO) from infranuclear nerve palsies or other disorders affecting the muscles associated with ocular motility.

Eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L\cdot\text{var } Y\text{top} = \text{Var}(\bar{y}_{1,average\ k=1:5,1})\tag{13}$$

$$R\cdot\text{var } Y\text{top} = \text{Var}(\bar{y}_{2,average\ k=1:5,1})\tag{14}$$

$$L\cdot\text{var } X\text{rit} = \text{Var}(\bar{x}_{1,average\ k=1:5,2})\tag{15}$$

$$R\cdot\text{var } X\text{rit} = \text{Var}(\bar{x}_{2,average\ k=1:5,2})\tag{16}$$

$$L\cdot\text{var } Y\text{bot} = \text{Var}(\bar{y}_{1,average\ k=1:5,3})\tag{17}$$

$$R\cdot\text{var } Y\text{bot} = \text{Var}(\bar{y}_{2,average\ k=1:5,3})\tag{18}$$

$$L\cdot\text{var } X\text{lef} = \text{Var}(\bar{x}_{1,average\ k=1:5,4})\tag{19}$$

$$R\cdot\text{var } X\text{lef} = \text{Var}(\bar{x}_{2,average\ k=1:5,4})\tag{20}$$

$$L\cdot\text{varTotal} = \text{Average}(\text{Var}(\bar{x}_{1,average\ k=1:5}) + \text{Var}(\bar{y}_{1,average\ k=1:5}))\tag{21}$$

$$R\cdot\text{varTotal} = \text{Average}(\text{Var}(\bar{y}_{2,average\ k=1:5}) + \text{Var}(\bar{y}_{2,average\ k=1:5}))\tag{22}$$

or segment standard deviation and segment skew such as, for instance, $$L\cdot\text{SkewTop} = \text{Skew}(\bar{y}_{1,average\ k=1:5,1})\tag{27}$$

$$R\cdot\text{SkewTop} = \text{Skew}(\bar{y}_{2,average\ k=1:5,1})\tag{28}$$

$$L\cdot\text{SkewRit} = \text{Skew}(\bar{x}_{1,average\ k=1:5,2})\tag{29}$$

$$R\cdot\text{SkewRit} = \text{Skew}(\bar{x}_{2,average\ k=1:5,2})\tag{30}$$

$$L\cdot\text{SkewBot} = \text{Skew}(\bar{y}_{1,average\ k=1:5,3})\tag{31}$$

$$R\cdot\text{SkewBot} = \text{Skew}(\bar{y}_{2,average\ k=1:5,3})\tag{32}$$

$$L\cdot\text{SkewLef} = \text{Skew}(\bar{x}_{1,average\ k=1:5,4})\tag{33}$$

$$R\cdot\text{SkewLef} = \text{Skew}(\bar{x}_{2,average\ k=1:5,4})\tag{34}$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}},\tag{35}$$

$$\text{SkewNorm}(\bar{y}_{j,k,l}) = \frac{\text{Skew}(\bar{y}_{j,k,l})}{\sigma_{\bar{y}_{j,k,l}}}.\tag{36}$$

$$L\cdot\text{SkewTopNorm} = \text{SkewNorm}(\bar{y}1, average\ k=1:5,1)\tag{37}$$

$$R\cdot\text{SkewTopNorm} = \text{SkewNorm}(\bar{y}2, average\ k=1:5,1)\tag{38}$$

$$L\cdot\text{SkewRitNorm} = \text{SkewNorm}(\bar{x}1, average\ k=1:5,2)\tag{39}$$

$$R\cdot\text{SkewRitNorm} = \text{SkewNorm}(\bar{x}2, average\ k=1:5,2)\tag{40}$$

$$L\cdot\text{SkewBotNorm} = \text{SkewNorm}(\bar{y}1, average\ k=1:5,3)\tag{41}$$

$$R\cdot\text{SkewBotNorm} = \text{SkewNorm}(\bar{y}2, average\ k=1:5,3)\tag{42}$$

$$L\cdot\text{SkewLefNorm} = \text{SkewNorm}(\bar{x}1, average\ k=1:5,4)\tag{43}$$

$$R\cdot\text{SkewLefNorm} = \text{SkewNorm}(\bar{x}2, average\ k=1:5,4)\tag{44}$$

The method may also feature calculating box height, box width, box area, or box aspect ratio.

Box Height $$\text{BoxHeight}_{j,k} = \bar{y}_{j,k,1} - \bar{y}_{j,k,3}\tag{45}$$

Box Width $$\text{BoxWidth}_{j,k} = \bar{x}_{j,k,2} - \bar{x}_{j,k,4}\tag{46}$$

Box Aspect Ratio $$AspectRatio_{j,k} = \frac{BoxHeight_{j,k}}{BoxWidth_{j,k}} \quad (47)$$

Box Area $$BoxArea_{j,k} = BoxHeight_{j,k} \times BoxWidth_{j,k} \quad (48)$$

The method may also feature calculating conjugacy of eye movement or variance from perfect conjugacy of eye movement, such as, for example, $$Conj\,var\,X\,top = \frac{\sum (\hat{x}_1)^2 - 0}{\sum \hat{x}_1}, \quad (57)$$

$$Conj\,var\,X\,rit = \frac{\sum (\hat{x}_2)^2 - 0}{\sum \hat{x}_2}, \quad (58)$$

$$Conj\,var\,X\,bot = \frac{\sum (\hat{x}_3)^2 - 0}{\sum \hat{x}_3}, \quad (59)$$

$$Conj\,var\,X\,lef = \frac{\sum (\hat{x}_4)^2 - 0}{\sum \hat{x}_4}, \quad (60)$$

$$Conj\,var\,Y\,top = \frac{\sum (\hat{y}_1)^2 - 0}{\sum \hat{y}_1}, \quad (61)$$

$$Conj\,var\,Y\,rit = \frac{\sum (\hat{y}_2)^2 - 0}{\sum \hat{y}_2}, \quad (62)$$

$$Conj\,var\,Y\,bot = \frac{\sum (\hat{y}_3)^2 - 0}{\sum \hat{y}_3}, \quad (63)$$

$$Conj\,var\,Y\,rit = \frac{\sum (\hat{y}_4)^2 - 0}{\sum \hat{y}_4}, \quad (64)$$

$$Conj\,Corr\,XY\,top = \frac{\sum \hat{x}_1 \hat{y}_1}{\sum \hat{x}_1 - 1}, \quad (65)$$

$$Conj\,Corr\,XY\,rit = \frac{\sum \hat{x}_2 \hat{y}_2}{\sum \hat{x}_2 - 1}, \quad (66)$$

$$Conj\,Corr\,XY\,bot = \frac{\sum \hat{x}_3 \hat{y}_3}{\sum \hat{x}_3 - 1}, \quad (67)$$

$$Conj\,Corr\,XY\,lef = \frac{\sum \hat{x}_4 \hat{y}_4}{\sum \hat{x}_4 - 1} \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing internuclear ophthalmoplegia (INO) or differentiating or distinguishing it from infranuclear nerve palsies. In some instances, two, three, four, five, six, seven, eight, nine, ten or more metrics may be observed or determined.

In a eighth aspect, the invention provides a kit useful for detecting, screening for or quantitating internuclear ophthalmoplegia (INO) and useful for differentiating internuclear ophthalmoplegia (INO) from infranuclear nerve palsies containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a ninth aspect, the invention provides methods for diagnosing or assessing attention deficit hyperactivity disorder (ADHD), chronic traumatic encephalopathy, or a schizophrenia spectrum disorder in a subject by
  a) Tracking eye movement of both eyes of the subject;
  b) Analyzing eye movement of both eyes of the subject;
  c) Comparing eye movement of a first eye of the subject to eye movement of a second eye of the subject; and
  d) Identifying the subject as having eye movement of a first eye that is significantly different from eye movement of a second eye.

In a tenth aspect, the invention provides methods for diagnosing and assessing attention deficit hyperactivity disorder (ADHD), chronic traumatic encephalopathy, or a schizophrenia spectrum disorder in a subject by
  a) Tracking eye movement of both eyes of the subject;
  b) Analyzing eye movement of both eyes of the subject;
  c) Comparing the x or y Cartesian coordinates at any time point for the eye movement of a first eye of the subject to the respective x or y Cartesian coordinates at the time point for the eye movement of a second eye of the subject;
  d) Providing a sum of the differences between all of the x coordinates of the first eye compared to the second eye over the time tested or providing a sum of the differences in y coordinates of the first eye compared to the second eye over the time tested or both; and, optionally
  e) Providing a total sum of the differences between both x and y coordinates of the first eye compared to the second eye over the time tested.

In some instances, the subject suffering from the attention deficit hyperactivity disorder (ADHD), chronic traumatic encephalopathy, or a schizophrenia spectrum disorder may have a total sum of the differences between both x and y coordinates of the first eye compared to the second eye over the time tested that is 10%, 20%, 30%, 40%, 50%, 60%, 70%, 80%, 90%, 100%, 150%, 200%, or two, three, four, five, six, eight, ten or more times greater than the total sum of the differences between both x and y coordinates of the first eye compared to the second eye over the time tested in a healthy control or in a reference value based upon one or more healthy controls or based upon the subject at a time before the disease.

In a eleventh aspect, the invention provides methods for diagnosing or assessing attention deficit hyperactivity disorder (ADHD), chronic traumatic encephalopathy, or a schizophrenia spectrum disorder by
  a) Tracking eye movement of at least one eye of the subject;
  b) Analyzing eye movement of at least one eye of the subject;
  c) Comparing eye movement of at least one eye of the subject to a normal or mean eye movement; and, optionally d) Calculating a standard deviation or p value for eye movement of at least one eye of the subject as compared to the normal or mean eye movement.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of the other eye of the subject or may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L \cdot \text{var } Y\text{top} = \text{Var}(\bar{y}_{1, average\ k=1:5,1}) \tag{13}$$

$$R \cdot \text{var } Y\text{top} = \text{Var}(\bar{y}_{2, average\ k=1:5,1}) \tag{14}$$

$$L \cdot \text{var } X\text{rit} = \text{Var}(\bar{x}_{1, average\ k=1:5,2}) \tag{15}$$

$$R \cdot \text{var } X\text{rit} = \text{Var}(\bar{x}_{2, average\ k=1:5,2}) \tag{16}$$

$$L \cdot \text{var } Y\text{bot} = \text{Var}(\bar{y}_{1, average\ k=1:5,3}) \tag{17}$$

$$R \cdot \text{var } Y\text{bot} = \text{Var}(\bar{y}_{2, average\ k=1:5,3}) \tag{18}$$

$$L \cdot \text{var } X\text{lef} = \text{Var}(\bar{x}_{1, average\ k=1:5,4}) \tag{19}$$

$$R \cdot \text{var } X\text{lef} = \text{Var}(\bar{x}_{2, average\ k=1:5,4}) \tag{20}$$

$$L \cdot \text{varTotal} = \text{Average}(\text{Var}(\bar{x}_{1, average\ k=1:5}) + \text{Var}(\bar{y}_{1, average\ k=1:5})) \tag{21}$$

$$R \cdot \text{varTotal} = \text{Average}(\text{Var}(\bar{x}_{2, average\ k=1:5}) + \text{Var}(\bar{y}_{2, average\ k=1:5})) \tag{22}$$

or segment standard deviation and segment skew such as, for instance, $$L \cdot \text{SkewTop} = \text{Skew}(\bar{y}_{1, average\ k=1:5,1}) \tag{27}$$

$$R \cdot \text{SkewTop} = \text{Skew}(\bar{y}_{2, average\ k=1:5,1}) \tag{28}$$

$$L \cdot \text{SkewRit} = \text{Skew}(\bar{x}_{1, average\ k=1:5,2}) \tag{29}$$

$$R \cdot \text{SkewRit} = \text{Skew}(\bar{x}_{2, average\ k=1:5,2}) \tag{30}$$

$$L \cdot \text{SkewBot} = \text{Skew}(\bar{y}_{1, average\ k=1:5,3}) \tag{31}$$

$$R \cdot \text{SkewBot} = \text{Skew}(\bar{y}_{2, average\ k=1:5,3}) \tag{32}$$

$$L \cdot \text{SkewLef} = \text{Skew}(\bar{x}_{1, average\ k=1:5,4}) \tag{33}$$

$$R \cdot \text{SkewLef} = \text{Skew}(\bar{x}_{2, average\ k=1:5,4}) \tag{34}$$

or segment normalized skew, such as, for instance, $$\text{SkewNorm}(\bar{x}_{j,k,l}) = \frac{\text{Skew}(\bar{x}_{j,k,l})}{\sigma_{x_{j,k,l}}}, \tag{35}$$

$$\text{SkewNorm}(\bar{y}_{j,k,l}) = \frac{\text{Skew}(\bar{y}_{j,k,l})}{\sigma_{y_{j,k,l}}}. \tag{36}$$

$$L \cdot \text{SkewTopNorm} = \text{SkewNorm}(\hat{y}1, \text{average } k=1:5,1) \tag{37}$$

$$R \cdot \text{SkewTopNorm} = \text{SkewNorm}(\hat{y}2, \text{average } k=1:5,1) \tag{38}$$

$$L \cdot \text{SkewRitNorm} = \text{SkewNorm}(\hat{x}1, \text{average } k=1:5,2) \tag{39}$$

$$R \cdot \text{SkewRitNorm} = \text{SkewNorm}(\hat{x}2, \text{average } k=1:5,2) \tag{40}$$

$$L \cdot \text{SkewBotNorm} = \text{SkewNorm}(\hat{y}1, \text{average } k=1:5,3) \tag{41}$$

$$R \cdot \text{SkewBotNorm} = \text{SkewNorm}(\hat{y}2, \text{average } k=1:5,3) \tag{42}$$

$$L \cdot \text{SkewLefNorm} = \text{SkewNorm}(\hat{x}1, \text{average } k=1:5,4) \tag{43}$$

$$R \cdot \text{SkewLefNorm} = \text{SkewNorm}(\hat{x}2, \text{average } k=1:5,4) \tag{44}$$

The method may also feature calculating box height, box width, box area, or box aspect ratio.

Box Height $$\text{BoxHeight}_{j,k} = \bar{\bar{y}}_{j,k,1} - \bar{\bar{y}}_{j,k,3} \tag{45}$$

Box Width $$\text{BoxWidth}_{j,k} = \bar{\bar{x}}_{j,k,2} - \bar{\bar{x}}_{j,k,4} \tag{46}$$

Box Aspect Ratio $$\text{AspectRatio}_{j,k} = \frac{\text{BoxHeight}_{j,k}}{\text{BoxWidth}_{j,k}} \tag{47}$$

Box Area $$\text{BoxArea}_{j,k} = \text{BoxHeight}_{j,k} \times \text{BoxWidth}_{j,k} \tag{48}$$

The method may also feature calculating conjugacy of eye movement or variance from perfect conjugacy of eye movement, such as, for example, $$\text{Conj var } X \text{ top} = \frac{\sum (\hat{x}_1)^2 - 0}{\sum \hat{x}_1}, \tag{57}$$

$$\text{Conj var } X \text{ rit} = \frac{\sum (\hat{x}_2)^2 - 0}{\sum \hat{x}_2}, \tag{58}$$

$$\text{Conj var } X \text{ bot} = \frac{\sum (\hat{x}_3)^2 - 0}{\sum \hat{x}_3}, \tag{59}$$

$$\text{Conj var } X \text{ lef} = \frac{\sum (\hat{x}_4)^2 - 0}{\sum \hat{x}_4}, \tag{60}$$

$$\text{Conj var } Y \text{ top} = \frac{\sum (\hat{y}_1)^2 - 0}{\sum \hat{y}_1}, \tag{61}$$

$$\text{Conj var } Y \text{ rit} = \frac{\sum (\hat{y}_2)^2 - 0}{\sum \hat{y}_2}, \tag{62}$$

-continued $$Conj \, \text{var} \, Y \, bot = \frac{\sum (\hat{y}_3)^2 - 0}{\sum \hat{y}_3},$$ (63)

$$Conj \, \text{var} \, Y \, rit = \frac{\sum (\hat{y}_4)^2 - 0}{\sum \hat{y}_4},$$ (64)

$$Conj \, \text{Corr} \, XY \, top = \frac{\sum \hat{x}_1 \hat{y}_1}{\sum \hat{x}_1 - 1},$$ (65)

$$Conj \, \text{Corr} \, XY \, rit = \frac{\sum \hat{x}_2 \hat{y}_2}{\sum \hat{x}_2 - 1},$$ (66)

$$Conj \, \text{Corr} \, XY \, bot = \frac{\sum \hat{x}_3 \hat{y}_3}{\sum \hat{x}_3 - 1},$$ (67)

$$Conj \, \text{Corr} \, XY \, lef = \frac{\sum \hat{x}_4 \hat{y}_4}{\sum \hat{x}_4 - 1}$$ (68)

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing attention deficit hyperactivity disorder (ADHD), chronic traumatic encephalopathy, or a schizophrenia spectrum disorder. In some instances, two, three, four, five, six, seven, eight, nine, ten or more metrics may be observed or determined.

A standard deviation or p value of 0.25, 0.3, 0.4, 0.5, 0.75. 0.8, 0.9, 1.0, 1.5, 2.0, 2.5 or more may reflect that a subject has attention deficit hyperactivity disorder (ADHD), chronic traumatic encephalopathy, or a schizophrenia spectrum disorder. As such, the methods described herein may be used to detect attention deficit hyperactivity disorder (ADHD), chronic traumatic encephalopathy, or a schizophrenia spectrum disorder and assess or determine the severity of the same.

In a twelfth aspect, the invention provides methods for diagnosing, assessing or quantitating attention deficit hyperactivity disorder (ADHD), chronic traumatic encephalopathy, or a schizophrenia spectrum disorder in a subject by
 a) Tracking eye movement of at least one eye of the subject;
 b) collecting raw x and y cartesian coordinates of pupil position;
 c) normalizing the raw x and y Cartesian coordinates; and
 d) calculating one or more individual metric.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In instances where the eye movement of both eyes are tracked, the method may additionally feature sorting the data by eye.

The one or more individual metric may be any one of $$L \cdot \text{var} \, Y\text{top} = \text{Var}(\bar{y}_{1,average \, k=1:5,1})$$ (13)

$$R \cdot \text{var} \, Y\text{top} = \text{Var}(\bar{y}_{2,average \, k=1:5,1})$$ (14)

$$L \cdot \text{var} \, X\text{rit} = \text{Var}(\bar{x}_{1,average \, k=1:5,2})$$ (15)

$$R \cdot \text{var} \, X\text{rit} = \text{Var}(\bar{x}_{2,average \, k=1:5,2})$$ (16)

$$L \cdot \text{var} \, Y\text{bot} = \text{Var}(\bar{y}_{1,average \, k=1:5,3})$$ (17)

$$R \cdot \text{var} \, Y\text{bot} = \text{Var}(\bar{y}_{2,average \, k=1:5,3})$$ (18)

$$L \cdot \text{var} \, X\text{lef} = \text{Var}(\bar{x}_{1,average \, k=1:5,4})$$ (19)

$$R \cdot \text{var} \, X\text{lef} = \text{Var}(\bar{x}_{2,average \, k=1:5,4})$$ (20)

$$L \cdot \text{varTotal} = \text{Average}(\text{Var}(\bar{x}_{1,average \, k=1:5}) + \text{Var}(\bar{y}_{1,average \, k=1:5}))$$ (21)

$$R \cdot \text{varTotal} = \text{Average}(\text{Var}(\bar{y}_{2,average \, k=1:5}) + \text{Var}(\bar{y}_{2,average \, k=1:5}))$$ (22)

or segment standard deviation and segment skew such as, for instance, $$L \cdot \text{SkewTop} = \text{Skew}(\bar{y}_{1,average \, k=1:5,1})$$ (27)

$$R \cdot \text{SkewTop} = \text{Skew}(\bar{y}_{2,average \, k=1:5,1})$$ (28)

$$L \cdot \text{SkewRit} = \text{Skew}(\bar{x}_{1,average \, k=1:5,2})$$ (29)

$$R \cdot \text{SkewRit} = \text{Skew}(\bar{x}_{2,average \, k=1:5,2})$$ (30)

$$L \cdot \text{SkewBot} = \text{Skew}(\bar{y}_{1,average \, k=1:5,3})$$ (31)

$$R \cdot \text{SkewBot} = \text{Skew}(\bar{y}_{2,average \, k=1:5,3})$$ (32)

$$L \cdot \text{SkewLef} = \text{Skew}(\bar{x}_{1,average \, k=1:5,4})$$ (33)

$$R \cdot \text{SkewLef} = \text{Skew}(\bar{x}_{2,average \, k=1:5,4})$$ (34)

or segment normalized skew, such as, for instance, $$SkewNorm(\bar{x}_{j,k,l}) = \frac{Skew(\bar{x}_{j,k,l})}{\sigma_{\bar{x}_{j,k,l}}},$$ (35)

$$SkewNorm(\bar{y}_{j,k,l}) = \frac{Skew(\bar{y}_{j,k,l})}{\sigma_{\bar{y}_{j,k,l}}}.$$ (36)

$$L \cdot \text{SkewTopNorm} = \text{SkewNorm}(\hat{y}1, average \, k=1:5,1)$$ (37)

$$R \cdot \text{SkewTopNorm} = \text{SkewNorm}(\hat{y}2, average \, k=1:5,1)$$ (38)

$$L \cdot \text{SkewRitNorm} = \text{SkewNorm}(\bar{x}1, average \, k=1:5,2)$$ (39)

$$R \cdot \text{SkewRitNorm} = \text{SkewNorm}(\bar{x}2, average \, k=1:5,2)$$ (40)

$$L \cdot \text{SkewBotNorm} = \text{SkewNorm}(\bar{y}1, average \, k=1:5,3)$$ (41)

$$R \cdot \text{SkewBotNorm} = \text{SkewNorm}(\bar{y}2, average \, k=1:5,3)$$ (42)

$$L \cdot \text{SkewLefNorm} = \text{SkewNorm}(\bar{x}1, average \, k=1:5,4)$$ (43)

$$R \cdot \text{SkewLefNorm} = \text{SkewNorm}(\bar{x}2, average \, k=1:5,4)$$ (44)

The method may also feature calculating box height, box width, box area, or box aspect ratio.

Box Height $$\text{BoxHeight}_{j,k} = \bar{y}_{j,k,1} - \bar{y}_{j,k,3}$$ (45)

Box Width $$\text{BoxWidth}_{j,k} = \bar{x}_{j,k,2} - \bar{x}_{j,k,4}$$ (46)

Box Aspect Ratio $$AspectRatio_{j,k} = \frac{BoxHeight_{j,k}}{BoxWidth_{j,k}} \quad (47)$$

Box Area $$BoxArea_{j,k} = BoxHeight_{j,k} \times BoxWidth_{j,k} \quad (48)$$

The method may also feature calculating conjugacy of eye movement or variance from perfect conjugacy of eye movement, such as, for example, $$Conj\,var\,X\,top = \frac{\sum (\hat{x}_1)^2 - 0}{\sum \hat{x}_1}, \quad (57)$$

$$Conj\,var\,X\,rit = \frac{\sum (\hat{x}_2)^2 - 0}{\sum \hat{x}_2}, \quad (58)$$

$$Conj\,var\,X\,bot = \frac{\sum (\hat{x}_3)^2 - 0}{\sum \hat{x}_3}, \quad (59)$$

$$Conj\,var\,X\,lef = \frac{\sum (\hat{x}_4)^2 - 0}{\sum \hat{x}_4}, \quad (60)$$

$$Conj\,var\,Y\,top = \frac{\sum (\hat{y}_1)^2 - 0}{\sum \hat{y}_1}, \quad (61)$$

$$Conj\,var\,Y\,rit = \frac{\sum (\hat{y}_2)^2 - 0}{\sum \hat{y}_2}, \quad (62)$$

$$Conj\,var\,Y\,bot = \frac{\sum (\hat{y}_3)^2 - 0}{\sum \hat{y}_3}, \quad (63)$$

$$Conj\,var\,Y\,rit = \frac{\sum (\hat{y}_4)^2 - 0}{\sum \hat{y}_4}, \quad (64)$$

$$Conj\,Corr\,XY\,top = \frac{\sum \hat{x}_1 \hat{y}_1}{\sum \hat{x}_1 - 1}, \quad (65)$$

$$Conj\,Corr\,XY\,rit = \frac{\sum \hat{x}_2 \hat{y}_2}{\sum \hat{x}_2 - 1}, \quad (66)$$

$$Conj\,Corr\,XY\,bot = \frac{\sum \hat{x}_3 \hat{y}_3}{\sum \hat{x}_3 - 1}, \quad (67)$$

$$Conj\,Corr\,XY\,lef = \frac{\sum \hat{x}_4 \hat{y}_4}{\sum \hat{x}_4 - 1}, \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing attention deficit hyperactivity disorder (ADHD), chronic traumatic encephalopathy, and schizophrenia spectrum disorders. In same instances, two, three, four, five, six, seven, eight, nine, ten or more metrics may be observed or determined.

A standard deviation or p value of 0.25, 0.3, 0.4, 0.5, 0.75. 0.8, 0.9, 1.0, 1.5, 2.0, 2.5 or more may reflect that a subject has attention deficit hyperactivity disorder (ADHD), chronic traumatic encephalopathy, or a schizophrenia spectrum disorder. As such, the methods described herein may be used to detect attention deficit hyperactivity disorder (ADHD), chronic traumatic encephalopathy, or a schizophrenia spectrum disorders and assess or determine the severity of the same.

In a thirteenth aspect, the invention provides a kit useful for detecting, screening for or quantitating attention deficit hyperactivity disorder, chronic traumatic encephalopathy, and schizophrenia spectrum disorders containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a fourteenth aspect, the invention provides methods for diagnosing, quantitating or identifying alcohol consumption or intoxication in a subject by
 a) Tracking eye movement of both eyes of the subject;
 b) Analyzing eye movement of both eyes of the subject;
 c) Comparing eye movement of a first eye of the subject to eye movement of a second eye of the subject; and
 d) Identifying the subject as having eye movement of a first eye that is significantly different from eye movement of a second eye.

In a fifteenth aspect, the invention provides methods for diagnosing, quantitating or identifying alcohol consumption or intoxication in a subject by
 a) Tracking eye movement of both eyes of the subject;
 b) Analyzing eye movement of both eyes of the subject;
 c) Comparing the x or y Cartesian coordinates at any time point for the eye movement of a first eye of the subject to the respective x or y Cartesian coordinates at the time point for the eye movement of a second eye of the subject;
 d) Providing a sum of the differences between all of the x coordinates of the first eye compared to the second eye over the time tested or providing a sum of the differences in y coordinates of the first eye compared to the second eye over the time tested or both; and, optionally
 e) Providing a total sum of the differences between both x and y coordinates of the first eye compared to the second eye over the time tested.

In some instances, the subject having consumed alcohol or being intoxicated may have a total sum of the differences between both x and y coordinates of the first eye compared to the second eye over the time tested that is 10%, 20%, 30%, 40%, 50%, 60%, 70%, 80%, 90%, 100%, 150%, 200%, or two, three, four, five, six, eight, ten or more times greater than the total sum of the differences between both x and y coordinates of the first eye compared to the second eye over the time tested in a control or in a reference value based upon one or more controls or based upon the subject at a time before the alcohol consumption or intoxication.

In a sixteenth aspect, the invention provides methods for diagnosing, quantitating or identifying alcohol consumption or intoxication by
 a) Tracking eye movement of at least one eye of the subject;
 b) Analyzing eye movement of at least one eye of the subject;

c) Comparing eye movement of at least one eye of the subject to a normal or mean eye movement; and, optionally d) Calculating a standard deviation or p value for eye movement of at least one eye of the subject as compared to the normal or mean eye movement.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of the other eye of the subject or may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x and y cartesian coordinates of pupil position, normalizing the raw x and y Cartesian coordinates, and sorting the data by eye.

The method may also feature calculating individual metrics, such as, for instance, segment mean, segment median, and segment variance. The method may also feature calculating specific metrics such as, for example, $$L\cdot\text{var }Y\text{top}=\text{Var}(\bar{y}_{1,average\ k=1:5,1}) \quad (13)$$

$$R\cdot\text{var }Y\text{top}=\text{Var}(\bar{y}_{2,average\ k=1:5,1}) \quad (14)$$

$$L\cdot\text{var }X\text{rit}=\text{Var}(\bar{x}_{1,average\ k=1:5,2}) \quad (15)$$

$$R\cdot\text{var }X\text{rit}=\text{Var}(\bar{x}_{2,average\ k=1:5,2}) \quad (16)$$

$$L\cdot\text{var }Y\text{bot}=\text{Var}(\bar{y}_{1,average\ k=1:5,3}) \quad (17)$$

$$R\cdot\text{var }Y\text{bot}=\text{Var}(\bar{y}_{2,average\ k=1:5,3}) \quad (18)$$

$$L\cdot\text{var }X\text{lef}=\text{Var}(\bar{x}_{1,average\ k=1:5,4}) \quad (19)$$

$$R\cdot\text{var }X\text{lef}=\text{Var}(\bar{x}_{2,average\ k=1:5,4}) \quad (20)$$

$$L\cdot\text{varTotal}=\text{Average}(\text{Var}(\bar{x}_{1,average\ k=1:5})+\text{Var}(\bar{y}_{1,average\ k=1:5})) \quad (21)$$

$$R\cdot\text{varTotal}=\text{Average}(\text{Var}(\bar{y}_{2,average\ k=1:5})+\text{Var}(\bar{y}_{2,average\ k=1:5})) \quad (22)$$

or segment standard deviation and segment skew such as, for instance, $$L\cdot\text{SkewTop}=\text{Skew}(\bar{y}_{1,average\ k=1:5,1}) \quad (27)$$

$$R\cdot\text{SkewTop}=\text{Skew}(\bar{y}_{2,average\ k=1:5,1}) \quad (28)$$

$$L\cdot\text{SkewRit}=\text{Skew}(\bar{x}_{1,average\ k=1:5,2}) \quad (29)$$

$$R\cdot\text{SkewRit}=\text{Skew}(\bar{x}_{2,average\ k=1:5,2}) \quad (30)$$

$$L\cdot\text{SkewBot}=\text{Skew}(\bar{y}_{1,average\ k=1:5,3}) \quad (31)$$

$$R\cdot\text{SkewBot}=\text{Skew}(\bar{y}_{2,average\ k=1:5,3}) \quad (32)$$

$$L\cdot\text{SkewLef}=\text{Skew}(\bar{x}_{1,average\ k=1:5,4}) \quad (33)$$

$$R\cdot\text{SkewLef}=\text{Skew}(\bar{x}_{2,average\ k=1:5,4}) \quad (34)$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}}, \quad (35)$$

$$\text{SkewNorm}(\bar{y}_{j,k,l}) = \frac{\text{Skew}(\bar{y}_{j,k,l})}{\sigma_{\bar{y}_{j,k,l}}}. \quad (36)$$

$$L\cdot\text{SkewTopNorm}=\text{SkewNorm}(\hat{y}1,average\ k=1:5,1) \quad (37)$$

$$R\cdot\text{SkewTopNorm}=\text{SkewNorm}(\bar{y}2,average\ k=1:5,1) \quad (38)$$

$$L\cdot\text{SkewRitNorm}=\text{SkewNorm}(\bar{x}1,average\ k=1:5,2) \quad (39)$$

$$R\cdot\text{SkewRitNorm}=\text{SkewNorm}(\bar{x}2,average\ k=1:5,2) \quad (40)$$

$$L\cdot\text{SkewBotNorm}=\text{SkewNorm}(\bar{y}1,average\ k=1:5,3) \quad (41)$$

$$R\cdot\text{SkewBotNorm}=\text{SkewNorm}(\bar{y}2,average\ k=1:5,3) \quad (42)$$

$$L\cdot\text{SkewLefNorm}=\text{SkewNorm}(\bar{x}1,average\ k=1:5,4) \quad (43)$$

$$R\cdot\text{SkewLefNorm}=\text{SkewNorm}(\bar{x}2,average\ k=1:5,4) \quad (44)$$

The method may also feature calculating box height, box width, box area, or box aspect ratio.

Box Height $$\text{BoxHeight}_{j,k}=\bar{\bar{y}}_{j,k,1}-\bar{\bar{y}}_{j,k,3} \quad (45)$$

Box Width $$\text{BoxWidth}_{j,k}=\bar{\bar{x}}_{j,k,2}-\bar{\bar{x}}_{j,k,4} \quad (46)$$

Box Aspect Ratio $$\text{AspectRatio}_{j,k} = \frac{\text{BoxHeight}_{j,k}}{\text{BoxWidth}_{j,k}} \quad (47)$$

Box Area $$\text{BoxArea}_{j,k}=\text{BoxHeight}_{j,k}\times\text{BoxWidth}_{j,k} \quad (48)$$

The method may also feature calculating conjugacy of eye movement or variance from perfect conjugacy of eye movement, such as, for example, $$\text{Conj var } X \text{ top} = \frac{\sum (\hat{x}_1)^2 - 0}{\sum \hat{x}_1}, \quad (57)$$

$$\text{Conj var } X \text{ rit} = \frac{\sum (\hat{x}_2)^2 - 0}{\sum \hat{x}_2}, \quad (58)$$

$$\text{Conj var } X \text{ bot} = \frac{\sum (\hat{x}_3)^2 - 0}{\sum \hat{x}_3}, \quad (59)$$

$$\text{Conj var } X \text{ lef} = \frac{\sum (\hat{x}_4)^2 - 0}{\sum \hat{x}_4}, \quad (60)$$

$$\text{Conj var } Y \text{ top} = \frac{\sum (\hat{y}_1)^2 - 0}{\sum \hat{y}_1}, \quad (61)$$

-continued $$\text{Conj var } Y \text{ rit} = \frac{\sum (\hat{y}_2)^2 - 0}{\sum \hat{y}_2}, \quad (62)$$

$$\text{Conj var } Y \text{ bot} = \frac{\sum (\hat{y}_3)^2 - 0}{\sum \hat{y}_3}, \quad (63)$$

$$\text{Conj var } Y \text{ rit} = \frac{\sum (\hat{y}_4)^2 - 0}{\sum \hat{y}_4}, \quad (64)$$

$$\text{Conj Corr } XY \text{ top} = \frac{\sum \hat{x}_1 \hat{y}_1}{\sum \hat{x}_1 - 1}, \quad (65)$$

$$\text{Conj Corr } XY \text{ rit} = \frac{\sum \hat{x}_2 \hat{y}_2}{\sum \hat{x}_2 - 1}, \quad (66)$$

$$\text{Conj Corr } XY \text{ bot} = \frac{\sum \hat{x}_3 \hat{y}_3}{\sum \hat{x}_3 - 1}, \quad (67)$$

$$\text{Conj Corr } XY \text{ lef} = \frac{\sum \hat{x}_4 \hat{y}_4}{\sum \hat{x}_4 - 1} \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the left.blink length.value, right.aspectRatiomean.value, right.skewTop.value, right.skewTopNorm.value, right.varTotal.value, right.varXrit.value, conj.varXbot.value, right.distTop.value, right.distRit.value, left.velTop.value, left.velRit.value may be especially useful for demonstrating or detecting or assessing alcohol consumption or intoxication. In some instances, two, three, four, five, six, seven, eight, nine, ten or more metrics may be observed or determined.

A standard deviation or p value of 0.05, 0.1, 0.2, 0.25, 0.3, 0.4, 0.5, 0.75. 0.8, 0.9, 1.0, 1.5, 2.0, 2.5 or more may reflect that a subject has consumed alcohol or is intoxicated. As such, the methods described herein may be used to detect, diagnose, quantitate or identify alcohol consumption or intoxication or determine the severity or extent of the same.

In a seventeenth aspect, the invention provides methods for diagnosing, assessing or quantitating alcohol consumption or intoxication in a subject by
  a) Tracking eye movement of at least one eye of the subject;
  b) collecting raw x and y cartesian coordinates of pupil position;
  c) normalizing the raw x and y Cartesian coordinates; and
  d) calculating one or more individual metric.

In some instances, eye movement of both eyes of the subject are tracked and analyzed. In some instances, both x and y coordinates of eye position for one or both eyes of a subject are collected for at least about 100, 500, 1,000, 5,000, 10,000, 50,000, 100,000, 200,000 or more eye positions. In instances where the eye movement of both eyes are tracked, the method may additionally feature sorting the data by eye.

The one or more individual metric may be any one of $$L \cdot \text{var } Y\text{top} = \text{Var}(\bar{y}_{1,\text{average } k=1:5,1}) \quad (13)$$

$$R \cdot \text{var } Y\text{top} = \text{Var}(\bar{y}_{2,\text{average } k=1:5,1}) \quad (14)$$

$$L \cdot \text{var } X\text{rit} = \text{Var}(\bar{x}_{1,\text{average } k=1:5,2}) \quad (15)$$

$$R \cdot \text{var } X\text{rit} = \text{Var}(\bar{x}_{2,\text{average } k=1:5,2}) \quad (16)$$

$$L \cdot \text{var } Y\text{bot} = \text{Var}(\bar{y}_{1,\text{average } k=1:5,3}) \quad (17)$$

$$R \cdot \text{var } Y\text{bot} = \text{Var}(\bar{y}_{2,\text{average } k=1:5,3}) \quad (18)$$

$$L \cdot \text{var } X\text{lef} = \text{Var}(\bar{x}_{1,\text{average } k=1:5,4}) \quad (19)$$

$$R \cdot \text{var } X\text{lef} = \text{Var}(\bar{x}_{2,\text{average } k=1:5,4}) \quad (20)$$

$$L \cdot \text{varTotal} = \text{Average}(\text{Var}(\bar{x}_{1,\text{average } k=1:5}) + \text{Var}(\bar{y}_{1,\text{average } k=1:5})) \quad (21)$$

$$R \cdot \text{varTotal} = \text{Average}(\text{Var}(\bar{y}_{2,\text{average } k=1:5}) + \text{Var}(\bar{y}_{2,\text{average } k=1:5})) \quad (22)$$

or segment standard deviation and segment skew such as, for instance, $$L \cdot \text{SkewTop} = \text{Skew}(\bar{y}_{1,\text{average } k=1:5,1}) \quad (27)$$

$$R \cdot \text{SkewTop} = \text{Skew}(\bar{y}_{2,\text{average } k=1:5,1}) \quad (28)$$

$$L \cdot \text{SkewRit} = \text{Skew}(\bar{x}_{1,\text{average } k=1:5,2}) \quad (29)$$

$$R \cdot \text{SkewRit} = \text{Skew}(\bar{x}_{2,\text{average } k=1:5,2}) \quad (30)$$

$$L \cdot \text{SkewBot} = \text{Skew}(\bar{y}_{1,\text{average } k=1:5,3}) \quad (31)$$

$$R \cdot \text{SkewBot} = \text{Skew}(\bar{y}_{2,\text{average } k=1:5,3}) \quad (32)$$

$$L \cdot \text{SkewLef} = \text{Skew}(\bar{x}_{1,\text{average } k=1:5,4}) \quad (33)$$

$$R \cdot \text{SkewLef} = \text{Skew}(\bar{x}_{2,\text{average } k=1:5,4}) \quad (34)$$

or segment normalized skew, such as, for instance, $$\text{SkewNorm}(\bar{x}_{j,k,l}) = \frac{\text{Skew}(\bar{x}_{j,k,l})}{\sigma_{x_{j,k,l}}}, \quad (35)$$

$$\text{SkewNorm}(\bar{y}_{j,k,l}) = \frac{\text{Skew}(\bar{y}_{j,k,l})}{\sigma_{y_{j,k,l}}}. \quad (36)$$

$$L \cdot \text{SkewTopNorm} = \text{SkewNorm}(\hat{y}1, \text{average } k=1:5,1) \quad (37)$$

$$R \cdot \text{SkewTopNorm} = \text{SkewNorm}(\bar{y}2, \text{average } k=1:5,1) \quad (38)$$

$$L \cdot \text{SkewRitNorm} = \text{SkewNorm}(\bar{x}1, \text{average } k=1:5,2) \quad (39)$$

$$R \cdot \text{SkewRitNorm} = \text{SkewNorm}(\bar{x}2, \text{average } k=1:5,2) \quad (40)$$

$$L \cdot \text{SkewBotNorm} = \text{SkewNorm}(\hat{y}1, \text{average } k=1:5,3) \quad (41)$$

$$R \cdot \text{SkewBotNorm} = \text{SkewNorm}(\bar{y}2, \text{average } k=1:5,3) \quad (42)$$

$$L \cdot \text{SkewLefNorm} = \text{SkewNorm}(\bar{x}1, \text{average } k=1:5,4) \quad (43)$$

$$R \cdot \text{SkewLefNorm} = \text{SkewNorm}(\bar{x}2, \text{average } k=1:5,4) \quad (44)$$

The method may also feature calculating box height, box width, box area, or box aspect ratio.

Box Height $$\text{BoxHeight}_{j,k} = \bar{y}_{j,k,1} - \bar{y}_{j,k,3} \quad (45)$$

Box Width $$\text{BoxWidth}_{j,k} = \bar{x}_{j,k,2} - \bar{x}_{j,k,4} \quad (46)$$

Box Aspect Ratio $$\text{AspectRatio}_{j,k} = \frac{\text{BoxHeight}_{j,k}}{\text{BoxWidth}_{j,k}} \quad (47)$$

Box Area $$BoxArea_{j,k} = BoxHeight_{j,k} \times BoxWidth_{j,k} \quad (48)$$

The method may also feature calculating conjugacy of eye movement or variance from perfect conjugacy of eye movement, such as, for example, $$Conj \, var \, X \, top = \frac{\sum (\hat{x}_1)^2 - 0}{\sum \hat{x}_1}, \quad (57)$$

$$Conj \, var \, X \, rit = \frac{\sum (\hat{x}_2)^2 - 0}{\sum \hat{x}_2}, \quad (58)$$

$$Conj \, var \, X \, bot = \frac{\sum (\hat{x}_3)^2 - 0}{\sum \hat{x}_3}, \quad (59)$$

$$Conj \, var \, X \, lef = \frac{\sum (\hat{x}_4)^2 - 0}{\sum \hat{x}_4}, \quad (60)$$

$$Conj \, var \, Y \, top = \frac{\sum (\hat{y}_1)^2 - 0}{\sum \hat{y}_1}, \quad (61)$$

$$Conj \, var \, Y \, rit = \frac{\sum (\hat{y}_2)^2 - 0}{\sum \hat{y}_2}, \quad (62)$$

$$Conj \, var \, Y \, bot = \frac{\sum (\hat{y}_3)^2 - 0}{\sum \hat{y}_3}, \quad (63)$$

$$Conj \, var \, Y \, rit = \frac{\sum (\hat{y}_4)^2 - 0}{\sum \hat{y}_4}, \quad (64)$$

$$Conj \, Corr \, XY \, top = \frac{\sum \hat{x}_1 \hat{y}_1}{\sum \hat{x}_1 - 1}, \quad (65)$$

$$Conj \, Corr \, XY \, rit = \frac{\sum \hat{x}_2 \hat{y}_2}{\sum \hat{x}_2 - 1}, \quad (66)$$

$$Conj \, Corr \, XY \, bot = \frac{\sum \hat{x}_3 \hat{y}_3}{\sum \hat{x}_3 - 1}, \quad (67)$$

$$Conj \, Corr \, XY \, lef = \frac{\sum \hat{x}_4 \hat{y}_4}{\sum \hat{x}_4 - 1}, \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the left.blinklength.value, right.aspectRatiomean.value, right.skewTop.value, right.skewTopNorm.value, right.varTotal.value, right.varXrit.value, conj.varXbot.value, right.distTop.value, right.distRit.value, left.velTop.value, left.velRit.value may be especially useful for demonstrating or detecting or assessing alcohol consumption or intoxication. In some instances, two, three, four, five, six, seven, eight, nine, ten or more metrics may be observed or determined.

A standard deviation or p value of 0.05, 0.1, 0.2, 0.25, 0.3, 0.4, 0.5, 0.75. 0.8, 0.9, 1.0, 1.5, 2.0, 2.5 or more may reflect that a subject has consumed alcohol or is intoxicated. As such, the methods described herein may be used to detect alcohol consumption or intoxication or determine the severity or extent of the same.

In a eighteenth aspect, the invention provides a kit useful for detecting, screening for or quantitating alcohol consumption or intoxication containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a nineteenth aspect, the invention provides a computer system. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

BRIEF DESCRIPTION OF THE FIGURES

FIG. 1 (A and B) demonstrates that as the aperture containing a video moves in a rectangular pattern, different nerves move the pupils. FIG. 1A demonstrates movement of the left eye, and FIG. 1B demonstrates movement of the right eye. Cranial nerve III moves the pupil up and down. Cranial nerve VI moves it laterally. This data was obtained on a monocular eye tracker with sequential tracking of each eye. The video goes around five times with each tracking recorded in a separate color (red; green, cyan, magenta, blue).

FIG. 2 C and D are time-course representations (FIG. 2C, left eye.

FIG. 17 represents findings from a subject affected by chronic methadone use. Chronic methadone use decreases disconjugacy (particularly in the "y" coordinates). A. Represents eye movement tracking box plots 1 day postoperative. B. Represents eye movement tracking box plots 4 days postoperative. C. Represents eye movement tracking box plots 66 days postoperative.

FIG. 25 represents the eye-box trajectories of a 19 year old male subject with ADHD tracked binocularly (FIG. 25A, left eye; FIG. 25B right eye). The aspect ratio is provided for each eye.

FIG. 27 represent the eye-box trajectories of a second 19 year old male subject with ADHD tracked binocularly (FIG. 27A, left eye; FIG. 27B right eye). The aspect ratio is provided for each eye.

FIG. 31 A and B represent the eye-box trajectories of a 31 year old male subject tracked binocularly (left eye; right eye). FIG. 31A represents the eye-box trajectories observed before drinking alcohol, and FIG. 31B represents the eye-box trajectories observed after drinking alcohol.

FIG. 32 A and B represent the eye-box trajectories of a 34 year old female subject tracked binocularly (left eye; right eye). FIG. 32A represents the eye-box trajectories observed before drinking alcohol, and FIG. 32B represents the eye-box trajectories observed after drinking alcohol.

DETAILED DESCRIPTION OF THE INVENTION

Figure 2A:
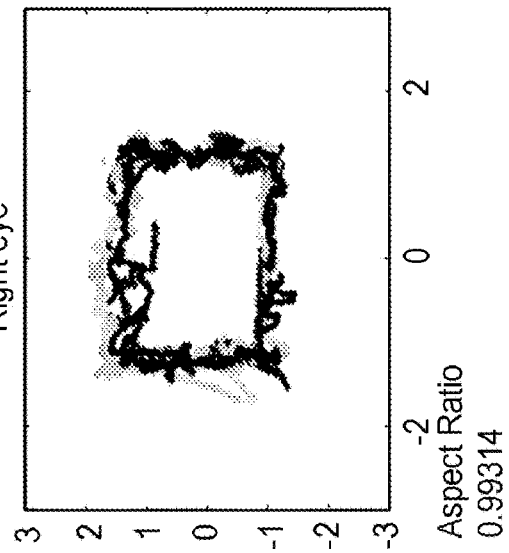
FIG. 2 A and B represent the eye-box trajectory of a normal subject tracked binocularly (FIG. 2A, left eye.
FIG. 2B right eye). Note that the eyes appear to be moving relatively the same, with some differences.
FIG. 2D right eye), in which the x-axis is the Cartesian coordinate of the eye position and the y-axis is time.
Figure 2B:
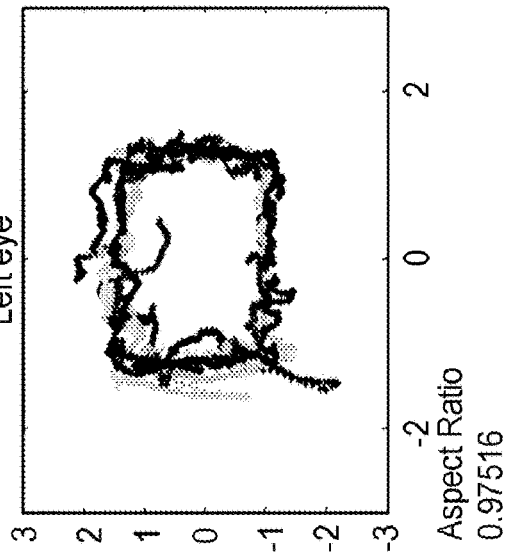
Figure 2C:
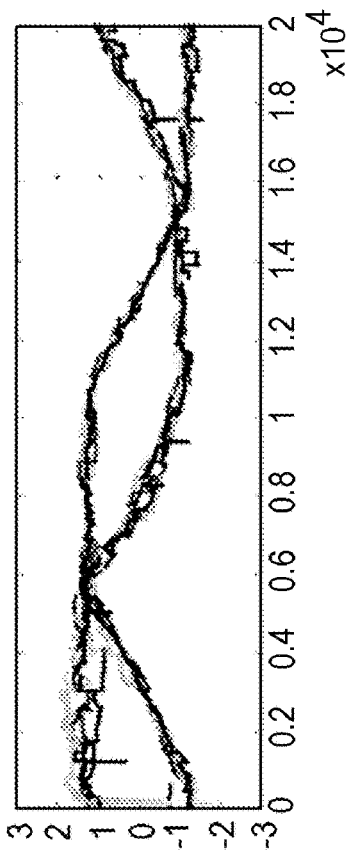
Figure 2D:
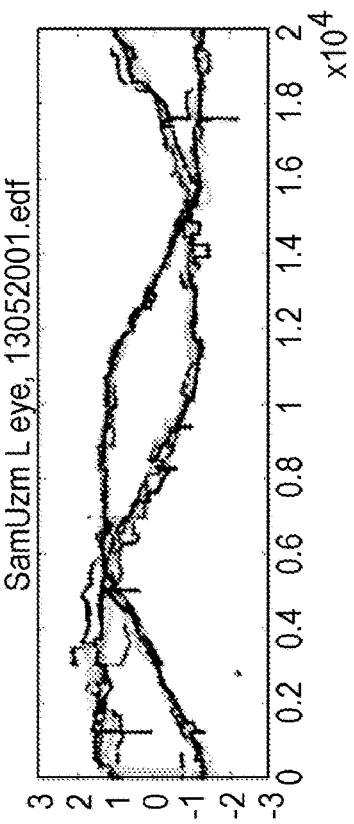

Before the present methods are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims. As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

Definitions

The terms used herein have the meanings recognized and known to those of skill in the art, however, for convenience and completeness, particular terms and their meanings are set forth below.

"Subject" or "patient" refers to a mammal, preferably a human, undergoing treatment or screening for a condition, disorder or disease such as, for instance, any condition characterized by or featuring disconjugate gaze or strabismus.

By "assessing or quantitating brain injury" or "assessing or quantitating structural and non-structural traumatic brain injury" is meant identifying, diagnosing, or determining the severity or physiological effects or sequelae of a traumatic brain injury such as, for instance, concussion, subconcussion or blast injury.

By "localizing a central nervous system lesion" is meant in some instances determining information that may predict a likely position of a lesion, for instance, determining the side of the body, for instance, left or right, where a lesion may likely be located within the central nervous system. In other instances, "localizing a central nervous system lesion" may mean determining a particular fossa or compartment, such as, for instance, a fascia compartment or brain ventricle in which a lesion is likely located within the central nervous system.

By "control" is meant a subject, individual or patient who has consumed substantially no alcohol or absolutely no alcohol in a particular preceding time frame such as, for instance, the last 1, 2, 3, 4, 5, 6, 8, 10, 12, 18, 24, 48 or 72 hours.

By "assessing central nervous system integrity" is meant identifying one or more symptoms that may indicate a pathology of or affecting the central nervous system, or identifying, assessing, quantifying or diagnosing a pathology of the central nervous system. The pathology may be, for instance, one or more of increased intracranial pressure, hydrocephalus, concussion, dementia, schizophrenia, amyotrophic lateral sclerosis, muscular sclerosis, autism and Fragile X disease.

By "vergence" or "vergence disorders" refers generally to convergence, when the eyes rotate inward as an object moves closer, and to divergence, when the eyes rotate outward as an object moves farther away. Both convergence and divergence are tested to some extent as an object moves around, effectively assessing sustained vergence. Most vergence disorders are due to the pathologies and causes described herein, for instance, trauma. Some vergence disorders may be congenital. The methods and algorithms described herein facilitate screening for such vergence and vergence disorders.

By "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that is at least 5%, 10%, 15%, 20%, 25%, 30%, 40%, 50%, 75%, or 100% or more variant compared to the corresponding eye movement observations tracked from the second eye. The 5%, 10%, 15%, 20%, 25%, 30%, 40%, 50%, 75%, or 100% or more variant may be calculated or observed either numerically or graphically. Alternatively, "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that, when graphically displayed in a scatterplot as described herein, is at least 5°, 10°, 15°, 20°, 25°, 30°, 40°, 50°, 60°, 75° or 90° or more variant compared to the corresponding eye movement observations tracked and graphically displayed on a scatterplot as described herein from the second eye.

By "narcosis" is meant unconsciousness, or a state of lacking normal awareness of the self or environment induced by one or more narcotic or anesthesia, or any mental status change or chronic behavioral affect that may be induced by acute or chronic use of narcotics.

By "narcotic" is meant any psychoactive compound with any sleep-inducing properties, or any drug that is prohibited, such as heroin or morphine. It is meant to include, for instance, opiates, opioids, morphine, heroin and their derivatives, such as hydrocodone as well as *Cannabis*, alcohol, and any other substance classified as a narcotic by the United States Controlled Substances Act.

By "schizophrenia spectrum disorders" is meant disorders featuring one or more symptoms of schizophrenia including positive symptoms like hallucinations, delusions, and disorganized thoughts and speech; negative symptoms like emotional and behavioral disturbances; and cognitive symptoms like difficulty paying attention, and understanding and utilizing information. The term encompasses and embraces different schizophrenia spectrum disorders, including, for instance, schizotypal personality disorder, schizoid personality disorder, delusional disorder, schizoaffective disorder, and schizophreniform disorder.

By "attention deficit hyperactivity disorder" (ADHD) is meant a psychiatric disorder of the neurodevelopmental type in which there are significant problems of attention, hyperactivity, or acting impulsively that are not appropriate for a person's age. Often, these symptoms begin by age six to twelve and persist for more than six months. The term specifically embraces all such diagnoses made according to DSM-IV criteria and all diagnoses made via the ICD-10 criteria. By "chronic traumatic encephalopathy (CTE)" is meant symptoms resulting from trauma, either as an isolated event or in the form of multiple prior injuries such as associated with concussion or subconcussion and associated with the syndrome named "chronic traumatic encephalopathy."

Eye Movement Tracking Device

According to the methods described, tracking eye movement may be performed using any suitable device such as, for example, an Eyelink® 1000 binocular eye tracker (500 Hz sampling, SR Research). The suitable device, i.e. the eye tracker, may be stationary or portable. The eye tracking movement samples may be obtained at any suitable frequency, such as for instance, 10 Hz to 10,000 Hz or more. The subject may be positioned an appropriate distance from the device, such as, for example, 10, 20, 30, 40, 50, 55, 60, 70, 80, 90 cm or more, or even a meter or more from the device screen. In some instances, the subject's head may be stabilized, such as, for instance by using a chinrest or similar stabilizing mechanism. The subject may be seated or reclining. Preferably, the presentation monitor of the device is adjusted so as to substantially match the subject's gaze direction. The tracking eye movement may be performed for a total of, for example, 30, 60, 90, 120, 150, 180, 200, 220, 240, 270, 300, 330, 360, 400, 450, 500 seconds or more, or for 5, 10, 15, 20, 25, 30, 45, 60, or 90 minutes or more. As such, according to the methods provided, 1,000, 5,000, 10,000, 20,000, 25,000, 50,000, 75,000, 100,000, 150,000, 200,000, 250,000, 300,000 or more samples of eye position may be obtained. Similarly, the tracking eye movement may be performed using a video oculography device, such as, for instance, goggles, or using a web-cam based tracking system.

According to the methods described, analyzing eye movement may be performed by any suitable means. In some instances, a stimulus and an analysis stream are provided that allows interpreting raw eye position data. In some instances, an algorithm may be provided for looking at pupil position directly thereby yielding information about ocular motility. Preferably, a device is adapted into a novel mobile system that may analyze eye movement close in time or substantially concurrent to the eye movement itself.

Tracking Eye Movement in Response to a Moving or Visual Stimulus

According to the methods described, eye movement may be tracked in response to a visual stimulus. In some instances, the visual stimulus may be, for instance, a video such as a music video that may move, for instance clockwise, along the outer edge, of a computer monitor. In some instances, such a video may be provided starting at the upper or lower, left or right hand corners, of a screen. The visual stimulus such as a video, e.g. a music video, may be provided in a substantially square aperture with an area of approximately 10, 12, 14, 16, 18, 20, 25, or degrees, for example, approximately ⅒, ⅛, ⅙, ⅕, ¼, ⅓, ½ of the size of the screen or so. The visual stimulus, such as, for example a music video, may play substantially continuously during the eye movement tracking, and it may in some instances move across the screen at a relatively or substantially constant speed. For instance, such a visual stimulus, for instance, a music video may cover each edge of a monitor in about 2, 5, 10, 15, 20, 30, 45 or 60 seconds or so. Therefore, in some instances, a full cycle may take, for instance, 10, 20, 30, 40, 50, 60, 75, 100, 120, 150, 180 seconds or so. Multiple cycles of such a visual stimulus, for instance a music video may be played, for instance, one, two, three, four, five, six, seven, eight, nine, ten, twelve, fifteen, twenty or more full cycles. As such, the visual stimulus may be provided, the eye movement may be tracked, in effect, in some instances the video may be played for a total of, for example, 30, 60, 90, 120, 150, 180, 200, 220, 240, 270, 300, 330, 360, 400, 450, 500 seconds or more. In instances where the visual stimulus is in the form of a video, a countdown video may be played in the starting position for, for instance, 5, 10, 15, 20, 25, or 30 seconds or more before beginning the visual stimulus, e.g. video, to provide subjects sufficient time to orient to the visual stimulus. Likewise, the visual stimulus, for instance a video, may be continued for an addition 2, 5, 10, 15, 20, 30, 45 or 60 seconds or so after the eye movement tracking is performed to reduce or substantially avoid boundary effects. The same result could be obtained by having the visual stimulus moving over any distance x relative to any amount of time t. The ideal stimulus would move however in the both the x and y Cartesian planes to optimize the assessment capability of the method.

Comparing Eye Movement of a First Eye of the Subject to Eye Movement of a Second Eye of the Subject or a Control According to the methods described, comparing eye movement of a first eye of the subject to eye movement of a second eye of the subject, may be performed by analyzing data. Data from the tracking eye movement may provide an indication of whether an individual subject's gaze is conjugate (eyes are moving together) versus disconjugate. Comparing eye movement of a first eye of the subject to eye movement of a second eye of the subject may feature generating scatterplots. Comparing eye movement of a first eye of the subject to eye movement of a second eye of the subject, may feature plotting the horizontal eye position along one axis and vertical eye position along an orthogonal axis. Such comparing eye movement of the subject to a control, or comparing eye movement of a first eye of the subject to eye movement of a second eye of the subject, may feature generating, plotting pairs of (x,y) values, for instance, 50,000, 100,000 or more pairs of values (x,y). Such pairs of values (x,y) may be plotted representing, for instance, the two components of the instantaneous angle of pupil reflection (horizontal, vertical) over a period of time, for instance, 100 or 200 seconds or more.

As such, comparing eye movement of a first eye of the subject to eye movement of a second eye of the subject, may feature generating figures substantially resembling boxes that reflect the trajectory traveled by the visual stimulation, such as when it moves across a screen. In healthy controls, these figures substantially resembling boxes may look like, for instance, substantially equilateral rectangles or squares, reflecting the trajectory traveled by the visual stimulus across a screen. In instances of neurological damage or increased intracranial pressure, such figures may not substantially resemble a box, a rectangle or a square. In fact, in some instances, the cranial nerve having reduced or impaired function or conduction may be identified. In some instances, the figures generated that reflect the trajectory traveled by the visual stimulation may demonstrate abnormal distribution of or absence of normal plotting pairs in particular areas. Increased variability along the y-axis may for example reflect cranial nerve II dysfunction. Decreased variability along the y-axis, or decreased height to width ratio may reflect CN III dysfunction. Increased height to width ratio may reflect CN IV or VI dysfunction. The height of the box may be mathematically determined by assessing the position of the pupil as the video traverses the top and bottom of the presented visual stimulus. This "actual" height may be different from the perceived height mathematically, since the perceived height can represent aberrant pupillary motion due to the patient's ocular motility dysfunction. The integrity of the box walls may also be indicative of other types of dysfunction. Both cranial nerve palsies and mass effect may cause defects in box trajectory. Supratentorial mass lesions and CN III defects may impact the top and/or bottom of the box. Infratentorial mass lesions or CN VI palsies may impact the sides of the box. For instance, in the case of the left eye, the upper left quadrant of the figure may reflect activity, function or conduction of cranial nerves III and VI, the lower left quadrant of the figure may reflect activity, function or conduction of cranial nerves III and IV, while the upper right quadrant and the lower right quadrants may reflect activity, function or conduction of cranial nerve III. In the case of the right eye, the upper and lower left quadrants of the figure may reflect activity, function or conduction of cranial nerve III, the lower right quadrant of the figure may reflect activity, function or conduction of cranial nerve III, while the upper right quadrant and the lower right quadrant may reflect activity, function or conduction of cranial nerves IV and VI.

Comparing eye movement of a first eye of the subject to eye movement of a second eye of the subject, may feature determining the distribution of certain measurements in the control population and comparing the subject with these control distributions. In such instances, visual stimulus trajectory may he divided into four time components, for instance, two, three, four, five, six or more repetitions of the first few, for instance, 2, 5, 10, 15, 20 or so seconds of each rotation cycle. In such instances, comparing eye movement of the subject to a control may feature evaluating such variables as the relative variance in each arm, and the relative integrity of each arm.

Comparing eye movement of the subject to a control, or comparing eye movement of a first eye of the subject to eye movement of a second eye of the subject, may also feature measuring the integrity of each subject's values. In instances featuring generating figures substantially resembling boxes that reflect the trajectory traveled by the visual stimulation, such as when it moves across a screen, the sides or arms of the figures (e.g. the top of the box and the bottom of the box) may be z-scored using the mean and standard deviation calculated from the control population. The resulting score may indicate how different the subject's values are compared with the control values, such as, for instance, in units of standard deviations.

According to the methods described, identifying the subject as having eye movement significantly different from the control, or identifying the subject as having eye movement of a first eye that is significantly different from eye movement of a second eye, may be performed using a z-score. Because 95% of all values in a normal distribution lie within two standard deviations of the mean, a z-score of 2 may be used as a significance threshold. Subjects with z-scores above, for instance, 2 in either or both, or 1, 2, 3, or 4 sides or arms of the figures may be judged to have significant disturbances of ocular motility. Similarly, identifying the subject as having eye movement significantly different from the control, or identifying the subject as having eye movement of a first eye that is significantly different from eye movement of a second eye, may be performed by assessing whether it has or there is a difference that exceeds a predetermined threshold.

Identifying the subject as having eye movement significantly different from the control, or identifying the subject as having eye movement of a first eye that is significantly different from eye movement of a second eye, may feature determining relative variance. In some instances, multiple such as 1,000, 2,000, 3,000, 5,000, 10,000, 20,000 or more point distributions may be generated by, for instance, taking multiple samples from a multiple number of values randomly chosen with replacement from the multiple control values. For each subject, the relative variance in either or both, or 1, 2, 3, or 4 sides or arms of the figures may be compared respectively with the corresponding control distribution, and the percent of the control distribution with variance below that of the test value may be determined. A p-value of 0.05 a widely accepted measure of statistical significance corresponds to 95% of control values falling below the test value. In such instances, subjects with variance higher than 95% of the values in the control distributions may be determined to have significant disturbances of ocular motility. The video may also move in other trajectories not resembling a rectangle, such as a triangle, circle or linear or nonlinear trajectories. As long as the trajectories can be resolved into vectors along Cartesian coordinates (horizontal vertical or x,y) the same principles will apply. In short, any trajectory (e.g. any shape, or line, or curve, etc.) studied over time may provide information about Central Nervous System function or dysfunction.

Comparing the movement of one eye of a subject to the other eye of a subject may be performed by comparing the x,y Cartesian coordinates at any time point t, for example, by subtracting the x coordinate of the left eye from the x coordinate of the right eye or vice versa, or by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested may be totaled to obtain a measure of total disconjugacy of gaze, which may be a surrogate marker for central nervous system integrity. In such a way, it is possible to quantitate the extent of central nervous system (CNS) integrity by quantitating the extent of disconjugate gaze.

Eye Movement Tracking without a Moving or Visual Stimulus

Eye movement may also be tracked without using a moving stimulus. It is possible to assess conjugacy without having the stimulus move at all, but by assessing the x, y coordinates over times during naturalistic viewing. For example, eye movement may be tracked during television watching or live viewing of an environment without a specific viewing apparatus such as a monitor or screen.

According to the methods described, comparing the x or y Cartesian coordinates at any time point for the eye movement of a first eye of the subject to the respective x or y Cartesian coordinates at any time point for the eye movement of a second eye of the subject, may be performed by analyzing data. Data from the tracking eye movement may provide an indication of whether an individual subject's gaze is conjugate (eyes are moving together) versus disconjugate. Comparing the x or y Cartesian coordinates at any time point for the eye movement of a first eye of the subject to the respective x or y Cartesian coordinates at any time point for the eye movement of a second eye of the subject, may feature generating scatterplots. Comparing the x or y Cartesian coordinates at any time point for the eye movement of a first eye of the subject to the respective x or y Cartesian coordinates at any time point for the eye movement of a second eye of the subject, may feature plotting the difference between the horizontal eye positions along one axis and time along an orthogonal axis, as well as the difference between the vertical eye positions along one axis and time along an orthogonal axis. Such comparing the x or y Cartesian coordinates at any time point for the eye movement of a first eye of the subject to the respective x or y Cartesian coordinates at any time point for the eye movement of a second eye of the subject; may feature generating, plotting pairs of (x, y) values, for instance, 25,000, 50,000, 75,000, 100,000, 150,000 or more pairs of values (x, y). Such pairs of values (x, y) may be plotted representing, for instance, the two components of the instantaneous angle of pupil reflection (horizontal, vertical) over a period of time, for instance, 100 or 200 or 250 or 300 seconds or more.

As such, comparing the x or y Cartesian coordinates at any time point for the eye movement of a first eye of the subject to the respective x or y Cartesian coordinates at the time point for the eye movement of a second eye of the subject, may allow generating plots assessing conjugacy of eye movements over time.

Comparing the x or y Cartesian coordinates at any time point for the eye movement of a first eye of the subject to the respective x or y Cartesian coordinates at the time point for the eye movement of a second eye of the subject, may feature determining the distribution of certain measurements in the control population and comparing the subject with these control distributions. In such instances, visual stimulus trajectory may be divided into four time components, for instance, two, three, four, five, six or more repetitions of the first few, for instance, 2, 5, 10, 15, 20 or so seconds of each rotation cycle. In such instances, comparing the x or y Cartesian coordinates at any time point for the eye movement of a first eye of the subject to the respective x or y Cartesian coordinates at any time point for the eye movement of a second eye of the subject may feature evaluating such variables as the relative variance in each arm, and the relative integrity of each arm.

Comparing the x or y Cartesian coordinates at any time point for the eye movement of a first eye of the subject to the respective x or y Cartesian coordinates at the time point for the eye movement of a second eye of the subject may be performed by comparing the x, y Cartesian coordinates at any time point t, for example, by subtracting the x coordinate of the left eye from the x coordinate of the right eye or vice versa, or by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested may be totaled to obtain a measure of total disconjugacy of gaze, which may be a surrogate marker for central nervous system integrity. In such a way, it is possible to quantitate the extent of central nervous system (CNS) integrity by quantitating the extent of disconjugate gaze.

Providing a sum of the differences between all of the x coordinates of the first eye compared to the second eye over the time tested or providing a sum of the differences in y coordinates of the first eye compared to the second eye over the time tested or both may be performed subsequent to comparing the x, y Cartesian coordinates at the time point t. For example, by subtracting the x coordinate of the left eye from the x coordinate of the right eye or vice versa. Also, by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested can be summed to obtain a measure of total disconjugacy of gaze, or as an average of five eyebox trajectory cycles formulaically represented as follows:

$$X_{Avg,ik} = \frac{\sum_{j=1}^{5} X_{ijk}}{5},$$

for all i=1:N, k=1:2,
where $X_{ijk}$ refers to the x-coordinate of the pupil, and k refers to the left or right eye of a subject. In cases where a subject's data was missing at any given time point in the five cycles, the denominator of the equation was the number of cycles where the data was present. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$Var_x = \frac{1}{N} \sum_{i=1}^{N} ([(X]_{Avg,i1} - X_{Avg,i2}) - 0)^2$$

Providing a total sum of the differences between both x and y coordinates of the first eye compared to the second eye over the time tested may be performed by calculating the total variance in both the horizontal and vertical planes between the first and the second eyes. The total variance may be computed as follows:

$$Var_{Tot} = Var_x + Var_y$$

In some instances, the $Var_x$ or the $Var_y$ or both, calculated as described herein, may be 0.05, 0.07, 0.1, 0.15, 0.20, 0.25, 0.30, 0.40, 0.50, 0.60, 0.75, 0.90, 1.0, 1.10, 1.25, 1.50, 1.75, or 2.0 or more. Similarly, in some instances, the $Var_{Tot}$ calculated as described herein, may be 0.1, 0.15, 0.20, 0.25, 0.30, 0.40, 0.50, 0.60, 0.75, 0.90, 1.0, 1.10, 1.25, 1.50, 1.75, 2.0, 2.50, 3.0 or 4.0 or more, in subjects having a neurological disease or condition characterized by or featuring disconjugacy of gaze or strabismus.

Tracking eye movement may feature generating figures substantially resembling boxes that reflect the trajectory traveled by the visual stimulation, such as when it moves across a screen, often called eye movement box trajectory. In healthy controls, these figures substantially resembling boxes may look like, for instance, substantially equilateral rectangles or squares, reflecting the trajectory traveled by the visual stimulus across a screen. In instances of structural and non-structural traumatic brain injury, neurological damage or increased intracranial pressure, such figures may not substantially resemble a box, a rectangle or a square. In fact, in some instances, the cranial nerve having reduced or impaired function or conduction may be identified. In some instances, the figures generated that reflect the trajectory traveled by the visual stimulation may demonstrate abnormal distribution of or absence of normal plotting pairs in particular areas. Increased variability along the y-axis may for example reflect cranial nerve II dysfunction. Decreased variability along the y-axis, or decreased height to width ratio may reflect CN III dysfunction. Increased height to width ratio may reflect CN IV or VI dysfunction. The height of the box may be mathematically determined by assessing the position of the pupil as the video traverses the top and bottom of the presented visual stimulus. This "actual" height may be different from the perceived height mathematically, since the perceived height can represent aberrant pupillary motion due to the patient's ocular motility dysfunction. The integrity of the box walls may also be indicative of other types of dysfunction. Both cranial nerve palsies and mass effect may cause defects in box trajectory. CN III defects may impact the top and/or bottom of the box. CN VI palsies may impact the sides of the box.

Traumatic Brain Injury

In addition to concussions, sub-concussive head hits also produce measurable changes in brain MRI. For instance, there may be persistent changes in white matter properties in athletes who did not experience a concussion during a season but had several blows to the head. A number of sub-concussive events may be as damaging as a frank concussion. The MRI changes reported in this study were causally related to the presence in serum of players of auto-antibodies against the brain protein S100B. Sub-concussion to leakage of the blood-brain barrier, extravasation of brain S100B in blood, activation of an immune response due to antigen unmasking and production of auto-antibodies. These auto-antibodies may be pathogenic as shown for example in epileptic human brain. (Phan et al., "Extracranial sources of S100B do not affect serum levels." PLoS One. 2010; 10 5(9); Carvalho-Tavares et al., Neurobiol Dis. 2013; 59:206-19) The link between S100B auto-antibodies and CTE needs experimental confirmation; however, antibodies against S100B or other brain protein have been found in patients affected by Alzheimer's disease.

Clinical symptoms of chronic traumatic encephalopathy are only beginning to be understood. They are thought to include changes in mood (i.e. depression, suicidality, apathy, anxiety), cognition (i.e. memory loss, executive dysfunction), behavior (short fuse, aggression), and in some cases motor disturbance (i.e. difficulty with balance and gait). The pathology of CTE has been broken up into stages, the clinical symptoms and clinical progression of CTE are not fully characterized.

The lack of in-vivo techniques to show distinct biomarkers for CTE is the reason CTE cannot be definitively diagnosed during lifetime. The only known diagnosis for CTE occurs by studying the brain tissue after death. Concussions are non-structural injuries and do not result in brain bleeding, which is why most concussions cannot be seen on routine neuroimaging tests such as CT or MRI. Acute concussion symptoms (those that occur shortly after an injury) should not be confused with CTE. Differentiating between prolonged post-concussion syndrome (PCS, where symptoms begin shortly after a concussion and last for weeks, months, and sometimes even years) and CTE symptoms can be difficult. (Poirier, *Clinical Pediatric Emergency Medicine* 2003; 4 (3): 179-85) Research studies are currently examining whether neuroimaging can detect subtle changes in axonal integrity and structural lesions that can occur in CTE. Recently, more progress in in-vivo diagnostic techniques for CTE has been made, using DTI, fMRI, MRI, and MRS imaging; however, more research needs to be done before any such techniques can be validated.

Drug Use, Drug Abuse and Narcosis

A patient may have altered mental status for a wide variety of reasons, which commonly include impairment due to the use of narcotics. The methods described herein demonstrate that an eye tracking algorithm performed while a subject watches television or a short film clip continuously playing in a moving aperture can distinguish between normal subjects and those administered the narcotic methadone. Eye tracking was performed on 93 methadone patients and 100 controls. These two populations were distinguishable by comparing the velocity of eye movements. Eye tracking was then performed on 53 of the methadone patients before and after their daily administration of narcotic. The observed eye tracking demonstrated that pupil velocity slowed as the eyes moved in one of four trajectories using a box trajectory. These data demonstrate that eye tracking may be useful for detecting narcotic use/abuse and to distinguish between altered mental status from narcotics versus other causes such as brain injury.

Structurally and Non-Structurally Brain Injured Subjects

A purpose of the prospective observational study described herein was to quantitate differences in eye tracking of structurally and non-structurally brain injured subjects relative to non-brain but bodily injured and healthy non-injured controls to identify the eye tracking parameters associated with structural and non-structural injury. Another purpose was to identify a correlation between impaired eye tracking and clinical neurologic functioning. Eye tracking and clinical concussion assessments were performed on 44 injured subjects, and eye tracking was performed only on 31 healthy normal controls. 51 eye tracking parameters were assessed in each patient. 10 parameters showed statistically significant differences between negative controls (healthy normal people and corporally injured trauma patients) and both positive controls (patients with structural brain injury) and patients with non-structural brain injury. 8 additional parameters showed statistically significant differences between negative controls (healthy normal people and corporally injured trauma patients) and patients with either structural or non-structural brain injury. 10 of the eye tracking measures showed statistically significant correlation between SCAT or SAC scores, demonstrating that these eye tracking parameters correlated with a validated clinical outcome measure.

In order to assess ocular motility including the function of cranial nerves III, IV, and VI and associated nuclei, a novel technique for automated eye movement tracking was developed using temporal rather than spatial calibration. The position of the pupil is predicted based on time elapsed since the start of the video rather than spatial calibration, enabling detection of impaired ability to move the pupil relative to normal controls or the opposite eye. Temporal calibration offers the additional advantage of utility to populations that may not be willing or able to cooperate with calibration instructions such as young children, foreign-language speakers, minimally conscious persons, or aphasics.

The data presented herein quantitates differences in eye tracking of structurally and non-structurally brain injured subjects relative to non-brain but bodily injured and healthy non-injured controls to identify the parameters associated with structural and non-structural injury. The data presented herein further establish a correlation between impaired eye tracking and clinical neurologic functioning.

Internuclear Ophthalmoplegia (INO)

The present methods provide an eye tracking algorithm that detects and quantitates the extent of internuclear ophthalmoplegia (INO) and differentiates it from an infranuclear palsy. The algorithm features having an individual observe a short film clip playing continuously in a moving aperture for a period of time while being eye tracked. The video is viewed with both eyes (binocular afferent), and both eyes are tracked. Pupil positions (Cartesian coordinates) are compared over time to determine if the eye movements are coordinated. Aspect ratio (the ratio of movements in the horizontal versus vertical plane) and/or horizontal and vertical conjugacy (the difference in coordinates between the left and right eyes in the x and y planes respectively) are assessed to identify whether the eyes are moving together. If they are not moving together, a lesion in the medial longitudinal fasciculus (MLF) resulting in INO can be distinguished from an infranuclear palsy by retracking the same individual with first one eye covered or closed (monocular afferent, monocular eye tracking) and then the other eye covered or closed. Thus by blocking the afferent information to one eye INO can be differentiated from infranuclear palsy.

An individual with an internuclear ophthalmoplegia (INO) will have normal motility (aspect ratio) in the eyes assessed separately (monocular afferent/monocular tracking) and abnormal tracking (abnormal aspect ratio/abnormal conjugacy) in the eyes assessed together.

The methods described herein feature first tracking the eye movement in a subject with both eyes trying to move together and then tracking the eye movement of each eye separately. The eye movement of each eye separately is tracked with the other eye covered or closed or otherwise maintained as unable to see by any suitable means or manner. The results obtained from such eye tracking indicate whether the pathology or problem impacting eye movement is with the movement of one eye (infranuclear, i.e. a problem with the nerve going to that eye, with muscles innervated by those nerves or with the ocular structures) versus a problem with eye movement coordination of both eyes (supranuclear).

An individual with an infranuclear palsy will demonstrate abnormal motility in the affected eye regardless of whether the eyes are tracked separately or together (with a monocular or binocular afferent) since the problem is occurring distal to the medial longitudinal fasciculus (MLF) 'coordination' center.

High resolution automated eye movement tracking, occurring over, for instance, about 220 seconds, is a powerful tool for detecting subclinically apparent ocular motility dysfunction, and thus aid in the rapid diagnosis of multiple neurological disorders or brain pathologies.

The data presented herein does not feature a calibration step in eye movement tracking. Thus patients need not reliably follow instructions, and the data does not filter out the possible effects of cranial neuropathy. Unlike other studies (Contreras et al., *Brain research* 2011; 1398:55-63; Maruta et al., *The Journal of Head Trauma Rehabilitation* 2010; 25(4):293-305; Contreras et al., *Journal of Biological Physics* 2008; 34(3-4):381-392 and Trojano et al., *J Neurol* 2012; (published online; ahead of print)) the data presented herein does not use saccade count or spatial accuracy as the measure. In addition to results based on the moving aperture's periodic envelope presented in this paper, the methodology also affords a very fine-scale data showing eye movements in response to the successive frames of the movie itself.

The methods described herein build on pre-existing methods that rely on intact ocular motility to address clinical questions. (Lee et al., *Brain research.* 2011; 1399:59-65; Contreras et al., *Brain research* 2011; 1398:55-63; Maruta et al., *The Journal of Head Trauma Rehabilitation* 2010; 25(4):293-305). The methods described herein differ in several ways. First, the present methods feature diagnosing specific clinical conditions related to vision and ocular motility reflecting the function of cranial nerves II, III, IV, VI and associated nuclei rather than measuring cognitive impairment due to primarily cortical mild to moderate traumatic brain injury. Second, the present methods use more fine-scale information, using, for instance, about 100,000 measurements to pull out subtle differences that can be lost through the somewhat arbitrary thresholding of velocity measures into saccades. Third, the present methods do not use measurements of spatial accuracy, which requires transforming the raw data by a series of scaling and rotating processes whose effectiveness depends on the ability of their subjects to follow precise commands reliably. In such methods previously used, it is necessary to exclude the vast majority of neurologically compromised patients. Further, such methods previously used lose any information related to the function of cranial nerves II, III, IV and VI, because the spatial distortions expected to result from damage to these nerves is reversed in the process of spatial calibration.

Trojano et al., *J Neurol* 2012; (published online; ahead of print) recently described uncalibrated eye movement measurements in a population of minimally conscious and persistently vegetative patients. The methods described herein differ in several ways. First, Trojano et al. report data from 11 rather than 25 healthy control subjects. Second, Trojano et al. evaluate chronic disorders of consciousness rather than acute changes in intracranial pressure. Third, Trojano et al. sample eye movements at 60 Hz rather than 500 Hz, effectively reducing the power of the data 100-fold. Fourth, Trojano et al. report differences in on-target and off-target fixations between the groups, despite not having spatially calibrated the data, making these values noisy. Finally, Trojano et al. use static stimuli moving in a quasi-periodic way. The methods described herein use moving images shown within an aperture that moves periodically and allows assessing both coarse and fine eye movement characteristics in both controls and patients.

The methods described herein provide a useful adjunct for diagnosis of internuclear ophthalmoplegia (INO) and prospective monitoring of such patients at risk for developing the same. The data presented herein demonstrate that patients with grossly intact extraocular movements on physical exam, and relatively minimal changes in pathology, may have profound disruption on high resolution tracking.

The data presented herein demonstrates in part that it is possible to diagnose internuclear ophthalmoplegia (INO) by analysis of eye movements during watching of a video. The methods described herein are significantly different from other technologies since imaging studies enable one to see the brain and invasive techniques enable determination of an arbitrary pressure or oxygenation number. The methods described herein actually assess physiologic functioning.

Attention Deficit Hyperactivity Disorder (ADHD), Chronic Traumatic Encephalopathy, and Schizophrenia Spectrum Disorders The present methods provide an eye tracking algorithm useful for detecting and diagnosing attention deficit hyperactivity disorder (ADHD), chronic traumatic encephalopathy, and schizophrenia spectrum disorders. The methods feature an eye tracking algorithm performed while someone watches a video playing continuously in an aperture on a viewing monitor that assesses how well the eyes move together.

Three individuals with ADHD demonstrated profoundly abnormal tracking particularly with regards to vertical ocular motility and conjugacy. Two of these people were diagnosed with ADHD in childhood. The third is a 62 year old male who was diagnosed with ADHD after a 12 year long career as a professional hockey player in the National Hockey League ending 21 years prior, with numerous prior concussions and one hypoxic incident over that time span. The former hockey player reports feeling off-balance and disoriented, in addition to having ADHD, raising the possibility that he has CTE or chronic traumatic encephalopathy from his many years of playing hockey.

In addition 30 patients were evaluated by a neurologist for elderly onset mild cognitive impairment. These patients were evaluated as having possible dementia and demonstrated eye tracking with metrics significantly deviated from 40 age matched control subjects.

High resolution automated eye movement tracking, occurring over, for instance, about 220 seconds, is a powerful tool for detecting subclinically apparent ocular motility dysfunction, and thus aid in the rapid diagnosis of multiple neurological disorders or brain pathologies.

The methods described herein provide a useful adjunct for diagnosis of and assessing attention deficit hyperactivity disorder (ADHD), chronic traumatic encephalopathy, and schizophrenia spectrum disorders and prospective monitoring of such patients at risk for developing the same. The data presented herein demonstrate that patients with grossly intact extraocular movements on physical exam, and relatively minimal changes in pathology, may have profound disruption on high resolution tracking.

The data presented herein demonstrates in part that it is possible to diagnose attention deficit hyperactivity disorder (ADHD), chronic traumatic encephalopathy, and schizophrenia spectrum disorders by analysis of eye movements during watching of a video. The methods described herein are significantly different from other technologies since imaging studies enable one to see the brain and invasive techniques enable determination of an arbitrary pressure or oxygenation number. The methods described herein actually assess physiologic functioning.

Alcohol Consumption

A patient may have altered mental status for a wide variety of reasons, which commonly include impairment due to consumption of alcohol. The data presented herein demonstrates that an eye tracking algorithm performed while a subject watches television or a short film clip continuously playing in a moving aperture can distinguish between normal subjects and those who have consumed or are intoxicated with alcohol. Eye tracking was performed on 33 normal healthy control subjects. These individuals were then enabled to consume alcohol if they so wished. Breathalyzer analysis was performed after consumption in all subjects, of whom 29 were intoxicated. Eye tracking was repeated using a different music video. Statistical analysis was performed to compare pre and post alcohol consumption eye tracking metrics. 11 of 90 eye tracking metrics were statistically significantly different in pre-versus post alcohol consumption eye tracking. This data demonstrates that eye tracking may be useful for detection of alcohol consumption and intoxication and to distinguish between altered mental status from alcohol versus other causes.

The present methods provide an eye tracking algorithm useful for detecting and diagnosing alcohol consumption and intoxication. The methods feature an eye tracking algorithm performed while someone watches a video playing continuously in an aperture on a viewing monitor that assesses how well the eyes move together.

Once again, the data presented herein does not feature a calibration step in eye movement tracking. Thus patients need not reliably follow instructions, and the data does not filter out the possible effects of cranial neuropathy. Unlike other studies (Contreras et al., *Brain research* 2011; 1398: 55-63; Maruta et al., *The Journal of Head Trauma Rehabilitation* 2010; 25(4):293-305; Contreras et al., *Journal of Biological Physics* 2008; 34(3-4):381-392 and Trojano et al., *J Neurol* 2012; (published online; ahead of print)) the data presented herein does not use saccade count or spatial accuracy as the measure. In addition to results based on the moving aperture's periodic envelope presented in this paper, the methodology also affords a very fine-scale data showing eye movements in response to the successive frames of the movie itself.

Once again, the methods described herein build on pre-existing methods that rely on intact ocular motility to address clinical questions. (Lee et al., *Brain research.* 2011; 1399:59-65; Contreras et al., *Brain research* 2011; 1398:55-63; Maruta et al., *The Journal of Head Trauma Rehabilitation* 2010; 25(4):293-305). The methods described herein differ in several ways. First, the present methods feature identifying alcohol consumption or intoxication or diagnosing specific clinical conditions related to vision and ocular motility reflecting the function of cranial nerves II, III, IV, VI and associated nuclei. Second, the present methods use more fine-scale information, using, for instance, about 100,000 measurements to pull out subtle differences that can be lost through the somewhat arbitrary thresholding of velocity measures into saccades. Third, the present methods do not use measurements of spatial accuracy, which requires transforming the raw data by a series of scaling and rotating processes whose effectiveness depends on the ability of their subjects to follow precise commands reliably. In such methods previously used, it is necessary to exclude the vast majority of neurologically compromised patients. Further, such methods previously used lose any information related to the function of cranial nerves II, III, IV and VI, because the spatial distortions expected to result from damage to these nerves is reversed in the process of spatial calibration.

The methods described herein provide a useful adjunct for diagnosis of and assessing alcohol consumption and intoxication. The data presented herein demonstrate that patients with grossly intact extraocular movements on physical exam, and relatively minimal changes in pathology, may have profound disruption on high resolution tracking.

The data presented herein demonstrates in part that it is possible to diagnose alcohol consumption and intoxication by analysis of eye movements during watching of a video. The methods described herein are significantly different from other technologies since imaging studies enable one to see the brain and invasive techniques enable determination of an arbitrary pressure or oxygenation number. The methods described herein actually assess physiologic functioning.

Conjugacy of Eye Movement

The present invention utilizes an eye movement tracking method that is useful for quantitating gaze conjugacy, and thus disconjugacy, during naturalistic viewing. Similarly, the method assesses vergence, or the ability of the eyes to focus on a single point. When the point moves closer the eyes converge and if it moves further away they diverge. Watching a moving stimulus on a monitor thus requires sustained vergence. It may be performed while a subject watches television or a video moving inside an aperture with a set trajectory for about 220 seconds at a fixed distance from a viewing monitor. It may also be performed as the subject views natural stimuli over time. The position of each pupil may be recorded over time elapsed as the video travels on its time course, enabling detection of impaired ability to move the pupils relative to time and therefore relative to each other. This method has high test-retest reliability in control subjects without significant neurologic or ophthalmic impairments using both a stationary and portable eye tracking device.

The present invention utilizes a technique for non-spatially calibrated tracking performed while subjects watch a music video moving inside an aperture on a computer monitor. The aperture moves around the monitor periphery at a known rate so that the position of the pupil can be predicted at any given time based on the time elapsed since the start of the video. By using elapsed time, rather than spatial calibration, the method detects impaired ability to move one pupil relative to the other. Uncalibrated tracking not only does not compensate for impaired motility, but also can be used in patients who do not follow commands such as aphasics, foreign-language speakers, persistently vegetative individuals and small children. It can also be used on animals.

If the subject's eyes are positioned about 55 cm from the center of the 30×35 cm viewing monitor, the method and associated algorithm elicits pupil movement in a maximum range of about 15° in any direction from midposition, or approximately 30° total from top to bottom or side to side. Thus, in some instances, the method and associated algorithm may not require or assess the full range of ocular motility, nor the entire visual field. Use of a larger monitor, or one positioned closer to the subject would enable assessment of these.

The observed and measured conjugacy was significantly higher in the horizontal plane than vertical. This may reflect any of multiple factors: (1) the shape of the monitor was not a perfect square but rather a 17" diameter rectangle. Each side was traversed in 10 seconds so the eyes had a greater distance to travel horizontally than vertically. Because the eyes were moving faster horizontally they may possibly be more conjugate. (2) Humans have stronger event related desynchronization on electroencephalogram with horizontal versus vertical eye movements (Kaiser, et al., *Clin Neurophysiol.*, 2009; 120: 1988-1993). Humans may have evolved to have higher conjugacy in the horizontal plane than in the vertical because more prey and predators are likely to be at near the same altitude rather than above or below. Other species have demonstrated differences in vertical versus horizontal eye movements (Lisberger, et al., *J Neurophysiol.*, 1989; 61: 173-185). (3) The control population is predominantly English speaking and thus reads from left to right, and reads faster horizontally than vertically (Seo, et al., *Vision Res.*, 2002; 42: 1325-1337). Testing of a population that reads vertically may potentially yield higher vertical conjugacy.

The technique described herein differs from uncalibrated tracking using static stimuli for on-target and off-target fixations in a population of minimally conscious and persistently vegetative patients that have open eyes (Trojano, et al., *J Neurol.*, 2012 (published online; ahead of print)). The moving images shown within an aperture that moves periodically allow assessing both coarse and fine eye movement characteristics in both controls and neurologically impaired subjects. Unlike other studies (Contreras, et al., *Brain Res.*, 2011; 1398: 55-63; Contreras, et al., *J Biol Phys.,* 2008; 34: 381-392; Maruta, et al., *J Head Trauma Rehabil.,* 2010; 25: 293-305; Trojano, et al., J Neural., 2012 (published online; ahead of print)) the present methods do not use saccade count or spatial accuracy which requires transformation of raw data by a series of scaling and rotating processes whose effectiveness depends on the ability of their subjects to follow precise commands reliably. The present methods also differ from gaze estimation, which requires either a fixed head position or multiple light sources and cameras to localize the pupil (Guestrin, et al., *IEEE Trans Biomed Eng.,* 2006; 53: 1124-1133).

Video oculography is a relatively newer technique that uses infrared cameras mounted in goggles to track the center of the pupil's position as the eye moves. It has been demonstrated to be useful in screening for neurovestibular and labyrinthine dysfunction and most recently in distinguishing these from vertebrobasilar stroke (Newman-Toker, et al., *Stroke,* 2013; 44: 1158-1161). Video oculography generally relies on spatial calibration (Hong, et al., *Behav Res Methods,* 2005; 37: 133-138; Schreiber, et al., *IEEE Trans Biomed Eng.,* 2004; 51: 676-679). The use of our non-calibrated stimulus algorithm with video oculography rather than a sole eye tracking camera might be an interesting subject for future study.

The methods described herein provide both sensitivity and specificity. Because so many different cortical functions are required for watching a video, any process impeding global cranial function or specific cranial nerve function will likely be revealed by the present methods. Tracking may be confounded in patients with a history of prior brain insult, who are intoxicated, or are under the influence of pharmacologic agents. Patients' cognitive abilities, attention span and distractibility will impact the quality of ocular motility data.

The methods described herein are useful for screening for strabismus. In a population of 14,006 consecutive patients examined at a pediatric eye clinic in Rome, 2.72% demonstrated either A or V-pattern strabismus (Dickmann, et al., *Ophthalmic Epidemiol.,* 2012; 19: 302-305). A-pattern was associated with a greater prevalence of neurological impairment, hydrocephalus and meningomyelocele, while those with V-pattern exhibited a greater prevalence of craniosynostosis and malformative syndromes (Dickmann, et al., *Ophthalmic Epidemiol.,* 2012; 19: 302-305). Delays in treatment of strabismus onset following binocular vision maturation may be associated with permanent disruption of stereopsis and sensory fusion (Fawcett, *Curr Opin Ophthalmol.,* 2005; 16: 298-302).

Given the relatively low prevalence of strabismus, the methods described herein are useful for the rapid automated assessment of acquired disconjugacy and vergence disorders. Such disconjugacy and vergence disorders may be due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases. As such, the methods described herein are useful for screening for strabismus or congenital disconjugate gaze, screening for acquired disconjugate gaze due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases, and assessing reading/learning disorders.

Binocular Eye Movement Monitoring

When the human brain is physiologically intact, the eyes move together with a conjugate gaze. Only by deliberate conscious effort can an individual overcome this mechanism (eg when they deliberately "cross" the eyes.) A failure of the eyes to move in complete synchrony is called disconjugate gaze.

Binocular tracking may be used to compare the non-spatially calibrated trajectory of one eye to the other. Subtle differences between the trajectories of the two eyes may be detected. These differences provide valuable information regarding the physiologic function or dysfunction of the movement of one eye relative to the other. In the absence of known structural ocular injury, such differences reflect physiologic differences in the function of the two sides of the brain. Since brain lesions due to stroke, trauma or concussion, tumors, demyelinating disease, hydrocephalus, degenerative disease, etc. are rarely completely symmetric, comparing the eye movement of one eye to the eye movement of the other eye may be used to either confirm the presence of a lesion, to differentiate the existence of a lesion from other more global factors that may affect a person's ability to participate in an eye tracking task, such as fatigue, intoxication, medications, drug abuse, malingering, or lack of willingness to participate in an eye tracking task.

Thus binocular tracking and directly comparing the trajectories obtained over time, rather than with spatial calibration, may be used to diagnose pathology and to distinguish between these diagnoses and global factors that may impact eye tracking. In addition to or instead of an eye tracking camera, a video oculography device such as goggles may be used to evaluate eye movements over time rather than with spatial calibration. The eye tracking device may also be located remotely and function via the internet or other visualization mechanism.

Computing System

A computing system according to the invention is described herein. Implementations of the observer matter and the functional operations described herein can be implemented in other types of digital electronic circuitry, or in computer software, firmware, or hardware, including the structures disclosed in this specification and their structural equivalents, or in combinations of one or more of them. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Implementations of the observer matter and the operations described herein can be implemented in digital electronic circuitry, or in computer software, firmware, or hardware, including the structures disclosed in this specification and their structural equivalents, or in combinations of one or more of them. The observer matter described herein can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described herein can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Described herein are many specific implementation details, these should not be construed as limitations on the scope of any inventions or of what may be claimed, but rather as descriptions of features specific to particular implementations of particular inventions. Certain features described herein in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

The Relationship of Aspect Ratio and Variance as Measures of the Signal.

When the (x, y) pairs are plotted to show the 'box plots,' they have been preprocessed because the absolute values of the raw data are of limited use since changes in the signal over time are most important. There are many ways to normalize data, including dividing by, the mean, by the standard deviation, or by the variance. Furthermore, the standard deviation or variance can be computed for all the data at once or x can be normalized using the variance of x and y can be normalized using the variance of y. Any normalization procedure for periodic data likely includes subtracting the mean, so the signal can be plotted as signal change alternating around zero. All of these transformations are conventional and widely used in data analysis by those of ordinary skill in the art. The details depend on the question being asked and the type of modeling or statistical testing being used.

In creating the box plots described herein, the raw data is preprocessed as follows: for the x (horizontal) and y (vertical) vectors independently, the mean is subtracted and divided by the standard deviation (which is the square root of the variance). This puts all the data in the same relative frame (zero-mean, max and min about 1 and −1). This is the reason the boxes look square (even if the stimulus presentation monitor is not square).

This means that 'long' and 'short' sides are reflecting relative variability. If the variability is high, the denominator is high and the measure value low. So, for example, if the variability of the horizontal (x) data is high relative to the variability of the vertical (y) data, the horizontal aspect of the box will be relatively smaller, and the result will be a tall skinny box (higher aspect ratio). Conversely, if the variability of the vertical (y) data is high relative to the variability of the horizontal (x) data, the vertical range will be reduced and the result will be a short fat box (lower aspect ratio).

Thus, particular implementations of the observer matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Disconjugate Eye Tracking Assessment

The methods described herein provide means for assessing or quantifying disconjugate gaze or disconjugate eye movement. These means feature receiving an array of pupil x and y coordinates that may be generated or obtained according to the methods described herein. These coordinates may be averaged across, for instance, five eyebox trajectory cycles. Formulaically this can be represented as follows:

$$X_{Avg,ik} = \frac{\sum_{j=1}^{5} X_{ijk}}{5},$$

for all i=1:N, k=1:2, where $X_{ijk}$ refers to the x-coordinate of the pupil, and k refers to the left or right eye of a subject. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero lateral or longitudinal pupil position difference between each eye. The variance may be computed as follows:

$$Var_x = \frac{1}{N}\sum_{i=1}^{N}(X_{Avg,i} - 0)^2.$$

The total variance may be computed as follows:

$$Var_{Tot} = Var_x + Var_y.$$

The variance in X, Y, and the total variance may be plotted in order to assess the amount of disconjugation (i.e. disconjugate gaze) present in a subject.

General Definitions

Raw x and y cartesian coordinates of pupil position are collected and stored in a one-dimensional vector:

$$x_i, \tag{1}$$

$$y_i. \tag{2}$$

This data is normalized according to the following form:

$$\bar{x}_i = \frac{x_i - \text{Mean}(x)}{\sigma_x}, \quad (3)$$

$$\bar{y}_i = \frac{y_i - \text{Mean}(x)}{\sigma_y}. \quad (4)$$

Index i corresponds to an individual data point. The size of i depends on the eye tracking hardware capture frequency and the time of tracking. The data is then sorted by eye (j=1:2, left, right), cycle (current stimulus method features an aperture that moves around the computer $$\bar{x}_i \to \bar{x}_{j,k,l}, \quad (5)$$

$$\bar{y}_i \to \bar{y}_{j,k,l}, \quad (6)$$

screen for five cycles) (k=1:5, first, second, third, fourth, fifth) and box segment (l=1:4, top, right, bottom, left). Implicit, is that each j, k, l has its own data points, n, whose size is also governed by the hardware tracking frequency and time length.

Individual Metrics

Segment Mean $$\bar{\bar{x}}_{j,k,l}, \quad (7)$$

$$\bar{\bar{y}}_{j,k,l}. \quad (8)$$

Corresponds to the arithmetic average of all data points on each segment l for all j, k. The result is one number representing each segment l.

Median

Corresponds to the statistical median of all data points on each segment l for all j, k. The result is one number representing each segment l.

$$\tilde{x}_{j,k,l}, \quad (9)$$

$$\tilde{y}_{j,k,l}. \quad (10)$$

Segment Variance $$\text{Var}(\bar{x}_{j,k,l}), \quad (11)$$

$$\text{Var}(\bar{y}_{j,k,l}). \quad (12)$$

Corresponds to the statistical variance of all data points on each segment l for all j, k. The result is one number representing each segment l.

Specific Metrics $$L\cdot\text{var } Y\text{top}=\text{Var}(\bar{y}_{1,average\ k=1:5,1}) \quad (13)$$

$$R\cdot\text{var } Y\text{top}=\text{Var}(\bar{y}_{2,average\ k=1:5,1}) \quad (14)$$

$$L\cdot\text{var } X\text{rit}=\text{Var}(\bar{x}_{1,average\ k=1:5,2}) \quad (15)$$

$$R\cdot\text{var } X\text{rit}=\text{Var}(\bar{x}_{2,average\ k=1:5,2}) \quad (16)$$

$$L\cdot\text{var } Y\text{bot}=\text{Var}(\bar{y}_{1,average\ k=1:5,3}) \quad (17)$$

$$R\cdot\text{var } Y\text{bot}=\text{Var}(\bar{y}_{2,average\ k=1:5,3}) \quad (18)$$

$$L\cdot\text{var } X\text{lef}=\text{Var}(\bar{x}_{1,average\ k=1:5,4}) \quad (19)$$

$$R\cdot\text{var } X\text{lef}=\text{Var}(\bar{x}_{2,average\ k=1:5,4}) \quad (20)$$

$$L\cdot\text{varTotal}=\text{Average}(\text{Var}(\bar{x}_{1,average\ k=1:5})+ \text{Var}(\bar{y}_{1,average\ k=1:5})) \quad (21)$$

$$R\cdot\text{varTotal}=\text{Average}(\text{Var}(\bar{y}_{2,average\ k=1:5})+ \text{Var}(\bar{y}_{2,average\ k=1:5})) \quad (22)$$

Segment Standard Deviation $$\sigma_{\bar{x}_{j,k,l}}, \quad (23)$$

$$\sigma_{\bar{y}_{j,k,l}}. \quad (24)$$

Corresponds to the statistical standard deviation of all data points on each segment/for all j, k. The result is one number representing each segment l.

Segment Skew $$\text{Skew}(\bar{x}_{j,k,l})=\bar{\bar{x}}_{j,k,l}-\tilde{x}_{j,k,l}, \quad (25)$$

$$\text{Skew}(\bar{y}_{j,k,l})=\bar{\bar{y}}_{j,k,l}-\tilde{y}_{j,k,l}, \quad (26)$$

Corresponds to the statistical skew (how far the mean is from the median) of all data points on each segment l for all j, k. The result is one number representing each segment l.

Specific Metrics $$L\cdot\text{SkewTop}=\text{Skew}(\bar{y}_{1,average\ k=1:5,1}) \quad (27)$$

$$R\cdot\text{SkewTop}=\text{Skew}(\bar{y}_{2,average\ k=1:5,1}) \quad (28)$$

$$L\cdot\text{SkewRit}=\text{Skew}(\bar{x}_{1,average\ k=1:5,2}) \quad (29)$$

$$R\cdot\text{SkewRit}=\text{Skew}(\bar{x}_{2,average\ k=1:5,2}) \quad (30)$$

$$L\cdot\text{SkewBot}=\text{Skew}(\bar{y}_{1,average\ k=1:5,3}) \quad (31)$$

$$R\cdot\text{SkewBot}=\text{Skew}(\bar{y}_{2,average\ k=1:5,3}) \quad (32)$$

$$L\cdot\text{SkewLef}=\text{Skew}(\bar{x}_{1,average\ k=1:5,4}) \quad (33)$$

$$R\cdot\text{SkewLef}=\text{Skew}(\bar{x}_{2,average\ k=1:5,4}) \quad (34)$$

Segment Normalized Skew $$\text{SkewNorm}(\bar{x}_{j,k,l}) = \frac{\text{Skew}(\bar{x}_{j,k,l})}{\sigma_{\bar{x}_{j,k,l}}}, \quad (35)$$

$$\text{SkewNorm}(\bar{y}_{j,k,l}) = \frac{\text{Skew}(\bar{y}_{j,k,l})}{\sigma_{\bar{y}_{j,k,l}}}. \quad (36)$$

Specific Metrics $$L\cdot\text{SkewTopNorm}=\text{SkewNorm}(\hat{y}1,average\ k=1:5,1) \quad (37)$$

$$R\cdot\text{SkewTopNorm}=\text{SkewNorm}(\bar{y}2,average\ k=1:5,1) \quad (38)$$

$$L\cdot\text{SkewRitNorm}=\text{SkewNorm}(\bar{x}1,average\ k=1:5,2) \quad (39)$$

$$R\cdot\text{SkewRitNorm}=\text{SkewNorm}(\bar{x}2,average\ k=1:5,2) \quad (40)$$

$$L\cdot\text{SkewBotNorm}=\text{SkewNorm}(\hat{y}1,average\ k=1:5,3) \quad (41)$$

$$R\cdot\text{SkewBotNorm}=\text{SkewNorm}(\bar{y}2,average\ k=1:5,3) \quad (42)$$

$$L\cdot\text{SkewLefNorm}=\text{SkewNorm}(\bar{x}1,average\ k=1:5,4) \quad (43)$$

$$R\cdot\text{SkewLefNorm}=\text{SkewNorm}(\bar{x}2,average\ k=1:5,4) \quad (44)$$

The method may also feature calculating box height, box width, box area, or box aspect ratio.

Box Height $$\text{BoxHeight}_{j,k}=\bar{\bar{y}}_{j,k,1}-\bar{\bar{y}}_{j,k,3} \quad (45)$$

Box Width $$\text{BoxWidth}_{j,k}=\bar{\bar{x}}_{j,k,2}-\bar{\bar{x}}_{j,k,4} \quad (46)$$

Box Aspect Ratio $$AspectRatio_{j,k} = \frac{BoxHeight_{j,k}}{BoxWidth_{j,k}} \quad (47)$$

Box Area $$BoxArea_{j,k} = BoxHeight_{j,k} \times BoxWidth_{j,k} \quad (48)$$

Conjugacy

The five cycles are averaged together to give one averaged cycle, rendering:

$$\bar{x}_{j,l}, \quad (49)$$

$$\bar{y}_{j,l}. \quad (50)$$

Then the data from the right eye is subtracted from the left eye to obtain a delta value:

$$\hat{x}_l = \bar{x}_{1,l} - \bar{x}_{2,l} \quad (51)$$

$$\hat{y}_l = \bar{y}_{1,l} - \bar{y}_{2,l}. \quad (52)$$

Here x represents the left normalized raw x pupil position minus the right normalized raw x pupil position. l corresponds to the top, right, bottom and left segments of the box.

Variance (Conjugacy)

The variance here does not follow the traditional form of statistical variance. In the traditional form, the average of the data points is subtracted from the sum of individual data points. In this case, the average is forced to zero, thus inferring that the hypothetical control patient has perfect conjugacy (left and right eye move precisely together).

$$Conj\,varX = Var(\hat{x}) = \frac{\sum_{l=1}^{4}(\hat{x}_l)^2 - 0}{\sum_{l=1}^{4}\hat{x}_l}, \quad (53)$$

$$Conj\,varY = Var(\hat{y}) = \frac{\sum_{l=1}^{4}(\hat{y}_l)^2 - 0}{\sum_{l=1}^{4}\hat{y}_l}, \quad (54)$$

$$TotalVariance = Conj\,totVar = Var(\hat{x}) + Var(\hat{y}), \quad (55)$$

$$CoVariance = Conj\,CorrXY = \frac{\sum_{l=1}^{4}\hat{x}_l\hat{y}_l}{\sum_{l=1}^{4}\hat{x}_l - 1} \quad (56)$$

Specific Metrics $$Conj\,varXtop = \frac{\sum(\hat{x}_1)^2 - 0}{\sum\hat{x}_1}, \quad (57)$$

$$Conj\,varXrit = \frac{\sum(\hat{x}_3)^2 - 0}{\sum\hat{x}_2}, \quad (58)$$

$$Conj\,varXbot = \frac{\sum(\hat{x}_?)^2 - 0}{\sum\hat{x}_3}, \quad (59)$$

$$Conj\,varXlef = \frac{\sum(\hat{x}_4)^2 - 0}{\sum\hat{x}_4}, \quad (60)$$

$$Conj\,varYtop = \frac{\sum(\hat{y}_1)^2 - 0}{\sum\hat{y}_1}, \quad (61)$$

$$Conj\,varYrit = \frac{\sum(\hat{y}_2)^2 - 0}{\sum\hat{y}_2}, \quad (62)$$

$$Conj\,varYbot = \frac{\sum(\hat{y}_3)^2 - 0}{\sum\hat{y}_3}, \quad (63)$$

$$Conj\,varYrit = \frac{\sum(\hat{y}_4)^2 - 0}{\sum\hat{y}_4}, \quad (64)$$

$$Conj\,CorrXYtop = \frac{\sum\hat{x}_1\hat{y}_1 - 0}{\sum\hat{x}_1 - 1}, \quad (65)$$

$$Conj\,CorrXYrit = \frac{\sum\hat{x}_2\hat{y}_2 - 0}{\sum\hat{x}_2 - 1}, \quad (66)$$

$$Conj\,CorrXYbot = \frac{\sum\hat{x}_3\hat{y}_3 - 0}{\sum\hat{x}_3 - 1}, \quad (67)$$

$$Conj\,CorrXYlef = \frac{\sum\hat{x}_4\hat{y}_4 - 0}{\sum\hat{x}_4 - 1} \quad (68)$$

Variance x Ratio Top/Bottom (Conjugacy)

$$Conj\,varXtopbotRatio = \frac{Var(\hat{x}_1)}{Var(\hat{x}_3)} \quad (69)$$

Variance y Ratio Top/Bottom (Conjugacy)

$$Conj\,varYtopbotRatio = \frac{Var(\hat{y}_1)}{Var(\hat{y}_3)} \quad (70)$$

Variance x Ratio Left/Right (Conjugacy)

$$Conj\,varXlefritRatio = \frac{Var(\hat{x}_4)}{Var(\hat{x}_2)} \quad (71)$$

Variance y Ratio Left/Right (Conjugacy)

$$Conj\,varYlefritRatio = \frac{Var(\hat{y}_4)}{Var(\hat{y}_2)} \quad (72)$$

The following examples are set forth to provide those of ordinary skill in the art with a description of how to make and use the methods, kits and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

EXAMPLE 1

Background

Eye movements contain clinically important information about neurological integrity. Clinical devices may take advantage of the relative ease of automated eye-movement tracking, for applications such as assessing recovery following clinical intervention. A technique was designed that can reliably measure eye movements with precision, without initial spatial calibration. Eye movements were tracked without spatial calibration in neurologically intact adults and in neurosurgical patients as they watched a short music video move around the perimeter of a screen for 220 s. Temporal features of the data were measured, rather than traditional spatial measures such as accuracy or speed.

The methods reliably discriminated between the presence and absence of neurological impairment using these uncalibrated measurements. The results indicate that this technique may be extended to assess neurologic integrity and quantify deficits, simply by having patients watch TV.

These methods are useful in a number of contexts, including rapid assessment of potentially neurologically injured individuals, monitoring of patients whose states might fluctuate between impairment and recovery, and measuring the efficacy of rehabilitation or intervention.

Eye movements have long been known to contain clinically relevant information about neurological integrity. Assessment of ocular motility is a standard part of any neurological exam, because it is easy and informative. However, there are some problems with the standard clinical exam including that it is normally administered by an expert, and generally is only qualitative, not quantitative.

The relative ease, portability, and noninvasiveness of automated eye-movement tracking devices has made it a promising area of translational research, for applications such as testing for concussion on athletic fields and assessing recovery following clinical intervention. Eye movement studies have provided insight into clinical fields from psychiatry to traumatic brain injury (TBI) and rehabilitation. (Trojano, et al., *J Neural.*, 2012, 259(9):1888-95; Gitchel, el al., *Arch Neurol.*, 2012, 69(8):1011-7; Qiu, et al., *PLoS One*, 2011, 6(10):e25805; Plow, et al., *PMR*, 3(9):825-35; Heitger, et al., *Brain.*, 2009, 132(Pt 10):2850-70; Pearson, et al., *Br J Sports Med.*, 2007, 41(9):610-2; Heitger, et al., *J Neurol Sci.*, 2007, 15; 253(1-39 2):34-47; Suh, et al., *Neurosci Lett.*, 2006, 401(1-2):108-13; Suh, et al., *Neurosci Lett.*, 2006, 410(3):203-7; Heitger, et al., *Brain inj.*, 2006, 20(8):807-24; Yang, et al., *Image and Vision Computing*, 2002, 20(4):273-87; and Heitger, et al., *Prog Brain Res.*, 2002, 40:433-12 48) Studies commonly measure accuracy of spatial fixation, time spent on particular fixation targets, and saccade count. (Trojano, et al., *J Neurol.*, 2012, 259(9):1888-95 and Foulsham, et al., *Vision Res.*, 2011, 51(1.7):1.920-31) Despite the promise, it has proven difficult to develop clinical applications based on quantitative measurements of eye-movements, (Heitger, et al., *Frog Brain Res.*, 2002, 40:433-12 48 and Foulsham. et al., *Vision Res.*, 2011, 51(17):1920-31) possibly because spatial calibration can be difficult in clinical settings, and because spatial calibration precludes the use of eye tracking for detection of dysfunctional ocular motility.

The standard use of an eye; tracker requires that the system be calibrated individually for every observer at the start of every measurement session. Calibration involves asking the observer to look at a series of high-contrast dots displayed on a computer monitor. The calibration process may be repeated several times until sufficient accuracy has been achieved. Only then can eye movements be recorded.

It has been difficult to use eye-tracking in clinical applications with observers for whom this calibration process is difficult (e.g., requiring many repetitions) or impossible. Calibration requires a willing observer who can follow commands reliably. Many clinical conditions that result in a loss of neural integrity, such as stroke or brain injury, also render the observer unwilling or unable to follow instruction.

Also problematic for using eye-tracking methods to brain injury or stroke patients, the calibration process itself may reduce the sensitivity of the eye tracking test. For example, consider a patient with impaired vertical ocular motility. Because the calibration process assumes that the eyes cover the full range of locations mapped out by the calibration points, it assigns the maximum pupil angle up and down incorrectly to the 'top' and 'bottom' of the monitor, respectively. In such instances, all future measurements for that observer are adjusted to conform to that incorrect assignment. Thus, impaired ocular motility may be undetected in tests that begin with a spatial calibration of the eye tracker.

Eye movement measurements may reflect severity of damage to the brain, as well as recovery following clinical intervention. The methods described herein were used to test patients from neurosurgery, emergency department and ophthalmology clinics as well as a control set of healthy volunteers. The success of the method involves two features. First, the methods described herein do not use spatial measures of accuracy as a variable of interest. By looking at eye movement trajectories in the time domain rather than the spatial domain, it is possible to quantify measures that do not rely on spatial calibration. Second, the measures are easily visualized and evaluated, making them immediately useful to the clinician or researcher.

Methods

Subjects. Healthy observers were recruited in New York University according to MB approved protocols as determined by the University Committee on Activities Involving Human Subjects (UCAIHS). All participants provided written informed consent, and the consent forms were approved by UCAIHS. Patients with neurological deficit were recruited from the neurosurgical practice at Bellevue Hospital. Written informed consent from the subjects or their legal proxies were obtained for prospective data collection according to guidelines established by the NYU IRB.

Observers. Because of the potential for uncalibrated eye-tracking to serve as an initial screen, the patient population was not restricted to a specific pathology. Rather, an arbitrary sample of patients who came through the clinic was recruited. The resulting sample was representative of the range of disorders seen in the clinic.

Eye Movement Tracking. Observers' eye movements were recorded using an Eyelink 1000 binocular eye tracker (500 Hz sampling, SR Research). All observers were seated approximately 55 cm from the screen. Some test patients were tracked on multiple visits at different stages of diagnosis, surgery, and recovery.

Visual Stimulus. The visual stimulus provided as a music video that played continuously while it moved clockwise along the outer edges of a computer monitor. Observers were instructed to watch the video. The stimulus was expected to evoke smooth pursuit eye movements as well as possible saccades and microsaccades as the observers scanned the video. The video was presented in a square aperture with an area approximately ⅛ of the size of the screen (about 16° of visual angle). This square aperture started at the upper left hand corner of the screen and moved at a constant speed, taking 10 seconds to traverse each edge of the monitor. A full cycle took 40 seconds, and five full cycles were played, for a total of 200 seconds. A countdown video played in the starting position for 10 seconds before the music video began, to give observers time to orient to the stimulus. Only the 200 seconds of the music video were used for analyses. The eye tracker sampled eye position at 500 Hz, yielding 100,000 samples of eye position over 200 seconds.

Axis Orientation. The camera and monitor were securely mounted, so that 'horizontal' for the camera was the same as 'horizontal' for the monitor. Therefore, the terms 'horizontal' and 'vertical.' are defined with respect to the monitor, not with respect to head-tilt. However, the head was typically aligned with the monitor, and a chinrest was used with all controls and about half of the patients, to ensure the continued alignment. The eyetracker converted changes of pupil angle into two orthogonal components which it labeled x, and y, and which in turn referred to horizontal and vertical change, due to the linked orientation of the monitor and camera. Therefore, we also refer to horizontal and vertical components as x and y respectively.

Data preprocessing. There was no spatial calibration so the units of the raw timecourses were of limited value. Therefore, for each observer, the timecourses were normalized by subtracting the mean and dividing by the standard deviation. This was done for each timecourse independently. The different timecourses were treated as distinct data sets from the same test patient or neurologically intact control.

Timecourses. The normalized x- and y-timecourses were plotted across time (FIGS. 1A and B). The clockwise movement of the visual stimulus alternated between horizontal changes and vertical changes, and the x- and y-timecourses in neurologically intact observers show the same alternation.

Visualization: Scatterplots. For visualization, scatterplots of the entire time series were created by plotting the 100,000 (x,y) pairs representing the two orthogonal components of the instantaneous angle of pupil reflection over 200 seconds. In neurologically intact controls, these figures look like boxes, reflecting the timing of the visual stimulus as it moved around the screen.

Quantitative data analysis and statistics. The x- and y-trajectories were fit with sinusoidal functions. The alternations in horizontal and vertical motion of the visual stimulus were thought to result in eye movement trajectories that were approximately sinusoidal with a period of 40 s, but with different phases for x and y. We further hypothesized that (1) the phase difference between x and y should be 45 degrees for neurologically intact controls, reflecting the 114 cycle alternation of horizontal and vertical eye movements; and (2) the model would fit data from the neurologically intact control observers better than it fit data from the patient group.

Degree of correlation (r) with a sinusoid was calculated for 1 each time course. The square of this value (r2) is a measure of goodness of fit of the model to the data. The correlation values were used because they better suited for statistical analysis. Throughout the text, 'model fit' refers to the correlation values (r).

Phase was calculated as phase of the sine function that best fit the data. The 8 following complementary procedures were used to assess the statistical significance of any differences in these two measures (phase difference and model fit) as compared between the neurologically intact control observers and the test patient observers.

(i) Statistical Analysis 1: hypothesis testing. For each measure, a statistical test was performed to determine whether the data from the test patient population could have come from the same underlying distributions as the data from the neurologically intact control population. For the phase measure, an unpaired t-test was used. For the sinusoidal fit measure, the Kruskal-Wallis analysis of variance (ANOVA) was used which is more appropriate for data that are not normally distributed.

(ii) Statistical Analysis 2: Fisher transformation. The correlation (r) values for each timecourse with the best fitting sinusoid were converted to z-scores using the Fisher transformation $((½)*\ln((1+r)/(1-r)))$. This normalization enables to complete the third step of the analysis.

(iii) Statistical Analysis 3: classification. The Fisher z-scores provided an estimate of the probability of seeing a particular correlation value for a given timecourse if the underlying population of timecourses had zero mean-correlation (the null hypothesis). The null hypothesis would be expected to be true for timecourses that were not fit well by sinusoids, e.g., timecourses from impaired observers. Timecourses with z-scores significantly above zero (e.g., well-matched to the stimulus trajectory) would be expected to come from unimpaired observers. A threshold of $z=2$ (corresponding to a significance level of alpha=0.05) was used to calculate the specificity and sensitivity of this test, as reported in the Results following.

Results

Eye movements were highly reliable and consistent across the group of neurologically intact control observers.

Discussion

Uncalibrated tracking may provide a quantitative measure of the ability to fixate, attend, and follow a stimulus. These date demonstrate that it is possible to collect reliable high-frequency eye movement data without first completing a spatial calibration for each observer. Many patients are not capable of calibrated eye tracking. The ability to track eye movements in these populations provides new insights about a variety of disorders that disturb the ocular-motor system, including but not limited to brain injury, stroke, and psychiatric disorders. Possible applications include clinical screening, diagnosis, monitoring the efficacy of treatment, and tracking progression of impairment and recovery.

EXAMPLE 2

Materials and Methods

Subjects. Healthy subjects were recruited in a university setting in accordance with IRB approved protocols. All other subjects were recruited directly from our neurosurgical practice. Informed consent from the subject or their legal proxy was obtained for prospective data collection in all cases in accordance with IRB guidelines.

Eye Movement Tracking. The subjects' eye movements were recorded using an Eyelink 1000 binocular eye tracker (500 Hz sampling, SR Research). Healthy volunteers were seated 55 cm from the screen with their head stabilized using a chinrest. Stimulus was presented on average 55 cm from patient eyes, with the presentation monitor adjusted to match gaze direction. Subjects used a chinrest.

Innovations for tracking patients. Two innovations were provided to measure ocular motility in a patient population. The first was a paradigm, consisting of a stimulus and an analysis stream that allows interpreting raw eye position data. With few exceptions, eye movement studies analyze transformed gaze position, which involves a loss of information and excludes many patients from study. A novel algorithm for looking at pupil position directly, yielding information about ocular motility was developed. A device that can be brought to patients was provided. With few exceptions, eye movement data are collected using a fixed eye tracker at an unchanging location, which requires subjects to travel to the tracker and to use the chair and chinrest setup that goes with it. The SR Research Eyelink 1000 was adapted into a novel mobile system that allows flexibility in location and subject position, without sacrificing data quality.

Visual Stimulus. A music video that moved clockwise along the outer edge of a computer monitor starting at the upper left hand corner of the screen was provided. Spatial calibration was not performed, and the distance varied between subjects, so that the size of the stimulus in degrees may only be approximated. For a healthy subject seated 55 cm from the screen with good spatial calibration, the stimulus was presented in a square aperture with an area of approximately 16 degrees (approximately ⅛ of the size of the screen). This square aperture, within which a music video played continuously, moved across the screen at a constant speed, taking 10 s to cover each edge of the monitor. A full cycle took 40 s, and five full cycles were played, for a total of 200 s. A countdown video played in the starting position for 10 s before the music video began, to provide all subjects time to orient to the stimulus. The movie continued for an addition 10 seconds after the 200 s trial, to avoid boundary effects from contaminating the data. Only the 200 s of the music video comprising 5 cycles of 40 s each were used in all analyses. At a rate of 500 Hz, this yielded 100,000 samples of eye position over 200 seconds.

Data analysis: (1) Visualization. To create a snapshot of the data from the entire trial that provided a vivid indication of whether an individual subject's ocular motility differs from that of healthy controls, scatterplots of the entire time series were created by plotting the horizontal eye position along one axis and vertical eye position along the orthogonal axis. The 100,000 pairs of values (x,y) were plotted representing the two components of the instantaneous angle of pupil reflection (horizontal, vertical) over 200 seconds. In healthy controls, these figures look like boxes, reflecting the trajectory traveled by the aperture as it moved across the screen. These visualizations confirmed that the raw eye traces did conform to the square spatial trajectory of the stimulus, except in cases of neurological damage.

Data analysis: (2) Time vs. Space. Without spatial calibration, exact measurements of error in the spatial domain are impossible. This problem was avoided by looking at the eye movement trajectories in the time domain, rather than the spatial domain. By using a constantly changing stimulus (a continuously playing movie) with a periodic envelope (the aperture trajectory), it was possible to look at relative eye movements over time. Effectively, each subject's mean trajectory over the path of the aperture served as its own calibration.

Data analysis: (3) Statistics. In order to quantitatively assess the statistical significance of our results, the distribution of certain measurements in the control population was determined, and each subject was compared with these control distributions for each measure. The stimulus trajectory was divided into four time components: The first arm consisted of five repetitions of the first 10 seconds of each rotation cycle (e.g., seconds 1:10, 41:50, 81:90, 121:130, and 161:170). The second, third and fourth arms were defined accordingly. Two variables were evaluated: the relative variance in each arm, and the relative integrity of each arm. Relative variance was calculated as mean variance across 5 repetitions within an arm divided by variance of the whole time course. Integrity was calculated as the percent of missing values in each arm. We defined 2 tests based on these measurements, and performed the same tests in the controls and the patients. The results of these tests in the control population were used to determine the control distributions. The results of these tests for each patient were compared to the appropriate control distribution, and confidence intervals were defined as follows.

Integrity. For the integrity measure, each patient's pair of values from arms 1 (the top of the box) and 3 (the bottom of the box) was z-scored using the mean and standard deviation calculated from the control population. The resulting score indicated how different the patient values were compared with the control values, in units of standard deviations. Because 95% of all values in a normal distribution lie within two standard deviations of the mean, a z-score of 2 was used as a significance threshold. Patients with z-scores above 2 in either or both arms were thus judged to have significant disturbances of ocular motility.

Relative variance. Because relative variance is a ratio, it cannot be analyzed using z-scores, since the assumption of a normal distribution does not hold for ratios. Instead, 5,000 point distributions were generated using a bootstrapping method that took 5,000 samples from 25 values randomly chosen with replacement from the 45 control values. For each subject, the relative variance in arms 1 and 3 were compared respectively with the corresponding control distribution, and the percent of the control distribution with variance below that of the test value was determined. A p-value of 0.05 (a widely accepted measure of statistical significance) corresponds to 95% of control values falling below the test value. Thus, subjects with variance higher than 95% of the values in the control distributions were determined to have significant disturbances of ocular motility.

Units. The units of relative variance are related to size in degree of visual angle, but are not exactly identical to degrees of visual angle, because there was no spatial calibration. These may be referred to as time-degrees units.

Results

Successful tracking. Visualization of the eye movement trajectories across healthy controls and patients confirmed that the method successfully measured eye movements without recourse to traditional calibration techniques.

Control distributions. As expected, the control distributions for the integrity measure were normally distributed with a mean of 0.2 and an average standard deviation of 0.05 (5% deviation). The control distributions of relative variance peaked at 0.25 (reflecting equal variance across the four arms).

Patient measurements. The integrity measures for the 'top' vs. 'bottom' arms of the trajectory for each subject, in units of standard deviation, as compared with the control distributions as described above were calculated. Subjects with cranial nerve palsies or mass effect showed defects in integrity of eye tracing box trajectory. Subjects with relatively greater cranial nerve II palsies due to either compression or papilledema showed streaking vertical lines due to scanning vision.

EXAMPLE 3

Materials and Methods

Patient Selection. Control subjects were employees, volunteers, visitors and patients at the Bellevue Hospital Center recruited in accordance with Institutional Review Board policy. Inclusion criteria for normal control subjects were: age 7 to 100 years, vision correctable to within 20/500 bilaterally, intact ocular motility, and ability to provide a complete ophthalmologic, medical and neurologic history as well as medications/drugs/alcohol consumed within the 24 hours prior to tracking. Parents were asked to corroborate details of the above for children aged 7-17. Exclusion criteria were history of: strabismus, diplopia, palsy of cranial nerves III, IV or VI, papilledema, optic neuritis or other known disorder affecting cranial nerve II, macular edema, retinal degeneration, dementia or cognitive impairment, hydrocephalus, sarcoidosis, myasthenia gravis, multiple sclerosis or other demyelinating disease, and active or acute epilepsy, stroke/hemorrhage or brain injury sufficiently significant to result in hospitalization. Subjects reporting any minor brain injury regardless of loss of consciousness within the previous week were also excluded.

Additional subjects were recruited from a neurophthalmic practice also in accordance with Institutional Review Board policy. These subjects were selected for participation specifically because they had known palsies of cranial nerves III, IV and VI respectively, or other specific ocular pathology.

Visual Stimulus. Each subjects' eye movements were recorded with an Eyelink 1000 eye tracker at a fixed distance of 55 cm from a computer monitor over a time period of 220 seconds. For the stationary tracker the subject was seated in an adjustable height chair, using an adjustable height chinrest. Portable tracker subjects were seated in either a height adjustable or height-fixed chair, with the monitor height adjusted to the subject. The portable tracker chinrest was attached to the monitor, while the stationary tracker chinrest was attached to the same table as the computer monitor. The visual stimuli were the music videos Shakira Waka-Waka, K'naan Wavin' Flag, or the Under the Sea song from the Little Mermaid. The video was played continuously in a square aperture with an area approximately ⅛ the screen size while moving clockwise along the outer edges of the monitor for five complete cycles of 40 seconds each. The first and last 10 seconds of each data set were discarded to yield 200 seconds of data. The afferent stimulus was presented binocularly and eye tracking was performed binocularly. Subjects were not spatially calibrated to the tracker to enable independent analysis of each pupil position over time.

In a separate example, subjects were assessed for gaze conjugacy using a naturalistic viewing stimulus. This consisted of watching television as eye movements were tracked over time. Subjects were not seated at a fixed distance from the monitor but were able to move their heads during viewing.

Data Analysis. The eye tracker sampled pupil position at 500 Hz, yielding 100,000 samples over 200 seconds. Scatterplots of the entire time series were created by plotting the 100,000 (x, y) pairs representing the two orthogonal components of the instantaneous angle of pupil reflection over time to create 'box trajectories' that reflected the temporal nature of the pupillary movement. These figures look like boxes, reflecting the timing of the aperture as it moved around the screen.

Analysis of Gaze Conjugacy. Comparing the movement of one eye of a subject to the other eye of a subject was performed by comparing the x, y Cartesian coordinates at any time point t. For example by subtracting the x coordinate of the left eye from the x coordinate of the right eye or vice versa. Also by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested can be summed to obtain a measure of total disconjugacy of gaze, or as an average of five eyebox trajectory cycles formulaically represented as follows:

$$X_{Avg,ik} = \frac{\sum_{j=1}^{5} X_{ijk}}{5},$$

for all i=1:N, k=1:2, where $X_{ijk}$ refers to the x-coordinate of the pupil, and k refers to the left or right eye of a subject. In cases where a subject's data was missing at any given time point in the five cycles, the denominator of the equation was the number of cycles where the data was present. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$Var_x = \frac{1}{N}\sum_{i=1}^{N} ([(X)]_{Avg,i1} - X_{Avg,i2}) - 0)^2$$

The total variance in both the horizontal and vertical planes may be computed as follows:

$$Var_{Tot} = Var_x + Var_y$$

The variance in X, Y, and the total variance may be plotted in order to assess the amount of disconjugation present in a subject.

Statistical Analyses

Statistics were evaluated using R. Conjugacy of eye movement versus age: Normal subjects demonstrated conjugate eye movement that was not impacted by age. A linear regression between total variance and age was calculated. A linear regression t-test was used to determine whether the slope of the regression line was statistically significantly different from 0.

Conjugacy of eye movement compared between genders: A Welch Two Sample t-test was used to determine if the true difference between the mean of male total variance and the mean of female total variance was statistically significantly different from 0.

X (horizontal eye movement) versus Y (vertical eye movement) conjugacy: A paired t-test was used to determine if the mean of the subject-paired differences between the total x-variance and total y-variance was statistically significantly different from 0.

Test-retest on the stationary tracker and from the stationary to the portable tracker: A paired t-test was used to determine if the mean of the subject-paired differences between the total variances for two separate eyetracking sessions was statistically significantly different from 0.

Results 125 unique subjects aged 7 to 75 (mean 34.3±15.7, median 28.2; 51.2% female) were surveyed regarding their past medical history (Table 1), past ophthalmic history (Table 2) and any medications, alcohol or drugs of abuse (Table 3) taken within the last 24 hours. The results indicated that many subjects disclosed prior medical and ophthalmic history and medication usage.

TABLE 1

Neurologic/Cranial History

| Condition/Symptoms | Number of Subjects |
| --- | --- |
| Concussion | 9 |
| Migraines | 4 |
| Hypertensin | 3 |
| Hypothryroidism | 3 |
| Unspecified Head injury | 3 |
| Vertigo | 2 |
| Diabetes Melitus | 1 |
| Dyslexia | 1 |
| Spinal Injury | 1 |
| 7, 8 Palsy | 1 |

*Note: Subjects may exhist in Multiple Categories

TABLE 2

Ophthalmic History

| Condition/Symptoms | Number of Subjects |
| --- | --- |
| Myopia | 26 |
| Astigmatism | 9 |
| Hyperopia | 6 |
| Cataracts | 5 |
| Glaucoma | 2 |
| Keratosis | 2 |
| Retinal Detachment | 2 |
| Adie Syndrome | 1 |
| Chalzion | 1 |
| Corneal Ulcers | 1 |
| Lasik | 1 |
| Orbital Myositis | 1 |
| Presbyopia | 1 |
| Sty | 1 |
| Trauma from foreign object | 1 |
| Other, unspecified | 9 |

*Note: Subjects may exhist in Multiple Categories

TABLE 3

Medication/Drug Usage in last 24 hrs

| Drugs | Number of Subjects |
| --- | --- |
| Multivitamin | 11 |
| Synthriod | 5 |
| Vitamin D | 5 |
| Aspirin | 6 |
| Advil | 3 |
| Lisinopril | 3 |
| Lipitor | 3 |
| Simvastatin | 3 |
| Adderall | 2 |
| Calcium | 2 |
| Flovent | 2 |
| Hydrocholorthiazide | 2 |
| Imuran | 2 |
| Insulin (unspecified) | 2 |
| Laxapro | 2 |
| Metoprolol | 2 |
| Norvasc | 2 |
| Spironolactone | 2 |
| Yaz | 2 |
| Albuterol | 1 |
| Allegra | 1 |
| Vitamin B12 | 1 |
| Calcitriol | 1 |
| chondroitin | 1 |
| Citrucel | 1 |
| Clopidogrel | 1 |
| Colcrys | 1 |
| Concerta | 1 |
| Cordia | 1 |
| Diovan | 1 |
| Doxycycline | 1 |
| Esomeprazole | 1 |
| Ferrous Sulfate | 1 |
| Fish Oil | 1 |
| Flonase | 1 |
| Furosemide | 1 |
| Gabapentin | 1 |
| Glyburide | 1 |
| Hydrocortisone | 1 |
| Kombigyze XR | 1 |
| Lantus | 1 |
| Losartan | 1 |
| Lutera | 1 |
| Magnesium Oxide | 1 |
| Methimazole | 1 |
| Motrin | 1 |
| Nexium | 1 |
| Niquil | 1 |
| Nit D | 1 |
| Novolog | 1 |
| OCP (unspecified) | 1 |
| Omezaprole | 1 |
| Plavix | 1 |
| Prandin | 1 |
| Prilosec | 1 |
| Singulair | 1 |
| Stribild | 1 |
| Toprol | 1 |
| Trimo-San | 1 |
| Welbutrin | 1 |
| Xyzal | 1 |
| Zyprexa | 1 |
| Zyrtec | 1 |
| Admit to Marijuana | 1 |
| Admit to Alcohol in past 24 | 6 |

*Note: Subjects may exhist in Multiple Categories

Figure 3:
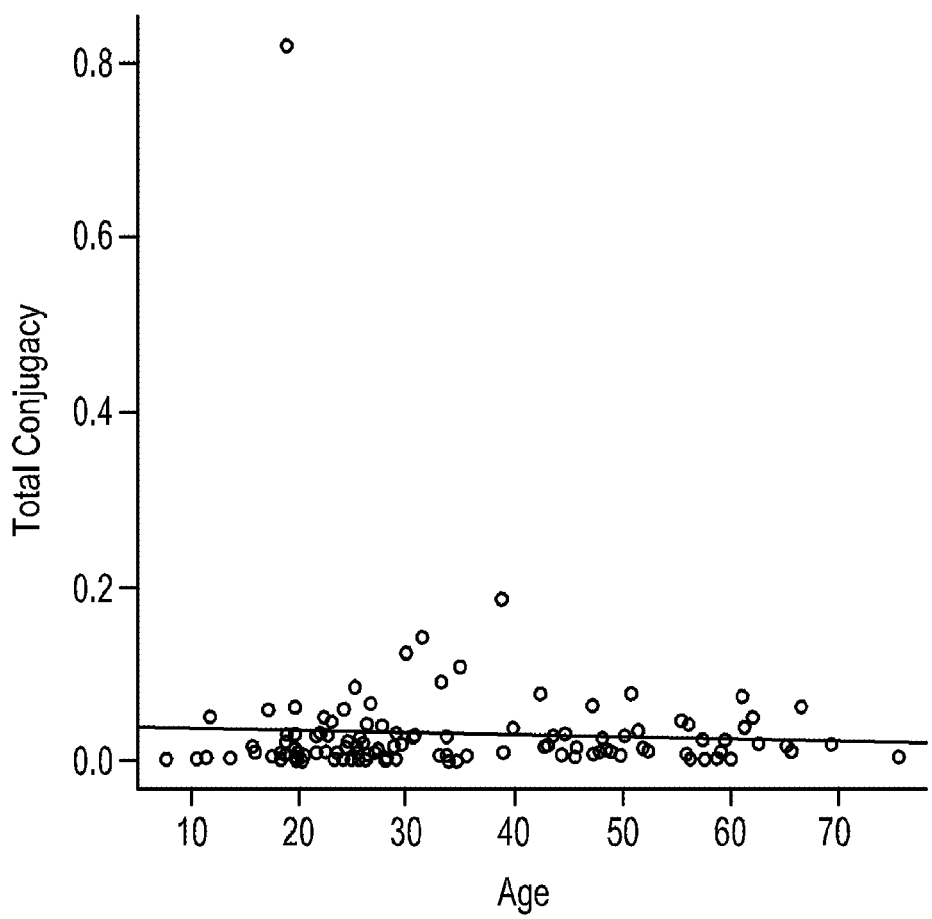
FIG. 3 represents total conjugacy versus age. Normal subjects demonstrated conjugate eye movement that was not impacted by age. A linear regression t-test was used to determine whether the slope of the relationship between total variance and age yielded a regression line statistically significantly different from 0. The test resulted in a t-statistic of −0.523 and a p-value of 0.6017 showing that the slope of the regression line was not statistically significantly different from 0. Thus in our subject population ranging in age from 7 to 75, there was no change in conjugacy of eye movements with age.

Normal subjects demonstrated conjugate eye movement that was not impacted by age (FIG. 3). A linear regression t-test was used to determine whether the slope of the relationship between total Variance and age yielded a regression line statistically significantly different from 0. The test resulted in a t-statistic of −0.523 and a p-value of 0.6017 showing that the slope of the regression line was not statistically significantly different from 0. Thus in the subject population ranging in age from 7 to 75, there was no change in conjugacy of eye movements with age.

The single greatest outlier (conjugacy of 0.8214) in the control population was a 23 year old male student who wears corrective contact lenses and takes adderall for attention deficit and hyperactivity disorder. This subject, underwent repeat tracking which remained disconjugate, (0.2600) however less than previously. The second greatest outlier (conjugacy 0.486) was a 39 year old male hospital employee who denied any ophthalmic or medical history, as well as the use of alcohol or drugs in the prior 24 hours. In both of these subjects the X-conjugacy was not a statistical outlier and only the y coordinates were disconjugate.

Figure 4:
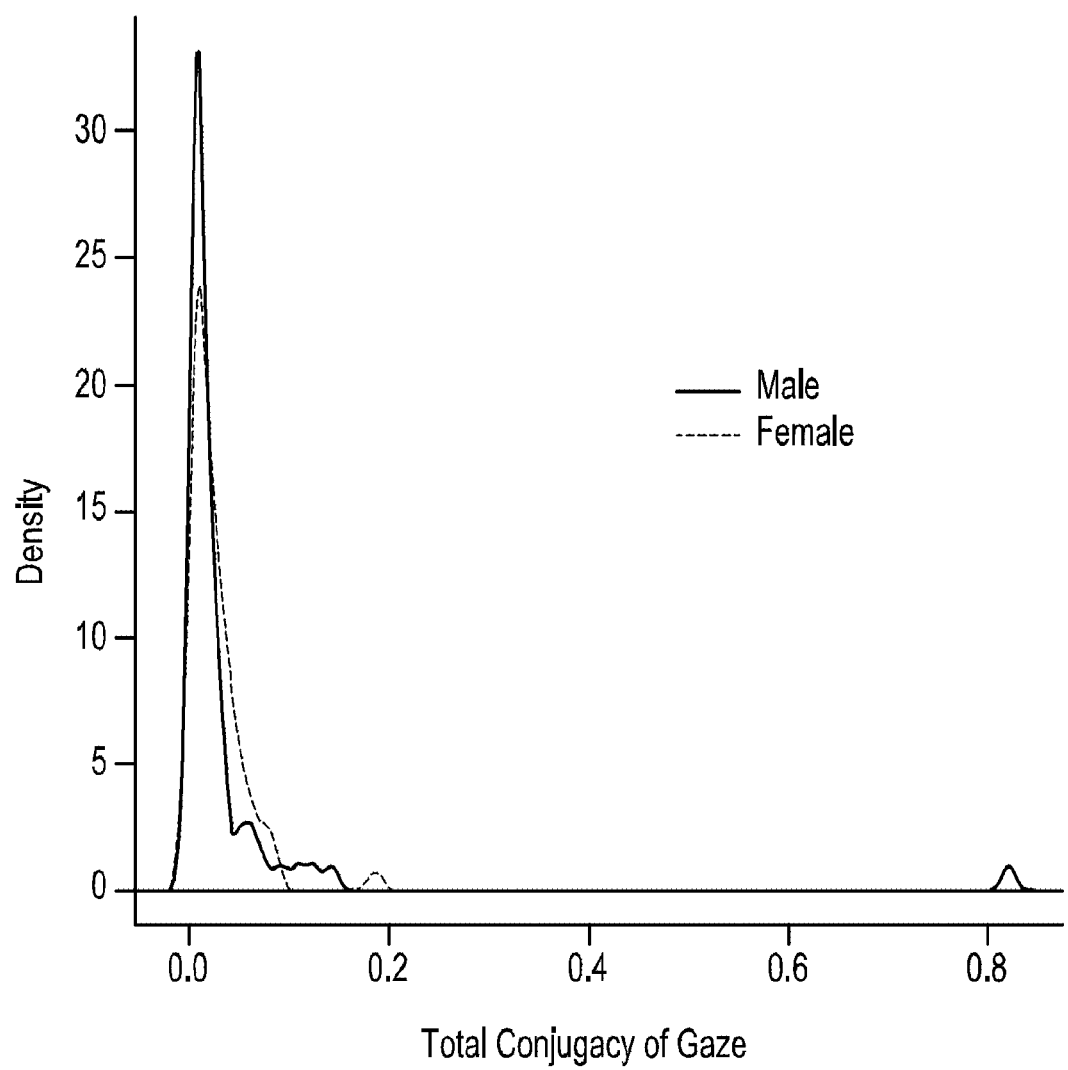
FIG. 4 represents male versus female conjugacy of eye movements. Normal subjects demonstrated conjugate eye movement that was not impacted by gender. A Welch Two Sample t-test with 68.49 degrees of freedom resulted in a t-statistic of 0.6734 and a p-value of 0.5029 showing that the difference in the means was not statistically significantly different from 0.

Normal subjects demonstrated conjugate eye movement that was not impacted by gender (FIG. 4). A Welch Two Sample t-test with 68.49 degrees of freedom resulted in a t-statistic of 0.6734 and a p-value of 0.5029 showing that the difference in the means was not statistically significantly different from 0.

Figure 5:
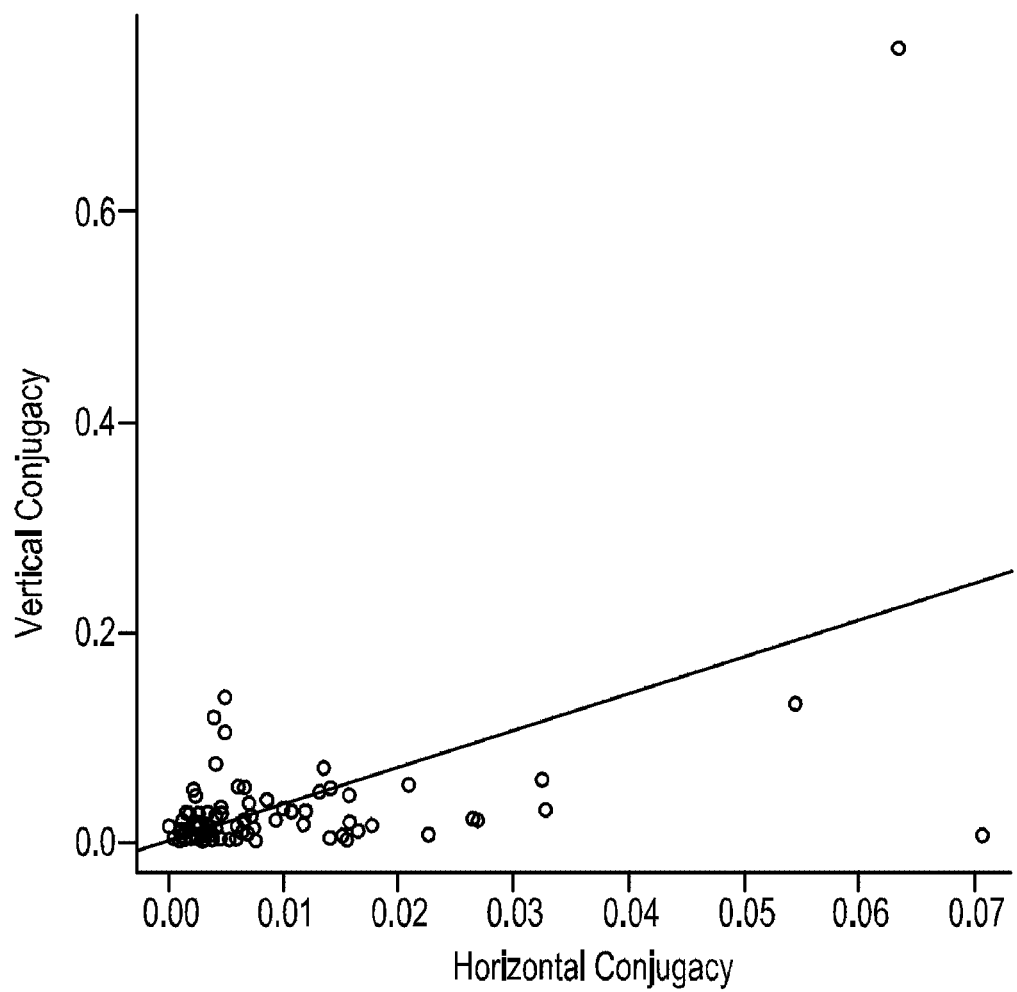
FIG. 5 represents X (horizontal) versus Y (vertical) conjugacy. Normal subjects demonstrated horizontal eye movement that was statistically highly significantly more conjugate than vertical eye movement. A paired t-test was used to determine if the mean of the subject-paired differences between the total x-variance and total y-variance was statistically significantly different from 0. With 124 degrees of freedom, the test resulted in a t-statistic of −3.0263 and a p-value of 0.003011 showing that the mean of the subject-paired differences was statistically highly significantly different from 0. Specifically, it was shown that for a particular subject, x-variance is statistically significantly less than y-variance.

Normal subjects demonstrated horizontal eye movement that was statistically highly significantly more conjugate than vertical eye movement (FIG. 5). A paired t-test was used to determine if the mean of the subject-paired differences between the total x-variance and total y-variance was statistically significantly different from 0. With 124 degrees of freedom, the test resulted in a t-statistic of −3.0263 and a p-value of 0.003011 showing that the mean of the subject-paired differences was statistically highly significantly different from 0. Specifically, it was shown that for a particular subject, x-variance is statistically significantly less than y-variance.

Figure 6:
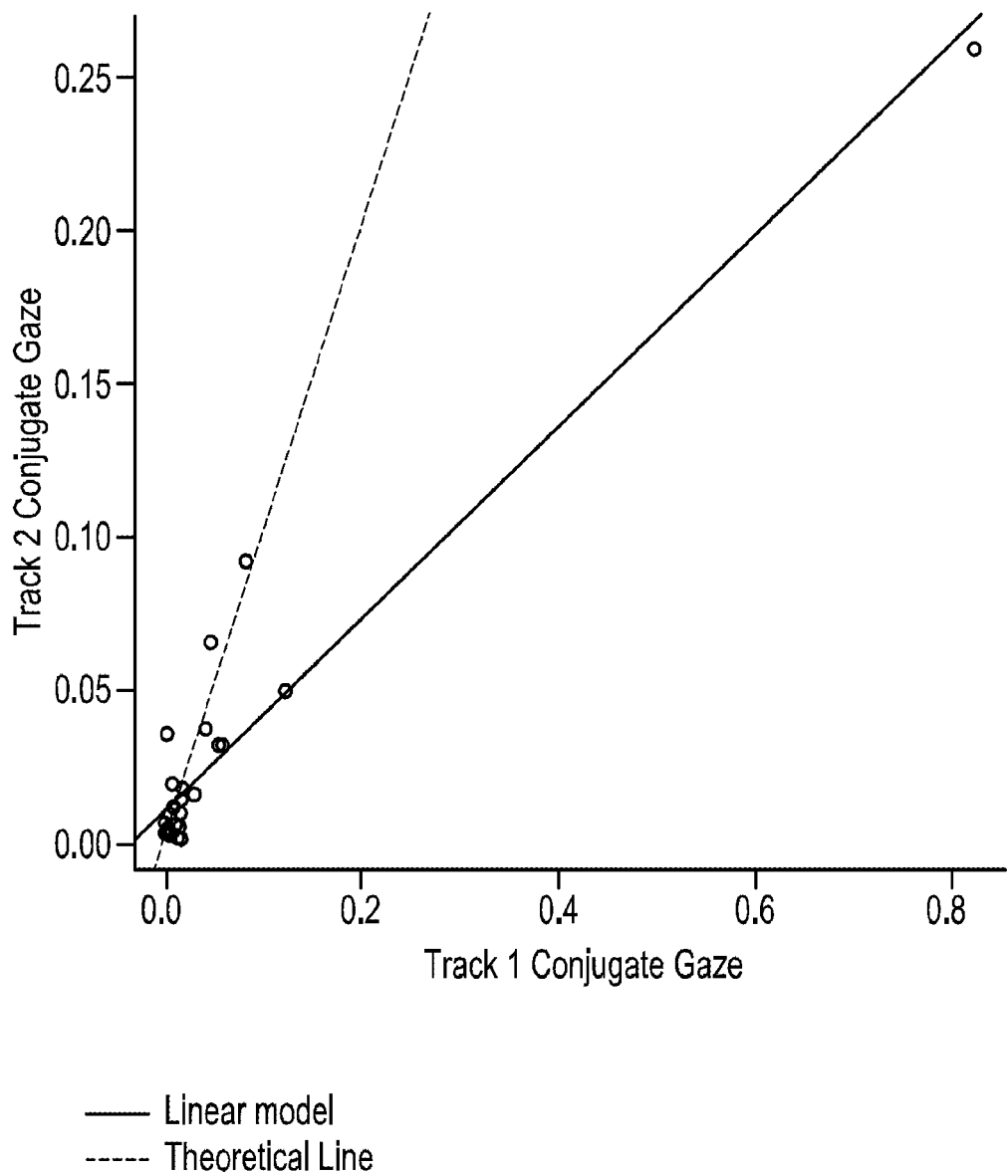
FIG. 6 demonstrates the test-retest reliability of a stationary to stationary tracker. Subjects (n=27) demonstrated high test-retest reliability between two separate eyetracking sessions on the stationary tracker. A paired t-test was used to determine if the mean of the subject-paired differences between the total variances for two separate eyetracking sessions was statistically significantly different from 0. With 26 degrees of freedom, the test resulted in a t-statistic of 1.2778 and a p-value of 0.2126 showing that the mean of the subject-paired differences was not statistically significantly different from 0.

Subjects (n=27) demonstrated high test-retest reliability between two separate eyetracking sessions on the stationary tracker (FIG. 6). A paired t-test was used to determine if the mean of the subject-paired differences between the total variances for two separate eyetracking sessions was statistically significantly different from 0. With 26 degrees of freedom, the test resulted in a t-statistic of 1.2778 and a p-value of 0.2126 showing that the mean of the subject-paired differences was not statistically significantly different from 0.

Figure 7:
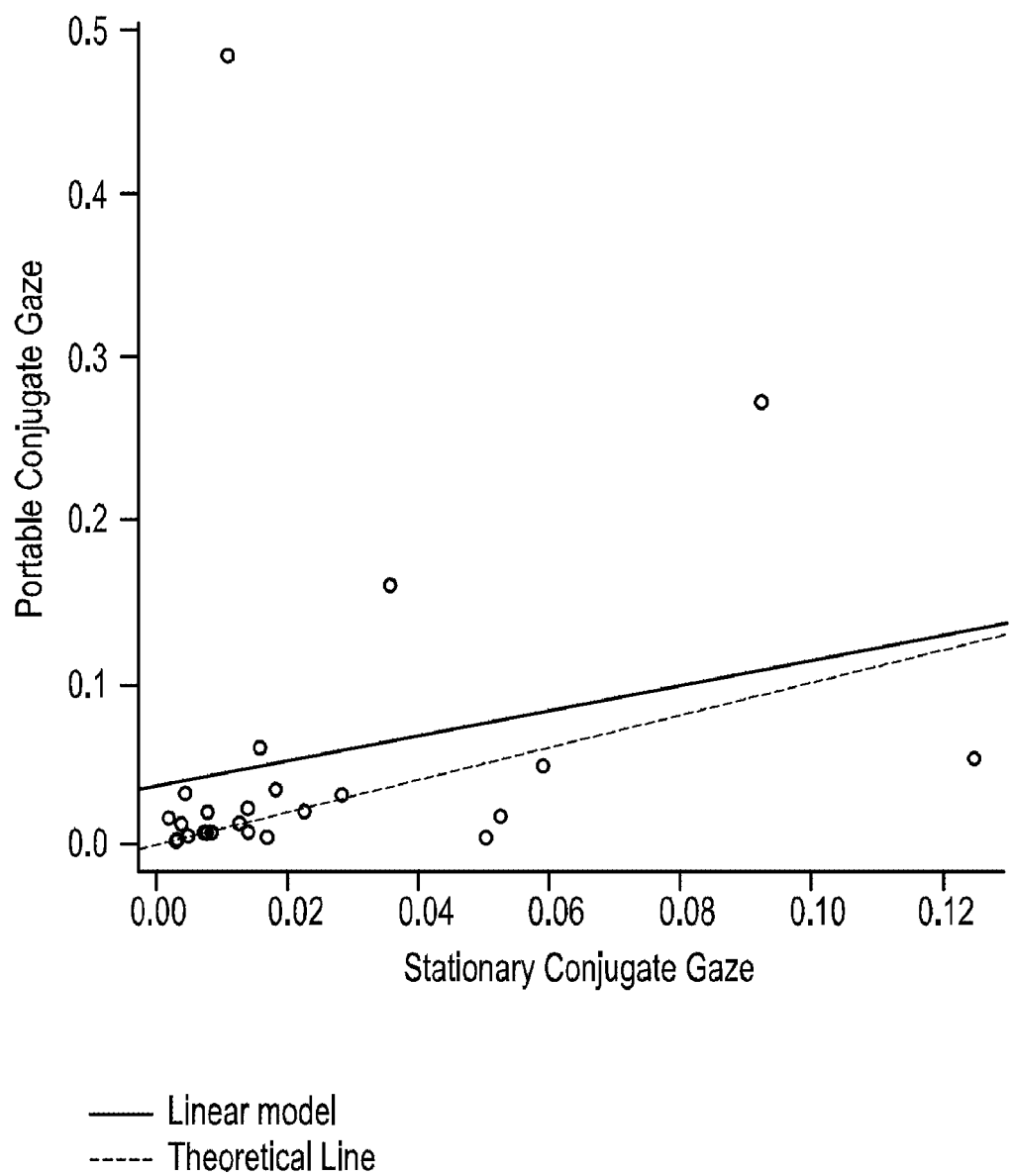
FIG. 7 demonstrates the test retest reliability of a stationary to portable tracker. Subjects (n=24) demonstrated high test-retest reliability between separate eyetracking sessions on the stationary tracker and the portable tracker. A paired t-test with 23 degrees of freedom (n=24), resulted in a t-statistic of 1.3661 and a p-value of 0.1851 showing that the mean of the subject-paired differences was not statistically significantly different from 0.
Figure 8:
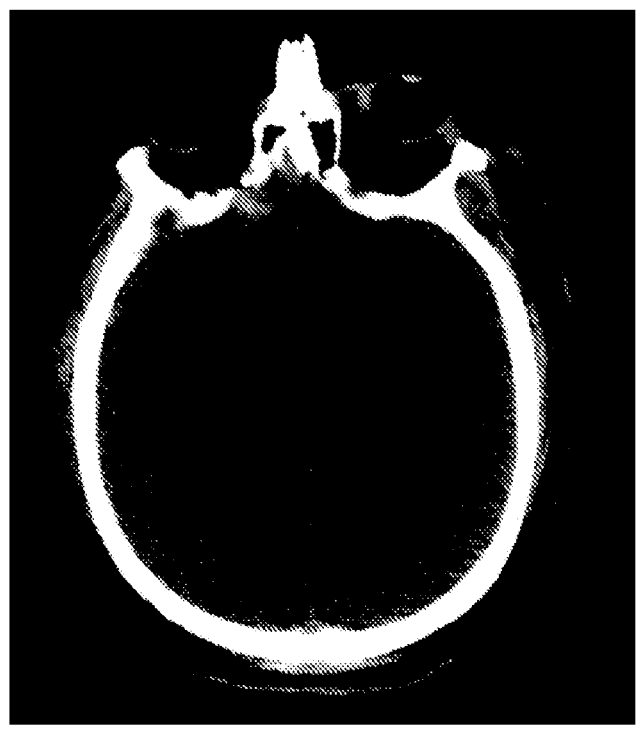
FIG. 8 represents findings from a 38 year old right-handed male recruited from the emergency room after being hit by a car while riding his bicycle. The patient was brought in with a backboard and C-collar, intoxicated with reported loss of consciousness and normal vitals but intermittent confusion with retrograde amnesia. On physical examination he was alert and oriented x3, had a right eye hematoma and a posterior vertex soft tissue hematoma. He had active bleeding over a 5 cm vertical laceration overlying the left maxilla. A. Head CT findings include bilateral parafalcine posterior vertex subdural hematomas measuring up to 8 mm in thickness. There were multiple punctuate-subcentimeter bifrontal contusions, right greater than left. There was a 4 mm left parafalcine subdural hematoma. He had no significant ophthalmic history following his last optometric visit 10 years prior. No other major body injuries. Quantitative serum alcohol level was 130 mg/dl. Medications administered up to 24 hours prior to recruitment included acetaminophen 325 mg, bacitracin, moxifloxacin hydrochloride. B. Represents eye movement tracking box plots 2 days after triage. The patient was positive for 12/22 symptoms according to SCAT3 with a severity score of 45/132 and GCS score of 13/15. Total SAC score of 17/30. C. Represent eye movement tracking box plots 13 days after triage. The patient was positive for 10/22 symptoms according to SCAT3 with a severity score of 27/132 and GCS score of 15/15. Total SAC score of 24/30. Medications administered up to 24 hours prior to eye tracking included ibuprofen.
Figure 8:
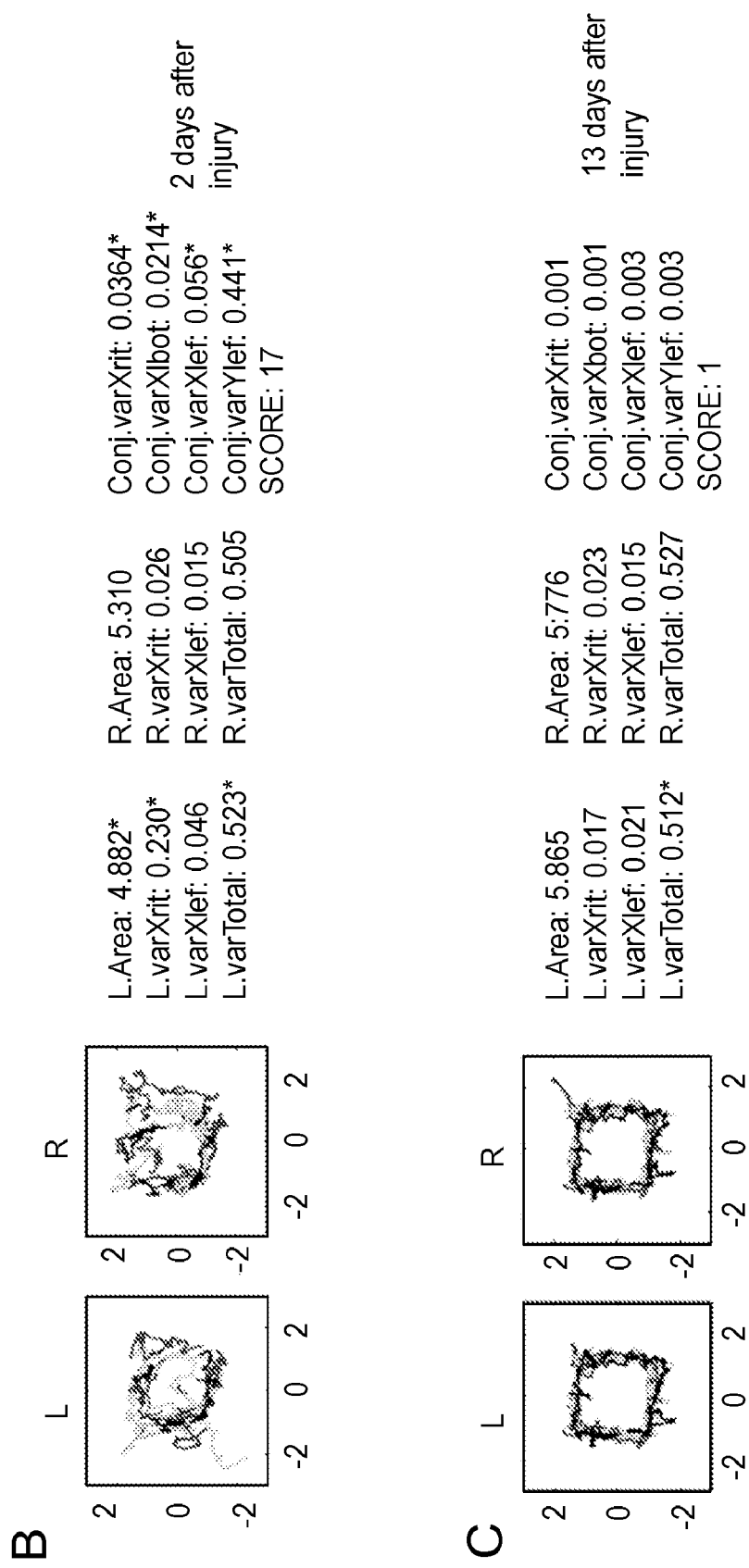
Figure 9:
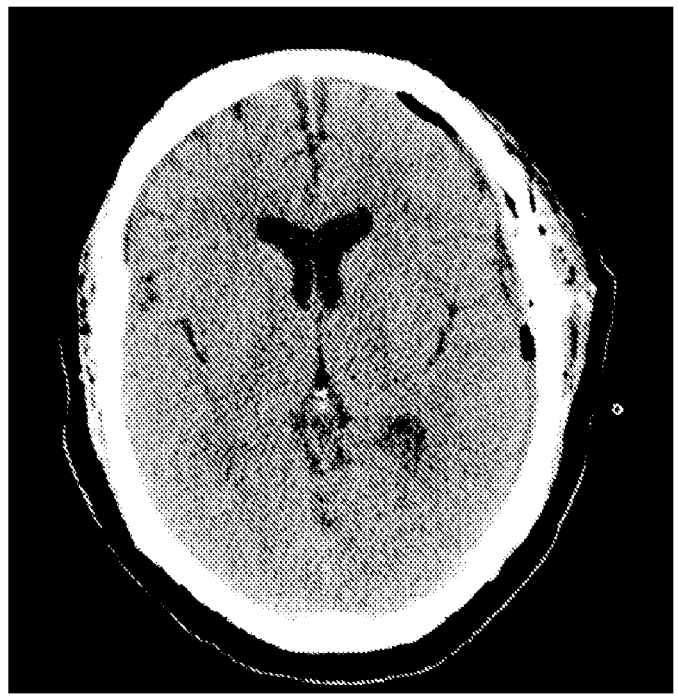
FIG. 9 represents findings from a 37 year old right-handed female. The patient fell 2 weeks prior to seeking medical care. She denied loss of consciousness at the time. After taking aspirin, she developed word finding difficulty 4 days prior to admission. She presented to the emergency room where her examination was otherwise non-focal. A. The head CT showed a mixed attenuation predominantly hyperdense subdural fluid collection over the left cerebral convexity measuring up to 1.7 cm in thickness with associated mass effect upon the left lateral ventricle and 7 mm left to right midline shift of the septum pellucidum. The patient underwent craniotomy and was recruited for the study from NSICU on the third postoperative day. She denied word finding difficulty and was neurologically non-focal at the time of recruitment and reported no ophthalmic history. Medications administered up to 24 hours prior to recruitment included Keppra, Ancef, Nexium, Heparin, Acetaminophen, Zofran. There were no drugs or alcohol reported for the past 24 hours. B. Represents eye movement tracking box plots 3 days post operatively and 17 days post injury patient. The patient was positive for 6/22 symptoms according to SCAT3 with a severity score of 17/132 and GCS score of 15/15. Total SAC score of 18/30. C. Represents eye movement tracking box plots at 35 days post surgery and 49 days post injury. The patient was positive for 13/22 symptoms according to SCAT3 with a severity score of 32/132 and GCS score of 15/15. Total SAC score of 27/30. No medications, drugs or alcohol 24 hours prior.
Figure 9:
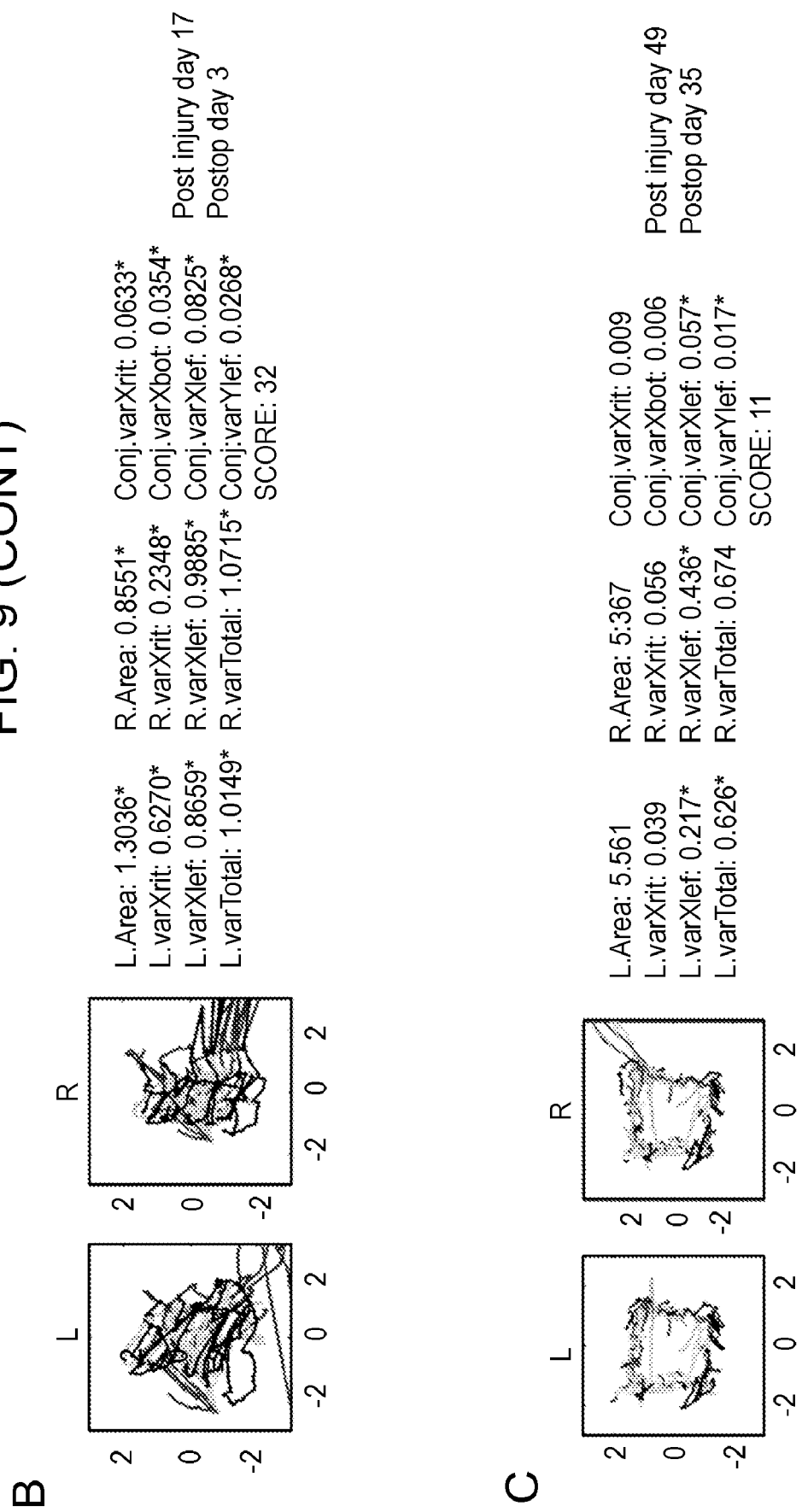
Figure 10:
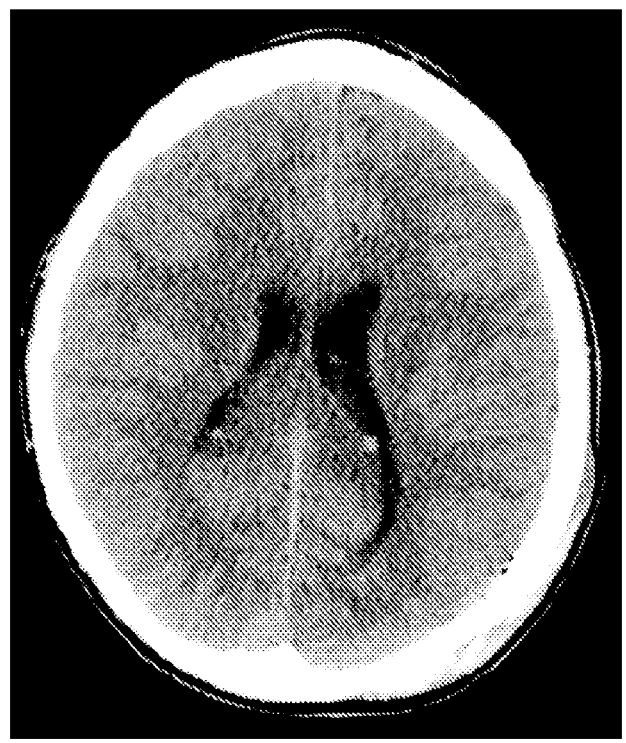
FIG. 10 represents findings from a 22 year old right-handed male recruited from the emergency room who was participating in a skateboard competition and experienced a fall from 10-15 feet landing on his unhelmeted head. He lost consciousness for approximately 30 minutes and then was agitated, confused and amnestic for the event. His trauma bay GCS was 15 and he had a moderate sized left scalp hematoma on physical examination. A. His head CT findings included a comminuted minimally displaced fracture of the left occipitoparietal bone with extension to the anterior aspect of the left temporal bone. There was also a small underlying left subdural hematoma with pneumocephalus. There was partial opacification of the left mastoid air cells, and a non-displaced fracture through the tympanic roof could not be completely excluded. He had no significant ophthalmic history other than eye pressure at the time of recruitment, and his last optometric visit was a year prior. His cranial trauma history included that 1.5 years ago he fell with loss of consciousness. Medications administered up to 24 hours prior to recruitment included levetiracetam 500 mg/100, 0.82% NaCl Premix, Ondansetron 4 mg/50 mL, Acetaminophen 325 mg. B. Represents eye movement tracking box plots 1 day after injury. The patient was positive for 13/22 SCAT3 symptoms with a severity score of 62/132 and GCS score of 14/15. The total SAC score was 19/30. C. Represents eye movement tracking box plots 12 days after injury. The patient was positive for 19/22 SCAT3 symptoms with a severity score of 81/132 and GCS score of 15/15. The total SAC score was 17/30. D. Represents eye movement tracking box plots 66 days after injury. The patient was positive for 19/22 SCAT3 symptoms with a severity score of 69/132 and GCS score of 15/15. The total SAC score was 24/30. No medications, drugs or alcohol were consumed in the 24 hours prior to tracking on any occasion.
Figure 11:
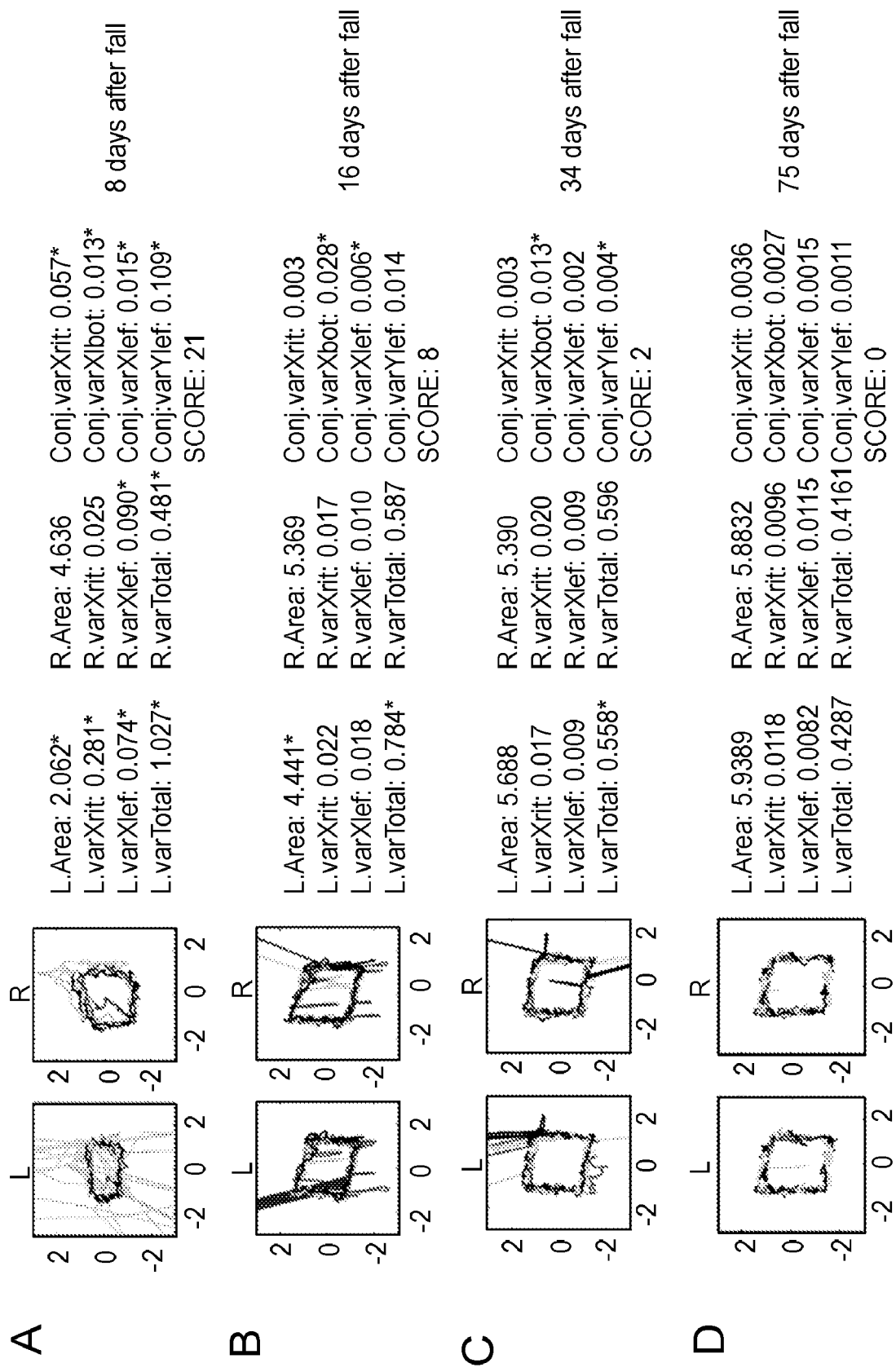
FIG. 11 represents the findings from a 23 year old right-handed male who fell from height of 30 feet. The Patient was awake, alert and hypotensive in the field, GCS 14. He reported diffuse pain including in head, no vomiting. The neurological examination was non-focal, but the patient was intubated for chest and pelvis injuries. He had no ophthalmic history other than an optometric visit 6 months prior. He wears corrective lenses for astigmatism and reports a learning disability. Medications administered within 24 hours prior to eye tracking included albuterol, vancomycin hydrochloride, piperacilin tazobactam, aztreonam, pentacel. A. Represents eye movement tracking box plots 8 days after injury. No SCAT was performed initially. B. Represents eye movement tracking box plots 16 days after injury. The patient was positive for 16/22 SCAT3 symptoms with a severity score of 18/132 and GCS of 15/15. Total SAC score of 22/30. C. Represents eye movement tracking box plots 34 days after injury. The patient was positive for 10/22 SCAT3 symptoms with a severity score of 27/132 and GCS of 15/15. Total SAC score of 22/30. D. Represents eye movement tracking box plots 75 days after injury. The patient was positive for 13/22 SCAT3 symptoms with a severity score of 39/132 and GCS of 15/15. Total SAC score of 26/30.
Figure 12:
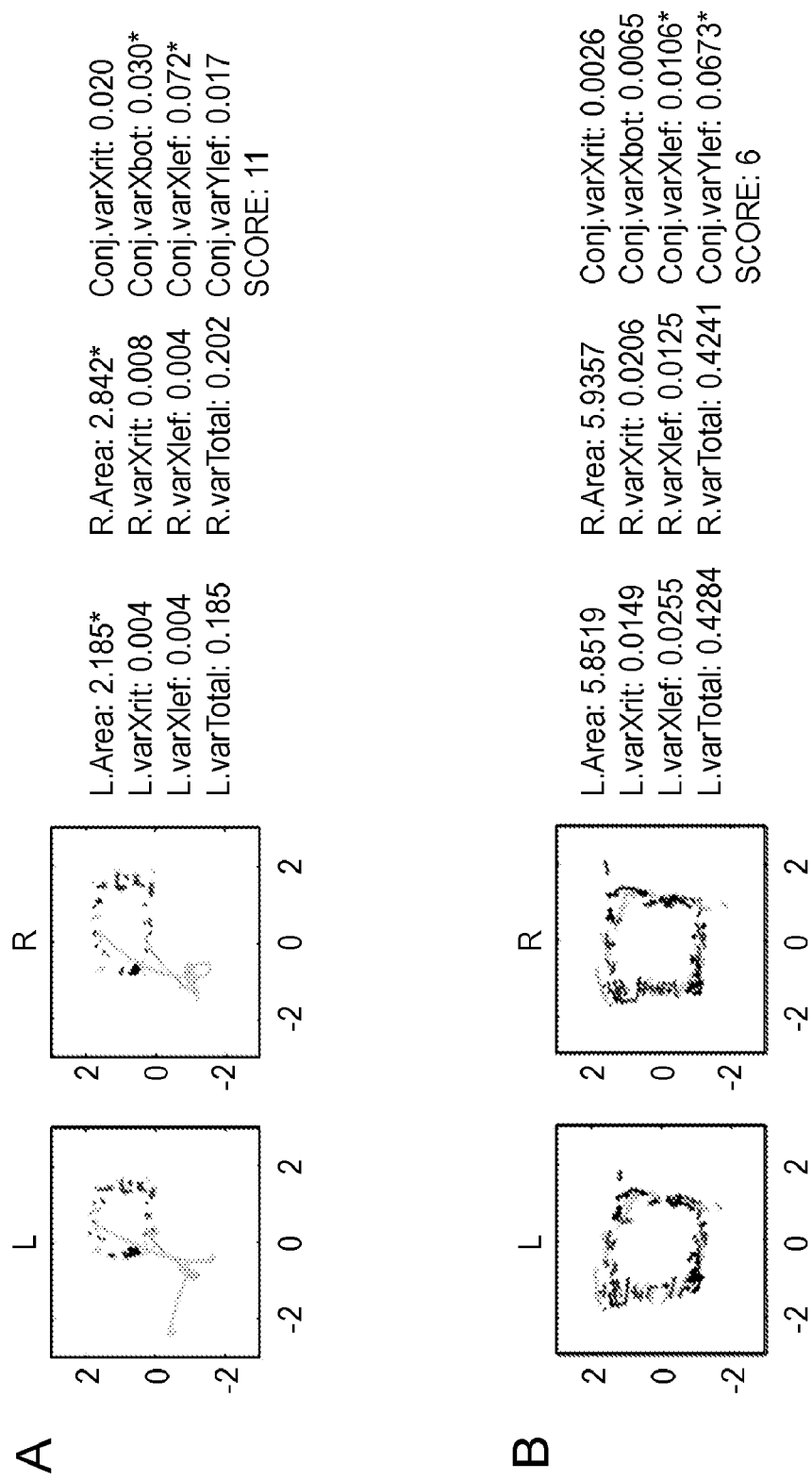
FIG. 12 represents the findings from a 47 year old right-handed male recruited from the emergency room. The patient was inebriated and crashed his bicycle into a parked truck. He was unhelmeted. He vomited and then became unresponsive. Upon arrival, he was intubated, GCS 3T. Radiograph revealed a broken clavicle. Quantitative serum alcohol level was 284 mg/dl. He had no ophthalmic history following an optometric visit many years ago. Upon recruitment 24 hours later the patient was extubated, alert and oriented x3. Medications administered up to 24 hours prior to recruitment included claritin and hydrocodone-acetaminophen, lidocaine, etomidate, and succinylcholine. A. Represents eye movement tracking box plots a few hours after triage. The patient was positive for 14/22 SCAT3 symptoms with a severity score of 72/132 and GCS score of 15/15. His total SAC score was 19/30. He reported feeling severely worse than baseline. B. Represents eye movement tracking box plots at 92 days post triage. The patient was positive for 10/22 SCAT3 symptoms with a severity score of 40/132 and GCS score of 15/15. His total SAC score was 21/30.

Subjects (n=24) demonstrated high test-retest reliability between separate eyetracking sessions on the stationary tracker and the portable tracker (FIG. 7). A paired t-test with 23 degrees of freedom (n=24), resulted in a t-statistic of 1.3661 and a p-value of 0.1851 showing that the mean of the subject-paired differences was not statistically significantly different from 0.

FIGS. 1 and 2 represent the eye tracking trajectories of subjects with normal eye movement.

EXAMPLE 4

Materials and Methods.

Four groups of subjects were selected as follows:

(1) subjects who have mild to moderate structural traumatic brain injury (TBI) as evidenced by CT scan demonstrating the presence of hemorrhage (subdural, epidural, subarachnoid or intraparenchymal), brain contusion, or skull fracture.

(2) non-structural TBI subjects (mild TBI/concussion), meaning they show no signs of structural injury on imaging; however, they complain of usual brain injury symptoms such as headache, dizziness, cognitive impairment, etc., A subject with mild traumatic brain injury is a person who has had a traumatically induced physiological disruption of brain function, as manifested by at least one of the following:

a. Any period of loss of consciousness (LOC).
 b. Any loss of memory for events immediately before or after the accident.
 c. Any alteration in mental state at the time of accident (i.e. feeling dazed, disoriented, or confused).
 d. Focal neurological deficit(s) that may or may not be transient, but where the severity of the injury does not exceed the following:
  1.) Loss of consciousness of approximately 30 minutes or less
  2.) After 30 minutes, an initial Glasgow Coma Scale (GCS) of 13-15
  3.) Posttraumatic amnesia (PTA) not greater than 24 hours.

(3) non-brain injured subjects that have suffered some type of injury such as to the extremities or other parts of the body. The subjects have sustained a blunt or penetrating trauma such as, to the corpus or extremities (i.e. car accident, falling, violent act excluding interpersonal violence).

(4) Healthy non injured control subjects were employees, volunteers, visitors and patients with intact ocular motility, and ability to provide a complete ophthalmologic, medical and neurologic history as well as medications/drugs/alcohol consumed within the 24 hours prior to tracking. Exclusion criteria included any minor brain injury regardless of loss of consciousness within the previous month.

Inclusion Criteria. All patients were recruited from the Bellevue Hospital Emergency Services (Emergency Room and Trauma Bay), trauma service and neurosurgery service. They were between the ages of 18 and 60, consentable and able/willing to participate and meet criteria for distribution into one of the three subject populations (structural TBI, non-structural TBI, injured/non-TBI) described above.

Exclusion Criteria. Subjects that received minor trauma insufficiently traumatizing to result in sufficient sequelae were excluded. Subjects suffering burns, anoxic injury or multiple/extensive injuries resulting in any medical, surgical or hemodynamic instability were also excluded. Particularly for the purposes of eye tracking all subjects that were blind (no light perception), missing eyes, and not opening eyes were excluded from the research. It is pertinent that subjects are able to detect light and have both eyes in order for the eye tracking data to be effective and significant. Any physical or mental injury or baseline disability rendering task completion difficult was excluded, also inability to participate in longtitudinal care, or obvious intoxication or blood alcohol level greater than 0.2. Pregnant individuals and prisoners were also excluded from the study. Subjects with a history of: strabismus, diplopia, palsy of cranial nerves III, IV or VI, papilledema, optic neuritis or other known disorder affecting cranial nerve II, macular edema, retinal degeneration, dementia or cognitive impairment, hydrocephalus, sarcoidosis, myasthenia gravis, multiple sclerosis or other demyelinating disease, and active or acute epilepsy, stroke/hemorrhage or prior brain injury sufficiently significant to result in hospitalization were also excluded.

Subjects underwent eye tracking and SCAT3 validated concussion outcome assessment as soon as possible after their injury, and then at regular intervals during recovery (1 week and 1 month).

Eye Tracking

A portable binocular eye movement tracker was constructed by attaching an adjustable arm to a rolling cart. A computer monitor was attached to the proximal portion of the arm, and a chinrest was attached to the distal aspect of the arm such that the chinrest centered the subject's eyes 55 cm away from the monitor.

Visual Stimulus. Subjects' eye movements were recorded with an Eyelink 1000 eye tracker over a time period of 220 seconds. Portable tracker subjects were seated in either a height adjustable or height-fixed chair or bed, with the monitor height adjusted to the subject. The visual stimuli were the music videos Shakira Waka-Waka, K'naan Wavin' Flag, Mission Kashmir Bhumbroo or Michael Jackson Man in the Mirror. The video was played continuously in a square aperture with an area approximately ⅛ the screen area while moving clockwise along the outer edges of the monitor for five complete cycles of 40 seconds each. The first and last 10 seconds of each data set were discarded to yield 200 seconds of data. The afferent stimulus was presented binocularly, and eye tracking was performed binocularly. Subjects were not spatially calibrated to the tracker to enable independent analysis of each pupil position over time.

Data Analysis. The eye tracker sampled pupil position at 500 Hz, yielding 100,000 samples over 200 seconds. Scatterplots of the entire time series were created by plotting the 100,000 (x,y) pairs representing the two orthogonal components of the instantaneous angle of pupil reflection over time to create 'box trajectories' that reflected the temporal nature of the pupillary movement. These figures look like boxes, reflecting the timing of the aperture as it moved around the screen.

Metrics: 51 eye-tracking parameters were measured per subject, looking at movement in each individual eye and conjugate movement between eyes. All data were analyzed using XLSTAT version 2012.6.02 (Addinsoft SARL, Paris, France) and MedCalc version 12.6.1 (MedCalc Software, Ostend, Belgium). A p-value of ≤0.05 was deemed as statistically significant.

Eye-tracking was performed on 46 patients and 31 controls. The patients were assigned to 1 of 4 groups (+CT n=13, −CT n=23, corpus injury n=10, and healthy control). Eye-tracking parameters were compared among the 4 groups using the Kruskal-Wallis test and multiple pairwise were performed using the Steel-Dwass-Crichlow-Fligner procedure to compare individual groups against controls.

The sports concussion assessment tool (SCAT) was administered, and standardized assessment of concussion (SAC) scores were obtained on thirty-seven subjects. Stepwise multiple regression analysis was performed to evaluate the impact of each eye-tracking parameter on the SCAT and SAC scores. Parameters with p-values >0.1 were removed from the model.

Results

Table 4 provides group means for each of the 51 measured parameters.

TABLE 4

Summary statistics

| Variable | n | Minimum | Maximum | Mean | Std. deviation |
|---|---|---|---|---|---|
| L.Aspect Ratio\|Corpus only | 10 | 0.961 | 1.643 | 1.388 | 0.207 |
| L.Aspect Ratio\|−CT | 22 | 0.089 | 1.614 | 0.940 | 0.316 |
| L.Aspect Ratio\|+CT | 12 | 0.944 | 1.896 | 1.111 | 0.253 |
| L.Aspect Ratio\|Control | 31 | 0.951 | 1.104 | 1.010 | 0.034 |
| L.Height\|Corpus only | 10 | 2.058 | 3.799 | 2.478 | 0.483 |
| L.Height\|−CT | 23 | −0.597 | 2.502 | 1.841 | 0.855 |
| L.Height\|+CT | 12 | 0.768 | 2.502 | 2.178 | 0.518 |
| L.Height\|Control | 31 | 1.830 | 2.578 | 2.387 | 0.163 |
| L.Width\|Corpus only | 10 | 1.874 | 2.452 | 2.289 | 0.197 |
| L.Width\|−CT | 22 | −1.222 | 2.486 | 1.876 | 0.898 |
| L.Width\|+CT | 12 | −1.464 | 2.358 | 1.838 | 1.021 |
| L.Width\|Control | 31 | 1.794 | 2.463 | 2.363 | 0.140 |
| L.Area\|Corpus only | 10 | 3.265 | 10.724 | 5.755 | 1.935 |
| L.Area\|−CT | 22 | −10.924 | 6.048 | 3.289 | 4.087 |
| L.Area\|+CT | 12 | −1.037 | 5.885 | 4.675 | 2.098 |
| L.Area\|Control | 31 | 3.283 | 6.503 | 5.379 | 0.321 |
| L.SkewTopNorm\|Corpus only | 10 | −0.290 | 0.083 | −0.109 | 0.109 |
| L.SkewTopNorm\|−CT | 23 | −0.336 | 0.203 | −0.063 | 0.132 |
| L.SkewTopNorm\|+CT | 13 | −0.361 | 0.238 | −0.057 | 0.172 |
| L.SkewTopNorm\|Control | 31 | −0.457 | 0.131 | −0.169 | 0.151 |
| L.SkewTop\|Corpus only | 10 | −0.148 | 0.008 | −0.030 | 0.015 |
| L.SkewTop\|−CT | 23 | −0.207 | 0.163 | −0.024 | 0.071 |
| L.SkewTop\|+CT | 13 | −0.323 | 0.060 | −0.034 | 0.096 |
| L.SkewTop\|Control | 31 | −0.187 | 0.053 | −0.027 | 0.040 |
| L.SkewRitNorm\|Corpus only | 10 | −0.425 | 0.007 | −0.167 | 0.131 |
| L.SkewRitNorm\|−CT | 23 | −0.688 | 0.183 | −0.095 | 0.193 |
| L.SkewRitNorm\|+CT | 13 | −0.549 | 0.265 | −0.051 | 0.206 |
| L.SkewRitNorm\|Control | 31 | −0.470 | 0.221 | −0.074 | 0.173 |
| L.SkewRitNorm\|Corpus only | 10 | −0.263 | −0.001 | −0.051 | 0.091 |
| L.SkewRitNorm\|−CT | 23 | −0.163 | 0.051 | −0.028 | 0.058 |
| L.SkewRitNorm\|+CT | 13 | −0.427 | 0.046 | −0.048 | 0.123 |
| L.SkewRit\|Control | 31 | −0.189 | 0.033 | −0.018 | 0.037 |
| L.SkewBotNorm\|Corpus only | 10 | −0.258 | 0.380 | −0.027 | 0.187 |
| L.SkewBotNorm\|−CT | 23 | 0.383 | 0.345 | −0.099 | 0.192 |
| L.SkewBotNorm\|+CT | 12 | −0.282 | 0.213 | 0.016 | 0.166 |
| L.SkewBotNorm\|Control | 31 | −0.539 | 0.264 | −0.058 | 0.171 |
| L.SkewBot\|Corpus only | 10 | −0.029 | 0.252 | 0.022 | 0.096 |
| L.SkewBot\|−CT | 23 | −0.235 | 0.128 | −0.034 | 0.083 |
| L.SkewBot\|+CT | 12 | −0.050 | 0.094 | 0.014 | 0.046 |
| L.SkewBot\|Control | 31 | −0.034 | 0.084 | −0.067 | 0.028 |
| L.SkewlefNorm\|Corpus only | 10 | −0.206 | 0.154 | 0.031 | 0.111 |
| L.SkewlefNorm\|−CT | 23 | −0.475 | 0.307 | −0.043 | 0.170 |
| L.SkewlefNorm\|+CT | 12 | −0.212 | 0.480 | 0.067 | 0.176 |
| L.SkewlefNorm\|Control | 31 | −0.321 | 0.333 | 0.006 | 0.180 |
| L.Skewlef\|Corpus only | 10 | −0.011 | 0.069 | 0.01 | 0.022 |
| L.Skewlef\|−CT | 23 | −0.276 | 0.306 | −0.001 | 0.110 |
| L.Skewlef\|+CT | 12 | −0.112 | 0.168 | 0.022 | 0.072 |
| L.Skewlef\|Control | 31 | −0.037 | 0.150 | 0.005 | 0.001 |
| L.varYtop\|Corpus only | 10 | 0.000 | 0.279 | 0.076 | 0.095 |
| L.varYtop\|−CT | 23 | 0.000 | 2.200 | 0.308 | 0.498 |
| L.varYtop\|+CT | 13 | 0.025 | 0.798 | 0.141 | 0.225 |
| L.varYtop\|Control | 31 | 0.001 | 0.898 | 0.065 | 0.158 |
| L.varXtit\|Corpus only | 10 | 0.002 | 0.749 | 0.133 | 0.272 |

TABLE 4-continued

Summary statistics

| Variable | n | Minimum | Maximum | Mean | Std. deviation |
|---|---|---|---|---|---|
| L.varXtit\|−CT | 23 | 0.004 | 3.337 | 0.259 | 0.702 |
| L.varXtit\|+CT | 13 | 0.005 | 1.049 | 0.192 | 0.306 |
| L.varXtit\|Control | 31 | 0.004 | 0.164 | 0.025 | 0.338 |
| L.varYbot\|Corpus only | 10 | 0.006 | 0.774 | 0.155 | 0.270 |
| L.varYbot\|−CT | 23 | 0.001 | 1.087 | 0.201 | 0.350 |
| L.varYbot\|+CT | 12 | 0.005 | 0.202 | 0.068 | 0.065 |
| L.varYbot\|Control | 31 | 0.005 | 0.325 | 0.042 | 0.063 |
| L.varXlef\|Corpus only | 10 | 0.007 | 0.204 | 0.036 | 0.060 |
| L.varXlef\|−CT | 23 | 0.005 | 1.167 | 0.218 | 0.324 |
| L.varXlef\|+CT | 12 | 0.007 | 0.665 | 0.169 | 0.221 |
| L.varXlef\|Control | 31 | 0.004 | 0.165 | 0.022 | 0.029 |
| L.varTotal\|Corpus only | 10 | 0.065 | 1.021 | 0.403 | 0.373 |
| L.varTotal\|−CT | 23 | 0.059 | 5.290 | 0.947 | 1.171 |
| L.varTotal\|+CT | 13 | 0.052 | 2.242 | 0.690 | 0.550 |
| L.varTotal\|Control | 31 | 0.024 | 1.252 | 0.218 | 0.259 |
| Conj varX\|Corpus only | 10 | 0.001 | 0.026 | 0.009 | 0.009 |
| Conj varX\|−CT | 23 | 0.001 | 0.476 | 0.046 | 0.103 |
| Conj varX\|+CT | 13 | 0.001 | 0.432 | 0.079 | 0.119 |
| Conj varX\|Control | 31 | 0.001 | 0.055 | 0.010 | 0.013 |
| Conj varXtop\|Corpus only | 10 | 0.001 | 0.035 | 0.009 | 0.010 |
| Conj varXtop\|−CT | 23 | 0.001 | 0.195 | 0.027 | 0.049 |
| Conj varXtop\|+CT | 13 | 0.002 | 0.413 | 0.062 | 0.122 |
| Conj varXtop\|Control | 31 | 0.001 | 0.044 | 0.007 | 0.008 |
| Conj varXrit\|Corpus only | 10 | 0.000 | 0.023 | 0.005 | 0.007 |
| Conj varXrit\|−CT | 23 | 0.000 | 0.132 | 0.025 | 0.077 |
| Conj varXrit\|+CT | 13 | 0.001 | 0.364 | 0.072 | 0.111 |
| Conj varXrit\|Control | 31 | 0.000 | 0.093 | 0.010 | 0.021 |
| Conj varXbot\|Corpus only | 10 | 0.000 | 0.069 | 0.011 | 0.021 |
| Conj varXbot\|−CT | 23 | 0.000 | 0.456 | 0.036 | 0.106 |
| Conj varXbot\|+CT | 12 | 0.001 | 0.095 | 0.109 | 0.205 |
| Conj varXbot\|Control | 31 | 0.000 | 0.034 | 0.004 | 0.006 |
| Conj varXlef\|Corpus only | 10 | 0.000 | 0.012 | 0.003 | 0.004 |
| Conj varXlef\|−CT | 23 | 0.000 | 0.205 | 0.019 | 0.046 |
| Conj varXlef\|+CT | 12 | 0.001 | 0.572 | 0.073 | 0.160 |
| Conj varXlef\|Control | 31 | 0.600 | 0.010 | 0.002 | 0.002 |
| Conj varY\|Corpus only | 10 | 0.002 | 0.109 | 0.032 | 0.043 |
| Conj varY\|−CT | 23 | 0.004 | 0.733 | 0.085 | 0.176 |
| Conj varY\|+CT | 13 | 0.002 | 0.357 | 0.086 | 0.121 |
| Conj varY\|Control | 31 | 0.001 | 0.229 | 0.036 | 0.056 |
| Conj varYtop\|Corpus only | 10 | 0.003 | 0.796 | 0.089 | 0.249 |
| Conj varYtop\|−CT | 23 | 0.002 | 1.129 | 0.100 | 0.250 |
| Conj varYtop\|+CT | 13 | 0.002 | 0.685 | 0.111 | 0.212 |
| Conj varYtop\|Control | 31 | 0.001 | 0.491 | 0.046 | 0.097 |
| Conj varYrit\|Corpus only | 10 | 0.002 | 0.111 | 0.028 | 0.042 |
| Conj varYrit\|−CT | 23 | 0.001 | 0.358 | 0.050 | 0.088 |
| Conj varYrit\|+CT | 13 | 0.001 | 0.246 | 0.059 | 0.078 |
| Conj varYrit\|Control | 31 | 0.001 | 0.450 | 0.032 | 0.099 |
| Conj varYbot\|Corpus only | 10 | 0.000 | 0.270 | 0.031 | 0.084 |
| Conj varYbot\|−CT | 23 | 0.000 | 0.962 | 0.068 | 0.203 |
| Conj varYbot\|−CT | 12 | 0.001 | 0.410 | 0.059 | 0.119 |
| Conj varYbot\|Control | 31 | 0.000 | 0.249 | 0.013 | 0.028 |
| Conj varYlef\|Corpus only | 10 | 0.000 | 0.037 | 0.011 | 0.012 |
| Conj varYlef\|−CT | 23 | 0.001 | 1.396 | 0.025 | 0.289 |
| Conj varYlef\|+CT | 12 | 0.002 | 0.441 | 0.065 | 0.126 |
| Conj varYlef\|Control | 31 | 0.800 | 0.036 | 0.006 | 0.003 |
| Conj lotVar\|Corpus only | 19 | 0.003 | 0.333 | 0.041 | 0.049 |
| Conj lotVar\|−CT | 23 | 0.006 | 0.335 | 0.131 | 0.347 |
| Conj lotVar\|+CT | 13 | 0.003 | 0.789 | 0.166 | 0.222 |
| Conj lotVar\|Control | 31 | 0.003 | 0.272 | 0.046 | 0.065 |
| Conj CorrXY\|Corpus only | 8 | −0.187 | 0.564 | 0.032 | 0.226 |
| Conj CorrXY\|−CT | 19 | −0.311 | 0.524 | −0.009 | 0.286 |
| Conj CorrXY\|+CT | 12 | −0.252 | 0.060 | −0.023 | 0.685 |
| Conj CorrXY\|Control | 30 | −0.324 | 0.621 | −0.032 | 0.321 |
| Conj CorrXYtop\|Corpus only | 4 | −0.336 | 0.686 | 0.238 | 0.536 |
| Conj CorrXYtop\|−CT | 10 | −0.956 | 0.935 | 0.105 | 0.628 |
| Conj CorrXYtop\|+CT | 3 | −0.228 | 0.103 | −0.033 | 0.166 |
| Conj CorrXYtop\|Control | 23 | −0.803 | 0.820 | 0.066 | 0.545 |
| Conj CorrXYrit\|Corpus only | 4 | −0.506 | 0.685 | −0.020 | 0.505 |
| Conj CorrXYrit\|−CT | 10 | −0.834 | 0.535 | −0.326 | 0.424 |
| Conj CorrXYrit\|+CT | 2 | 0.157 | 0.335 | 0.247 | 0.128 |
| Conj CorrXYrit\|Control | 23 | −0.983 | 0.327 | −0.288 | 0.191 |
| Conj CorrXYbot\|Corpus only | 4 | −0.691 | 0.429 | 0.017 | 0.493 |
| Conj CorrXYbot\|−CT | 7 | −0.907 | 0.704 | −0.166 | 0.573 |
| Conj CorrXYbot\|+CT | 3 | −0.264 | 0.021 | 0.234 | 0.453 |
| Conj CorrXYbot\|Control | 24 | −0.948 | 0.957 | −0.152 | 0.621 |
| Conj CorrXYlef\|Corpus only | 4 | −0.553 | 0.129 | −0.162 | 0.289 |

TABLE 4-continued

Summary statistics

| Variable | n | Minimum | Maximum | Mean | Std. deviation |
|---|---|---|---|---|---|
| Conj CorrXYlef\|−CT | 9 | −0.708 | 0.240 | 0.098 | 0.620 |
| Conj CorrXYlef\|+CT | 3 | −0.210 | 0.613 | 0.243 | 0.417 |
| Conj CorrXYlef\|Control | 24 | −0.823 | 0.942 | 0.078 | 0.620 |
| Conj varXtopbotRatio\|Corpus only | 10 | 0.132 | 20.531 | 2.889 | 6.923 |
| Conj varXtopbotRatio\|−CT | 23 | 0.505 | 30.325 | 5.719 | 4.726 |
| Conj varXtopbotRatio\|+CT | 12 | 0.052 | 13.072 | 2.187 | 3.694 |
| Conj varXtopbotRatio\|Control | 31 | 0.272 | 23.023 | 3.694 | 2.098 |
| Conj varYtopbotRatio\|Corpus only | 10 | 0.036 | 36.220 | 14.147 | 26.741 |
| Conj varYtopbotRatio\|−CT | 23 | 0.072 | 29.052 | 4.674 | 7.287 |
| Conj varYtopbotRatio\|+CT | 12 | 0.258 | 21.781 | 3.156 | 6.004 |
| Conj varYtopbotRatio\|Control | 31 | 0.099 | 62.984 | 9.846 | 15.751 |
| Conj varXlefritRatio\|Corpus only | 10 | 0.033 | 7.522 | 1.382 | 2.198 |
| Conj varXlefritRatio\|−CT | 23 | 0.027 | 5.017 | 1.176 | 1.584 |
| Conj varXlefritRatio\|+CT | 12 | 0.073 | 6.814 | 1.991 | 2.408 |
| Conj varXlefritRatio\|Control | 31 | 0.031 | 5.415 | 0.999 | 1.348 |
| Conj varYlefritRatio\|Corpus only | 10 | 0.138 | 3.160 | 0.893 | 0.909 |
| Conj varYlefritRatio\|−CT | 23 | 0.092 | 49.468 | 3.009 | 10.185 |
| Conj varYlefritRatio\|+CT | 12 | 0.227 | 7.013 | 1.716 | 1.899 |
| Conj varYlefritRatio\|Control | 31 | 0.015 | 3.351 | 1.011 | 1.033 |
| R.Aspect Ratio\|Corpus only | 10 | 0.948 | 2.073 | 1.133 | 0.338 |
| R.Aspect Ratio\|−CT | 22 | −0.920 | 9.401 | 1.297 | 1.881 |
| R.Aspect Ratio\|+CT | 12 | 0.558 | 2.196 | 1.187 | 0.441 |
| R.Aspect Ratio\|Control | 31 | 0.829 | 1.090 | 0.995 | 0.062 |
| R.Height\|Corpus only | 10 | 2.100 | 4.782 | 2.594 | 0.768 |
| R.Height\|−CT | 23 | −0.517 | 2.638 | 1.957 | 0.734 |
| R.Height\|+CT | 12 | 2.134 | 2.553 | 2.223 | 0.471 |
| R.Height\|Control | 31 | 1.692 | 2.547 | 2.342 | 0.189 |
| R.Width\|Corpus only | 10 | 1.845 | 2.459 | 2.303 | 0.189 |
| R.Width\|−CT | 22 | −1.293 | 2.522 | 1.819 | 0.961 |
| R.Width\|+CT | 12 | −2.852 | 2.398 | 1.653 | 1.493 |
| R.Width\|Control | 31 | 1.758 | 2.457 | 2.354 | 0.116 |
| R.Area\|Corpus only | 10 | 3.875 | 3.445 | 5.636 | 1.205 |
| R.Area\|−CT | 22 | −3.462 | 3.977 | 3.841 | 2.588 |
| R.Area\|+CT | 12 | −3.241 | 5.642 | 4.125 | 2.743 |
| R.Area\|Control | 31 | 1.782 | 11.738 | 5.590 | 1.491 |
| R.SkewTopNorm\|Corpus only | 10 | −0.247 | 0.050 | −0.120 | 0.109 |
| R.SkewTopNorm\|−CT | 23 | −0.492 | 0.227 | −0.099 | 0.213 |
| R.SkewTopNorm\|+CT | 13 | −0.507 | 0.115 | −0.118 | 0.153 |
| R.SkewTopNorm\|Control | 31 | −0.487 | 0.164 | −0.141 | 0.169 |
| R.SkewTop\|Corpus only | 10 | −0.127 | 0.007 | −0.031 | 0.039 |
| R.SkewTop\|−CT | 23 | −0.156 | 0.168 | −0.031 | 0.105 |
| R.SkewTop\|+CT | 13 | −0.296 | 0.021 | −0.036 | 0.082 |
| R.SkewTop\|Control | 31 | −0.198 | 0.030 | −0.025 | 0.046 |
| R.SkewRitNorm\|Corpus only | 10 | −0.432 | 0.027 | −0.097 | 0.141 |
| R.SkewRitNorm\|−CT | 23 | −0.615 | 0.255 | −0.036 | 0.202 |
| R.SkewRitNorm\|+CT | 13 | −0.541 | 0.295 | −0.016 | 0.203 |
| R.SkewRitNorm\|−Control | 31 | −0.440 | 0.264 | −0.035 | 0.195 |
| R.SkewRitNorm\|Corpus only | 10 | −0.182 | 0.002 | −0.036 | 0.065 |
| R.SkewRitNorm\|−CT | 23 | −0.140 | 0.135 | −0.002 | 0.059 |
| R.SkewRitNorm\|+CT | 13 | −0.389 | 0.145 | −0.034 | 0.125 |
| R.SkewRit\|Control | 31 | −0.192 | 0.080 | −0.007 | 0.043 |
| R.SkewBotNorm\|Corpus only | 10 | −0.231 | 0.355 | 0.000 | 0.157 |
| R.SkewBotNorm\|−CT | 23 | −0.397 | 0.373 | −0.048 | 0.201 |
| R.SkewBotNorm\|+CT | 12 | −0.287 | 0.195 | −0.090 | 0.255 |
| R.SkewBotNorm\|Control | 31 | −0.391 | 0.326 | −0.021 | 0.387 |
| R.SkewBot\|Corpus only | 10 | −0.029 | 0.257 | 0.019 | 0.085 |
| R.SkewBot\|−CT | 23 | −0.163 | 0.136 | −0.007 | 0.072 |
| R.SkewBot\|+CT | 12 | −0.074 | 0.038 | −0.014 | 0.030 |
| R.SkewBot\|Control | 31 | −0.214 | 0.095 | −0.008 | 0.046 |
| R.SkewlefNorm\|Corpus only | 10 | −0.145 | 0.126 | −0.009 | 0.098 |
| R.SkewlefNorm\|−CT | 23 | −0.670 | 0.359 | −0.069 | 0.218 |
| R.SkewlefNorm\|+CT | 12 | −0.580 | 0.238 | 0.027 | 0.137 |
| R.SkewlefNorm\|Control | 31 | −0.482 | 0.387 | 0.019 | 0.195 |
| R.Skewlef\|Corpus only | 10 | −0.008 | 0.075 | 0.007 | 0.025 |
| R.Skewlef\|−CT | 23 | −0.515 | 0.461 | −0.014 | 0.162 |
| R.Skewlef\|+CT | 12 | −0.063 | 0.100 | 0.015 | 0.043 |
| R.Skewlef\|Control | 31 | −0.089 | 0.159 | 0.004 | 0.037 |
| R.varYtop\|Corpus only | 10 | 0.000 | 0.287 | 0.072 | 0.089 |
| R.varYtop\|−CT | 23 | 0.012 | 0.930 | 0.232 | 0.292 |
| R.varYtop\|+CT | 13 | 0.015 | 0.341 | 0.100 | 0.117 |
| R.varYtop\|Control | 31 | 0.007 | 1.465 | 0.097 | 0.264 |
| R.varXtit\|Corpus only | 10 | 0.006 | 0.584 | 0.113 | 0.214 |
| R.varXtit\|−CT | 23 | 0.002 | 0.633 | 0.146 | 0.387 |
| R.varXtit\|+CT | 13 | 0.003 | 1.217 | 0.325 | 0.463 |
| R.varXtit\|Control | 31 | 0.005 | 0.444 | 0.042 | 0.089 |
| R.varYbot\|Corpus only | 10 | 0.003 | 0.478 | 0.084 | 0.143 |

TABLE 4-continued

Summary statistics

| Variable | n | Minimum | Maximum | Mean | Std. deviation |
|---|---|---|---|---|---|
| R.varYbot\|−CT | 23 | 0.008 | 2.629 | 0.235 | 0.573 |
| R.varYbot\|+CT | 12 | 0.011 | 0.231 | 0.059 | 0.063 |
| R.varYbot\|Control | 31 | 0.005 | 1.531 | 0.084 | 0.271 |
| R.varXlef\|Corpus only | 10 | 0.008 | 0.236 | 0.038 | 0.070 |
| R.varXlef\|−CT | 23 | 0.005 | 2.152 | 0.302 | 0.341 |
| R.varXlef\|+CT | 12 | 0.006 | 0.859 | 0.143 | 0.255 |
| R.varXlef\|Control | 31 | 0.004 | 0.155 | 0.021 | 0.031 |
| R.varTotal\|Corpus only | 10 | 0.076 | 0.893 | 0.417 | 0.292 |
| R.varTotal\|−CT | 23 | 0.064 | 3.816 | 0.937 | 0.573 |
| R.varTotal\|+CT | 13 | 0.039 | 2.894 | 0.820 | 0.831 |
| R.varTotal\|Control | 31 | 0.028 | 1.565 | 0.312 | 0.371 |

Table 5 provides p-values. Ten of the 51 measured parameters demonstrated statistically significant differences between negative controls (either normal healthy people, or corporally injured but not brain injured controls) and both positive controls (structurally brain injured) and non-structurally brain injured people. 8 additional parameters showed statistically significant differences between negative controls (healthy normal people and corporally injured trauma patients) and patients with either structural or non-structural brain injury. 10 of the eye tracking measures showed statistically significant correlation between SCAT or SAC scores, suggesting that these eye tracking parameters correlated with a validated clinical outcome measure.

| | Corpus | CT− | CT+ | SCAT | SAC |
|---|---|---|---|---|---|
| L.Aspect Ratio | 0.962 | 0.365 | 0.125 | 0.0028 | |
| L.Height | 0.845 | 0.011 | 0.280 | | |
| L.Width | 0.873 | 0.161 | 0.001 | | |
| L.Area | 0.427 | 0.001 | 0.004 | 0.0288 | |
| L.SkewTopNorm | 0.656 | 0.064 | 0.305 | | 0.0030 |
| L.SkewTop | 0.993 | 0.776 | 0.709 | <0.0001 | |
| L.SkewRitNorm | 0.482 | 0.996 | 0.989 | | |
| L.SkewRit | 0.356 | 0.924 | 0.993 | | |
| L.SkewBotNorm | 0.999 | 0.840 | 0.494 | | |
| L.SkewBot | 0.998 | 0.694 | 0.529 | 0.0027 | |
| L.SkewLefNorm | 0.896 | 0.725 | 0.822 | | |
| L.SkewLef | 0.712 | 0.617 | 0.666 | | |
| L.varYtop | 0.766 | 0.073 | 0.059 | | |
| L.varXrit | 0.987 | 0.009 | 0.005 | | |
| L.varYbot | 0.845 | 0.330 | 0.219 | | |
| L.varXlef | 0.962 | 0.009 | 0.005 | 0.0255 | |
| L.varTotal | 0.145 | 0.801 | 0.003 | | |
| R.Aspect Ratio | 0.712 | 0.666 | 0.111 | | |
| R.Height | 1.000 | 0.024 | 0.666 | | |
| R.Width | 0.999 | 0.088 | 0.002 | | |
| R.Area | 0.694 | 0.025 | 0.010 | | |
| R.SkewTopNorm | 0.974 | 0.864 | 0.938 | | |
| R.SkewTop | 0.398 | 1.000 | 1.000 | <0.0001 | |
| R.SkewRitNorm | 0.712 | 1.000 | 0.992 | | |
| R.SkewRit | 0.482 | 0.925 | 0.995 | | |
| R.SkewBotNorm | 0.962 | 0.955 | 0.748 | | |
| R.SkewBot | 0.995 | 0.986 | 0.779 | | |
| R.SkewLefNorm | 0.955 | 0.339 | 0.998 | | |
| R.SkewLef | 0.998 | 0.359 | 0.836 | | |
| R.varYtop | 0.766 | 0.028 | 0.498 | | |
| R.varXrit | 0.987 | 0.011 | 0.011 | <0.0001 | |
| R.varYbot | 0.198 | 0.102 | 0.411 | | |
| R.varXlef | 0.675 | 0.002 | 0.017 | 0.0003 | |
| R.varTotal | 0.236 | 0.001 | 0.027 | | |
| Conj varX | 0.999 | 0.086 | 0.011 | | |
| Conj varXtop | 0.898 | 0.174 | 0.131 | | |
| Conj varXrit | 0.998 | 0.021 | 0.016 | | |
| Conj varXbot | 0.830 | 0.053 | 0.002 | | |
| Conj varXlef | 0.999 | 0.033 | 0.003 | 0.0002 | |
| Conj varY | 0.939 | 0.814 | 0.547 | | |
| Conj varYtop | 0.948 | 0.988 | 0.964 | | 0.0095 |
| Conj varYrit | 0.637 | 0.151 | 0.081 | | |
| Conj varYbot | 0.995 | 0.339 | 0.303 | | |
| Conj varYlef | 0.308 | 0.086 | 0.006 | | 0.0011 |
| Conj totVar | 0.993 | 0.550 | 0.676 | | |
| Conj CorrXY | 0.876 | 0.977 | 1.000 | | |
| Conj CorrXYtop | 0.934 | 0.966 | 0.904 | | |
| Conj CorrXYrit | 0.175 | 0.999 | 0.377 | | |
| Conj CorrXYbot | 0.953 | 1.000 | 0.702 | | |
| Conj CorrXYlef | 0.953 | 1.000 | 0.980 | | |
| Conj varXtopbotRatio | 0.979 | 0.848 | 0.098 | | |
| Conj varYtopbotRatio | 1.000 | 0.483 | 0.197 | | |
| Conj varXlefritRatio | 0.873 | 0.986 | 0.808 | | |

These data demonstrate the usefulness of these mathematical algorithms to detect and quantitate the extent of structural and non-structural brain injury.

EXAMPLE 5

The results and data demonstrate the effect of methadone on eye movements assessed during watching a short film clip. This methodology was established using the narcotic methadone. Methadone is one of the mu opioid receptor binding drugs, which include morphine, heroin, fentanyl, and morphine 6-β-glucuronide (M6G). This class of narcotics has a complex mechanism of action, may not bind to a single receptor and have differences in their potency, effectiveness, and tolerability among patients (Pasternak, *Pain Med* 13 Suppl 2012; 1:S4a-11).

Methods

The same eye tracking algorithm was performed with a binocular eye tracker as described above, including in Example 4. The same eye tracking algorithm may also be performed with a monocular eye tracker.

Calculating Velocity. The coordinates of the pupil at time 1 are $x_1$, $y_1$ and at time 2 are $x_2$, $y_2$ The distance ($z_1$) traveled by the pupil between times 1 and 2 may be determined as the square root of:

$$(x_2-x_1)^2+(y_2-y_1)^2$$

The sum of the z's may be obtained to obtain the distance traveled by the eye pupil over any time period of interest. The sum of the z's over 10 second intervals may be obtained to look at the distance traveled during each segment of the rectangular box trajectory. Pupil velocity may be determined by dividing by the amount of time in seconds.

Whether eye pupil velocities change in different directions eye movement reflected in a box trajectory travels around the box. A $z_{total}$, $z_{top}$, $z_{left}$, $z_{right}$, $z_{bottom}$ with reference to the box trajectory may be provided for each eye. Groups may then be compared using the Wilcoxon statistical analysis.

Results

The eye tracking velocity of 93 methadone patients when compared to 100 controls demonstrates that when the aperture moves clockwise around a rectangular box trajectory, movement in the left eye on ¾ box trajectories is slower in methadone patients than in control subjects. The top segment of the box trajectory was the most significantly different between methadone patients and controls:

The p-values for velocity comparison in control and methadone groups is provided below in Table 6.

TABLE 6

| S. NO | Segment | P-Value |
|---|---|---|
| 1 | Left Eye Top | 0.000352 |
| 2 | Left Eye Right | 0.580132 |
| 3 | Left Eye Bottom | 0.027431 |
| 4 | Left Eye Left | 0.046586 |
| 5 | Right Eye Top | 0.001296 |
| 6 | Right Eye Right | 0.211476 |
| 7 | Right Eye Bottom | 0.147633 |
| 8 | Right Eye Left | 0.078633 |

The eye tracking velocity was measured in 53 chronic methadone consuming patients before and after administration of their daily dosage of methadone. The top trajectory of the box was most sensitive to an individual dose of methadone.

The p-values for before and after methadone velocity calculations are provided below in Table 7.

TABLE 7

| S. NO | Segment | P-Value |
|---|---|---|
| 1 | Left Eye Top | 0.090069 |
| 2 | Left Eye Right | 0.765767 |
| 3 | Left Eye Bottom | 0.807321 |
| 4 | Left Eye Left | 0.881353 |
| 5 | Right Eye Top | 0.072061 |
| 6 | Right Eye Right | 0.179416 |
| 7 | Right Eye Bottom | 0.319482 |
| 8 | Right Eye Left | 0.524585 |

Discussion

The results provided above demonstrate that methadone decreases the velocity of eye movements. The results provided above further demonstrate that methadone decreases the velocity of eye movements in the top segment of the box trajectory more so than in the other segments of the box trajectory. These results demonstrate that eye movement tracking while watching a short film clip can detect narcosis.

EXAMPLE 6

Eye movement tracking was performed in 80 methadone patients and 116 controls generally in accordance with the procedures set forth herein including in Examples 4 and 5. Observations of the metrics measured in methadone patients are provided in Table 8. The p-values are included demonstrating the difference in 51 metrics of eye movement measured between 80 methadone patients and 116 controls. Skew and variability were most affected.

TABLE 8

| Variable | Observations | Minimum | Maximum | Mean | Std. deviation | |
|---|---|---|---|---|---|---|
| L.Aspect Ratio|0 | 80 | 0.847 | 1.654 | 1.020 | 0.082 | 1 |
| L.Aspect Ratio|1 | 116 | −3.573 | 1.791 | 0.964 | 0.465 | 0.048 |
| L.Height|0 | 80 | 1.723 | 2.547 | 2.341 | 0.168 | 1 |
| L.Height|1 | 116 | 1.027 | 2.761 | 2.364 | 0.213 | 0.374 |
| L.Width|0 | 80 | 0.999 | 2.464 | 2.312 | 0.211 | 1 |
| L.Width|1 | 116 | −1.443 | 2.649 | 2.315 | 0.446 | 0.008 |
| L.Area|0 | 80 | 1.738 | 6.245 | 5.442 | 0.755 | 1 |
| L.Area|1 | 116 | −1.482 | 6.675 | 5.550 | 0.959 | 0.199 |
| L.SkewTopNorm|0 | 80 | −0.418 | 0.228 | −0.091 | 0.136 | 1 |
| L.SkewTopNorm|1 | 116 | −0.270 | 0.392 | −0.007 | 0.127 | <0.0001 |
| L.SkewTop|0 | 80 | −0.190 | 0.117 | −0.021 | 0.045 | 1 |
| L.SkewTop|1 | 116 | −0.108 | 0.289 | 0.003 | 0.041 | <0.0001 |
| L.SkewRitNorm|0 | 80 | −0.493 | 0.221 | −0.087 | 0.163 | 1 |
| L.SkewRitNorm|1 | 116 | −0.233 | 0.269 | −0.004 | 0.110 | 0.001 |
| L.SkewRit|0 | 80 | −0.233 | 0.033 | −0.023 | 0.049 | 1 |
| L.SkewRit|1 | 116 | −0.119 | 0.077 | −0.002 | 0.027 | 0.001 |
| L.SkewBotNorm|0 | 80 | −0.250 | 0.397 | 0.023 | 0.140 | 1 |
| L.SkewBotNorm|1 | 116 | −0.518 | 0.226 | −0.004 | 0.118 | 0.277 |
| L.SkewBot|0 | 80 | −0.080 | 0.337 | 0.009 | 0.052 | 1 |
| L.SkewBot|1 | 116 | −0.132 | 0.147 | −0.001 | 0.025 | 0.420 |
| L.SkewLetNorm|0 | 80 | −0.272 | 0.522 | 0.111 | 0.166 | 1 |
| L.SkewLefNorm|1 | 116 | −0.305 | 0.295 | 0.015 | 0.108 | <0.0001 |
| L.SkewLef|0 | 80 | −0.114 | 0.226 | 0.023 | 0.050 | 1 |
| L.SkewLef|1 | 116 | −0.102 | 0.210 | 0.004 | 0.031 | <0.0001 |
| L.varYtop|0 | 80 | 0.003 | 0.256 | 0.050 | 0.054 | 1 |
| L.varYtop|1 | 116 | 0.004 | 0.876 | 0.047 | 0.106 | 0.005 |
| L.varXrit|0 | 80 | 0.004 | 1.172 | 0.044 | 0.134 | 1 |
| L.varXrit|1 | 116 | 0.005 | 0.910 | 0.039 | 0.093 | 0.229 |
| L.varYbot|0 | 80 | 0.004 | 1.123 | 0.048 | 0.128 | 1 |
| L.varYbot|1 | 116 | 0.001 | 0.563 | 0.030 | 0.068 | 0.006 |
| L.varXlef|0 | 80 | 0.003 | 0.919 | 0.045 | 0.112 | 1 |
| L.varXlef|1 | 116 | 0.006 | 0.680 | 0.046 | 0.110 | 0.451 |
| L.varTotal|0 | 80 | 0.258 | 1.223 | 0.479 | 0.116 | 1 |
| L.varTotal|1 | 116 | 0.330 | 1.316 | 0.526 | 0.104 | <0.0001 |
| R.Aspect Ratio|0 | 80 | 0.725 | 1.476 | 1.013 | 0.076 | 1 |
| R.Aspect Ratio|1 | 116 | −3.791 | 1.996 | 0.970 | 0.495 | 0.381 |

TABLE 8-continued

| Variable | Observations | Minimum | Maximum | Mean | Std. deviation | |
|---|---|---|---|---|---|---|
| R.Height\|0 | 80 | 1.617 | 2.485 | 2.323 | 0.185 | 1 |
| R.Height\|1 | 116 | 1.008 | 2.616 | 2.355 | 0.192 | 0.411 |
| R.Width\|0 | 80 | 1.603 | 2.467 | 2.305 | 0.172 | 1 |
| R.Width\|1 | 116 | −1.291 | 2.524 | 2.302 | 0.438 | 0.024 |
| R.Area\|0 | 80 | 2.637 | 6.061 | 5.376 | 0.703 | 1 |
| R.Area\|1 | 116 | −1.423 | 6.190 | 5.497 | 0.944 | 0.156 |
| R.SkewTopNorm\|0 | 80 | −0.500 | 0.238 | −0.115 | 0.150 | 1 |
| R.SkewTopNorm\|1 | 116 | −0.283 | 0.424 | −0.004 | 0.147 | <0.0001 |
| R.SkewTop\|0 | 80 | −0.198 | 0.094 | −0.025 | 0.043 | 1 |
| R.SkewTop\|1 | 116 | −0.078 | 0.255 | 0.004 | 0.044 | <0.0001 |
| R.SkewRitNorm\|0 | 80 | −0.529 | 0.334 | −0.072 | 0.182 | 1 |
| R.SkewRitNorm\|1 | 116 | −0.286 | 0.395 | 0.013 | 0.115 | 0.001 |
| R.SkewRit\|0 | 80 | −0.249 | 0.213 | −0.017 | 0.060 | 1 |
| R.SkewRit\|1 | 116 | −0.083 | 0.119 | 0.006 | 0.027 | 0.001 |
| R.SkewBotNorm\|0 | 80 | −0.263 | 0.388 | −0.004 | 0.147 | 1 |
| R.SkewBotNorm\|1 | 116 | −0.280 | 0.273 | −0.023 | 0.112 | 0.665 |
| R.SkewBot\|0 | 80 | −0.061 | 0.340 | 0.010 | 0.063 | 1 |
| R.SkewBot\|1 | 116 | −0.051 | 0.060 | −0.002 | 0.019 | 0.682 |
| R.SkewLefNorm\|0 | 80 | −0.198 | 0.522 | 0.109 | 0.159 | 1 |
| R.SkewLefNorm\|1 | 116 | −0.251 | 0.322 | 0.025 | 0.111 | 0.000 |
| R.SkewLef\|0 | 80 | −0.019 | 0.210 | 0.026 | 0.047 | 1 |
| R.SkewLef\|1 | 116 | −0.041 | 0.287 | 0.011 | 0.042 | 0.002 |
| R.varYtop\|0 | 80 | 0.007 | 0.397 | 0.053 | 0.067 | 1 |
| R.varYtop\|1 | 116 | 0.005 | 0.879 | 0.043 | 0.091 | 0.003 |
| R.varXrit\|0 | 80 | 0.006 | 0.577 | 0.057 | 0.109 | 1 |
| R.varXrit\|1 | 116 | 0.006 | 0.889 | 0.048 | 0.109 | 0.601 |
| R.varYbot\|0 | 80 | 0.005 | 2.031 | 0.085 | 0.282 | 1 |
| R.varYbot\|1 | 116 | 0.002 | 0.581 | 0.031 | 0.073 | 0.002 |
| r.varXlef\|0 | 80 | 0.004 | 0.442 | 0.039 | 0.066 | 1 |
| r.varXlef\|1 | 116 | 0.006 | 1.193 | 0.050 | 0.137 | 0.447 |
| R.varTotal\|0 | 80 | 0.259 | 1.189 | 0.492 | 0.123 | 1 |
| R.varTotal\|1 | 116 | 0.333 | 1.352 | 0.537 | 0.118 | <0.0001 |
| Conj varX\|0 | 80 | 0.000 | 0.328 | 0.010 | 0.040 | 1 |
| Conj varX\|1 | 116 | 0.000 | 0.138 | 0.012 | 0.021 | 0.001 |
| Conj varXtop 0 | 80 | 0.000 | 0.186 | 0.007 | 0.021 | 1 |
| Conj varXtop 1 | 116 | 0.001 | 0.200 | 0.014 | 0.030 | 0.027 |
| Conj varXrit\|0 | 80 | 0.000 | 1.074 | 0.020 | 0.121 | 1 |
| Conj varXrit\|1 | 116 | 0.000 | 0.162 | 0.010 | 0.022 | 0.071 |
| Conj varXbot\|0 | 80 | 0.000 | 0.251 | 0.007 | 0.029 | 1 |
| Conj varXbot\|1 | 116 | 0.000 | 0.232 | 0.013 | 0.029 | <0.0001 |
| Conj varXrit\|0 | 80 | 0.000 | 0.157 | 0.006 | 0.023 | 1 |
| Conj varXrit\|1 | 116 | 0.000 | 0.110 | 0.009 | 0.019 | 0.000 |
| Conj varY\|0 | 80 | 0.001 | 0.148 | 0.022 | 0.033 | 1 |
| Conj varY\|1 | 116 | 0.001 | 0.125 | 0.012 | 0.016 | 0.044 |
| Conj varYtop\|0 | 80 | 0.000 | 0.280 | 0.017 | 0.036 | 1 |
| Conj varYtop\|1 | 116 | 0.000 | 0.273 | 0.012 | 0.028 | 0.076 |
| Conj varYrit\|0 | 80 | 0.001 | 0.460 | 0.032 | 0.073 | 1 |
| Conj varYrit\|1 | 116 | 0.001 | 0.172 | 0.017 | 0.025 | 0.188 |
| Conj varYbot\|0 | 80 | 0.000 | 0.386 | 0.022 | 0.061 | 1 |
| Conj varYbot\|1 | 116 | 0.000 | 0.118 | 0.008 | 0.016 | 0.514 |
| Conj varYrit\|0 | 80 | 0.001 | 0.156 | 0.017 | 0.025 | 1 |
| Conj varYrit\|1 | 116 | 0.001 | 0.112 | 0.012 | 0.017 | 0.161 |
| Conj totVar\|0 | 80 | 0.002 | 0.454 | 0.032 | 0.064 | 1 |
| Conj tolVar\|1 | 116 | 0.002 | 0.177 | 0.024 | 0.031 | 0.880 |
| Conj CorrXY\|0 | 80 | −0.052 | 0.109 | 0.003 | 0.016 | 1 |
| Conj CorrXY\|1 | 116 | −0.016 | 0.056 | 0.000 | 0.006 | 0.144 |
| Conj varXtopbotRatio\|0 | 80 | 0.179 | 19.432 | 2.469 | 3.016 | 1 |
| Conj varXtopbotRatio\|1 | 116 | 0.042 | 32.506 | 2.199 | 3.631 | 0.071 |
| Conj varYtopbotRatio\|0 | 80 | 0.055 | 304.849 | 9.665 | 35.251 | 1 |
| Conj varYtopbotRalio\|1 | 116 | 0.016 | 90.616 | 4.741 | 10.397 | 0.836 |
| Conj varXlefritRatio\|0 | 80 | 0.017 | 19.894 | 1.800 | 2.827 | 1 |
| Conj varXlefritRatio\|1 | 116 | 0.028 | 39.405 | 2.597 | 4.995 | 0.076 |
| Conj varYlefritRatio\|0 | 80 | 0.013 | 22.554 | 1.671 | 3.199 | 1 |
| Conj varYlefritRatio\|1 | 116 | 0.040 | 8.671 | 1.041 | 1.066 | 0.931 |
| BOX SCORE\|0 | 80 | 0.000 | 27.000 | 3.525 | 5.356 | 1 |
| BOX SCORE\|1 | 116 | 0.000 | 29.000 | 4.060 | 5.556 | 0.062 |

EXAMPLE 7

Internuclear Ophthalmoplegia

A 65 year old male presented to the emergency room with acute onset of double vision. On examination he had L to R nystagmus, and L impaired adduction on rightward gaze. He was diagnosed in the ophthalmology clinic with INO due to a midbrain ischemic stroke. Binocular afferent eye tracking was performed and revealed abnormal aspect ratios and conjugacy (FIG. 19). Monocular afferent eye tracking was performed and revealed normal aspect ratios (FIGS. 20 and 21).

EXAMPLE 8

Infranuclear Nerve Palsies

A 61 year old female presented with a tumor affecting her L VIth and IIIrd nerves as confirmed by ophthalmic examination. Binocular afferent tracking was performed and revealed abnormal aspect rations and conjugacy (FIG. 22). Monocular afferent eye tracking was performed and revealed abnormal aspect ratios (FIGS. 23, 24).

EXAMPLE 9

Materials and Methods

Mild cognitive impairment subjects were recruited from a private neurologic practice to which they were referred for suspicion of dementia. Subjects were evaluated with standard clinical dementia assessment measures in addition to eye tracking measures and compared to an age matched control group.

Data analysis was performed using SAS version 9.3. Data from TOBII and EYELINK trackers were analyzed separately. Wilcoxon rank-sum two sample test was used to compare the eye-tracking parameters between the normal control group and the asymptomatic group. The Wilcoxon test is a non-parametric test comparing the distributions of two groups and it does not require the assumption of normality. To get more accurate results, the exact Wilcoxon test was used to obtain the two-sided p-values. Statistical significance was claimed when the p-value was less than 0.05. A significant result indicated a difference between the groups.

Results

Figure 26A:
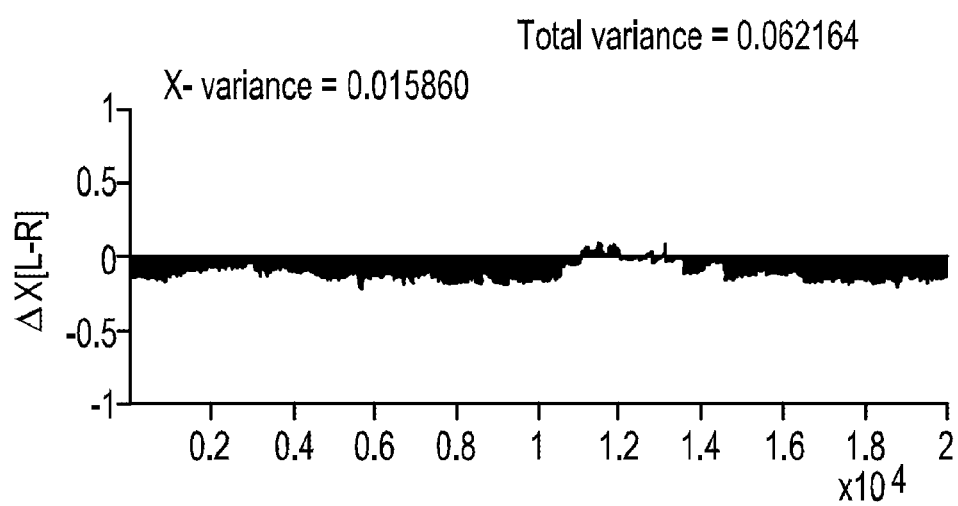
FIG. 26 demonstrates the conjugacy of left and right eye movement represented by $\Delta x$ (FIG. 26A) and $\Delta y$ (FIG. 26B) for the 1.9 year old male subject with ADHD tracked binocularly demonstrated in FIG. 25.
Figure 26B:
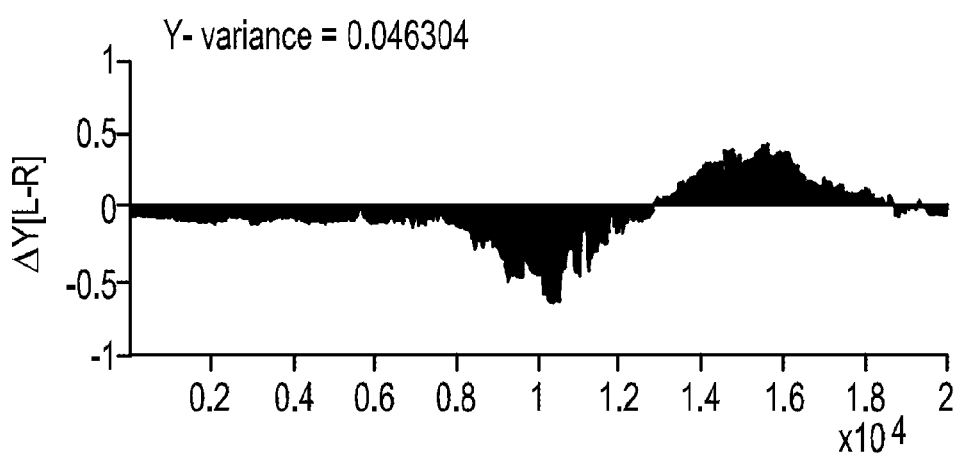
Figure 28A:
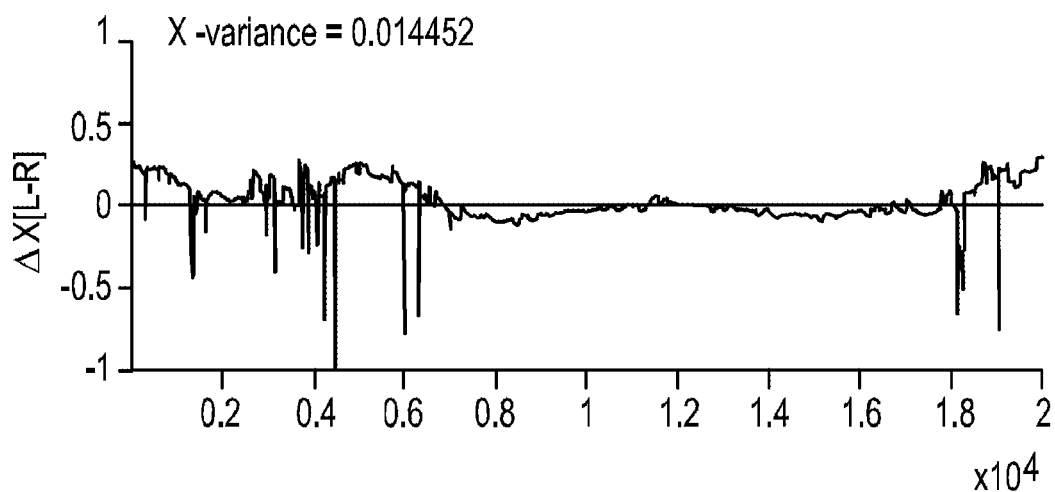
FIG. 28 demonstrates the conjugacy of left and right eye movement represented by $\Delta x$ (FIG. 28A) and $\Delta y$ (FIG. 28B) for the 19 year old male subject with ADHD tracked binocularly demonstrated in FIG. 27.
Figure 28B:
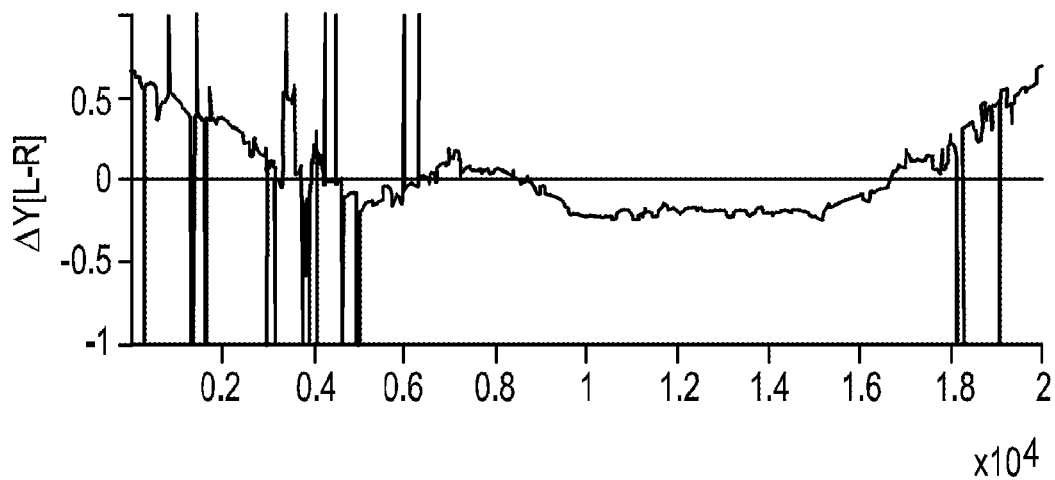

ADHD Cases 1 and 2: Both patients are 19 year old males, and both were diagnosed in childhood with ADHD which is currently controlled by medication. The eye movement tracking of case 1 is demonstrated in FIG. 25 (FIG. 25A, left eye; FIG. 25B right eye). The aspect ratio is provided for each eye. FIG. 26 demonstrates the conjugacy of left and right eye movement of case 1 represented by Δx (FIG. 26A) and Δy (FIG. 26B). FIG. 27 represents the eye-box trajectories of case 2 (FIG. 27A, left eye; FIG. 27B right eye). The aspect ratio is provided for each eye. FIG. 28 demonstrates the conjugacy of left and right eye movement of case 2 represented by Δx (FIG. 28A) and Δy (FIG. 28B).

Figure 13:
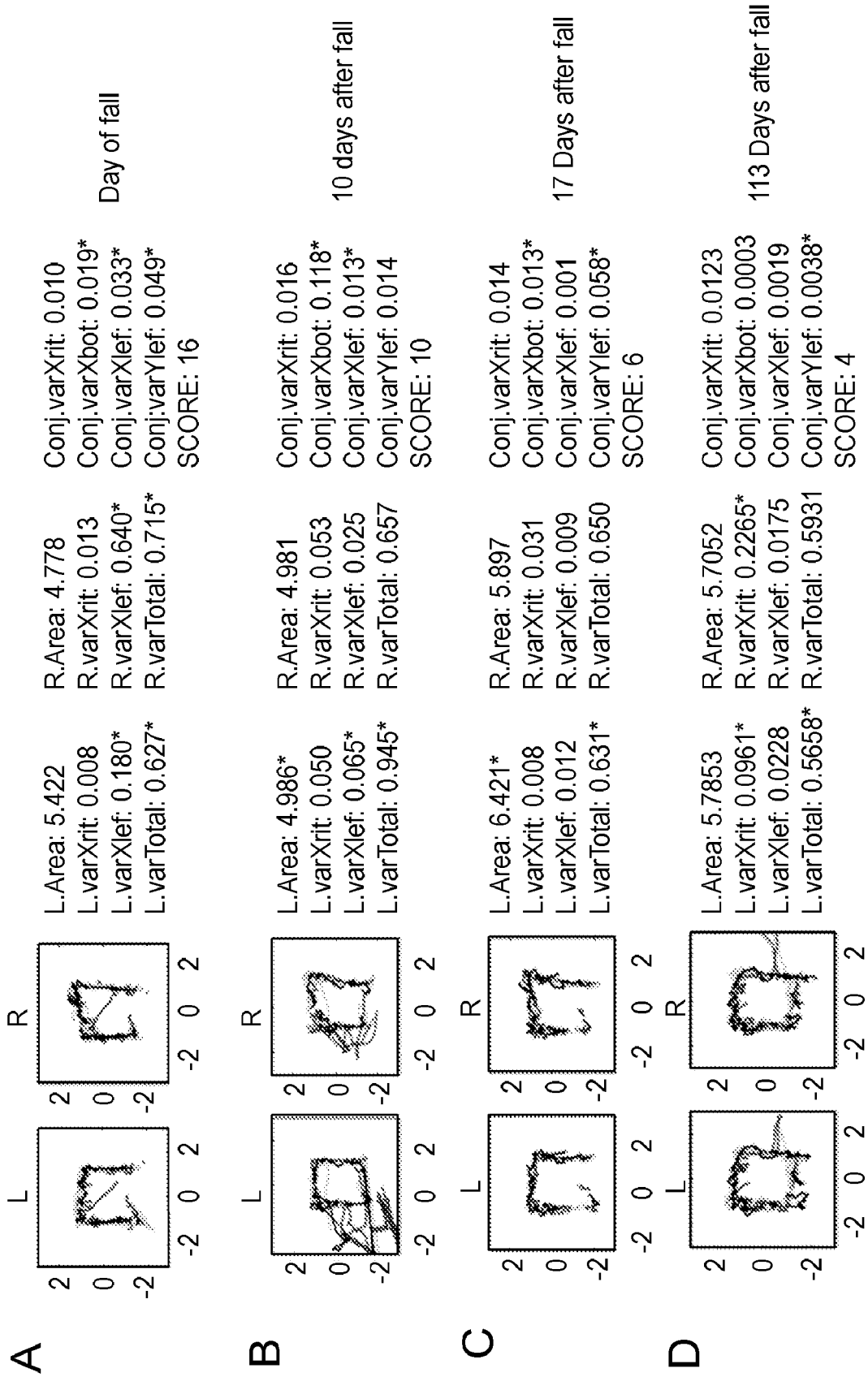
FIG. 13 represents the findings from a 53 year old right-handed female recruited from the ER after falling on the street down bus steps, impacting her face. She denied loss of conscious or amnesia and presented immobilized with cervical collar. On examination she had a lip laceration. She had a medical history significant for migraines and bitemporal hemianopsia due to benign pituitary adenoma. Head CT showed moderate multifocal white matter disease to right putamen, posteriorly in the right caudate head and left frontal corona radiate, maybe ischemic in origin, and bilateral proptosis. Her last optometric visit was one month prior to recruitment, and she wears corrective lenses and bifocal contact in right eye. Medications administered up to 24 hours prior to recruitment included diovan, lidocaine, hydrochloide 600 mg, acetaminphen 650 mg, vitamins, and tylenol. A. Represents eye movement tracking box plots a few hours after triage. The patient was positive for 16/22 SCAT3 symptoms with a severity score of 40/132 and GCS score of 15/15. The total SAC score was 23/30. B. Represents eye movement tracking box plots at 10 days post injury. The patient was positive for 4/22 SCAT3 symptoms with a severity score of 17/132 and GCS of 15/15. The total SAC score was 20/30. C. Represents eye movement tracking box plots 17 days post injury. D. Represents eye movement tracking box plots at 113 days post injury. The patient was positive for 16/22 SCAT3 symptoms with a severity score of 48/132 and GCS score of 15/15. The total SAC score was 27/30.
Figure 14:
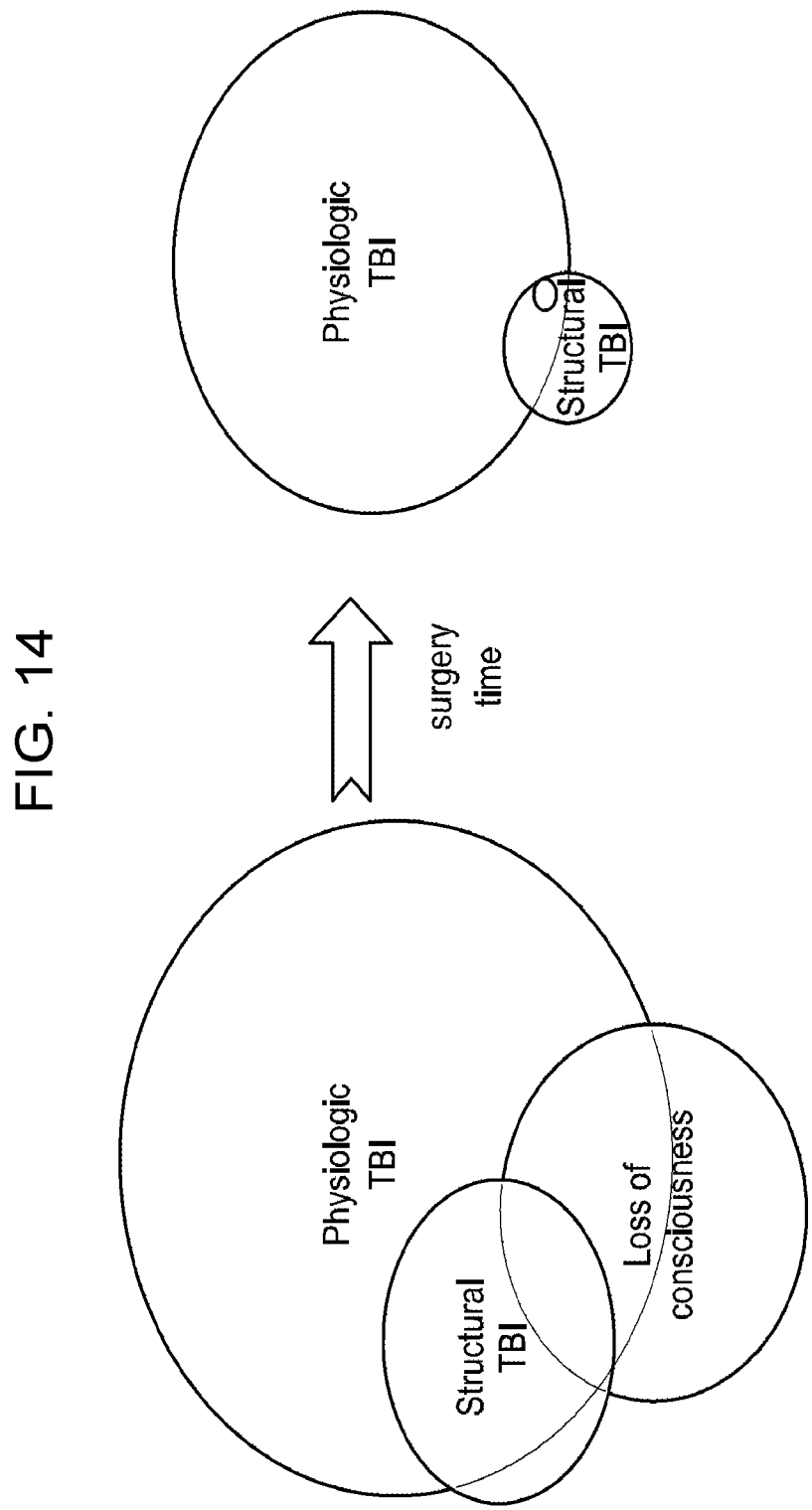
FIG. 14 represents graphically that while MRI and CT can detect structural traumatic brain injury (TBI), eye tracking can detect physiologic disruption of cerebral function.
Figure 15:
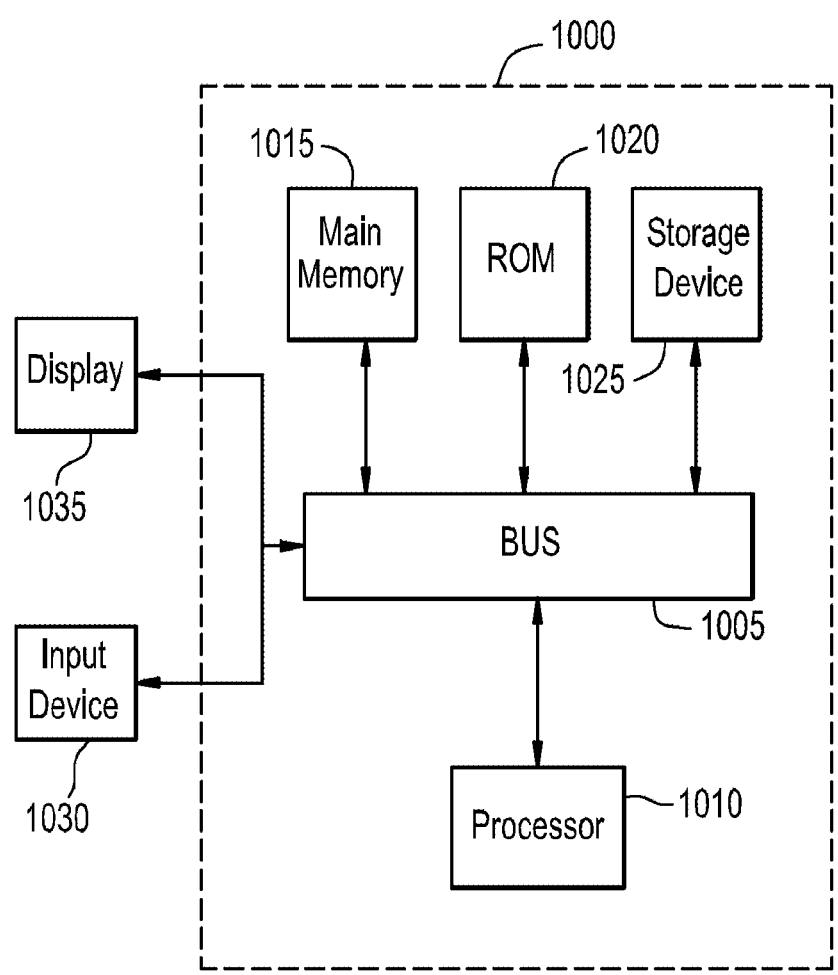
FIG. 15 is a block diagram of a computer system in accordance with an illustrative implementation.
Figure 16:
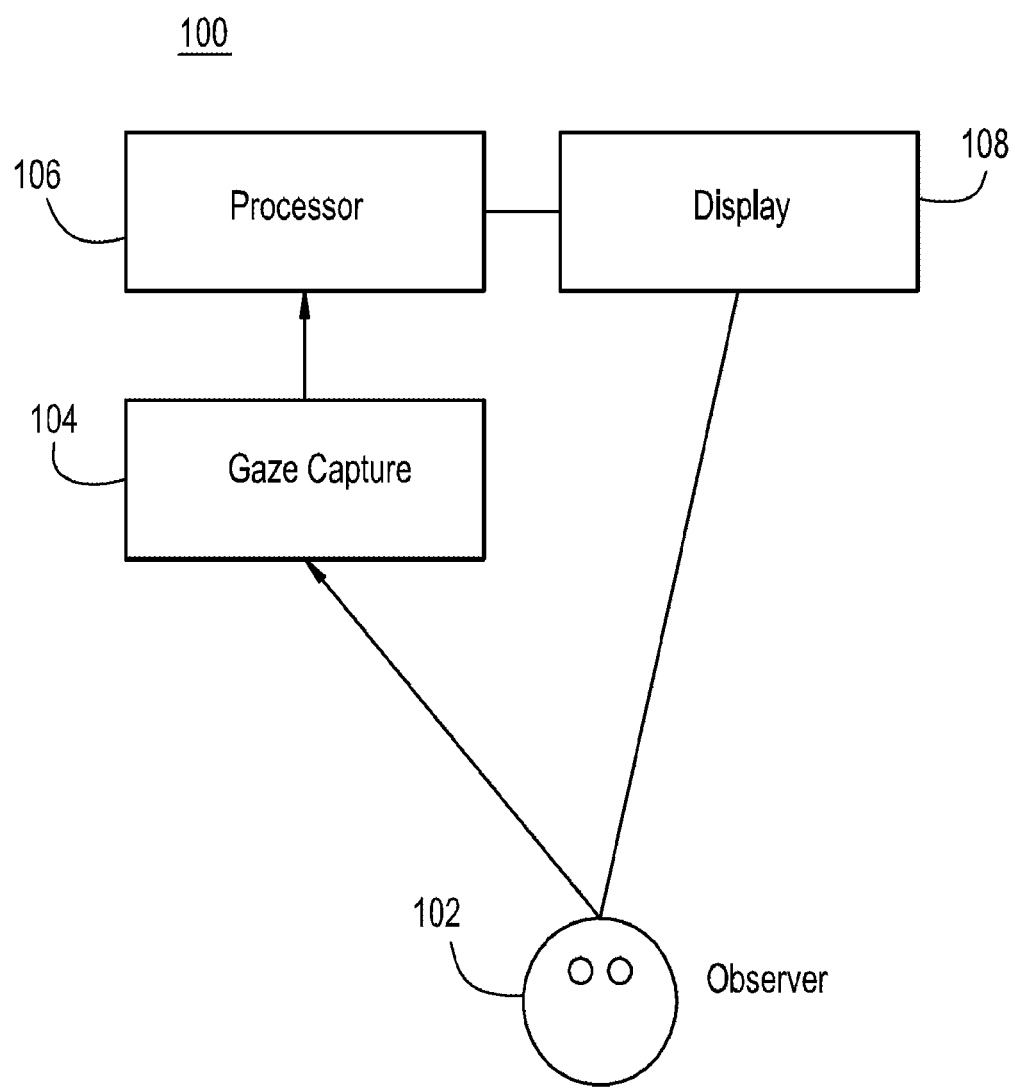
FIG. 16 is a schematic diagram showing a configuration of how a subject's eye movements are measured, analyzed and displayed by such a computer system as shown in FIG. 8.
Figure 18A:
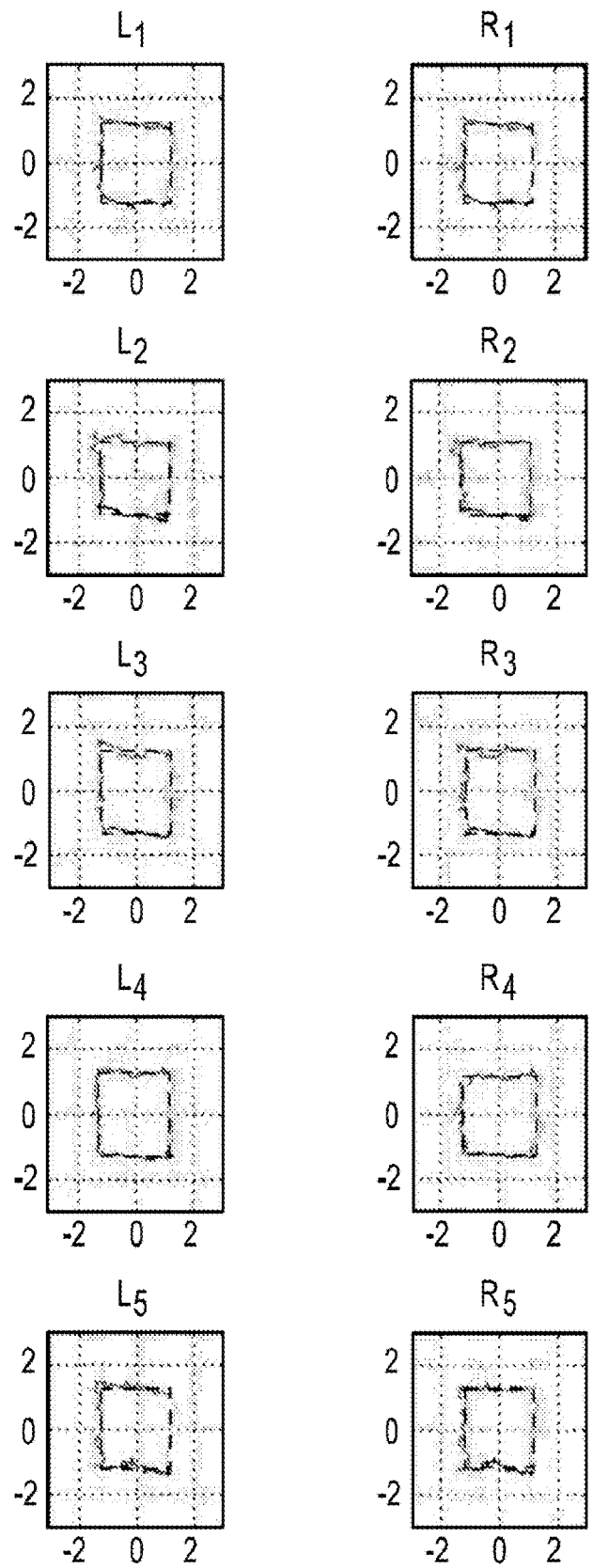
FIG. 18 represents findings from a 41 year old male chronic methadone user who fell, hit his head and sustained an epidural hematoma and skull fracture. He underwent surgery and was recruited for eye-tracking on post-op day 1. Despite use of daily methadone, which is associated with decreased disconjugacy, he had a sustained disconjugate eye movements even at 66 days postoperatively. A. Represents eye movement tracking box plots at points 1-5. B. Provides a composite of eye movement tracking box plots 1-5. C. Provides Left and Right Aspect determined as described herein. D. Represents ΔX [L-R] and Conj. varX determined as described herein. E. Provides a plot of Left-X, Right-X, Left-Y and Right-Y determined as described herein. F. Represents ΔY [L-R] and Conj. varY determined as described herein.
Figure 18B:
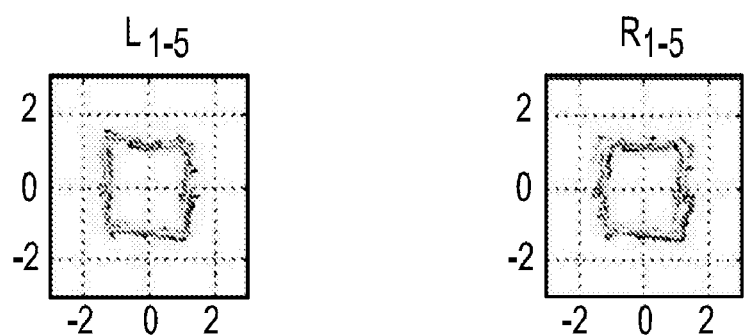
Figure 18C:
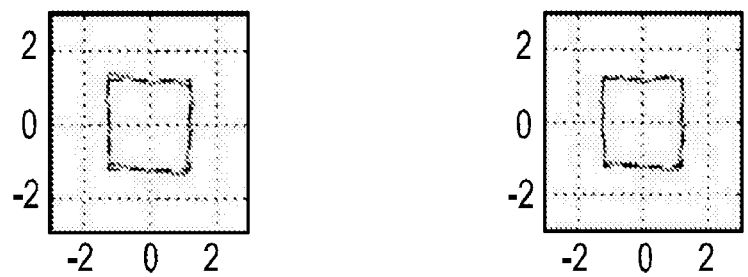
Figure 18D:
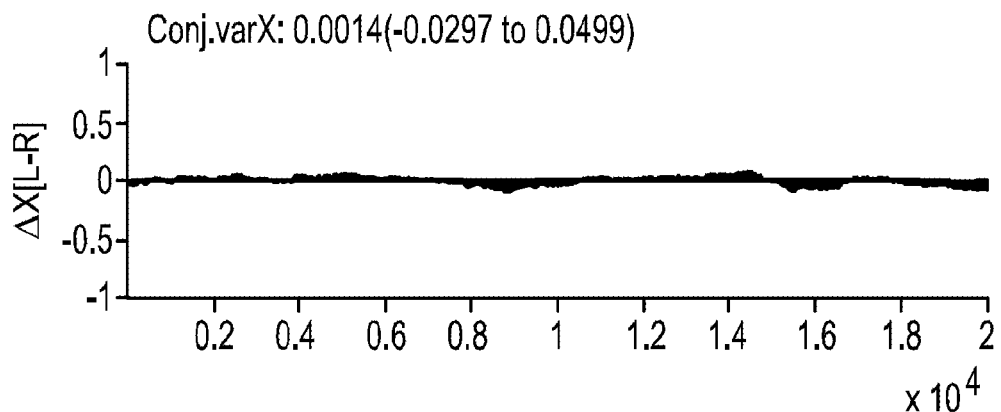
Figure 18E:
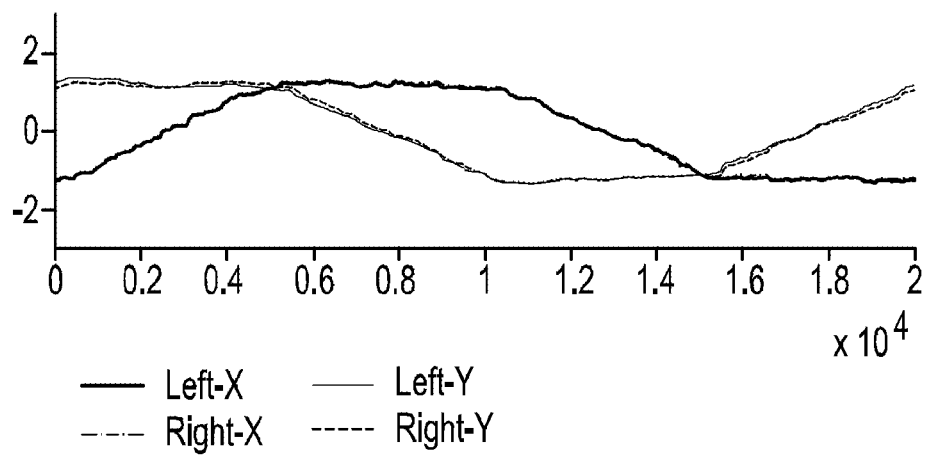
Figure 18F:
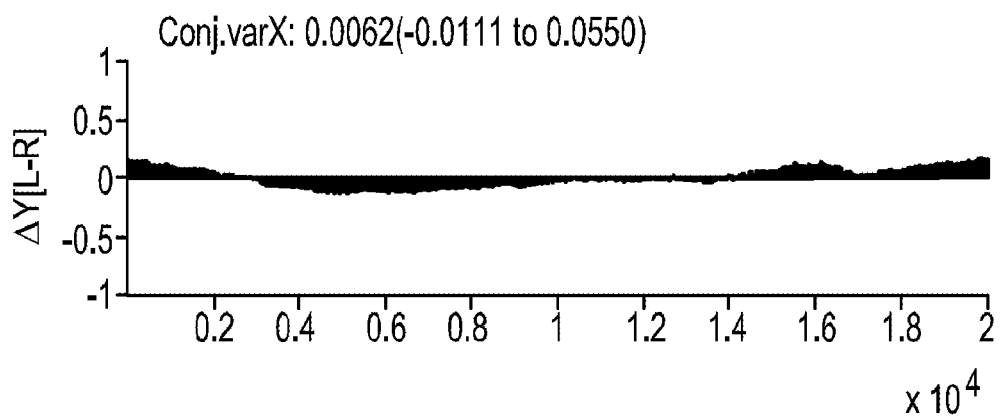
Figure 19A:
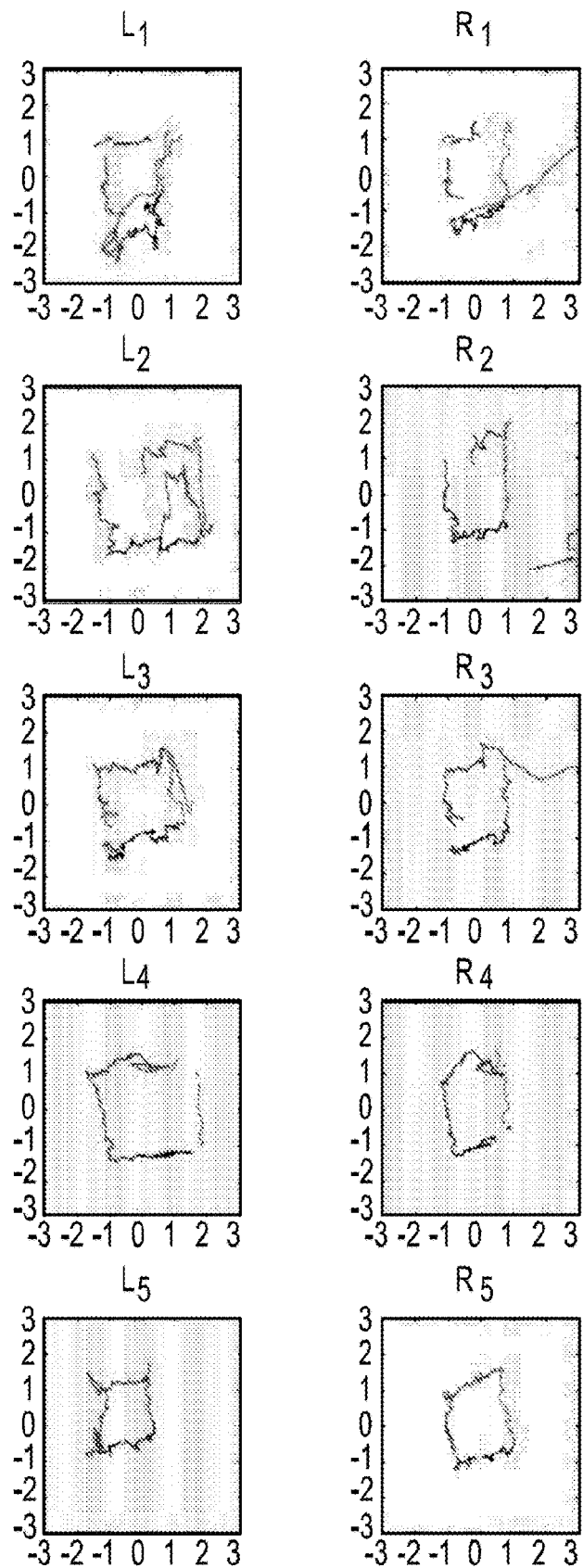
FIG. 19 provides the eye movement tracking trajectories of a 65 year old male presented to the emergency room with acute onset of double vision. On examination he had left to right (L to R) nystagmus, and L impaired adduction on rightward gaze. He was diagnosed in the ophthalmology clinic with INO due to a midbrain ischemic stroke. Binocular afferent eye tracking was performed and revealed abnormal aspect ratios and conjugacy.
Figure 19B:
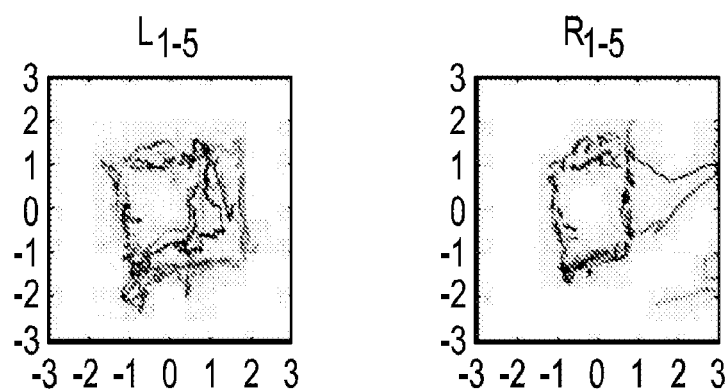
Figure 19C:
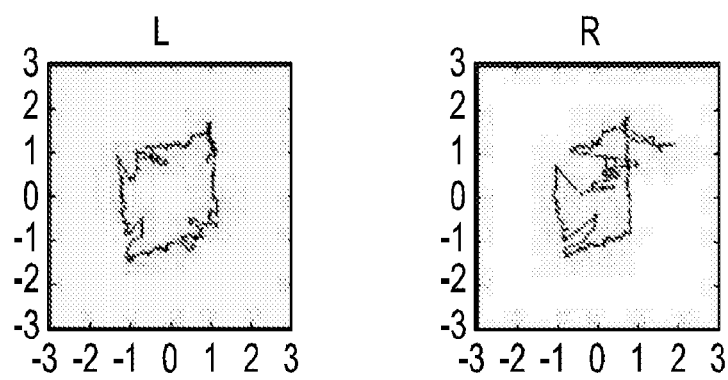
Figure 19D:
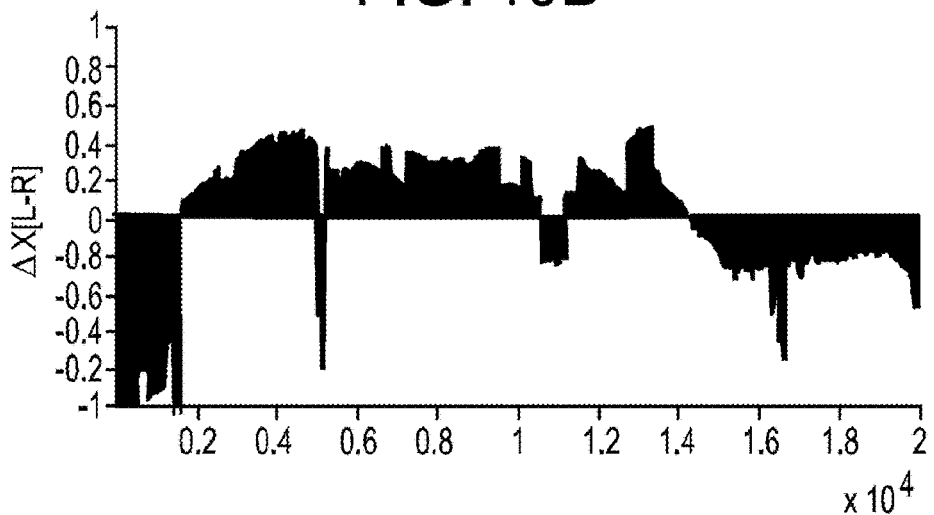
Figure 19E:
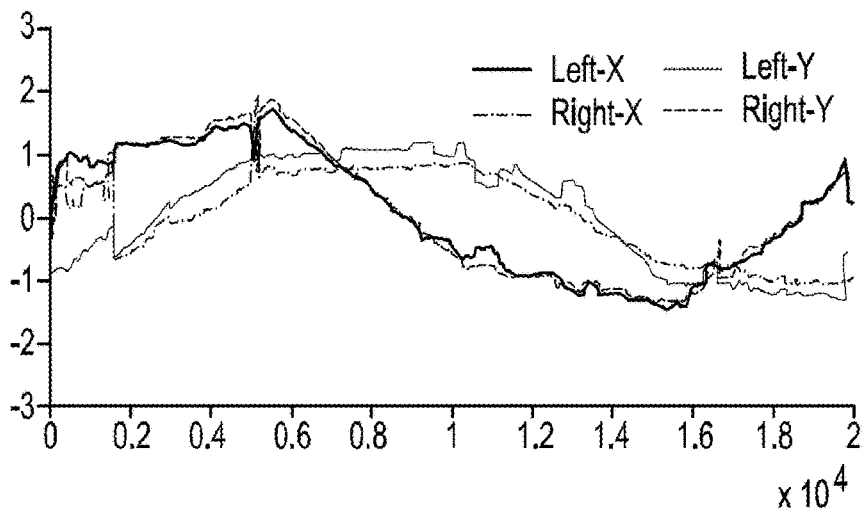
Figure 19F:
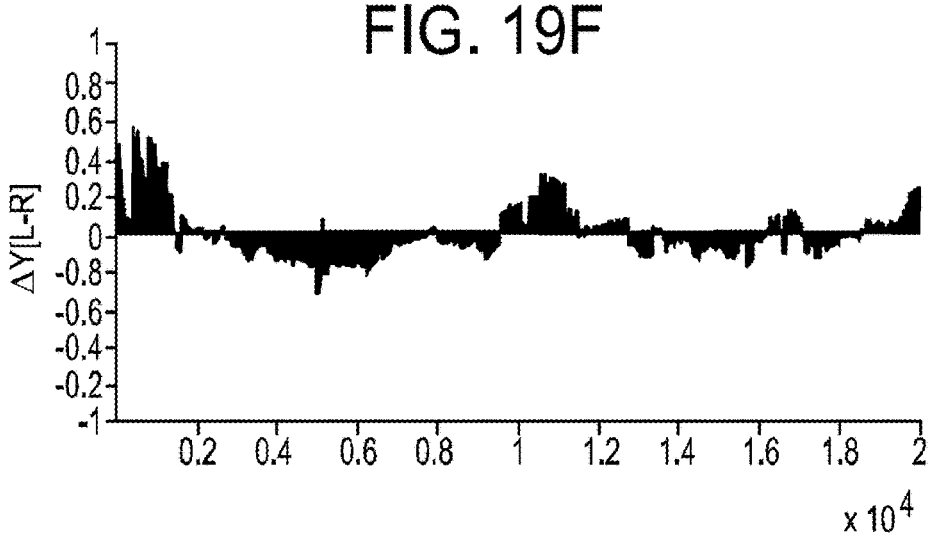
Figure 20A:
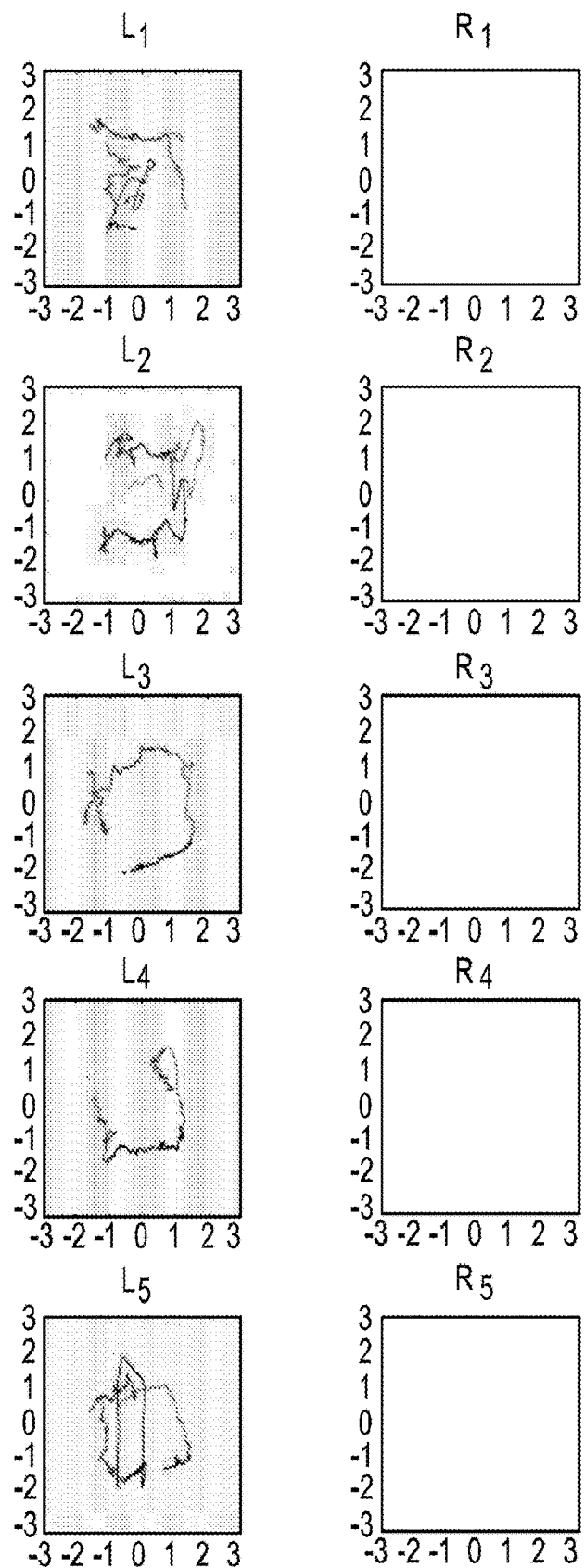
FIG. 20 also provides the eye movement tracking trajectories of a 65 year old male presented to the emergency room with acute onset of double vision. On examination he had left to right (L to R) nystagmus, and L impaired adduction on rightward gaze. He was diagnosed in the ophthalmology clinic with INO due to a midbrain ischemic stroke. Monocular afferent eye tracking was performed and revealed normal aspect ratios.
Figure 20B:
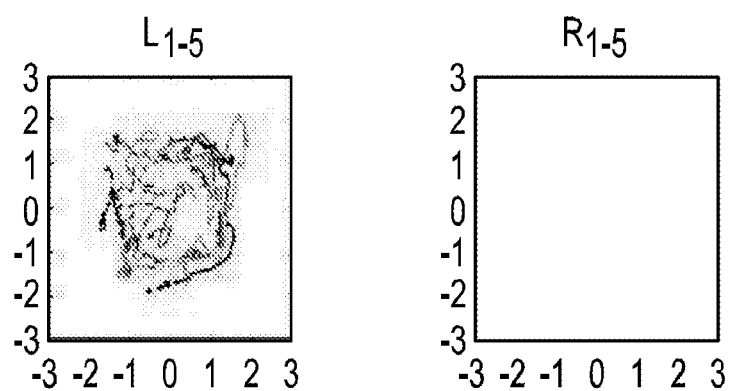
Figure 20C:
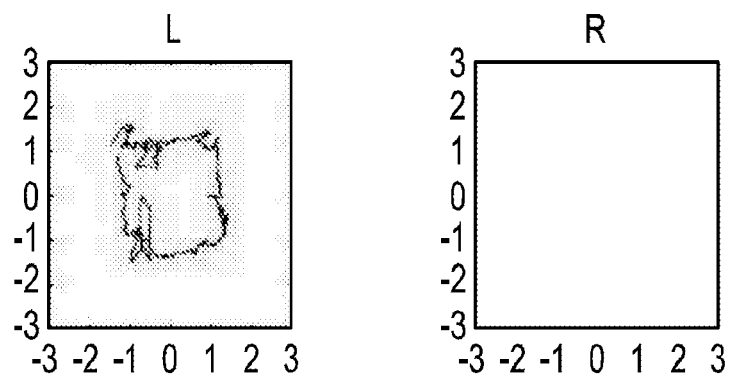
Figure 20D:
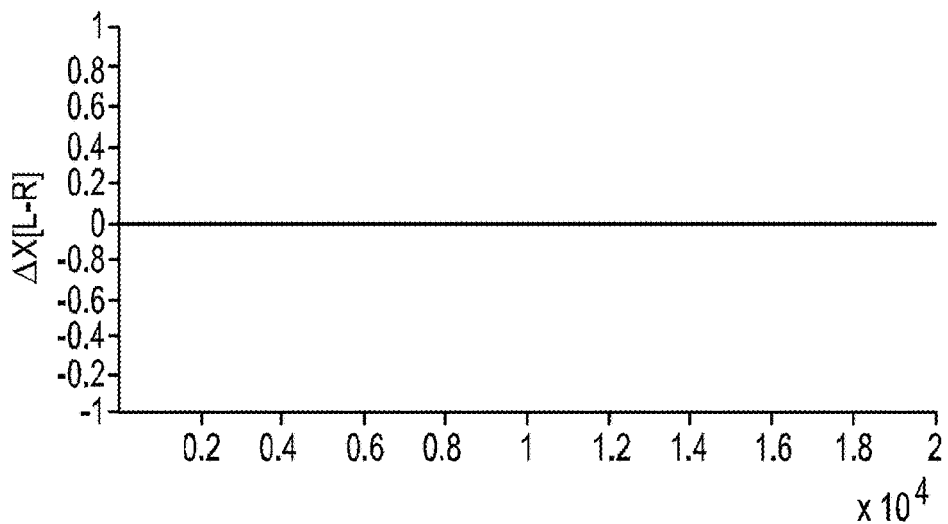
Figure 20E:
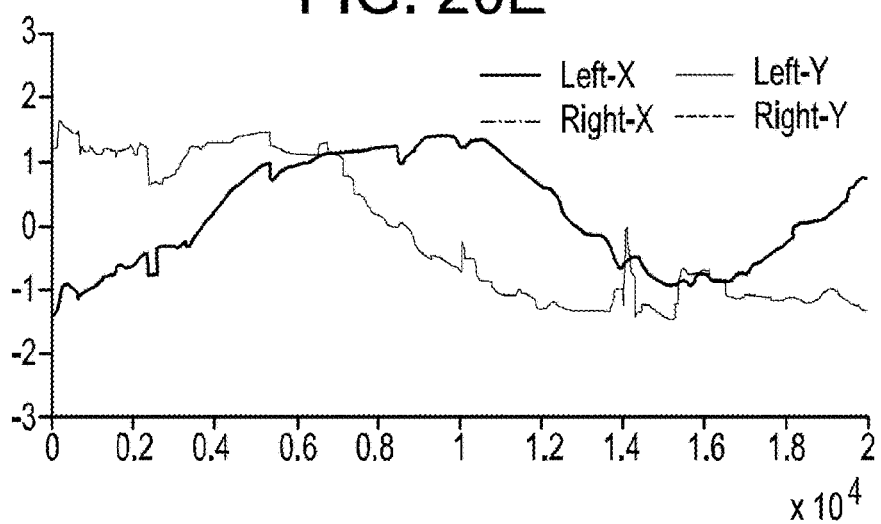
Figure 20F:
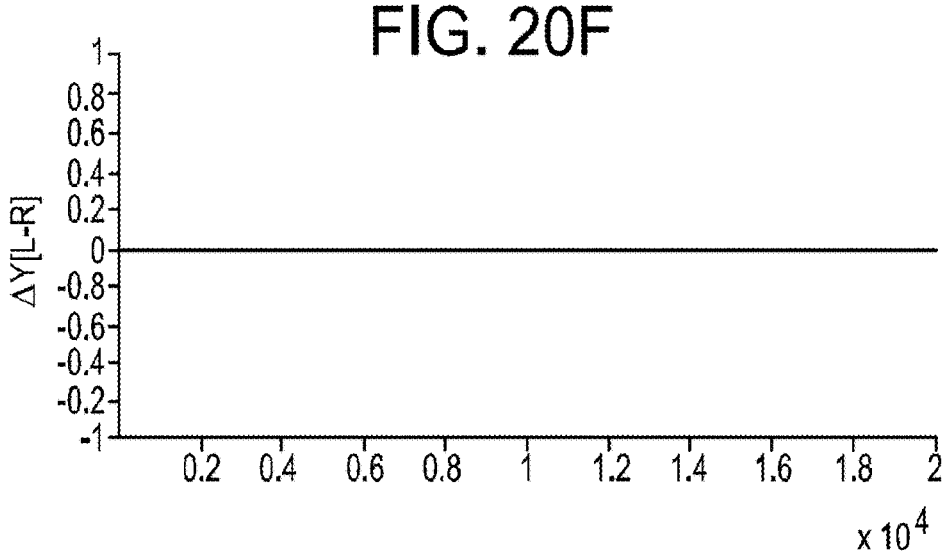
Figure 21A:
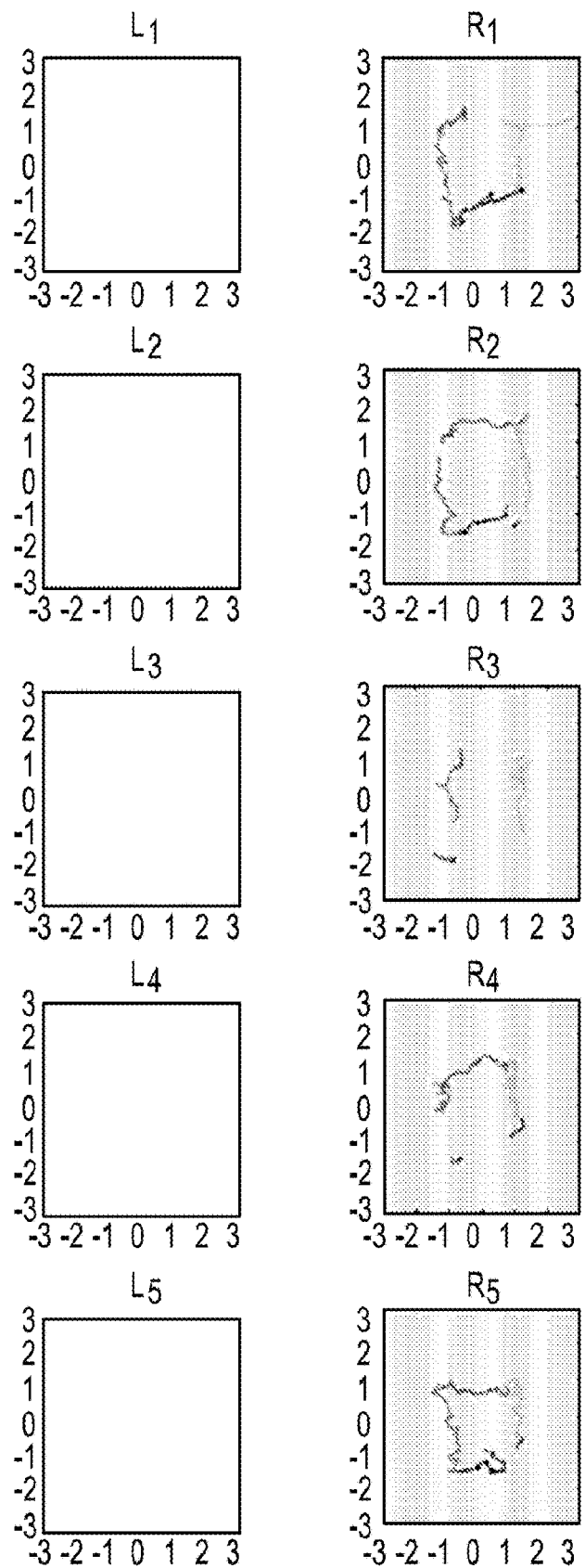
FIG. 21 also provides the eye movement tracking trajectories of a 65 year old male presented to the emergency room with acute onset of double vision. On examination he had left to right (L to R) nystagmus, and L impaired adduction on rightward gaze. He was diagnosed in the ophthalmology clinic with INO due to a midbrain ischemic stroke. Monocular afferent eye tracking was performed and revealed normal aspect ratios.
Figure 21B:
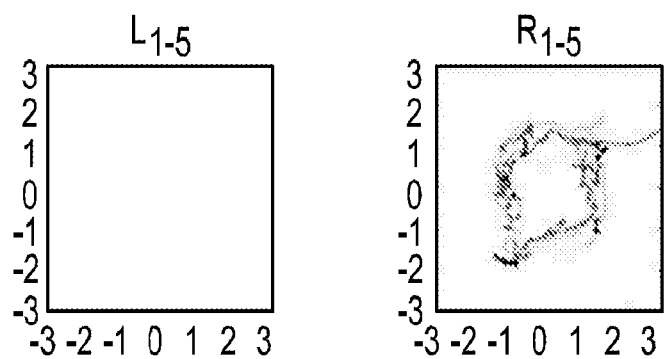
Figure 21C:
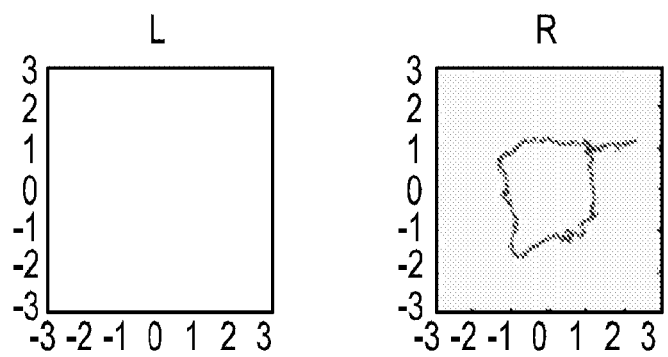
Figure 21D:
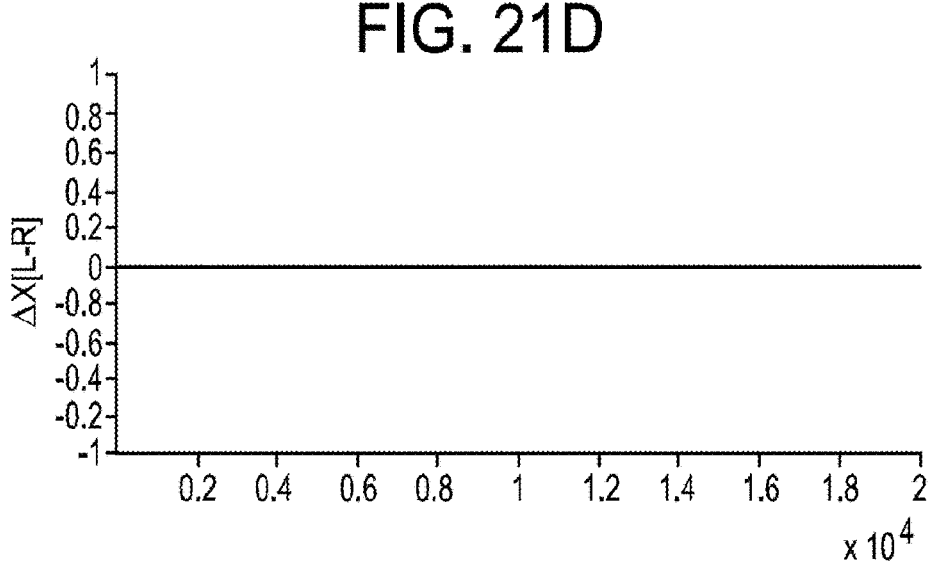
Figure 21E:
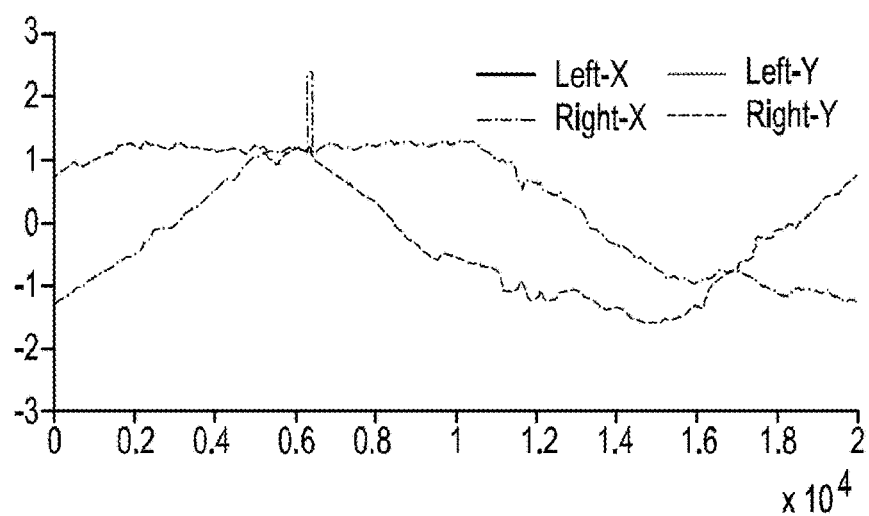
Figure 21F:
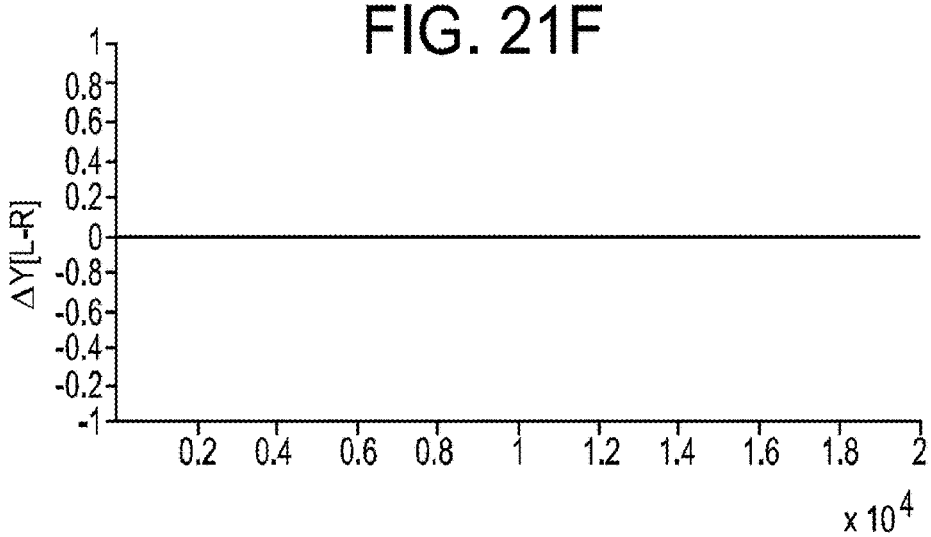
Figure 22A:
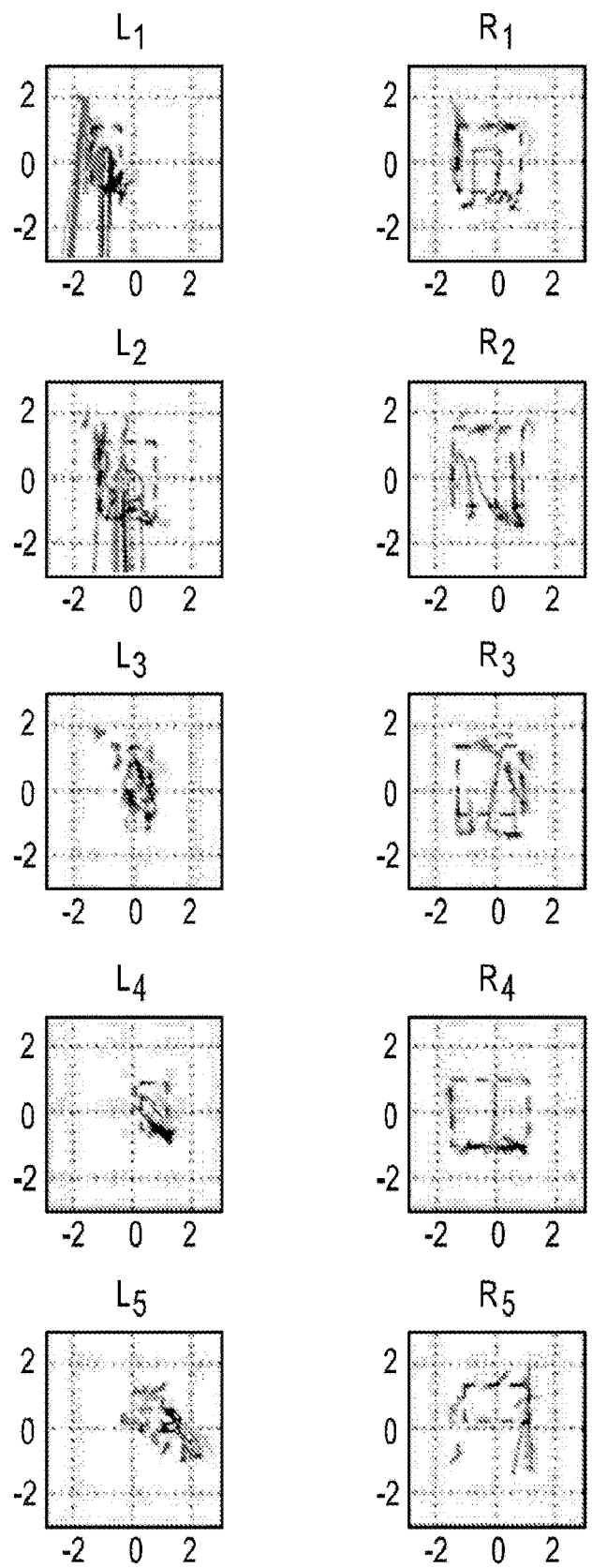
FIG. 22 provides the eye movement tracking trajectories of a 61 year old female who presented with a tumor affecting her left (L) VIth and IIIrd nerves as confirmed by ophthalmic examination. Binocular afferent tracking was performed and revealed abnormal aspect ratios and conjugacy.
Figure 22B:
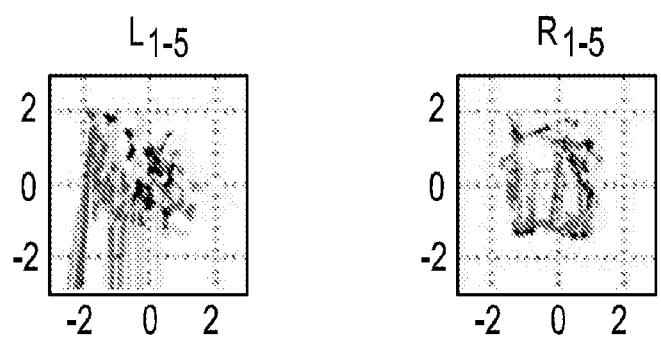
Figure 22C:
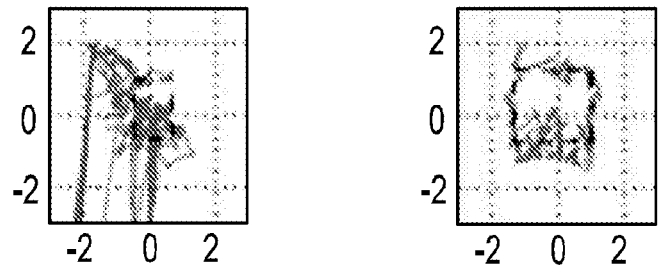
Figure 22D:
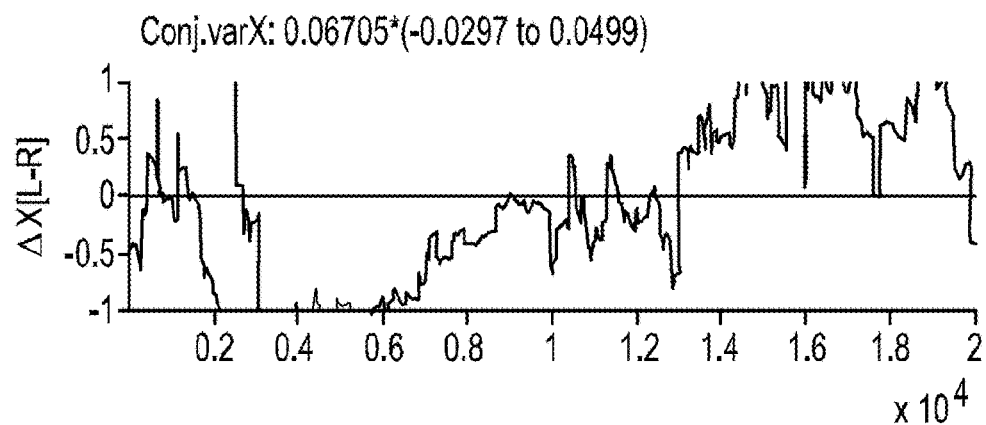
Figure 22E:
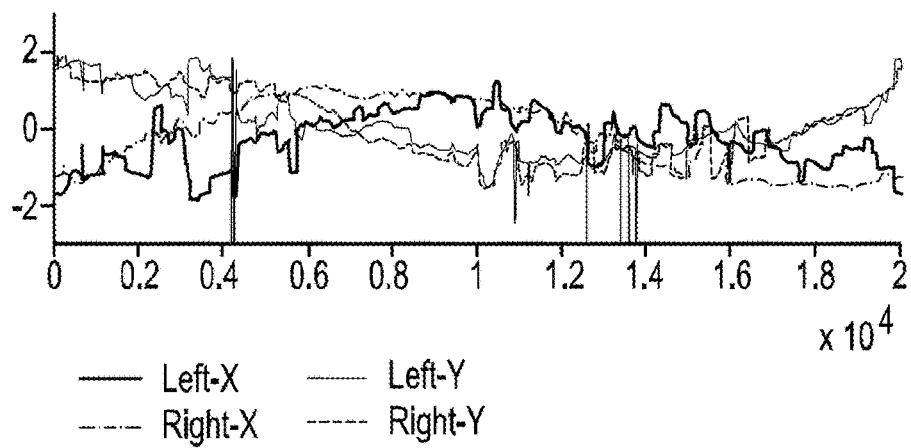
Figure 22F:
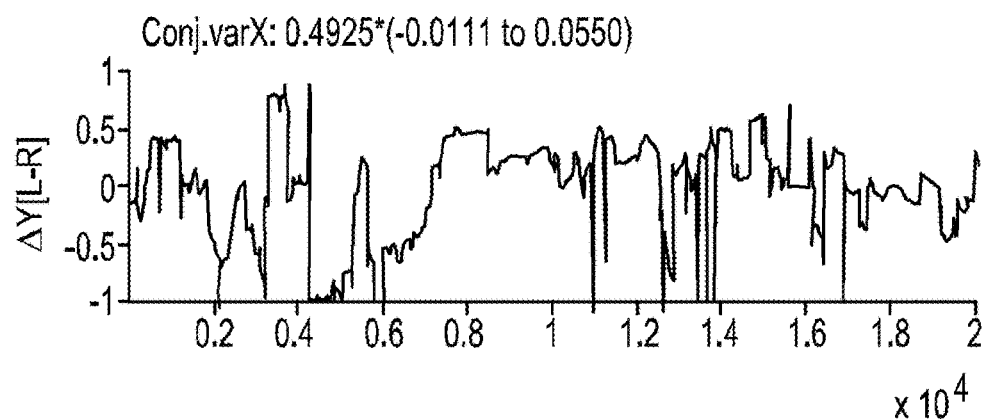
Figure 23A:
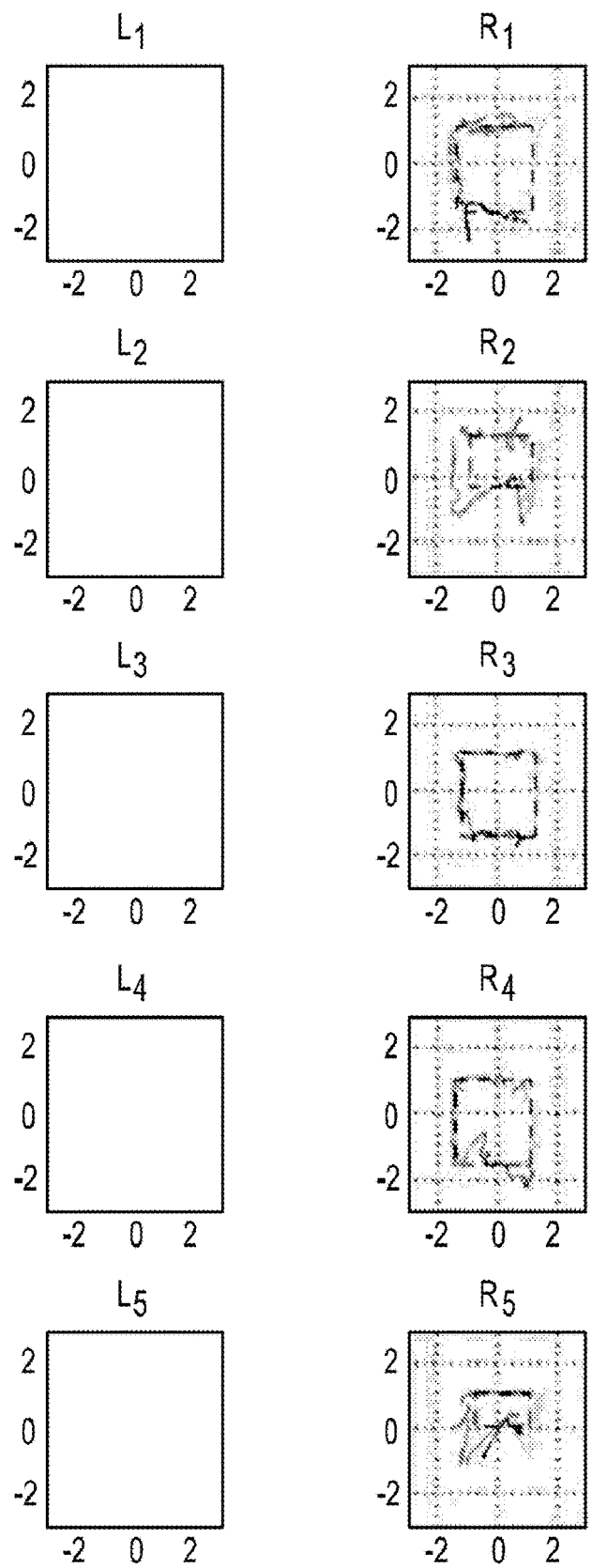
FIG. 23 also provides the eye movement tracking trajectories of a 61 year old female who presented with a tumor affecting her left (L) VIth and IIIrd nerves as confirmed by ophthalmic examination. Monocular afferent eye tracking was performed and revealed abnormal aspect ratios.
Figure 23B:
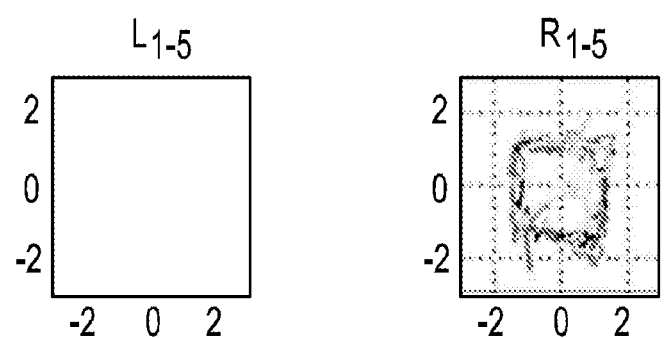
Figure 23C:
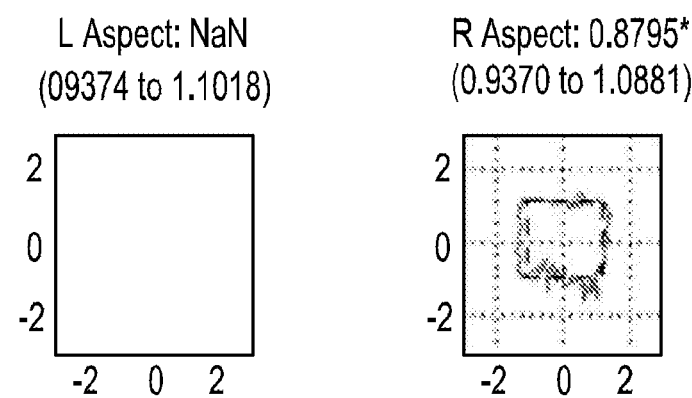
Figure 23D:
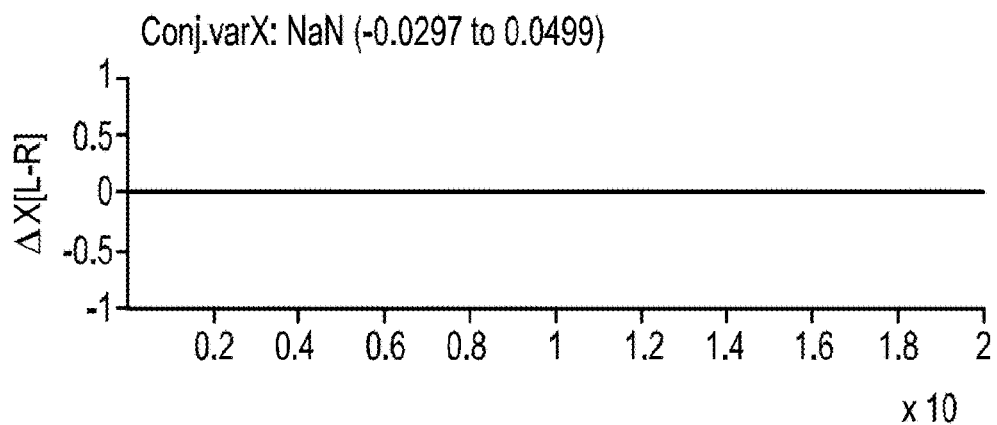
Figure 23E:
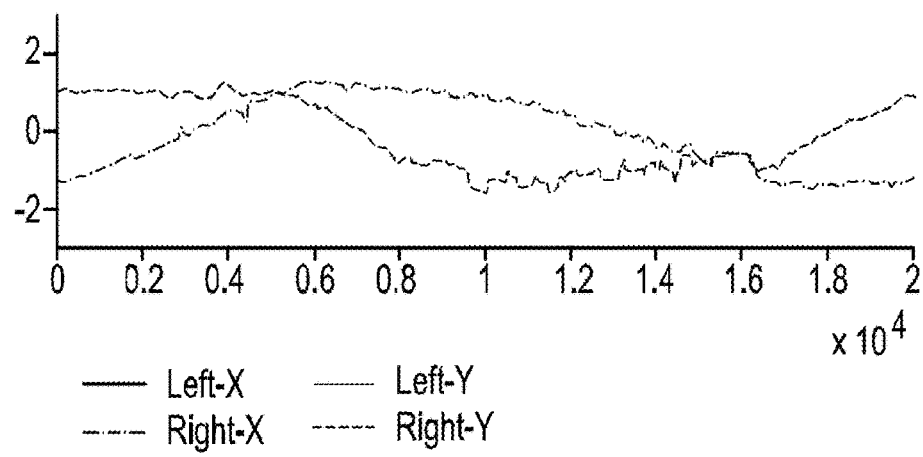
Figure 23F:
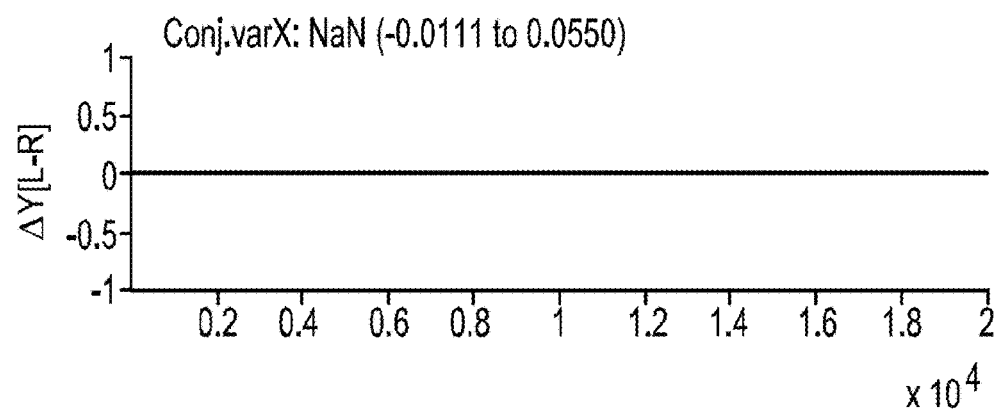
Figure 24A:
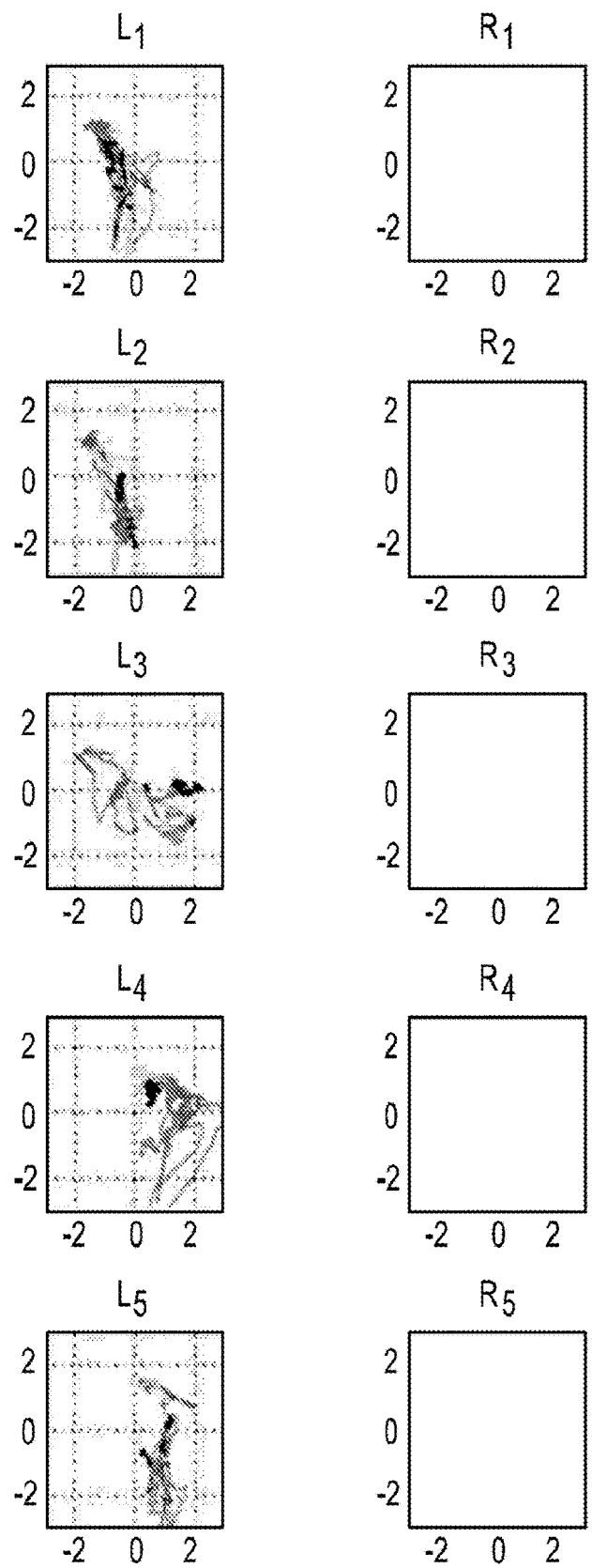
FIG. 24 also provides the eye movement tracking trajectories of a 61 year old female who presented with a tumor affecting her left (L) VIth and IIIrd nerves as confirmed by ophthalmic examination. Monocular afferent eye tracking was performed and revealed abnormal aspect ratios.
Figure 24D:
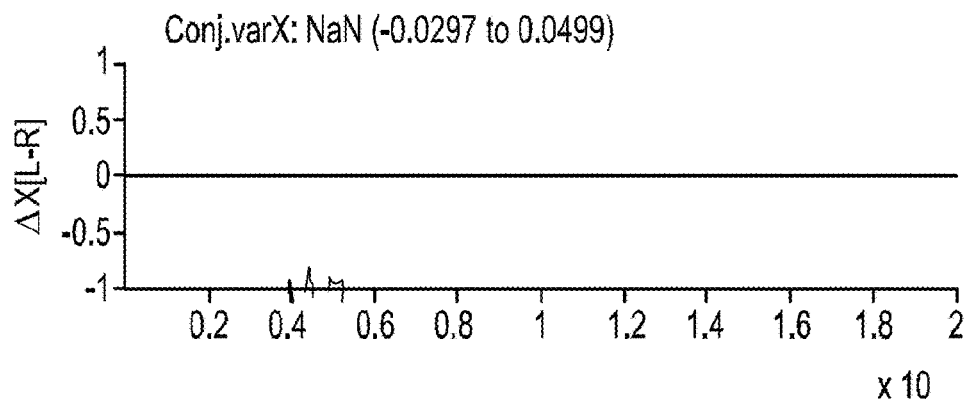
Figure 24E:
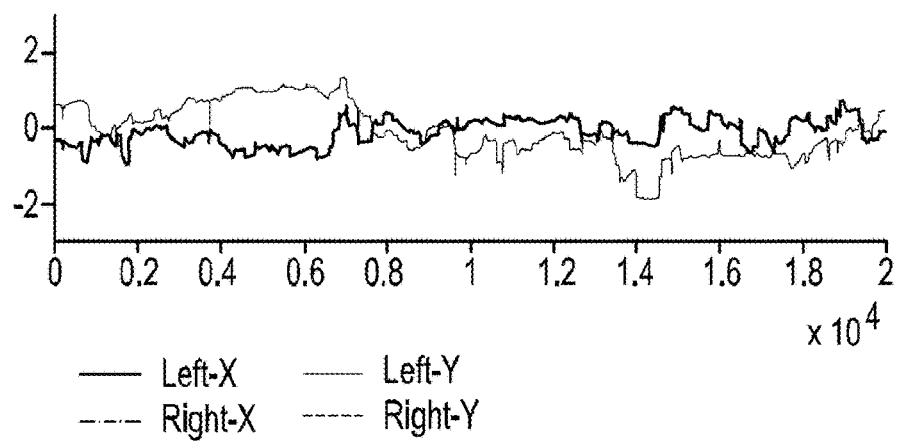
Figure 24F:
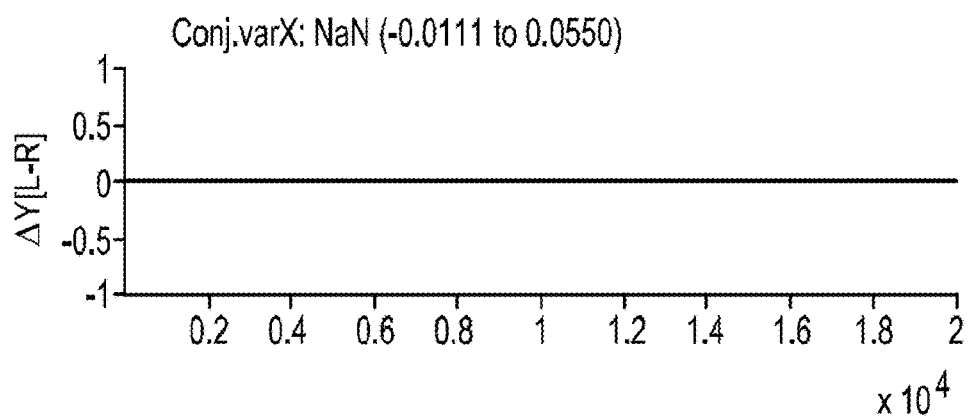
Figure 29E:
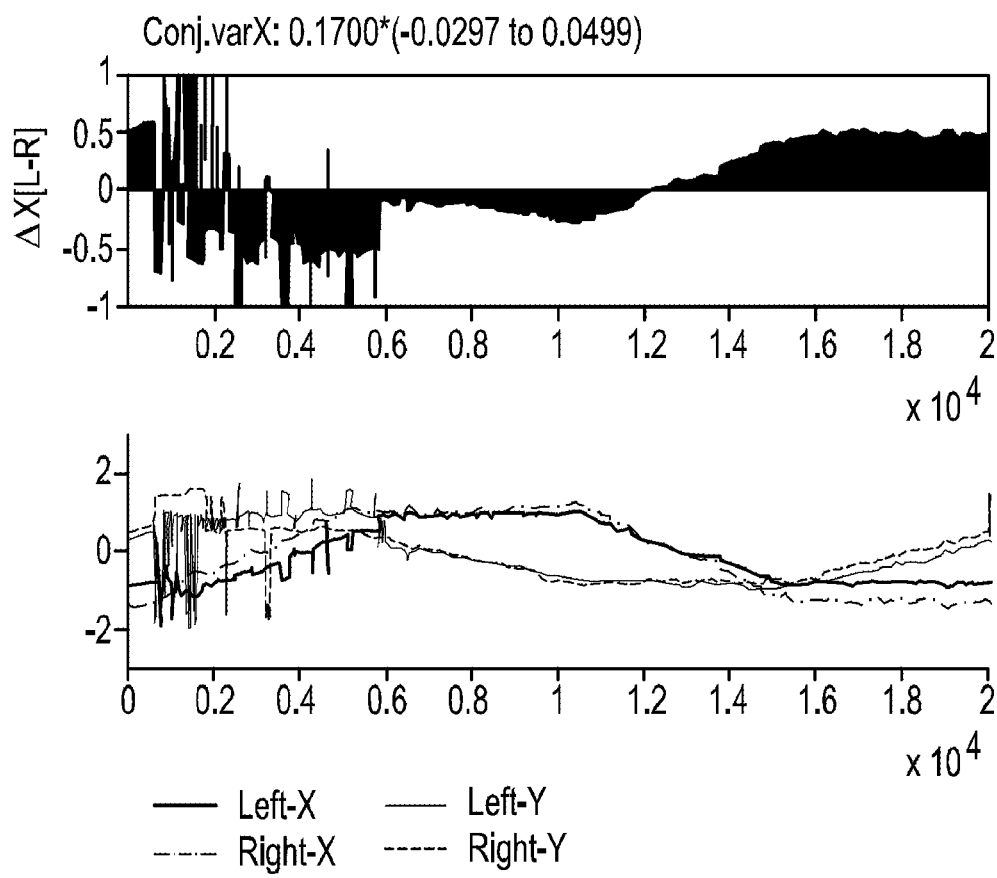
FIG. 29 represents the eye-box trajectories and conjugacy of eye movement of a subject with possible chronic traumatic encephalopathy (CTE) and ADHD tracked, binocularly (FIG. 29A, left eye.
FIG. 29B right eye). The aspect ratio is provided for each eye (FIGS. 29C, 29D). The conjugacy of left and right eye movement represented by $\Delta x$ (FIG. 29E) and $\Delta y$ (FIG. 29F) is represented.
Figure 29F:
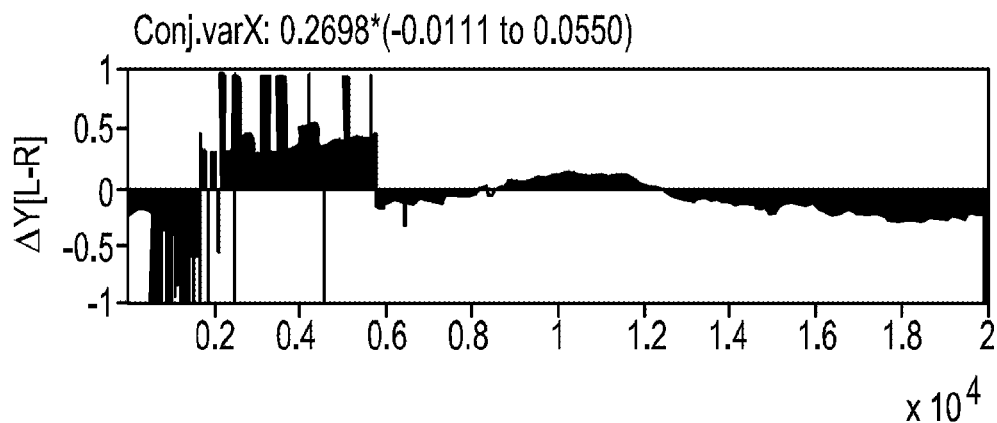
Figure 30E:
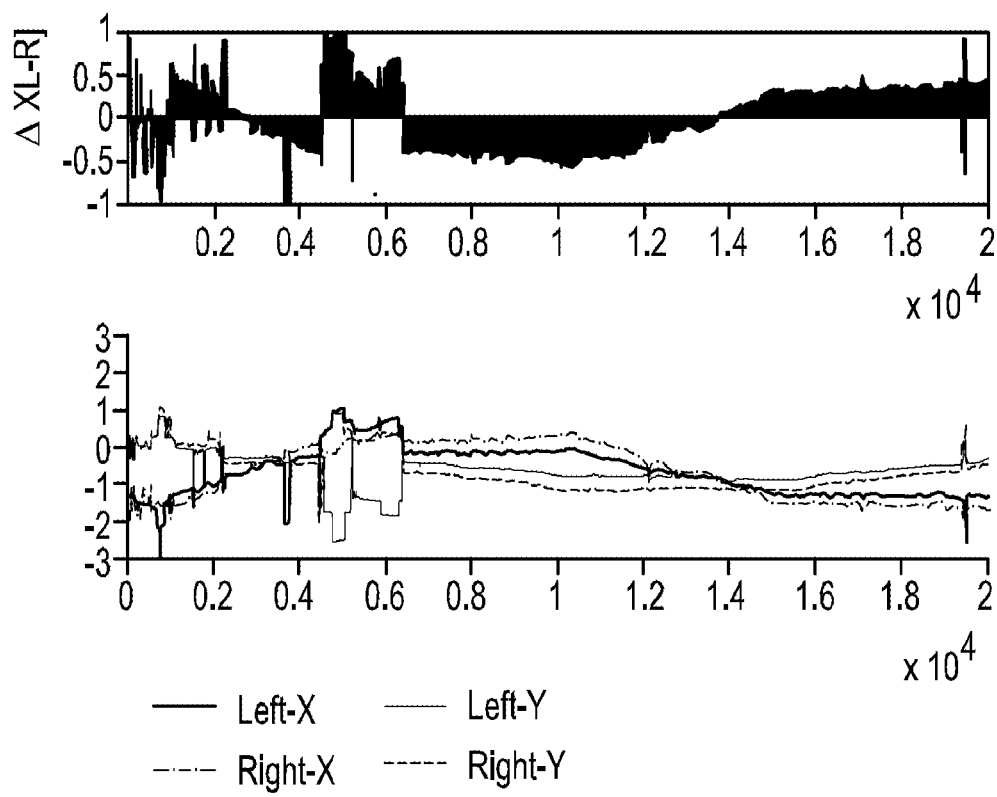
FIG. 30 represents a second testing or repeat of the eye-box trajectories and conjugacy of eye movement of the subject with possible chronic traumatic encephalopathy (CTE) and ADHD tracked binocularly as represented in FIG. 30.
(FIG. 30A, left eye.
FIG. 30B right eye) The aspect ratio is provided for each eye (FIGS. 30C, 30D). The conjugacy of left and right eye movement represented by $\Delta x$ (FIG. 30E) and $\Delta y$ (FIG. 30F) is represented.
Figure 30F:
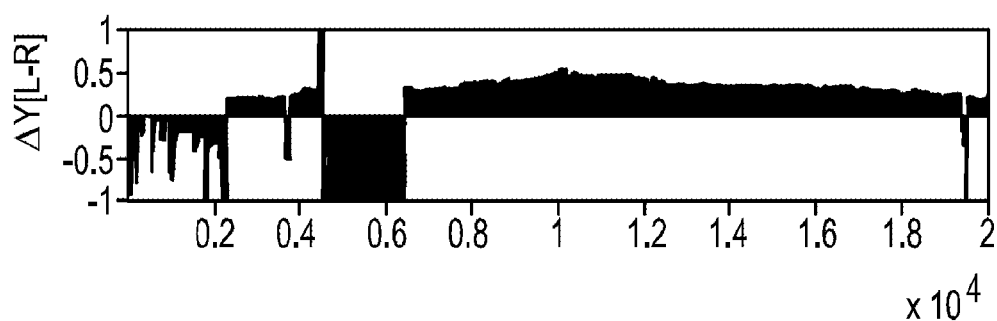

Case 3 is a 62 year old former professional hockey player (12 years in NHL) with occasional sensations of feeling off-balance and disoriented, as well as having ADHD. FIG. 29 represents the eye-box trajectories and conjugacy of eye movement of a subject with possible chronic traumatic encephalopathy (CTE) and ADHD tracked binocularly (FIG. 29A, left eye; FIG. 29B right eye). The aspect ratio is provided for each eye (FIGS. 29C, 29D). The conjugacy of left and right eye movement represented by Δx (FIG. 29E) and Δy (FIG. 29F) is represented. FIG. 13 represents a second testing or repeat of the eye-box trajectories and conjugacy of eye movement of the subject with possible chronic traumatic encephalopathy (CTE) and ADHD tracked binocularly as represented in FIG. 29. (FIG. 30A, left eye; FIG. 30B right eye) The aspect ratio is provided for each eye (FIGS. 30C, 30D). The conjugacy of left and right eye movement represented by Δx (FIG. 30E) and Δy (FIG. 30F) is represented.

Table 9: statistical comparisons of p-values between normal healthy controls and subjects being evaluated in a neurology practice with mild cognitive impairment reveals that numerous metrics are markedly different between these groups.

TABLE 9

| Variable | Controls (N = 40) vs MCI (N = 30) |
| --- | --- |
| left__area__value | 0.683838314 |
| left__aspectRatio__value | 0.276765067 |
| left__height__value | 0.918940207 |
| left__width__value | 0.024577153 |
| left__skewTop__value | 0.730834374 |
| left__skewTopNorm__value | 0.790752851 |
| left__skewRit__value | 0.125967649 |
| left__skewRitNorm__value | 0.122620352 |
| left__skewBot__value | 0.083764878 |
| left__skewBotNorm__value | 0.109563339 |
| left__skewLef__value | 0.161908877 |
| left__skewLefNorm__value | 0.235422747 |
| left__varTotal__value | 0.125585311 |
| left__varXlef__value | 0.154070763 |
| left__varXrit__value | 0.922413851 |
| left__varYbot__value | 0.012438452 |
| left__varYtop__value | 0.220110373 |
| right__area__value | 0.103235574 |
| right__aspcetRatio__value | 0.986390881 |
| right__height__value | 0.440632018 |
| right__width__value | 0.101295878 |
| right__skewTop__value | 0.526856958 |
| right__skewTopNorm__value | 0.55292087 |
| right__skewRit__value | 0.606822362 |
| right__skewRitNorm__value | 0.552910245 |
| right__skewBot__value | 0.910105645 |
| right__skewBotNorm__value | 0.8992745 |
| right__skewLef__value | 0.48484475 |
| right__skewLefNorm__value | 0.476668635 |
| right__varTotal__value | 0.30400133 |
| right__varXlef__value | 0.053170921 |
| right__varXrit__value | 0.750642587 |
| right__varYbot__value | 0.014323155 |
| right__varYtop__value | 0.966073028 |
| conj__CorrXY__value | 0.299001512 |
| conj__totVar__value | 0.029506073 |
| conj__varX__value | 0.016645475 |
| conj__varXbot__value | 0.026356193 |
| conj__varXlef__value | 0.033797709 |
| conj__varXlefritRatio__value | 0.704197445 |
| conj__varXrit__value | 0.045756631 |
| conj__varXtop__value | 0.020746067 |
| Conj__varXtopbotRatio__value | 0.506630234 |
| conj__varY__value | 0.038604875 |
| conj__varYbot__value | 0.001041257 |

EXAMPLE 10

The present data demonstrates that an eye tracking algorithm performed while a subject watches television or a short film clip continuously playing in a moving aperture can distinguish between normal subjects and those who have consumed alcohol or are intoxicated.

Methods:

Patient Selection.

Subjects were volunteers recruited in accordance with Institutional Review Board policy. Inclusion criteria were:

age >21 years, vision correctable to within 20/50 bilaterally, intact ocular motility, and ability to provide a complete ophthalmologic, medical and neurologic history as well as medications/drugs/alcohol consumed within the 24 hours prior to tracking. Exclusion criteria were history of: strabismus, diplopia, palsy of cranial nerves III, IV or VI, papilledema, optic neuropathy, macular edema, retinal degeneration, dementia or cognitive impairment, hydrocephalus, sarcoidosis, myasthenia gravis, multiple sclerosis or other demyelinating disease. Pregnant individuals and prisoners were excluded from the study as were subjects who were missing eyes, not opening eyes, or wearing excessive mascara/false eyelashes. Subjects reporting any minor brain injury regardless of loss of consciousness within the previous week were also excluded from participating as controls.

Alcohol Consumption.

Subjects were permitted to consume alcohol and food ad lib during the study and were periodically assessed for Breath-Alcohol Content (BAC) using the AlcoHAWK pro Breathalyzer analysis device.

Visual Stimulus.

Subjects' eye movements were recorded with an Eyelink 1000 eye tracker at a fixed distance of 55 cm from a computer monitor over a time period of 220 seconds. Subjects were seated in either a height adjustable or height-fixed chair or bed, with the monitor height adjusted to the subject. The tracker chinrest was attached to the monitor. The visual stimuli were the music videos "I Just Can't Wait to be King" from the Lion King and Puss in Boots (soundtrack). The video was played continuously in a square aperture with an area approximately ⅛ the screen size while moving clockwise along the outer edges of the monitor for five complete cycles of 40 seconds each. The first and last 10 seconds of each data set were discarded to yield 200 seconds of data. The afferent stimulus was presented binocularly and eye tracking was performed binocularly. Subjects were not spatially calibrated to the tracker to enable independent analysis of each pupil position over time.

Data Analysis.

The eye tracker sampled pupil position at 500 Hz, yielding 100,000 samples over 200 seconds. Scatterplots of the entire time series were created by plotting the 100,000 (x,y) pairs representing the two orthogonal components of the instantaneous angle of pupil reflection over time to create 'box trajectories' that reflected the temporal nature of the pupillary movement. These figures look like boxes, reflecting the timing of the aperture as it moved around the screen. 200 data points prior to and following each blink were removed prior to creating the measures of disconjugacy and aspect ratio to limit noise in the data from the blink event.

Analysis of Gaze Conjugacy.

Comparing the movement of one eye of a subject to the other eye of a subject was performed by comparing the x,y Cartesian coordinates at any time point t. For example by subtracting the x coordinate of the left eye from the x coordinate of the right eye or vice versa. Also by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested can be summed to obtain a measure of total disconjugacy of gaze, or as an average of five eyebox trajectory cycles formulaically represented as follows:

$$X_{Avg,ik} = \frac{\sum_{j=1}^{5} X_{ijk}}{5},$$

for all i=1:N, k=1:2, where $X_{ijk}$ refers to the x-coordinate of the pupil, and k refers to the left or right eye of a subject. In cases where a subject's data was missing at any given time point in the five cycles (including blinks), the denominator of the equation was the number of cycles where the data was present. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$Var_x = \frac{1}{N} \sum_{i=1}^{N} ((X_{Avg,i1} - X_{Avg,i2}) - 0)^2$$

The total variance in both the horizontal and vertical planes may be computed as follows:

$$Var_{Tot} = Var_x + Var_y.$$

The variance in X, Y, and the total variance may be plotted in order to assess the amount of disconjugacy present in a subject.

Velocity is calculated in a similar manner. If the coordinates of the pupil at time 1 are $x_1$, $y_1$ and at time 2 are $x_2$, $y_2$, then the distance ($z_1$) traveled by the pupil between times 1 and 2 is the square root of:

$$(x_2-x_1)^2+(y_2-y_1)^2$$

The sum of the z's is then obtained to get distance traveled by the pupil over any time period of interest. To look at the distance traveled during each segment of the rectangular trajectory, the sum of the z's over 10 second intervals is obtained. To calculate pupil velocity, one can then divide by the amount of time in seconds. It is then possible to determine whether pupil velocities change in different directions as the pupil travels around the box, obtaining a $z_{total}$, $z_{top}$, $z_{left}$, $z_{right}$, $z_{bottom}$ for each eye.

Statistical Analyses

Data analysis was performed using R version 3.0.3 and SAS version 9.3. A p-value of <0.05 after adjusted for multiple comparisons was deemed statistically significant.

The Kruskal-Wallis test was used to compare age, eye-tracking parameters across the groups. A significant result indicated a difference between at least two of the groups. P-values adjusted for multiple comparisons were obtained using the bootstrap method, a resampling-based multiple testing method for correlated variables. (Pollard et al., *Journal of Statistical Planning and Inference* 2004; 125:85-100; van der Laan et al., *Stat Appl Genet Mol Biol* 5: Article 14, 2006)

Multiple pairwise comparisons for eye-tracking parameters were made using the Wilcoxon two sample tests. P-values were first adjusted by the bootstrap method for correlated variables and then adjusted by the Bonferroni method for multiple testing within a single variable.

Results:

8 of 90 eye tracking metrics were statistically significantly different after subjects were intoxicated versus pre-intoxication metrics in 33 normally healthy controls versus 29 intoxicated normal healthy controls. The 29 intoxicated subjects achieved breath alcohol content levels of 0.08 to 0.29. Three non/minimally drinking subjects had levels <0.02. The metrics determined are provided in Table 10.

TABLE 10

Summary statistics

| Variable | Observation | Minimum | Maximum | Mean | Std. Deviation |
|---|---|---|---|---|---|
| left.areamean.value\|EtOH | 29 | 4.5203 | 6.0883 | 5.5777 | 0.3936 |
| left.areamean.value\|Pre-EtOH | 33 | 4.4339 | 13.9577 | 5.9838 | 1.4923 |
| left.areamedian.value\|EtOH | 29 | 4.7456 | 5.9483 | 5.5955 | 0.3080 |
| left.areamedian.value\|Pre-EtOH | 33 | 4.5335 | 14.8343 | 6.0006 | 1.6313 |
| left.aspectRatiomean.value\|EtOH | 29 | 0.8162 | 1.2606 | 0.9940 | 0.0744 |
| left.aspectRatiomean.value\|Pre-EtOH | 33 | 0.7723 | 1.4074 | 1.0102 | 0.0879 |
| left.aspectRatiomedian.value\|EtOH | 29 | 0.8482 | 1.1811 | 0.9979 | 0.0661 |
| left.aspectRatiomedian.value\|Pre-EtOH | 33 | 0.7867 | 1.4337 | 1.0080 | 0.0912 |
| left.heightmean.value\|EtOH | 29 | 0.0320 | 0.2490 | 0.1083 | 0.0558 |
| left.heightmean.value\|Pre-EtOH | 33 | 0.0140 | 0.1520 | 0.0826 | 0.0304 |
| left.heightmedian.value\|EtOH | 29 | 0.0700 | 2.6400 | 0.7290 | 0.5496 |
| left.heightmedian.value\|Pre-EtOH | 33 | 0.0300 | 4.2250 | 0.6895 | 0.7735 |
| left.widthmean.value\|EtOH | 29 | 0.0012 | 0.0133 | 0.0026 | 0.0023 |
| left.widthmean.value\|Pre-EtOH | 33 | 0.0008 | 0.0059 | 0.0020 | 0.0009 |
| left.widthmedian.value\|EtOH | 29 | 0.0013 | 0.0088 | 0.0023 | 0.0014 |
| left.widthmedian.value\|Pre-EtOH | 33 | 0.0008 | 0.0250 | 0.0028 | 0.0041 |
| left.skewTop.value\|EtOH | 29 | 0.0014 | 0.0127 | 0.0027 | 0.0022 |
| left.skewTop.value\|Pre-EtOH | 33 | 0.0008 | 0.0046 | 0.0021 | 0.0010 |
| left.skewTopNorm.value\|EtOH | 29 | 0.0011 | 0.0046 | 0.0023 | 0.0009 |
| left.skewTopNorm.value\|Pre-EtOH | 33 | 0.0011 | 0.0115 | 0.0023 | 0.0018 |
| left.skewRit.value\|EtOH | 29 | 1.9208 | 2.5503 | 2.3518 | 0.1227 |
| left.skewRit.value\|Pre-EtOH | 33 | 1.8504 | 4.4322 | 2.4529 | 0.3801 |
| left.skewRitNorm.value\|EtOH | 29 | 2.0514 | 2.5683 | 2.3611 | 0.1066 |
| left.skewRitNorm.value\|Pre-EtOH | 33 | 1.8886 | 4.6118 | 2.4527 | 0.4061 |
| left.skewBot.value\|EtOH | 29 | 14.0000 | 528.0000 | 145.7931 | 109.9296 |
| left.skewBot.value\|Pre-EtOH | 33 | 6.0000 | 845.0000 | 137.9091 | 154.7044 |
| left.skewBotNorm.value\|EtOH | 29 | −0.0536 | 0.0971 | 0.0062 | 0.0353 |
| left.skewBotNorm.value\|Pre-EtOH | 33 | −0.1542 | 0.1242 | −0.0071 | 0.0458 |
| left.skewLef.value\|EtOH | 29 | −1.4730 | 1.3323 | 0.0680 | 0.6243 |
| left.skewLef.value\|Pre-EtOH | 33 | −1.4095 | 2.2410 | −0.0987 | 0.7880 |
| left.skewLefNorm.value\|EtOH | 29 | −0.0205 | 0.0289 | −0.0003 | 0.0129 |
| left.skewLefNorm.value\|Pre-EtOH | 33 | −0.0199 | 0.0693 | 0.0052 | 0.0197 |
| left.varTotal.value\|EtOH | 29 | −0.6458 | 0.7596 | −0.0442 | 0.4167 |
| left.varTotal.value\|Pre-EtOH | 33 | −0.7901 | 0.8269 | 0.0635 | 0.4687 |
| left.varXlef.value\|EtOH | 29 | −0.1139 | 0.0595 | 0.0008 | 0.0306 |
| left.varXlef.value\|Pre-EtOH | 33 | −0.0563 | 0.0577 | 0.0011 | 0.0194 |
| left.varXrit.value\|EtOH | 29 | −0.8021 | 1.1655 | 0.1040 | 0.5126 |
| left.varXrit.value\|Pre-EtOH | 33 | −1.1208 | 1.1400 | −0.0066 | 0.4536 |
| left.varYbot.value\|EtOH | 29 | −0.1498 | 0.0792 | −0.0032 | 0.0418 |
| left.varYbot.value\|Pre-EtOH | 33 | −0.0616 | 0.0404 | −0.0068 | 0.0238 |
| left.varYtop.value\|EtOH | 29 | −1.2160 | 0.9195 | 0.0091 | 0.5052 |
| left.varYtop.value\|Pre-EtOH | 33 | −0.8624 | 0.7247 | −0.1074 | 0.4616 |
| left.nblinks.value\|EtOH | 29 | 0.4404 | 0.5811 | 0.5017 | 0.0303 |
| left.nblinks.value\|Pre-EtOH | 33 | 0.4162 | 0.7086 | 0.5093 | 0.0456 |
| left.blinkrate.value\|EtOH | 29 | 0.0009 | 0.0380 | 0.0084 | 0.0091 |
| left.blinkrate.value\|Pre-EtOH | 33 | 0.0007 | 0.0883 | 0.0122 | 0.0168 |
| left.blinklength.value\|EtOH | 29 | 0.0029 | 0.1814 | 0.0229 | 0.0334 |
| left.blinklength.value\|Pre-EtOH | 33 | 0.0014 | 0.0820 | 0.0122 | 0.0157 |
| right.areamean.value\|EtOH | 29 | 0.0039 | 0.0870 | 0.0243 | 0.0238 |
| right.areamean.value\|Pre-EtOH | 33 | 0.0014 | 0.1169 | 0.0217 | 0.0276 |
| right.areamedian.value\|EtOH | 29 | 0.0031 | 0.2493 | 0.0369 | 0.0531 |
| right.areamedian.value\|Pre-EtOH | 33 | 0.0021 | 0.1192 | 0.0236 | 0.0251 |
| right.aspectRatiomean.value\|EtOH | 29 | 0.3233 | 1.0724 | 0.6029 | 0.1716 |
| right.aspectRatiomean.value\|Pre-EtOH | 33 | 0.1776 | 0.8423 | 0.5134 | 0.1393 |
| right.aspectRatiomedian.value\|EtOH | 29 | 0.3414 | 0.8544 | 0.5458 | 0.1312 |
| right.aspectRatiomedian.value\|Pre-EtOH | 33 | 0.1600 | 0.8756 | 0.5447 | 0.1328 |
| right.heightmean.value\|EtOH | 29 | 0.3056 | 0.8362 | 0.5854 | 0.1450 |
| right.heightmean.value\|Pre-EtOH | 33 | 0.1384 | 0.8328 | 0.5163 | 0.1591 |
| right.heightmedian.value\|EtOH | 29 | 0.2311 | 0.8736 | 0.5718 | 0.1432 |
| right.heightmedian.value\|Pre-EtOH | 33 | 0.2373 | 0.9088 | 0.5343 | 0.1434 |
| right.widthmean.value\|EtOH | 29 | 1.9093 | 2.5100 | 2.3715 | 0.1086 |
| right.widthmean.value\|Pre-EtOH | 33 | 2.2592 | 3.1491 | 2.4196 | 0.1469 |

TABLE 10-continued

| Summary statistics | | | | | |
|---|---|---|---|---|---|
| Variable | Observation | Minimum | Maximum | Mean | Std. Deviation |
| right.widthmedian.value\|EtOH | 29 | 2.0045 | 2.4862 | 2.3704 | 0.0914 |
| right.widthmedian.value\|Pre-EtOH | 33 | 2.2363 | 3.2166 | 2.4236 | 0.1584 |
| right.skewTop.value\|EtOH | 29 | 4.6677 | 6.2958 | 5.6003 | 0.3903 |
| right.skewTop.value\|Pre-EtOH | 33 | 5.2297 | 13.4197 | 6.0231 | 1.3533 |
| right.skewTopNorm.value\|EtOH | 29 | 4.6739 | 6.3522 | 5.6109 | 0.3394 |
| right.skewTopNorm.value\|Pre-EtOH | 33 | 5.3237 | 13.4777 | 6.0247 | 1.3573 |
| right.skewRit.value\|EtOH | 29 | 0.8075 | 1.1791 | 0.9972 | 0.0763 |
| right.skewRit.value\|Pre-EtOH | 33 | 0.9698 | 1.4652 | 1.0255 | 0.0849 |
| right.skewRitNorm.value\|EtOH | 29 | 0.8042 | 1.1230 | 1.0016 | 0.0685 |
| right.skewRitNorm.value\|Pre-EtOH | 33 | 0.9481 | 1.3902 | 1.0223 | 0.0746 |
| right.skewBot.value\|EtOH | 29 | 0.0320 | 0.2490 | 0.1083 | 0.0558 |
| right.skewBot.value\|Pre-EtOH | 33 | 0.0140 | 0.1520 | 0.0826 | 0.0304 |
| right.skewBotNorm.value\|EtOH | 29 | 0.0700 | 2.6400 | 0.7290 | 0.5496 |
| right.skewBotNorm.value\|Pre-EtOH | 33 | 0.0300 | 4.2250 | 0.6895 | 0.7735 |
| right.skewLef.value\|EtOH | 29 | 0.0012 | 0.0088 | 0.0024 | 0.0015 |
| right.skewLef.value\|Pre-EtOH | 33 | 0.0007 | 0.0059 | 0.0021 | 0.0010 |
| right.skewLefNorm.value\|EtOH | 29 | 0.0010 | 0.0382 | 0.0033 | 0.0068 |
| right.skewLefNorm.value\|Pre-EtOH | 33 | 0.0009 | 0.0050 | 0.0020 | 0.0010 |
| right.varTotal.value\|EtOH | 29 | 0.0014 | 0.0056 | 0.0025 | 0.0010 |
| right.varTotal.value\|Pre-EtOH | 33 | 0.0009 | 0.0053 | 0.0020 | 0.0009 |
| right.varXlef.value\|EtOH | 29 | 0.0011 | 0.0104 | 0.0025 | 0.0017 |
| right.varXlef.value\|Pre-EtOH | 33 | 0.0011 | 0.0047 | 0.0021 | 0.0008 |
| right.varXrit.value\|EtOH | 29 | 1.9552 | 2.6794 | 2.3609 | 0.1382 |
| right.varXrit.value\|Pre-EtOH | 33 | 2.2836 | 4.4343 | 2.4808 | 0.3566 |
| right.varYbot.value\|EtOH | 29 | 1.9388 | 2.5701 | 2.3692 | 0.1262 |
| right.varYbot.value\|Pre-EtOH | 33 | 2.2852 | 4.3286 | 2.4766 | 0.3378 |
| right.varYtop.value\|EtOH | 29 | 14.0000 | 528.0000 | 145.7931 | 109.9296 |
| right.varYtop.value\|Pre-EtOH | 33 | 6.0000 | 845.0000 | 137.9091 | 154.7044 |
| right.nblinks.value\|EtOH | 29 | −0.1156 | 0.0705 | −0.0014 | 0.0369 |
| right.nblinks.value\|Pre-EtOH | 33 | −0.1605 | 0.0497 | −0.0082 | 0.0388 |
| right.blinkrate.value\|EtOH | 29 | −1.1502 | 0.9404 | −0.0793 | 0.6308 |
| right.blinkrate.value\|Pre-EtOH | 33 | −1.7333 | 1.0785 | −0.1312 | 0.6299 |
| right.blinklength.value\|EtOH | 29 | −0.0202 | 0.0408 | 0.0040 | 0.0170 |
| right.blinklength.value\|Pre-EtOH | 33 | −0.0253 | 0.0940 | 0.0079 | 0.0225 |
| conj.CorrXY.value\|EtOH | 29 | −1.0950 | 0.9516 | 0.0503 | 0.5614 |
| conj.CorrXY.value\|Pre-EtOH | 33 | −0.7848 | 1.1550 | 0.1369 | 0.4560 |
| conj.CorrXYbot.value\|EtOH | 29 | −0.1192 | 0.0712 | 0.0077 | 0.0323 |
| conj.CorrXYbot.value\|Pre-EtOH | 33 | −0.0441 | 0.0684 | 0.0039 | 0.0179 |
| conj.CorrXYlef.value\|EtOH | 29 | −0.8539 | 1.1384 | 0.2152 | 0.5085 |
| conj.CorrXYlef.value\|Pre-EtOH | 33 | −0.5197 | 1.0719 | 0.1158 | 0.3837 |
| conj.CorrXYrit.value\|EtOH | 29 | −0.1607 | 0.0339 | −0.0096 | 0.0401 |
| conj.CorrXYrit.value\|Pre-EtOH | 33 | −0.0548 | 0.0368 | −0.0040 | 0.0209 |
| conj.CorrXYtop.value\|EtOH | 29 | −1.1948 | 0.7125 | −0.0534 | 0.5140 |
| conj.CorrXYtop.value\|Pre-EtOH | 33 | −0.7522 | 0.8306 | 0.0468 | 0.4439 |
| conj.totVar.value\|EtOH | 29 | 0.4322 | 0.5636 | 0.5016 | 0.0349 |
| conj.totVar.value\|Pre-EtOH | 33 | 0.4068 | 0.7315 | 0.5044 | 0.0482 |
| conj.varX.value\|EtOH | 29 | 0.0031 | 0.0484 | 0.0092 | 0.0096 |
| conj.varX.value\|Pre-EtOH | 33 | 0.0008 | 0.0604 | 0.0126 | 0.0155 |
| conj.varXbot.value\|EtOH | 29 | 0.0031 | 0.2016 | 0.0296 | 0.0477 |
| conj.varXbot.value\|Pre-EtOH | 33 | 0.0011 | 0.0861 | 0.0121 | 0.0157 |
| conj.varXlef.value\|EtOH | 29 | 0.0027 | 0.1103 | 0.0269 | 0.0296 |
| conj.varXlef.value\|Pre-EtOH | 33 | 0.0023 | 0.0858 | 0.0194 | 0.0209 |
| conj.varXlefritRatio.value\|EtOH | 29 | 0.0015 | 0.2394 | 0.0305 | 0.0481 |
| conj.varXlefritRatio.value\|Pre-EtOH | 33 | 0.0013 | 0.1074 | 0.0200 | 0.0245 |
| conj.varXrit.value\|EtOH | 29 | 0.1223 | 1.1381 | 0.5597 | 0.2232 |
| conj.varXrit.value\|Pre-EtOH | 33 | 0.3108 | 0.9043 | 0.5314 | 0.1344 |
| conj.varXtop.value\|EtOH | 29 | 0.1667 | 0.8384 | 0.5108 | 0.1614 |
| conj.varXtop.value\|Pre-EtOH | 33 | 0.3213 | 0.9875 | 0.5385 | 0.1254 |
| conj.varXtopbotRatio.value\|EtOH | 29 | 0.0721 | 0.9043 | 0.5726 | 0.1938 |
| conj.varXtopbotRatio.value\|Pre-EtOH | 33 | 0.3510 | 0.8511 | 0.5415 | 0.1256 |
| conj.varY.value\|EtOH | 29 | 0.2076 | 0.9087 | 0.5544 | 0.1644 |
| conj.varY.value\|Pre-EtOH | 33 | 0.3161 | 0.9006 | 0.5513 | 0.1234 |
| conj.varYbot.value\|EtOH | 29 | 2.0645 | 2.5704 | 2.3725 | 0.1012 |
| conj.varYbot.value\|Pre-EtOH | 33 | 2.2017 | 3.0263 | 2.4121 | 0.1284 |
| conj.varYlef.value\|EtOH | 29 | 2.1376 | 2.5419 | 2.3689 | 0.0836 |
| conj.varYlef.value\|Pre-EtOH | 33 | 2.2539 | 3.1136 | 2.4161 | 0.1409 |
| conj.varYlefritRatio.value\|EtOH | 29 | 0.0000 | 8.0000 | 0.9655 | 1.9545 |
| conj.varYlefritRatio.value\|Pre-EtOH | 33 | 0.0000 | 7.0000 | 0.4242 | 1.4149 |
| conj.varYrit.value\|EtOH | 29 | 0.0000 | 9.0000 | 1.2069 | 2.2261 |

TABLE 10-continued

Summary statistics

| Variable | Observation | Minimum | Maximum | Mean | Std. Deviation |
|---|---|---|---|---|---|
| conj.varYrit.value\|Pre-EtOH | 33 | 0.0000 | 10.0000 | 0.9091 | 2.3233 |
| conj.varYtop.value\|EtOH | 29 | 0.0000 | 18.0000 | 3.2414 | 4.6954 |
| conj.varYtop.value\|Pre-EtOH | 33 | 0.0000 | 18.0000 | 2.7273 | 4.6588 |
| conj.varYtopbotRatio.value\|EtOH | 29 | −0.0112 | 0.0169 | 0.0016 | 0.0055 |
| conj.varYtopbotRatio.value\|Pre-EtOH | 33 | −0.0250 | 0.0070 | −0.0004 | 0.0049 |
| conj.boxscore.value\|EtOH | 29 | | | | |
| conj.boxscore.value\|Pre-EtOH | 33 | | | | |
| left.distBot.value\|EtOH | 29 | 0.0000 | 2.0000 | 0.1724 | 0.5391 |
| left.distBot.value\|Pre-EtOH | 33 | 0.0000 | 1.0000 | 0.0303 | 0.1741 |
| left.distLef.value\|EtOH | 29 | 0.0033 | 0.1866 | 0.0345 | 0.0438 |
| left.distLef.value\|Pre-EtOH | 33 | 0.0020 | 0.4767 | 0.0310 | 0.0817 |
| right.distTop.value\|EtOH | 29 | 0.0006 | 0.0575 | 0.0093 | 0.0140 |
| right.distTop.value\|Pre-EtOH | 33 | 0.0002 | 0.0832 | 0.0067 | 0.0159 |
| right.distRit.value\|EtOH | 29 | 0.0009 | 0.0289 | 0.0069 | 0.0078 |
| right.distRit.value\|Pre-EtOH | 33 | 0.0007 | 0.0093 | 0.0032 | 0.0023 |
| right.distBot.value\|EtOH | 29 | 0.0005 | 0.1513 | 0.0132 | 0.0296 |
| right.distBot.value\|Pre-EtOH | 33 | 0.0004 | 0.0236 | 0.0041 | 0.0047 |
| right.distLef.value\|EtOH | 29 | 0.0003 | 0.0381 | 0.0038 | 0.0069 |
| right.distLef.value\|Pre-EtOH | 33 | 0.0003 | 0.0229 | 0.0029 | 0.0041 |
| left.velTop.value\|EtOH | 29 | 0.0528 | 8.8761 | 1.6318 | 1.9969 |
| left.velTop.value\|Pre-EtOH | 33 | 0.2431 | 17.0838 | 2.5358 | 3.1025 |
| left.velRit.value\|EtOH | 29 | 0.0003 | 0.0770 | 0.0071 | 0.0152 |
| left.velRit.value\|Pre-EtOH | 33 | 0.0002 | 0.0076 | 0.0017 | 0.0017 |
| left.velBot.value\|EtOH | 29 | 0.0011 | 0.0197 | 0.0059 | 0.0041 |
| left.velBot.value\|Pre-EtOH | 33 | 0.0007 | 0.0233 | 0.0050 | 0.0047 |
| left.velLef.value\|EtOH | 29 | 0.0318 | 6.6717 | 1.5277 | 1.3926 |
| left.velLef.value\|Pre-EtOH | 33 | 0.1686 | 11.9799 | 2.1248 | 2.2258 |
| right.velTop.value\|EtOH | 29 | 0.0011 | 0.1813 | 0.0275 | 0.0419 |
| right.velTop.value\|Pre-EtOH | 33 | 0.0010 | 0.4732 | 0.0278 | 0.0814 |
| right.velRit.value\|EtOH | 29 | 0.0010 | 0.0827 | 0.0173 | 0.0210 |
| right.velRit.value\|Pre-EtOH | 33 | 0.0007 | 0.2063 | 0.0246 | 0.0492 |
| right.velBot.value\|EtOH | 29 | 0.0014 | 0.4057 | 0.0390 | 0.0815 |
| right.velBot.value\|Pre-EtOH | 33 | 0.0008 | 1.6090 | 0.0683 | 0.2783 |
| right.velLef.value\|EtOH | 29 | 0.1093 | 7.9867 | 1.5497 | 1.6999 |
| right.velLef.value\|Pre-EtOH | 33 | 0.2652 | 22.0486 | 2.1207 | 3.7692 |
| conj.velTop.value\|EtOH | 29 | 0.0013 | 0.3327 | 0.0371 | 0.0653 |
| conj.velTop.value\|Pre-EtOH | 33 | 0.0009 | 0.0730 | 0.0153 | 0.0178 |
| conj.velRit.value\|EtOH | 29 | 0.0005 | 0.1099 | 0.0177 | 0.0259 |
| conj.velRit.value\|Pre-EtOH | 33 | 0.0003 | 0.1133 | 0.0107 | 0.0217 |
| conj.velBot.value\|EtOH | 29 | 0.1233 | 9.4359 | 1.5080 | 2.0405 |
| conj.velBot.value\|Pre-EtOH | 33 | 0.0082 | 4.7438 | 1.1951 | 1.2999 |
| conj.velLef.value\|EtOH | 29 | −0.5667 | 0.7252 | 0.0431 | 0.2363 |
| conj.velLef.value\|Pre-EtOH | 33 | −0.5536 | 0.2262 | −0.0179 | 0.1285 |
| conj.velLef.value\|EtOH | 29 | −0.3613 | 0.3917 | 0.0350 | 0.1490 |
| conj.velLef.value\|Pre-EtOH | 33 | −0.1613 | 0.2353 | 0.0062 | 0.0779 |
| conj.velRit.value\|EtOH | 29 | −0.3083 | 0.6047 | 0.0128 | 0.1688 |
| conj.velRit.value\|Pre-EtOH | 33 | −0.6586 | 0.2554 | −0.0253 | 0.1385 |
| conj.velTop.value\|EtOH | 29 | −0.4972 | 0.3426 | 0.0174 | 0.1699 |
| conj.velTop.value\|Pre-EtOH | 33 | −0.2188 | 0.2594 | −0.0170 | 0.0758 |

The invention claimed is:

1. A method for diagnosing, assessing or quantitating drug use, drug abuse or narcosis in a subject comprising:
    a) tracking eye pupil movement of at least one of a first eye and a second eye of the subject using a device suitable for tracking eye pupil movement;
    b) analyzing eye pupil movement of the at least one of the first eye and the second eye of the subject using a computer in electronic communication with the device suitable for tracking eye pupil movement;
    c) generating a box plot that reflects a trajectory traveled of each of the at least one of the first eye and the second eye in response to a visual stimuli, the box plot having four segments that represent different directions;
    d) comparing eye pupil movement of the at least one of the first eye and the second eye of the subject to a normal or mean eye pupil movement;
    e) calculating a standard deviation or p value for eye pupil movement of the at least one of the first eye and the second eye of the subject as compared to the normal or mean eye pupil movement; and
    f) calculating a plurality of velocities including a segment velocity of eye pupil movement in each of the four segments of the box plot, and comparing a first segment velocity of eye pupil movement with other segment velocities of the four segments.

2. The method according to claim 1 wherein eye pupil movement of the first eye and the second eye of the subject are tracked and analyzed.

3. The method according to claim 1 wherein both x and y coordinates of eye position for the first eye and the second eye of the subject are collected.

4. The method according to claim 1 wherein the eye pupil movement is tracked for at least about 100 or more seconds.

5. The method according to claim 1 wherein the tracking, analyzing and comparing comprises collecting raw x and y Cartesian coordinates of pupil position, normalizing the raw x and y Cartesian coordinates, and sorting data by eye.

6. The method according to claim 5 wherein the x and y Cartesian coordinates of pupil position represent two components of an instantaneous angle of pupil reflection.

7. The method according to claim 1 wherein the analyzing and comparing comprises calculating velocity of the eye pupil movement.

8. The method according to claim 1 wherein the comparing eye pupil movement of at least one of the first eye and the second eye of the subject to a normal or mean eye pupil movement comprises comparing eye pupil movement of at least one of the first eye and the second eye of the subject to the eye pupil movement of an eye of one or more other subjects or controls.

9. The method according to claim 1, further comprising the step of determining the presence of drug use, drug abuse or narcosis in the subject if the segment velocity in one of the four segments is less than a segment velocity in others of the four segments.

10. The method according to claim 1 wherein the comparing further comprises comparing the segment velocity of eye pupil movement in each of the four segments to control velocities for each of the four segments.

11. The method according to claim 1, further comprising the step of determining the presence of drug use, drug abuse or narcosis in the subject based on the shape of the box plot.

12. The method according to claim 1, wherein comparing a first segment velocity of eye pupil movement with other segment velocities of the four segments includes comparing segment velocities of the first eye pupil to other segment velocities of the first eye pupil.

13. The method according to claim 1, further comprising the step of temporally calibrating pupil movement by predicting positions of the eye pupil based on time elapsed since a start of the visual stimuli.

* * * * *